(12) United States Patent
Messerly et al.

(10) Patent No.: US 12,708,427 B2
(45) Date of Patent: Aug. 18, 2026

(54) ULTRASONIC ENERGY DEVICE WHICH VARIES PRESSURE APPLIED BY CLAMP ARM TO PROVIDE THRESHOLD CONTROL PRESSURE AT A CUT PROGRESSION LOCATION

(71) Applicant: Cilag GmbH International, Zug (CH)

(72) Inventors: Jeffrey D. Messerly, Cincinnati, OH (US); Frederick E. Shelton, IV, Hillsboro, OH (US); David C. Yates, Morrow, OH (US); Jason L. Harris, Lebanon, OH (US); James M. Wilson, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 736 days.

(21) Appl. No.: 17/734,496

(22) Filed: May 2, 2022

(65) Prior Publication Data

US 2022/0370117 A1 Nov. 24, 2022

Related U.S. Application Data

(63) Continuation of application No. 16/182,238, filed on Nov. 6, 2018, now Pat. No. 11,419,667.

(Continued)

(51) Int. Cl.

| | |
|---|---|
| ***A61B 18/14*** | (2006.01) |
| ***A61B 17/32*** | (2006.01) |

(Continued)

(52) U.S. Cl.

CPC .. *A61B 18/1445* (2013.01); *A61B 17/320068* (2013.01); *A61B 17/320092* (2013.01);

(Continued)

(58) Field of Classification Search

CPC ............ A61B 18/1445; A61B 18/1206; A61B 17/320068; A61B 17/320092;

(Continued)

(56) References Cited

U.S. PATENT DOCUMENTS

| | | | |
|---|---|---|---|
| 969,528 | A | 9/1910 | Disbrow |
| 1,570,025 | A | 1/1926 | Young |

(Continued)

FOREIGN PATENT DOCUMENTS

| | | | |
|---|---|---|---|
| AU | 2015201140 | A1 | 3/2015 |
| CA | 2795323 | A1 | 5/2014 |

(Continued)

OTHER PUBLICATIONS

US 10,504,709 B2, 12/2019, Karancsi et al. (withdrawn)

(Continued)

*Primary Examiner* — Joanne M Rodden
*Assistant Examiner* — Bo Ouyang
(74) *Attorney, Agent, or Firm* — Condo Roccia Koptiw LLP

(57) ABSTRACT

Surgical instruments and system and methods for using surgical instruments are disclosed. A surgical instrument comprises an end effector comprising an ultrasonic blade and clamp arm, an ultrasonic transducer, and a control circuit. The ultrasonic transducer ultrasonically oscillates the ultrasonic blade in response to a drive signal from a generator. The end effector receives electrosurgical energy to weld tissue. The control circuit determines a resonant frequency measure indicative of a thermally induced change in resonant frequency and a electrical continuity measure; calculates a weld focal point based on the determined measures, controls closure of the clamp arm to vary a pressure applied by the clamp arm to provide a threshold control pressure to the tissue loaded into the end effector, (Continued)

and maintains a gap between the ultrasonic blade and clamp arm at a point proximal to the proximal end of the tissue. Pressure is varied based on corresponding weld focal point.

10 Claims, 34 Drawing Sheets

Related U.S. Application Data

(60) Provisional application No. 62/729,195, filed on Sep. 10, 2018, provisional application No. 62/692,768, filed on Jun. 30, 2018, provisional application No. 62/692,748, filed on Jun. 30, 2018, provisional application No. 62/692,747, filed on Jun. 30, 2018, provisional application No. 62/659,900, filed on Apr. 19, 2018, provisional application No. 62/650,877, filed on Mar. 30, 2018, provisional application No. 62/650,887, filed on Mar. 30, 2018, provisional application No. 62/650,898, filed on Mar. 30, 2018, provisional application No. 62/650,882, filed on Mar. 30, 2018, provisional application No. 62/640,417, filed on Mar. 8, 2018, provisional application No. 62/640,415, filed on Mar. 8, 2018, provisional application No. 62/611,341, filed on Dec. 28, 2017, provisional application No. 62/611,340, filed on Dec. 28, 2017, provisional application No. 62/611,339, filed on Dec. 28, 2017.

(51) Int. Cl.

| | |
|---|---|
| ***A61B 18/12*** | (2006.01) |
| *A61B 17/00* | (2006.01) |
| *A61B 18/00* | (2006.01) |
| *A61B 34/30* | (2016.01) |
| *A61B 34/37* | (2016.01) |
| *A61B 50/10* | (2016.01) |
| *A61B 50/13* | (2016.01) |
| *A61B 50/18* | (2016.01) |
| *A61B 90/00* | (2016.01) |
| *G16H 40/63* | (2018.01) |
| *G16H 40/67* | (2018.01) |
| *H04L 67/10* | (2022.01) |

(52) U.S. Cl.

CPC *A61B 18/1206* (2013.01); *A61B 2017/00017* (2013.01); *A61B 2017/00022* (2013.01); *A61B 2017/00199* (2013.01); *A61B 2017/00504* (2013.01); *A61B 2017/320073* (2017.08); *A61B 2017/320094* (2017.08); *A61B 2017/320095* (2017.08); *A61B 2018/00619* (2013.01); *A61B 2018/00636* (2013.01); *A61B 2018/00642* (2013.01); *A61B 2018/00678* (2013.01); *A61B 2018/00702* (2013.01); *A61B 2018/00875* (2013.01); *A61B 2018/0088* (2013.01); *A61B 2018/00994* (2013.01); *A61B 2018/1253* (2013.01); *A61B 2018/126* (2013.01); *A61B 2018/1273* (2013.01); *A61B 34/30* (2016.02); *A61B 34/37* (2016.02); *A61B 50/10* (2016.02); *A61B 50/13* (2016.02); *A61B 2050/185* (2016.02); *A61B 2090/032* (2016.02); *A61B 90/361* (2016.02); *A61B 90/37* (2016.02); *A61B 2090/376* (2016.02); *A61B 2218/002* (2013.01); *A61B 2218/008* (2013.01); *G16H 40/63* (2018.01); *G16H 40/67* (2018.01); *H04L 67/10* (2013.01)

(58) Field of Classification Search

CPC ......... A61B 34/30; A61B 34/37; A61B 50/10; A61B 50/13; A61B 90/361; A61B 90/37; A61B 2050/185; A61B 2090/032; A61B 2090/376; A61B 2017/320094; A61B 2017/320073; A61B 2017/320095; A61B 2017/00017; A61B 2017/00022; A61B 2017/00199; A61B 2017/00504; A61B 2018/00619; A61B 2018/00636; A61B 2018/00642; A61B 2018/00678; A61B 2018/00702; A61B 2018/00875; A61B 2018/0088; A61B 2018/00994; A61B 2018/1253; A61B 2018/126; A61B 2018/1273; H04L 67/10

See application file for complete search history.

(56) References Cited

U.S. PATENT DOCUMENTS

| | | | |
|---|---|---|---|
| 1,853,416 | A | 4/1932 | Hall |
| 2,222,125 | A | 11/1940 | Stehlik |
| 2,704,333 | A | 3/1955 | Calosi et al. |
| 2,736,960 | A | 3/1956 | Armstrong |
| 2,849,788 | A | 9/1958 | Oliver |
| RE25,033 | E | 8/1961 | Balamuth et al. |
| 3,015,961 | A | 1/1962 | Roney |
| 3,082,426 | A | 3/1963 | Miles |
| 3,503,396 | A | 3/1970 | Pierie et al. |
| 3,513,848 | A | 5/1970 | Winston et al. |
| 3,526,219 | A | 9/1970 | Balamuth |
| 3,584,628 | A | 6/1971 | Green |
| 3,614,484 | A | 10/1971 | Shoh |
| 3,626,457 | A | 12/1971 | Duerr et al. |
| 3,633,584 | A | 1/1972 | Farrell |
| 3,636,943 | A | 1/1972 | Balamuth |
| 3,759,017 | A | 9/1973 | Young |
| 3,776,238 | A | 12/1973 | Peyman et al. |
| 3,805,787 | A | 4/1974 | Banko |
| 3,830,098 | A | 8/1974 | Antonevich |
| 3,854,737 | A | 12/1974 | Gilliam |
| 3,862,630 | A | 1/1975 | Balamuth |
| 3,863,118 | A | 1/1975 | Lander et al. |
| 3,898,545 | A | 8/1975 | Coppa et al. |
| 3,900,823 | A | 8/1975 | Sokal et al. |
| 3,912,121 | A | 10/1975 | Steffen |
| 3,915,271 | A | 10/1975 | Harper |
| 3,918,442 | A | 11/1975 | Nikolaev et al. |
| 3,932,812 | A | 1/1976 | Milligan |
| 3,946,738 | A | 3/1976 | Newton et al. |
| 3,955,859 | A | 5/1976 | Stella et al. |
| 3,956,826 | A | 5/1976 | Perdreaux, Jr. |
| 4,041,362 | A | 8/1977 | Ichiyanagi |
| 4,052,649 | A | 10/1977 | Greenwell et al. |
| 4,087,730 | A | 5/1978 | Goles |
| 4,156,187 | A | 5/1979 | Brumbach et al. |
| 4,157,859 | A | 6/1979 | Terry |
| 4,171,700 | A | 10/1979 | Farin |
| 4,188,927 | A | 2/1980 | Harris |
| 4,200,106 | A | 4/1980 | Dinkelkamp et al. |
| 4,202,722 | A | 5/1980 | Paquin |
| 4,306,570 | A | 12/1981 | Matthews |
| 4,412,539 | A | 11/1983 | Jarvik |
| 4,445,063 | A | 4/1984 | Smith |
| 4,448,193 | A | 5/1984 | Ivanov |
| 4,491,132 | A | 1/1985 | Aikins |
| 4,504,264 | A | 3/1985 | Kelman |
| 4,523,695 | A | 6/1985 | Braun et al. |
| 4,574,615 | A | 3/1986 | Bower et al. |
| 4,608,160 | A | 8/1986 | Zoch |
| 4,614,366 | A | 9/1986 | North et al. |
| 4,617,927 | A | 10/1986 | Manes |
| 4,633,119 | A | 12/1986 | Thompson |
| 4,633,874 | A | 1/1987 | Chow et al. |
| 4,634,420 | A | 1/1987 | Spinosa et al. |
| 4,640,279 | A | 2/1987 | Beard |

(56) References Cited

U.S. PATENT DOCUMENTS 4,649,919 A 3/1987 Thimsen et al.
4,701,193 A 10/1987 Robertson et al.
4,708,127 A 11/1987 Abdelghani
4,712,722 A 12/1987 Hood et al.
4,735,603 A 4/1988 Goodson et al.
4,788,977 A 12/1988 Farin et al.
4,827,911 A 5/1989 Broadwin et al.
4,832,683 A 5/1989 Idemoto et al.
4,838,853 A 6/1989 Parisi
4,849,752 A 7/1989 Bryant
4,850,354 A 7/1989 Mcgurk-Burleson et al.
4,865,159 A 9/1989 Jamison
D303,787 S 10/1989 Messenger et al.
4,892,244 A 1/1990 Fox et al.
4,896,009 A 1/1990 Pawlowski
4,903,696 A 2/1990 Stasz et al.
4,922,902 A 5/1990 Wuchinich et al.
4,954,960 A 9/1990 Lo et al.
4,965,532 A 10/1990 Sakurai
4,976,173 A 12/1990 Yang
4,979,952 A 12/1990 Kubota et al.
4,981,756 A 1/1991 Rhandhawa
5,010,341 A 4/1991 Huntley et al.
5,026,387 A 6/1991 Thomas
5,035,692 A 7/1991 Lyon et al.
5,042,460 A 8/1991 Sakurai et al.
5,047,043 A 9/1991 Kubota et al.
5,084,057 A 1/1992 Green et al.
5,100,402 A 3/1992 Fan
5,109,819 A 5/1992 Custer et al.
5,112,300 A 5/1992 Ureche
D327,061 S 6/1992 Soren et al.
5,123,903 A 6/1992 Quaid et al.
5,126,618 A 6/1992 Takahashi et al.
5,129,570 A 7/1992 Schulze et al.
5,151,102 A 9/1992 Kamiyama et al.
5,156,315 A 10/1992 Green et al.
5,158,585 A 10/1992 Saho et al.
5,162,044 A 11/1992 Gahn et al.
5,163,537 A 11/1992 Radev
5,171,247 A 12/1992 Hughett et al.
D332,660 S 1/1993 Rawson et al.
5,176,677 A 1/1993 Wuchinich
5,176,695 A 1/1993 Dulebohn
5,184,605 A 2/1993 Grzeszykowski
5,188,102 A 2/1993 Idemoto et al.
5,189,277 A 2/1993 Boisvert et al.
5,197,962 A 3/1993 Sansom et al.
5,204,669 A 4/1993 Dorfe et al.
5,213,569 A 5/1993 Davis
5,217,003 A 6/1993 Wilk
5,221,282 A 6/1993 Wuchinich
5,226,909 A 7/1993 Evans et al.
5,226,910 A 7/1993 Kajiyama et al.
5,241,236 A 8/1993 Sasaki et al.
5,242,474 A 9/1993 Herbst et al.
5,253,793 A 10/1993 Green et al.
5,257,988 A 11/1993 Esperance
5,261,922 A 11/1993 Hood
5,271,543 A 12/1993 Grant et al.
RE34,519 E 1/1994 Fox et al.
5,275,323 A 1/1994 Schulze et al.
5,275,609 A 1/1994 Pingleton et al.
5,282,800 A 2/1994 Foshee et al.
5,304,115 A 4/1994 Pflueger et al.
D347,474 S 5/1994 Olson
5,318,516 A 6/1994 Cosmescu
5,318,563 A 6/1994 Malis et al.
5,322,055 A 6/1994 Davison et al.
5,324,299 A 6/1994 Davison et al.
5,326,342 A 7/1994 Pflueger et al.
5,342,349 A 8/1994 Kaufman
5,344,420 A 9/1994 Hilal et al.
5,346,502 A 9/1994 Estabrook et al.
5,353,474 A 10/1994 Good et al.
5,357,164 A 10/1994 Imabayashi et al.
5,357,423 A 10/1994 Weaver et al.
5,364,003 A 11/1994 Williamson, IV
5,366,466 A 11/1994 Christian et al.
5,371,429 A 12/1994 Manna
D354,564 S 1/1995 Medema
5,381,067 A 1/1995 Greenstein et al.
5,383,880 A 1/1995 Hooven
5,385,544 A 1/1995 Edwards et al.
5,396,900 A 3/1995 Slater et al.
5,397,046 A 3/1995 Savage et al.
5,403,312 A 4/1995 Yates et al.
5,403,327 A 4/1995 Thornton et al.
D358,887 S 5/1995 Feinberg
5,411,481 A 5/1995 Allen et al.
5,413,267 A 5/1995 Solyntjes et al.
5,415,335 A 5/1995 Knodell, Jr.
5,417,699 A 5/1995 Klein et al.
5,419,761 A 5/1995 Narayanan et al.
5,421,829 A 6/1995 Olichney et al.
5,438,997 A 8/1995 Sieben et al.
5,439,468 A 8/1995 Schulze et al.
5,445,304 A 8/1995 Plyley et al.
5,447,509 A 9/1995 Mills et al.
5,449,370 A 9/1995 Vaitekunas
5,462,545 A 10/1995 Wang et al.
5,465,895 A 11/1995 Knodel et al.
5,467,911 A 11/1995 Tsuruta et al.
5,471,988 A 12/1995 Fujio et al.
5,474,566 A 12/1995 Alesi et al.
5,483,501 A 1/1996 Park et al.
5,485,947 A 1/1996 Olson et al.
5,486,162 A 1/1996 Brumbach
5,496,315 A 3/1996 Weaver et al.
5,496,317 A 3/1996 Goble et al.
5,500,216 A 3/1996 Julian et al.
5,501,654 A 3/1996 Failla et al.
5,503,320 A 4/1996 Webster et al.
5,505,693 A 4/1996 Mackool
5,507,738 A 4/1996 Ciervo
5,527,331 A 6/1996 Kresch et al.
5,529,235 A 6/1996 Boiarski et al.
5,531,743 A 7/1996 Nettekoven et al.
5,545,148 A 8/1996 Wurster
5,552,685 A 9/1996 Young et al.
5,560,372 A 10/1996 Cory
5,562,609 A 10/1996 Brumbach
5,562,610 A 10/1996 Brumbach
5,584,425 A 12/1996 Savage et al.
5,601,601 A 2/1997 Tal et al.
5,603,773 A 2/1997 Campbell
5,607,436 A 3/1997 Pratt et al.
5,610,379 A 3/1997 Muz et al.
5,610,811 A 3/1997 Honda
5,613,966 A 3/1997 Makower et al.
5,618,492 A 4/1997 Auten et al.
5,624,452 A 4/1997 Yates
D379,346 S 5/1997 Mieki
5,626,587 A 5/1997 Bishop et al.
5,628,760 A 5/1997 Knoepfler
5,630,420 A 5/1997 Vaitekunas
D381,077 S 7/1997 Hunt
5,643,291 A 7/1997 Pier et al.
5,651,780 A 7/1997 Jackson et al.
5,653,713 A 8/1997 Michelson
5,654,750 A 8/1997 Weil et al.
5,669,922 A 9/1997 Hood
5,673,841 A 10/1997 Schulze et al.
5,673,842 A 10/1997 Bittner et al.
5,674,235 A 10/1997 Parisi
5,675,227 A 10/1997 Roos et al.
5,690,269 A 11/1997 Bolanos et al.
5,693,042 A 12/1997 Boiarski et al.
5,693,052 A 12/1997 Weaver
5,694,936 A 12/1997 Fujimoto et al.
5,695,502 A 12/1997 Pier et al.
5,697,926 A 12/1997 Weaver
5,706,998 A 1/1998 Plyley et al.
5,713,896 A 2/1998 Nardella

(56) References Cited

U.S. PATENT DOCUMENTS 5,718,359 A 2/1998 Palmer et al.
5,724,468 A 3/1998 Leone et al.
5,725,536 A 3/1998 Oberlin et al.
5,725,542 A 3/1998 Yoon
5,730,752 A 3/1998 Alden et al.
5,733,074 A 3/1998 Stoeck et al.
5,735,445 A 4/1998 Vidal et al.
5,735,848 A 4/1998 Yates et al.
5,741,226 A 4/1998 Strukel et al.
5,746,209 A 5/1998 Yost et al.
5,749,362 A 5/1998 Funda et al.
5,749,893 A 5/1998 Vidal et al.
5,752,644 A 5/1998 Bolanos et al.
5,762,255 A 6/1998 Chrisman et al.
5,762,458 A 6/1998 Wang et al.
5,766,186 A 6/1998 Faraz et al.
5,769,791 A 6/1998 Benaron et al.
5,775,331 A 7/1998 Raymond et al.
5,792,165 A 8/1998 Klieman et al.
5,797,537 A 8/1998 Oberlin et al.
5,800,350 A 9/1998 Coppleson et al.
5,808,396 A 9/1998 Boukhny
5,810,859 A 9/1998 Dimatteo et al.
D399,561 S 10/1998 Ellingson
5,817,084 A 10/1998 Jensen
5,817,093 A 10/1998 Williamson, IV et al.
5,817,119 A 10/1998 Klieman et al.
5,820,009 A 10/1998 Melling et al.
5,827,323 A 10/1998 Klieman et al.
5,828,160 A 10/1998 Sugishita
5,833,690 A 11/1998 Yates et al.
5,833,696 A 11/1998 Whitfield et al.
5,836,849 A 11/1998 Mathiak et al.
5,836,869 A 11/1998 Kudo et al.
5,836,897 A 11/1998 Sakurai et al.
5,836,909 A 11/1998 Cosmescu
5,843,080 A 12/1998 Fleenor et al.
5,843,109 A 12/1998 Mehta et al.
5,846,237 A 12/1998 Nettekoven
5,849,022 A 12/1998 Sakashita et al.
5,873,873 A 2/1999 Smith et al.
5,878,938 A 3/1999 Bittner et al.
5,879,364 A 3/1999 Bromfield et al.
5,883,615 A 3/1999 Fago et al.
5,893,835 A 4/1999 Witt et al.
5,893,849 A 4/1999 Weaver
5,897,523 A 4/1999 Wright et al.
5,897,569 A 4/1999 Kellogg et al.
5,906,625 A 5/1999 Bito et al.
5,906,628 A 5/1999 Miyawaki et al.
5,911,699 A 6/1999 Anis et al.
5,935,143 A 8/1999 Hood
5,935,144 A 8/1999 Estabrook
5,938,633 A 8/1999 Beaupre
5,942,333 A 8/1999 Arnett et al.
5,944,718 A 8/1999 Austin et al.
5,944,737 A 8/1999 Tsonton et al.
5,947,996 A 9/1999 Logeman
5,954,736 A 9/1999 Bishop et al.
5,954,746 A 9/1999 Holthaus et al.
5,957,882 A 9/1999 Nita et al.
5,957,943 A 9/1999 Vaitekunas
5,968,007 A 10/1999 Simon et al.
5,968,032 A 10/1999 Sleister
5,968,060 A 10/1999 Kellogg
D416,089 S 11/1999 Medema et al.
5,980,510 A 11/1999 Tsonton et al.
5,987,346 A 11/1999 Benaron et al.
5,989,274 A 11/1999 Davison et al.
5,989,275 A 11/1999 Estabrook et al.
5,993,972 A 11/1999 Reich et al.
5,997,528 A 12/1999 Bisch et al.
6,004,269 A 12/1999 Crowley et al.
6,010,054 A 1/2000 Johnson et al.
6,027,515 A 2/2000 Cimino
6,030,437 A 2/2000 Gourrier et al.
6,033,375 A 3/2000 Brumbach
6,036,637 A 3/2000 Kudo
6,039,734 A 3/2000 Goble
6,039,735 A 3/2000 Greep
6,050,943 A 4/2000 Slayton et al.
6,051,010 A 4/2000 Dimatteo et al.
6,056,735 A 5/2000 Okada et al.
6,059,799 A 5/2000 Aranyi et al.
6,063,098 A 5/2000 Houser et al.
6,066,132 A 5/2000 Chen et al.
6,066,137 A 5/2000 Greep
6,066,151 A 5/2000 Miyawaki et al.
6,068,647 A 5/2000 Witt et al.
6,077,285 A 6/2000 Boukhny
6,079,606 A 6/2000 Milliman et al.
6,083,191 A 7/2000 Rose
6,086,584 A 7/2000 Miller
6,090,107 A 7/2000 Borgmeier et al.
6,090,120 A 7/2000 Wright et al.
6,099,537 A 8/2000 Sugai et al.
6,102,907 A 8/2000 Smethers et al.
6,109,500 A 8/2000 Alli et al.
6,110,127 A 8/2000 Suzuki
6,113,594 A 9/2000 Savage
6,113,598 A 9/2000 Baker
6,117,152 A 9/2000 Huitema
6,126,592 A 10/2000 Proch et al.
6,126,629 A 10/2000 Perkins
6,126,658 A 10/2000 Baker
6,129,735 A 10/2000 Okada et al.
6,131,789 A 10/2000 Schulze et al.
6,139,320 A 10/2000 Hahn
6,139,561 A 10/2000 Shibata et al.
6,142,615 A 11/2000 Qiu et al.
6,147,560 A 11/2000 Erhage et al.
6,152,902 A 11/2000 Christian et al.
6,155,473 A 12/2000 Tompkins et al.
6,159,160 A 12/2000 Hsei et al.
6,159,175 A 12/2000 Strukel et al.
6,165,150 A 12/2000 Banko
6,204,592 B1 3/2001 Hur
6,206,844 B1 3/2001 Reichel et al.
6,210,403 B1 4/2001 Klicek
6,214,000 B1 4/2001 Fleenor et al.
6,214,023 B1 4/2001 Whipple et al.
6,231,565 B1 5/2001 Tovey et al.
6,233,476 B1 5/2001 Strommer et al.
6,238,366 B1 5/2001 Savage et al.
6,252,110 B1 6/2001 Uemura et al.
D444,365 S 7/2001 Bass et al.
6,254,623 B1 7/2001 Haibel et al.
6,258,034 B1 7/2001 Hanafy
6,258,105 B1 7/2001 Hart et al.
6,267,761 B1 7/2001 Ryan
6,269,411 B1 7/2001 Reasoner
6,270,831 B2 8/2001 Kumar et al.
6,273,852 B1 8/2001 Lehe et al.
6,273,887 B1 8/2001 Yamauchi et al.
6,274,963 B1 8/2001 Estabrook et al.
6,277,115 B1 8/2001 Saadat
6,278,218 B1 8/2001 Madan et al.
6,283,960 B1 9/2001 Ashley
6,283,981 B1 9/2001 Beaupre
6,301,495 B1 10/2001 Gueziec et al.
6,302,881 B1 10/2001 Farin
6,308,089 B1 10/2001 von der Ruhr et al.
6,309,400 B2 10/2001 Beaupre
6,319,221 B1 11/2001 Savage et al.
6,325,808 B1 12/2001 Bernard et al.
6,325,811 B1 12/2001 Messerly
6,328,751 B1 12/2001 Beaupre
6,331,181 B1 12/2001 Tierney et al.
6,340,352 B1 1/2002 Okada et al.
6,341,164 B1 1/2002 Dilkie et al.
6,352,532 B1 3/2002 Kramer et al.
6,379,320 B1 4/2002 Lafon et al.
D457,958 S 5/2002 Dycus et al.
6,383,194 B1 5/2002 Pothula

(56) References Cited

U.S. PATENT DOCUMENTS 6,387,109 B1 5/2002 Davison et al.
6,388,657 B1 5/2002 Natoli
6,391,042 B1 5/2002 Cimino
6,391,102 B1 5/2002 Bodden et al.
6,405,733 B1 6/2002 Fogarty et al.
6,416,486 B1 7/2002 Wampler
6,423,057 B1 7/2002 He et al.
6,423,073 B2 7/2002 Bowman
6,423,082 B1 7/2002 Houser et al.
6,428,539 B1 8/2002 Baxter et al.
6,432,118 B1 8/2002 Messerly
6,434,416 B1 8/2002 Mizoguchi et al.
6,436,114 B1 8/2002 Novak et al.
6,436,115 B1 8/2002 Beaupre
6,443,969 B1 9/2002 Novak et al.
6,443,973 B1 9/2002 Whitman
6,451,015 B1 9/2002 Rittman, III et al.
6,454,781 B1 9/2002 Witt et al.
6,454,782 B1 9/2002 Schwemberger
6,457,625 B1 10/2002 Tormala et al.
6,458,142 B1 10/2002 Faller et al.
6,461,352 B2 10/2002 Morgan et al.
6,466,817 B1 10/2002 Kaula et al.
6,480,796 B2 11/2002 Wiener
6,485,490 B2 11/2002 Wampler et al.
6,491,708 B2 12/2002 Madan et al.
6,497,715 B2 12/2002 Satou
6,500,188 B2 12/2002 Harper et al.
6,524,251 B2 2/2003 Rabiner et al.
6,524,307 B1 2/2003 Palmerton et al.
6,524,316 B1 2/2003 Nicholson et al.
6,527,736 B1 3/2003 Attinger et al.
6,530,933 B1 3/2003 Yeung et al.
6,533,784 B2 3/2003 Truckai et al.
6,537,291 B2 3/2003 Friedman et al.
6,543,452 B1 4/2003 Lavigne
6,543,456 B1 4/2003 Freeman
6,544,260 B1 4/2003 Markel et al.
6,551,243 B2 4/2003 Bocionek et al.
6,561,983 B2 5/2003 Cronin et al.
6,569,109 B2 5/2003 Sakurai et al.
6,572,632 B2 6/2003 Zisterer et al.
6,575,969 B1 6/2003 Rittman et al.
6,582,424 B2 6/2003 Fleenor et al.
6,582,451 B1 6/2003 Marucci et al.
6,584,358 B2 6/2003 Carter et al.
6,585,791 B1 7/2003 Garito et al.
6,589,200 B1 7/2003 Schwemberger et al.
6,589,232 B1 7/2003 Mueller
6,589,239 B2 7/2003 Khandkar et al.
6,610,059 B1 8/2003 West et al.
6,611,793 B1 8/2003 Burnside et al.
6,616,450 B2 9/2003 Moessle et al.
6,618,626 B2 9/2003 West, Jr. et al.
6,623,501 B2 9/2003 Heller et al.
6,626,926 B2 9/2003 Friedman et al.
6,633,234 B2 10/2003 Wiener et al.
6,648,223 B2 11/2003 Boukhny et al.
6,662,127 B2 12/2003 Wiener et al.
6,663,941 B2 12/2003 Brown et al.
6,669,690 B1 12/2003 Okada et al.
6,676,660 B2 1/2004 Wampler et al.
6,678,552 B2 1/2004 Pearlman
6,678,621 B2 1/2004 Wiener et al.
6,679,875 B2 1/2004 Honda et al.
6,679,899 B2 1/2004 Wiener et al.
6,682,544 B2 1/2004 Mastri et al.
6,685,704 B2 2/2004 Greep
6,689,146 B1 2/2004 Himes
6,699,187 B2 3/2004 Webb et al.
6,716,215 B1 4/2004 David et al.
6,731,047 B2 5/2004 Kauf et al.
6,731,514 B2 5/2004 Evans
6,733,506 B1 5/2004 Mcdevitt et al.
6,742,895 B2 6/2004 Robin
6,752,816 B2 6/2004 Culp et al.
6,760,616 B2 7/2004 Hoey et al.
6,762,535 B2 7/2004 Take et al.
6,770,072 B1 8/2004 Truckai et al.
6,773,443 B2 8/2004 Truwit et al.
6,773,444 B2 8/2004 Messerly
6,775,575 B2 8/2004 Bommannan et al.
6,778,846 B1 8/2004 Martinez et al.
6,781,683 B2 8/2004 Kacyra et al.
6,783,524 B2 8/2004 Anderson et al.
6,783,525 B2 8/2004 Greep et al.
6,786,382 B1 9/2004 Hoffman
6,786,383 B2 9/2004 Stegelmann
6,790,216 B1 9/2004 Ishikawa
6,793,652 B1 9/2004 Whitman et al.
6,793,663 B2 9/2004 Kneifel et al.
D496,997 S 10/2004 Dycus et al.
6,802,843 B2 10/2004 Truckai et al.
6,824,539 B2 11/2004 Novak
6,827,712 B2 12/2004 Tovey et al.
6,828,712 B2 12/2004 Battaglin et al.
6,846,308 B2 1/2005 Whitman et al.
6,849,074 B2 2/2005 Chen et al.
6,852,219 B2 2/2005 Hammond
6,863,650 B1 3/2005 Irion
6,869,430 B2 3/2005 Balbierz et al.
6,869,435 B2 3/2005 Blake, III
6,869,439 B2 3/2005 White et al.
6,875,220 B2 4/2005 Du et al.
6,908,472 B2 6/2005 Wiener et al.
6,911,033 B2 6/2005 de Guillebon et al.
6,913,471 B2 7/2005 Smith
6,923,804 B2 8/2005 Eggers et al.
6,929,632 B2 8/2005 Nita et al.
6,933,656 B2 8/2005 Matsushita et al.
6,937,892 B2 8/2005 Leyde et al.
D509,589 S 9/2005 Wells
6,942,677 B2 9/2005 Nita et al.
6,945,981 B2 9/2005 Donofrio et al.
6,951,559 B1 10/2005 Greep
D511,145 S 11/2005 Donofrio et al.
6,962,587 B2 11/2005 Johnson et al.
6,974,450 B2 12/2005 Weber et al.
6,976,844 B2 12/2005 Hickok et al.
6,978,921 B2 12/2005 Shelton, IV et al.
6,984,220 B2 1/2006 Wuchinich
6,988,649 B2 1/2006 Shelton, IV et al.
7,000,818 B2 2/2006 Shelton, IV et al.
7,001,335 B2 2/2006 Adachi et al.
7,009,511 B2 3/2006 Mazar et al.
7,030,146 B2 4/2006 Baynes et al.
7,032,798 B2 4/2006 Whitman et al.
7,033,357 B2 4/2006 Baxter et al.
7,041,083 B2 5/2006 Chu et al.
7,041,088 B2 5/2006 Nawrocki et al.
7,041,941 B2 5/2006 Faries, Jr. et al.
7,044,352 B2 5/2006 Shelton, IV et al.
7,044,911 B2 5/2006 Drinan et al.
7,044,949 B2 5/2006 Orszulak et al.
7,048,775 B2 5/2006 Jornitz et al.
7,053,752 B2 5/2006 Wang et al.
7,055,730 B2 6/2006 Ehrenfels et al.
7,073,765 B2 7/2006 Newkirk
7,074,219 B2 7/2006 Levine et al.
7,077,039 B2 7/2006 Gass et al.
7,077,853 B2 7/2006 Kramer et al.
7,077,856 B2 7/2006 Whitman
7,081,096 B2 7/2006 Brister et al.
7,087,054 B2 8/2006 Truckai et al.
7,090,672 B2 8/2006 Underwood et al.
7,097,640 B2 8/2006 Wang et al.
7,101,371 B2 9/2006 Dycus et al.
7,101,378 B2 9/2006 Salameh et al.
7,103,688 B2 9/2006 Strong
7,104,949 B2 9/2006 Anderson et al.
D531,311 S 10/2006 Guerra et al.
7,118,564 B2 10/2006 Ritchie et al.
7,121,460 B1 10/2006 Parsons et al.
7,124,932 B2 10/2006 Isaacson et al.

(56) References Cited

U.S. PATENT DOCUMENTS 7,135,018 B2 11/2006 Ryan et al.
7,135,030 B2 11/2006 Schwemberger et al.
7,137,980 B2 11/2006 Buysse et al.
7,140,528 B2 11/2006 Shelton, IV
7,143,923 B2 12/2006 Shelton, IV et al.
7,143,925 B2 12/2006 Shelton, IV et al.
7,144,403 B2 12/2006 Booth
7,147,139 B2 12/2006 Schwemberger et al.
7,153,315 B2 12/2006 Miller
7,155,316 B2 12/2006 Sutherland et al.
D536,093 S 1/2007 Nakajima et al.
7,156,189 B1 1/2007 Bar-Cohen et al.
7,156,853 B2 1/2007 Muratsu
7,157,058 B2 1/2007 Marhasin et al.
7,159,750 B2 1/2007 Racenet et al.
7,160,299 B2 1/2007 Baily
7,163,548 B2 1/2007 Stulen et al.
7,164,940 B2 1/2007 Hareyama et al.
7,169,145 B2 1/2007 Isaacson et al.
7,169,146 B2 1/2007 Truckai et al.
7,177,533 B2 2/2007 McFarlin et al.
7,179,271 B2 2/2007 Friedman et al.
7,182,775 B2 2/2007 de Guillebon et al.
D541,418 S 4/2007 Schechter et al.
7,204,820 B2 4/2007 Akahoshi
7,207,472 B2 4/2007 Wukusick et al.
7,208,005 B2 4/2007 Frecker et al.
7,217,269 B2 5/2007 El-Galley et al.
7,223,229 B2 5/2007 Inman et al.
7,229,455 B2 6/2007 Sakurai et al.
7,230,529 B2 6/2007 Ketcherside, Jr. et al.
7,232,447 B2 6/2007 Gellman et al.
7,236,817 B2 6/2007 Papas et al.
7,246,734 B2 7/2007 Shelton, IV
7,252,664 B2 8/2007 Nasab et al.
7,273,483 B2 9/2007 Wiener et al.
7,278,563 B1 10/2007 Green
7,285,895 B2 10/2007 Beaupre
7,294,106 B2 11/2007 Birkenbach et al.
7,294,116 B1 11/2007 Ellman et al.
7,296,724 B2 11/2007 Green et al.
7,317,955 B2 1/2008 McGreevy
7,326,236 B2 2/2008 Andreas et al.
7,328,828 B2 2/2008 Ortiz et al.
7,331,410 B2 2/2008 Yong et al.
7,334,717 B2 2/2008 Rethy et al.
7,343,565 B2 3/2008 Ying et al.
7,344,532 B2 3/2008 Goble et al.
7,353,068 B2 4/2008 Tanaka et al.
7,362,228 B2 4/2008 Nycz et al.
7,371,227 B2 5/2008 Zeiner
7,380,695 B2 6/2008 Doll et al.
7,383,088 B2 6/2008 Spinelli et al.
7,390,317 B2 6/2008 Taylor et al.
7,391,173 B2 6/2008 Schena
7,407,074 B2 8/2008 Ortiz et al.
7,408,288 B2 8/2008 Hara
7,408,439 B2 8/2008 Wang et al.
D576,725 S 9/2008 Shumer et al.
7,422,136 B1 9/2008 Marczyk
7,422,139 B2 9/2008 Shelton, IV et al.
7,423,972 B2 9/2008 Shaham et al.
D578,643 S 10/2008 Shumer et al.
D578,644 S 10/2008 Shumer et al.
D578,645 S 10/2008 Shumer et al.
7,431,704 B2 10/2008 Babaev
7,441,684 B2 10/2008 Shelton et al.
D579,876 S 11/2008 Novotney et al.
7,451,904 B2 11/2008 Shelton, IV
7,455,208 B2 11/2008 Wales et al.
7,457,804 B2 11/2008 Uber, III et al.
D583,328 S 12/2008 Chiang
7,464,847 B2 12/2008 Viola et al.
7,464,849 B2 12/2008 Shelton, IV et al.
7,472,815 B2 1/2009 Shelton et al.
7,473,263 B2 1/2009 Johnston et al.
7,479,148 B2 1/2009 Beaupre
7,479,160 B2 1/2009 Branch et al.
7,488,285 B2 2/2009 Honda et al.
7,494,468 B2 2/2009 Rabiner et al.
7,496,418 B2 2/2009 Kim et al.
D589,447 S 3/2009 Sasada et al.
7,503,893 B2 3/2009 Kucklick
7,503,895 B2 3/2009 Rabiner et al.
7,515,961 B2 4/2009 Germanson et al.
7,518,502 B2 4/2009 Austin et al.
7,530,986 B2 5/2009 Beaupre et al.
7,534,243 B1 5/2009 Chin et al.
D594,983 S 6/2009 Price et al.
7,549,564 B2 6/2009 Boudreaux
7,554,343 B2 6/2009 Bromfield
7,559,450 B2 7/2009 Wales et al.
7,563,259 B2 7/2009 Takahashi
7,567,012 B2 7/2009 Namikawa
7,568,604 B2 8/2009 Ehrenfels et al.
7,575,144 B2 8/2009 Ortiz et al.
7,578,820 B2 8/2009 Moore et al.
7,597,731 B2 10/2009 Palmerton et al.
7,617,137 B2 11/2009 Kreiner et al.
7,621,192 B2 11/2009 Conti et al.
7,621,898 B2 11/2009 Lalomia et al.
7,631,793 B2 12/2009 Rethy et al.
7,637,410 B2 12/2009 Marczyk
7,637,907 B2 12/2009 Blaha
7,641,092 B2 1/2010 Kruszynski et al.
7,644,848 B2 1/2010 Swayze et al.
7,654,431 B2 2/2010 Hueil et al.
7,667,592 B2 2/2010 Ohyama et al.
7,667,839 B2 2/2010 Bates
7,670,334 B2 3/2010 Hueil et al.
7,674,263 B2 3/2010 Ryan
7,694,865 B2 4/2010 Scirica
7,699,860 B2 4/2010 Huitema et al.
7,714,481 B2 5/2010 Sakai
7,717,915 B2 5/2010 Miyazawa
7,720,306 B2 5/2010 Gardiner et al.
7,721,934 B2 5/2010 Shelton, IV et al.
7,721,936 B2 5/2010 Shalton, IV et al.
D618,797 S 6/2010 Price et al.
7,736,357 B2 6/2010 Lee, Jr. et al.
7,742,176 B2 6/2010 Braunecker et al.
7,743,960 B2 6/2010 Whitman et al.
7,749,240 B2 7/2010 Takahashi et al.
7,751,115 B2 7/2010 Song
7,753,245 B2 7/2010 Boudreaux et al.
7,757,028 B2 7/2010 Druke et al.
D621,503 S 8/2010 Otten et al.
7,766,207 B2 8/2010 Mather et al.
7,766,905 B2 8/2010 Paterson et al.
7,770,773 B2 8/2010 Whitman et al.
7,770,774 B2 8/2010 Mastri et al.
7,771,429 B2 8/2010 Ballard et al.
7,776,037 B2 8/2010 Odom
7,780,054 B2 8/2010 Wales
7,780,659 B2 8/2010 Okada et al.
7,782,789 B2 8/2010 Stultz et al.
7,784,662 B2 8/2010 Wales et al.
7,784,663 B2 8/2010 Shelton, IV
7,798,386 B2 9/2010 Schall et al.
7,803,151 B2 9/2010 Whitman
7,803,152 B2 9/2010 Honda et al.
7,810,692 B2 10/2010 Hall et al.
7,810,693 B2 10/2010 Broehl et al.
7,818,041 B2 10/2010 Kim et al.
7,819,298 B2 10/2010 Hall et al.
D627,066 S 11/2010 Romero
7,832,612 B2 11/2010 Baxter, III et al.
7,833,219 B2 11/2010 Tashiro et al.
7,836,085 B2 11/2010 Petakov et al.
7,837,079 B2 11/2010 Holsten et al.
7,837,680 B2 11/2010 Isaacson et al.
7,837,699 B2 11/2010 Yamada et al.
7,841,980 B2 11/2010 Minosawa et al.
7,845,537 B2 12/2010 Shelton, IV et al.

(56) References Cited

U.S. PATENT DOCUMENTS 7,854,735 B2 12/2010 Houser et al.
7,857,185 B2 12/2010 Swayze et al.
D631,155 S 1/2011 Peine et al.
D631,252 S 1/2011 Leslie
7,861,906 B2 1/2011 Doll et al.
7,862,560 B2 1/2011 Marion
7,862,579 B2 1/2011 Ortiz et al.
7,865,236 B2 1/2011 Cory et al.
7,876,030 B2 1/2011 Taki et al.
D631,965 S 2/2011 Price et al.
7,884,735 B2 2/2011 Newkirk
7,887,530 B2 2/2011 Zemlok et al.
7,892,337 B2 2/2011 Palmerton et al.
7,892,606 B2 2/2011 Thies et al.
7,905,881 B2 3/2011 Masuda et al.
7,907,166 B2 3/2011 Lamprecht et al.
7,913,891 B2 3/2011 Doll et al.
7,918,230 B2 4/2011 Whitman et al.
7,918,377 B2 4/2011 Measamer et al.
7,920,706 B2 4/2011 Asokan et al.
7,922,651 B2 4/2011 Yamada et al.
7,927,014 B2 4/2011 Dehler
7,932,826 B2 4/2011 Fritchie et al.
D637,288 S 5/2011 Houghton
D638,540 S 5/2011 Ljiri et al.
7,942,300 B2 5/2011 Rethy et al.
7,945,065 B2 5/2011 Menzl et al.
7,945,342 B2 5/2011 Tsai et al.
7,951,148 B2 5/2011 McClurken
7,954,682 B2 6/2011 Giordano et al.
7,955,322 B2 6/2011 Devengenzo et al.
7,956,620 B2 6/2011 Gilbert
7,959,626 B2 6/2011 Hong et al.
7,963,433 B2 6/2011 Whitman et al.
7,966,269 B2 6/2011 Bauer et al.
7,967,180 B2 6/2011 Scirica
7,976,553 B2 7/2011 Shelton, IV et al.
7,979,157 B2 7/2011 Anvari
7,980,443 B2 7/2011 Scheib et al.
7,982,776 B2 7/2011 Dunki-Jacobs et al.
7,988,028 B2 8/2011 Farascioni et al.
7,993,140 B2 8/2011 Sakezles
7,995,045 B2 8/2011 Dunki-Jacobs
8,005,947 B2 8/2011 Morris et al.
8,007,494 B1 8/2011 Taylor et al.
8,007,513 B2 8/2011 Nalagatla et al.
8,010,180 B2 8/2011 Quaid et al.
8,012,170 B2 9/2011 Whitman et al.
8,015,976 B2 9/2011 Shah
8,016,855 B2 9/2011 Whitman et al.
8,019,094 B2 9/2011 Hsieh et al.
8,025,199 B2 9/2011 Whitman et al.
8,027,710 B1 9/2011 Dannan
8,035,685 B2 10/2011 Jensen
8,038,686 B2 10/2011 Huitema et al.
8,038,693 B2 10/2011 Allen
8,043,560 B2 10/2011 Okumoto et al.
8,054,184 B2 11/2011 Cline et al.
8,054,752 B2 11/2011 Druke et al.
8,062,306 B2 11/2011 Nobis et al.
8,062,330 B2 11/2011 Prommersberger et al.
8,066,721 B2 11/2011 Kortenbach et al.
8,074,861 B2 12/2011 Ehrenfels et al.
8,075,571 B2 12/2011 Vitali et al.
8,089,107 B2 1/2012 Okubora
8,089,197 B2 1/2012 Rinner et al.
8,096,459 B2 1/2012 Ortiz et al.
8,118,206 B2 2/2012 Zand et al.
8,120,301 B2 2/2012 Goldberg et al.
8,123,764 B2 2/2012 Meade et al.
D655,678 S 3/2012 Kobayashi et al.
8,128,625 B2 3/2012 Odom
8,131,565 B2 3/2012 Dicks et al.
8,136,712 B2 3/2012 Zingman
D657,368 S 4/2012 Magee et al.
8,147,486 B2 4/2012 Honour et al.
8,155,479 B2 4/2012 Hoffman et al.
8,157,145 B2 4/2012 Shelton, IV et al.
8,157,150 B2 4/2012 Viola et al.
8,157,151 B2 4/2012 Ingmanson et al.
8,160,098 B1 4/2012 Yan et al.
8,160,690 B2 4/2012 Wilfley et al.
8,161,977 B2 4/2012 Shelton, IV et al.
8,170,396 B2 5/2012 Kuspa et al.
8,172,836 B2 5/2012 Ward
8,177,800 B2 5/2012 Spitz et al.
8,181,839 B2 5/2012 Beetel
8,185,409 B2 5/2012 Putnam et al.
D661,801 S 6/2012 Price et al.
D661,802 S 6/2012 Price et al.
D661,803 S 6/2012 Price et al.
D661,804 S 6/2012 Price et al.
8,206,345 B2 6/2012 Abboud et al.
8,208,707 B2 6/2012 Mendonca et al.
8,210,411 B2 7/2012 Yates et al.
8,214,007 B2 7/2012 Baker et al.
8,216,849 B2 7/2012 Petty
8,220,688 B2 7/2012 Laurent et al.
8,225,643 B2 7/2012 Abboud et al.
8,225,979 B2 7/2012 Farascioni et al.
8,229,549 B2 7/2012 Whitman et al.
8,231,042 B2 7/2012 Hessler et al.
8,239,066 B2 8/2012 Jennings et al.
8,241,322 B2 8/2012 Whitman et al.
8,255,045 B2 8/2012 Gharib et al.
D667,838 S 9/2012 Magee et al.
8,257,387 B2 9/2012 Cunningham
8,260,016 B2 9/2012 Maeda et al.
8,262,560 B2 9/2012 Whitman
8,287,485 B2 10/2012 Kimura et al.
8,292,639 B2 10/2012 Achammer et al.
8,292,888 B2 10/2012 Whitman
8,295,902 B2 10/2012 Salahieh et al.
8,308,040 B2 11/2012 Huang et al.
8,321,581 B2 11/2012 Katis et al.
8,322,590 B2 12/2012 Patel et al.
8,328,065 B2 12/2012 Shah
8,335,590 B2 12/2012 Costa et al.
D675,164 S 1/2013 Kobayashi et al.
8,343,065 B2 1/2013 Bartol et al.
8,346,392 B2 1/2013 Walser et al.
8,360,299 B2 1/2013 Zemlok et al.
8,364,222 B2 1/2013 Cook et al.
D676,392 S 2/2013 Gassauer
8,365,975 B1 2/2013 Manoux et al.
8,372,102 B2 2/2013 Stulen et al.
D678,196 S 3/2013 Miyauchi et al.
D678,304 S 3/2013 Yakoub et al.
8,388,652 B2 3/2013 Viola
8,393,514 B2 3/2013 Shelton, IV et al.
8,397,972 B2 3/2013 Kostrzewski
8,398,541 B2 3/2013 DiMaio et al.
8,403,944 B2 3/2013 Pain et al.
8,403,945 B2 3/2013 Whitfield et al.
8,403,946 B2 3/2013 Whitfield et al.
8,406,859 B2 3/2013 Zuzak et al.
8,411,034 B2 4/2013 Boillot et al.
8,413,871 B2 4/2013 Racenet et al.
8,422,035 B2 4/2013 Hinderling et al.
8,423,182 B2 4/2013 Robinson et al.
8,428,722 B2 4/2013 Verhoef et al.
8,429,153 B2 4/2013 Birdwell et al.
8,439,910 B2 5/2013 Greep et al.
8,444,663 B2 5/2013 Houser et al.
8,452,615 B2 5/2013 Abri
8,454,506 B2 6/2013 Rothman et al.
8,461,744 B2 6/2013 Wiener et al.
8,468,030 B2 6/2013 Stroup et al.
8,469,973 B2 6/2013 Meade et al.
8,472,630 B2 6/2013 Konrad et al.
D687,146 S 7/2013 Juzkiw et al.
8,476,227 B2 7/2013 Kaplan et al.
8,478,418 B2 7/2013 Fahey
8,489,235 B2 7/2013 Moll et al.

(56) References Cited

U.S. PATENT DOCUMENTS

D687,549 S 8/2013 Johnson et al.
8,499,992 B2 8/2013 Whitman et al.
8,500,728 B2 8/2013 Newton et al.
8,500,756 B2 8/2013 Papa et al.
8,503,759 B2 8/2013 Greer et al.
8,505,801 B2 8/2013 Ehrenfels et al.
8,506,478 B2 8/2013 Mizuyoshi
8,512,325 B2 8/2013 Mathonnet
8,512,365 B2 8/2013 Wiener et al.
8,515,520 B2 8/2013 Brunnett et al.
8,517,239 B2 8/2013 Scheib et al.
8,521,331 B2 8/2013 Itkowitz
8,523,043 B2 9/2013 Ullrich et al.
8,540,709 B2 9/2013 Allen
8,546,996 B2 10/2013 Messerly et al.
8,554,697 B2 10/2013 Claus et al.
8,560,047 B2 10/2013 Haider et al.
8,561,870 B2 10/2013 Baxter, III et al.
8,562,598 B2 10/2013 Falkenstein et al.
8,566,115 B2 10/2013 Moore
8,567,393 B2 10/2013 Hickle et al.
8,571,598 B2 10/2013 Valavi
8,573,459 B2 11/2013 Smith et al.
8,573,465 B2 11/2013 Shelton, IV
8,574,229 B2 11/2013 Eder et al.
8,585,631 B2 11/2013 Dacquay
8,585,694 B2 11/2013 Amoah et al.
8,590,762 B2 11/2013 Hess et al.
8,591,536 B2 11/2013 Robertson
8,595,607 B2 11/2013 Nekoomaram et al.
8,596,513 B2 12/2013 Olson et al.
8,596,515 B2 12/2013 Okoniewski
8,604,709 B2 12/2013 Jalbout et al.
8,608,044 B2 12/2013 Hueil et al.
8,608,045 B2 12/2013 Smith et al.
8,616,431 B2 12/2013 Timm et al.
8,617,155 B2 12/2013 Johnson et al.
8,620,055 B2 12/2013 Barratt et al.
8,620,473 B2 12/2013 Diolaiti et al.
8,622,275 B2 1/2014 Baxter, III et al.
8,623,027 B2 1/2014 Price et al.
8,627,483 B2 1/2014 Rachlin et al.
8,627,993 B2 1/2014 Smith et al.
8,627,995 B2 1/2014 Smith et al.
8,628,518 B2 1/2014 Blumenkranz et al.
8,628,545 B2 1/2014 Cabrera et al.
8,631,987 B2 1/2014 Shelton, IV et al.
8,632,525 B2 1/2014 Kerr et al.
8,636,190 B2 1/2014 Zemlok et al.
8,636,736 B2 1/2014 Yates et al.
8,641,621 B2 2/2014 Razzaque et al.
8,652,086 B2 2/2014 Gerg et al.
8,652,121 B2 2/2014 Quick et al.
8,652,128 B2 2/2014 Ward
8,657,176 B2 2/2014 Shelton, IV et al.
8,657,177 B2 2/2014 Scirica et al.
8,663,220 B2 3/2014 Wiener et al.
8,666,544 B2 3/2014 Moll et al.
8,679,114 B2 3/2014 Chapman et al.
8,682,049 B2 3/2014 Zhao et al.
8,682,489 B2 3/2014 Itkowitz et al.
8,685,056 B2 4/2014 Evans et al.
8,688,188 B2 4/2014 Heller et al.
8,690,864 B2 4/2014 Hoarau
8,701,962 B2 4/2014 Kostrzewski
D704,839 S 5/2014 Juzkiw et al.
8,719,061 B2 5/2014 Birchall
8,720,766 B2 5/2014 Hess et al.
8,733,613 B2 5/2014 Huitema et al.
8,740,840 B2 6/2014 Foley et al.
8,740,866 B2 6/2014 Reasoner et al.
8,747,238 B2 6/2014 Shelton, IV et al.
8,752,749 B2 6/2014 Moore et al.
8,757,465 B2 6/2014 Woodard, Jr. et al.
8,761,717 B1 6/2014 Buchheit
8,763,879 B2 7/2014 Shelton, IV et al.
8,768,251 B2 7/2014 Claus et al.
8,771,270 B2 7/2014 Burbank
8,775,196 B2 7/2014 Simpson et al.
8,779,648 B2 7/2014 Giordano et al.
8,790,253 B2 7/2014 Sunagawa et al.
8,794,497 B2 8/2014 Zingman
8,795,001 B1 8/2014 Lam et al.
8,795,274 B2 8/2014 Hanna
8,799,008 B2 8/2014 Johnson et al.
8,799,009 B2 8/2014 Mellin et al.
8,800,838 B2 8/2014 Shelton, IV
8,801,703 B2 8/2014 Gregg et al.
8,814,996 B2 8/2014 Giurgiutiu et al.
8,818,556 B2 8/2014 Sanchez et al.
8,819,581 B2 8/2014 Nakamura et al.
8,820,603 B2 9/2014 Shelton, IV et al.
8,820,608 B2 9/2014 Miyamoto
8,827,134 B2 9/2014 Viola et al.
8,840,003 B2 9/2014 Morgan et al.
D716,333 S 10/2014 Chotin et al.
8,851,354 B2 10/2014 Swensgard et al.
8,852,174 B2 10/2014 Burbank
8,875,973 B2 11/2014 Whitman
8,876,857 B2 11/2014 Burbank
8,882,662 B2 11/2014 Charles
8,886,790 B2 11/2014 Harrang et al.
8,893,949 B2 11/2014 Shelton, IV et al.
8,899,479 B2 12/2014 Cappuzzo et al.
8,905,977 B2 12/2014 Shelton et al.
8,912,746 B2 12/2014 Reid et al.
8,914,098 B2 12/2014 Brennan et al.
8,917,513 B1 12/2014 Hazzard
8,918,207 B2 12/2014 Prisco
8,920,186 B2 12/2014 Shishikura
8,920,414 B2 12/2014 Stone et al.
8,920,433 B2 12/2014 Barrier et al.
8,930,203 B2 1/2015 Kiaie et al.
8,930,214 B2 1/2015 Woolford
8,931,679 B2 1/2015 Kostrzewski
8,936,614 B2 1/2015 Allen, IV
8,945,095 B2 2/2015 Blumenkranz et al.
8,945,163 B2 2/2015 Voegele et al.
8,955,732 B2 2/2015 Zemlok et al.
8,956,581 B2 2/2015 Rosenbaum et al.
8,960,519 B2 2/2015 Whitman et al.
8,960,520 B2 2/2015 McCuen
8,962,062 B2 2/2015 Podhajsky et al.
8,967,443 B2 3/2015 McCuen
8,967,455 B2 3/2015 Zhou
8,968,276 B2 3/2015 Zemlok et al.
8,968,296 B2 3/2015 McPherson
8,968,309 B2 3/2015 Roy et al.
8,968,312 B2 3/2015 Marczyk et al.
8,968,337 B2 3/2015 Whitfield et al.
8,968,358 B2 3/2015 Reschke
8,974,429 B2 3/2015 Gordon et al.
8,979,890 B2 3/2015 Boudreaux
8,986,288 B2 3/2015 Konishi
8,986,302 B2 3/2015 Aldridge et al.
8,989,903 B2 3/2015 Weir et al.
8,991,678 B2 3/2015 Wellman et al.
8,992,565 B2 3/2015 Brisson et al.
8,998,797 B2 4/2015 Omori
9,002,518 B2 4/2015 Manzo et al.
9,010,608 B2 4/2015 Casasanta, Jr. et al.
9,010,611 B2 4/2015 Ross et al.
9,011,366 B2 4/2015 Dean et al.
9,011,427 B2 4/2015 Price et al.
9,016,539 B2 4/2015 Kostrzewski et al.
9,017,326 B2 4/2015 DiNardo et al.
9,020,240 B2 4/2015 Pettersson et al.
D729,267 S 5/2015 Yoo et al.
9,023,032 B2 5/2015 Robinson
9,023,071 B2 5/2015 Miller et al.
9,027,431 B2 5/2015 Tang et al.
9,028,494 B2 5/2015 Shelton, IV et al.
9,035,568 B2 5/2015 Ganton et al.
9,038,882 B2 5/2015 Racenet et al.

(56) References Cited

U.S. PATENT DOCUMENTS 9,043,027 B2 5/2015 Durant et al.
9,044,227 B2 6/2015 Shelton, IV et al.
9,044,244 B2 6/2015 Ludwin et al.
9,044,261 B2 6/2015 Houser
9,050,063 B2 6/2015 Roe et al.
9,050,083 B2 6/2015 Yates et al.
9,050,120 B2 6/2015 Swarup et al.
9,052,809 B2 6/2015 Vesto
9,055,035 B2 6/2015 Porsch et al.
9,055,870 B2 6/2015 Meador et al.
9,060,770 B2 6/2015 Shelton, IV et al.
9,060,775 B2 6/2015 Wiener et al.
9,066,650 B2 6/2015 Sekiguchi
9,072,523 B2 7/2015 Houser et al.
9,072,535 B2 7/2015 Shelton, IV et al.
9,072,536 B2 7/2015 Shelton, IV et al.
9,078,653 B2 7/2015 Leimbach et al.
9,078,727 B2 7/2015 Miller
9,084,606 B2 7/2015 Greep
9,089,360 B2 7/2015 Messerly et al.
9,095,362 B2 8/2015 Dachs, II et al.
9,095,367 B2 8/2015 Olson et al.
9,099,863 B2 8/2015 Smith et al.
9,101,358 B2 8/2015 Kerr et al.
9,101,359 B2 8/2015 Smith et al.
9,101,374 B1 8/2015 Hoch et al.
9,106,270 B2 8/2015 Puterbaugh et al.
9,107,573 B2 8/2015 Birnkrant
9,107,662 B2 8/2015 Kostrzewski
9,107,684 B2 8/2015 Ma
9,107,688 B2 8/2015 Kimball et al.
9,107,689 B2 8/2015 Robertson et al.
9,107,694 B2 8/2015 Hendriks et al.
9,111,548 B2 8/2015 Nandy et al.
9,113,880 B2 8/2015 Zemlok et al.
9,114,494 B1 8/2015 Mah
9,116,597 B1 8/2015 Gulasky
9,119,617 B2 9/2015 Souls et al.
9,119,655 B2 9/2015 Bowling et al.
9,119,657 B2 9/2015 Shelton, IV et al.
9,123,155 B2 9/2015 Cunningham et al.
9,125,644 B2 9/2015 Lane et al.
9,129,054 B2 9/2015 Nawana et al.
9,137,254 B2 9/2015 Bilbrey et al.
9,138,129 B2 9/2015 Diolaiti
9,138,225 B2 9/2015 Huang et al.
9,149,322 B2 10/2015 Knowlton
9,155,503 B2 10/2015 Cadwell
9,160,853 B1 10/2015 Daddi et al.
9,161,803 B2 10/2015 Yates et al.
9,168,054 B2 10/2015 Turner et al.
9,168,091 B2 10/2015 Janssen et al.
9,168,104 B2 10/2015 Dein
9,179,912 B2 11/2015 Yates et al.
9,183,723 B2 11/2015 Sherman et al.
9,186,143 B2 11/2015 Timm et al.
9,192,375 B2 11/2015 Skinlo et al.
9,192,447 B2 11/2015 Choi et al.
9,192,707 B2 11/2015 Gerber et al.
9,198,711 B2 12/2015 Joseph
9,202,078 B2 12/2015 Abuelsaad et al.
9,204,830 B2 12/2015 Zand et al.
9,204,879 B2 12/2015 Shelton, IV
9,204,995 B2 12/2015 Scheller et al.
9,211,120 B2 12/2015 Scheib et al.
9,216,062 B2 12/2015 Duque et al.
9,218,053 B2 12/2015 Komuro et al.
9,220,502 B2 12/2015 Zemlok et al.
9,226,689 B2 1/2016 Jacobsen et al.
9,226,751 B2 1/2016 Shelton, IV et al.
9,226,766 B2 1/2016 Aldridge et al.
9,226,767 B2 1/2016 Stulen et al.
9,226,791 B2 1/2016 McCarthy et al.
9,232,883 B2 1/2016 Ozawa et al.
9,237,891 B2 1/2016 Shelton, IV
9,237,921 B2 1/2016 Messerly et al.
9,241,728 B2 1/2016 Price et al.
9,241,730 B2 1/2016 Babaev
9,241,731 B2 1/2016 Boudreaux et al.
9,247,996 B1 2/2016 Merana et al.
9,250,172 B2 2/2016 Harris et al.
9,255,907 B2 2/2016 Heanue et al.
9,265,429 B2 2/2016 St. Pierre et al.
9,265,585 B2 2/2016 Wingardner et al.
9,272,406 B2 3/2016 Aronhalt et al.
9,277,956 B2 3/2016 Zhang
9,277,961 B2 3/2016 Panescu et al.
9,277,969 B2 3/2016 Brannan et al.
9,280,884 B1 3/2016 Schultz et al.
9,282,962 B2 3/2016 Schmid et al.
9,282,974 B2 3/2016 Shelton, IV
9,283,045 B2 3/2016 Rhee et al.
9,283,054 B2 3/2016 Morgan et al.
9,289,211 B2 3/2016 Williams et al.
9,289,212 B2 3/2016 Shelton, IV et al.
9,295,514 B2 3/2016 Shelton, IV et al.
9,301,691 B2 4/2016 Hufnagel et al.
9,301,753 B2 4/2016 Aldridge et al.
9,301,759 B2 4/2016 Spivey et al.
9,301,810 B2 4/2016 Amiri et al.
9,302,213 B2 4/2016 Manahan et al.
9,307,894 B2 4/2016 von Grunberg et al.
9,307,914 B2 4/2016 Fahey
9,307,986 B2 4/2016 Hall et al.
9,314,246 B2 4/2016 Shelton, IV et al.
9,314,308 B2 4/2016 Parihar et al.
9,320,563 B2 4/2016 Brustad et al.
9,325,732 B1 4/2016 Stickle et al.
9,326,767 B2 5/2016 Koch et al.
9,326,770 B2 5/2016 Shelton, IV et al.
9,331,422 B2 5/2016 Nazzaro et al.
9,332,987 B2 5/2016 Leimbach et al.
9,333,042 B2 5/2016 Diolaiti et al.
9,336,385 B1 5/2016 Spencer et al.
9,341,704 B2 5/2016 Picard et al.
9,345,481 B2 5/2016 Hall et al.
9,345,490 B2 5/2016 Ippisch
9,345,546 B2 5/2016 Toth et al.
9,345,900 B2 5/2016 Wu et al.
9,351,726 B2 5/2016 Leimbach et al.
9,351,727 B2 5/2016 Leimbach et al.
9,358,003 B2 6/2016 Hall et al.
9,358,685 B2 6/2016 Meier et al.
9,360,449 B2 6/2016 Duric
9,364,230 B2 6/2016 Shelton, IV et al.
9,364,231 B2 6/2016 Wenchell
9,364,249 B2 6/2016 Kimball et al.
9,364,294 B2 6/2016 Razzaque et al.
9,370,400 B2 6/2016 Parihar
9,375,282 B2 6/2016 Nau, Jr. et al.
9,375,539 B2 6/2016 Stearns et al.
9,381,003 B2 7/2016 Todor et al.
9,381,058 B2 7/2016 Houser et al.
9,386,984 B2 7/2016 Aronhalt et al.
9,386,988 B2 7/2016 Baxter, III et al.
9,387,295 B1 7/2016 Mastri et al.
9,393,017 B2 7/2016 Flanagan et al.
9,393,037 B2 7/2016 Olson et al.
9,398,905 B2 7/2016 Martin
9,398,911 B2 7/2016 Auld
9,402,629 B2 8/2016 Ehrenfels et al.
9,414,776 B2 8/2016 Sillay et al.
9,414,940 B2 8/2016 Stein et al.
9,419,018 B2 8/2016 Sasagawa et al.
9,421,014 B2 8/2016 Ingmanson et al.
9,433,470 B2 9/2016 Choi
9,439,622 B2 9/2016 Case et al.
9,439,668 B2 9/2016 Timm et al.
9,439,736 B2 9/2016 Olson
9,445,764 B2 9/2016 Gross et al.
9,445,813 B2 9/2016 Shelton, IV et al.
9,450,701 B2 9/2016 Do et al.
9,451,949 B2 9/2016 Gorek et al.
9,451,958 B2 9/2016 Shelton, IV et al.

(56) References Cited

U.S. PATENT DOCUMENTS 9,463,022 B2 10/2016 Swayze et al.
9,463,646 B2 10/2016 Payne et al.
9,468,438 B2 10/2016 Baber et al.
9,474,565 B2 10/2016 Shikhman et al.
D772,252 S 11/2016 Myers et al.
9,480,492 B2 11/2016 Aranyi et al.
9,485,475 B2 11/2016 Speier et al.
9,486,271 B2 11/2016 Dunning
9,492,146 B2 11/2016 Kostrzewski et al.
9,492,237 B2 11/2016 Kang et al.
9,493,807 B2 11/2016 Little et al.
9,498,182 B2 11/2016 Case et al.
9,498,215 B2 11/2016 Duque et al.
9,498,231 B2 11/2016 Haider et al.
9,516,239 B2 12/2016 Blanquart et al.
9,519,753 B1 12/2016 Gerdeman et al.
9,522,003 B2 12/2016 Weir et al.
9,526,407 B2 12/2016 Hoeg et al.
9,526,499 B2 12/2016 Kostrzewski et al.
9,526,587 B2 12/2016 Zhao et al.
9,532,827 B2 1/2017 Morgan et al.
9,532,845 B1 1/2017 Dossett et al.
9,539,007 B2 1/2017 Dhakad et al.
9,539,020 B2 1/2017 Conlon et al.
9,542,481 B2 1/2017 Halter et al.
9,546,662 B2 1/2017 Shener-Irmakoglu et al.
9,549,781 B2 1/2017 He et al.
9,554,692 B2 1/2017 Levy
9,554,794 B2 1/2017 Baber et al.
9,554,854 B2 1/2017 Yates et al.
9,561,038 B2 2/2017 Shelton, IV et al.
9,561,045 B2 2/2017 Hinman et al.
9,561,082 B2 2/2017 Yen et al.
9,561,982 B2 2/2017 Enicks et al.
9,566,708 B2 2/2017 Kurnianto
9,572,592 B2 2/2017 Price et al.
9,579,099 B2 2/2017 Penna et al.
9,579,503 B2 2/2017 McKinney et al.
9,585,657 B2 3/2017 Shelton, IV et al.
9,592,095 B2 3/2017 Panescu et al.
9,597,081 B2 3/2017 Swayze et al.
9,600,031 B2 3/2017 Kaneko et al.
9,600,138 B2 3/2017 Thomas et al.
9,603,024 B2 3/2017 Wang et al.
9,603,277 B2 3/2017 Morgan et al.
D783,675 S 4/2017 Yagisawa et al.
D784,270 S 4/2017 Bhattacharya
9,610,114 B2 4/2017 Baxter, III et al.
9,610,412 B2 4/2017 Zemlok et al.
9,615,877 B2 4/2017 Tyrrell et al.
9,622,684 B2 4/2017 Wybo
9,622,808 B2 4/2017 Beller et al.
9,628,501 B2 4/2017 Datta Ray et al.
9,629,560 B2 4/2017 Joseph
9,629,623 B2 4/2017 Lytle, IV et al.
9,629,628 B2 4/2017 Aranyi
9,629,629 B2 4/2017 Leimbach et al.
9,630,318 B2 4/2017 Ibarz Gabardos et al.
9,636,112 B2 5/2017 Penna et al.
9,636,188 B2 5/2017 Gattani et al.
9,636,239 B2 5/2017 Durand et al.
9,636,825 B2 5/2017 Penn et al.
9,641,596 B2 5/2017 Unagami et al.
9,641,815 B2 5/2017 Richardson et al.
9,642,620 B2 5/2017 Baxter, III et al.
9,643,022 B2 5/2017 Mashiach et al.
9,649,110 B2 5/2017 Parihar et al.
9,649,111 B2 5/2017 Shelton, IV et al.
9,649,126 B2 5/2017 Robertson et al.
9,649,169 B2 5/2017 Cinquin et al.
9,652,655 B2 5/2017 Satish et al.
9,655,616 B2 5/2017 Aranyi
9,656,092 B2 5/2017 Golden
9,662,116 B2 5/2017 Smith et al.
9,662,177 B2 5/2017 Weir et al.
9,668,729 B2 6/2017 Williams et al.
9,668,732 B2 6/2017 Patel et al.
9,668,765 B2 6/2017 Grace et al.
9,671,860 B2 6/2017 Ogawa et al.
9,675,264 B2 6/2017 Acquista et al.
9,675,354 B2 6/2017 Weir et al.
9,681,870 B2 6/2017 Baxter, III et al.
9,686,306 B2 6/2017 Chizeck et al.
9,687,230 B2 6/2017 Leimbach et al.
9,690,362 B2 6/2017 Leimbach et al.
9,700,292 B2 7/2017 Nawana et al.
9,700,309 B2 7/2017 Jaworek et al.
9,700,312 B2 7/2017 Kostrzewski et al.
9,700,320 B2 7/2017 Dinardo et al.
9,706,993 B2 7/2017 Hessler et al.
9,710,214 B2 7/2017 Lin et al.
9,710,644 B2 7/2017 Reybok et al.
9,713,424 B2 7/2017 Spaide
9,713,503 B2 7/2017 Goldschmidt
9,717,141 B1 7/2017 Tegg
9,717,498 B2 8/2017 Aranyi et al.
9,717,525 B2 8/2017 Ahluwalia et al.
9,717,548 B2 8/2017 Couture
9,724,094 B2 8/2017 Baber et al.
9,724,100 B2 8/2017 Scheib et al.
9,724,118 B2 8/2017 Schulte et al.
9,733,663 B2 8/2017 Leimbach et al.
9,737,301 B2 8/2017 Baber et al.
9,737,310 B2 8/2017 Whitfield et al.
9,737,335 B2 8/2017 Butler et al.
9,737,355 B2 8/2017 Yates et al.
9,740,826 B2 8/2017 Raghavan et al.
9,743,016 B2 8/2017 Nestares et al.
9,743,929 B2 8/2017 Leimbach et al.
9,743,946 B2 8/2017 Faller et al.
9,743,947 B2 8/2017 Price et al.
9,750,499 B2 9/2017 Leimbach et al.
9,750,500 B2 9/2017 Malkowski
9,750,522 B2 9/2017 Scheib et al.
9,750,523 B2 9/2017 Tsubuku
9,750,563 B2 9/2017 Shikhman et al.
9,753,135 B2 9/2017 Bosch
9,753,568 B2 9/2017 McMillen
9,757,126 B2 9/2017 Cappola
9,757,128 B2 9/2017 Baber et al.
9,757,142 B2 9/2017 Shimizu
9,757,152 B2 9/2017 Ogilvie et al.
9,763,741 B2 9/2017 Alvarez et al.
9,764,164 B2 9/2017 Wiener et al.
9,770,541 B2 9/2017 Carr et al.
9,775,611 B2 10/2017 Kostrzewski
9,777,913 B2 10/2017 Talbert et al.
9,782,164 B2 10/2017 Mumaw et al.
9,782,169 B2 10/2017 Kimsey et al.
9,782,212 B2 10/2017 Wham et al.
9,782,214 B2 10/2017 Houser et al.
9,788,835 B2 10/2017 Morgan et al.
9,788,836 B2 10/2017 Overmyer et al.
9,788,851 B2 10/2017 Dannaher et al.
9,788,902 B2 10/2017 Inoue et al.
9,788,907 B1 10/2017 Alvi et al.
9,795,436 B2 10/2017 Yates et al.
9,797,486 B2 10/2017 Zergiebel et al.
9,801,531 B2 10/2017 Morita et al.
9,801,626 B2 10/2017 Parihar et al.
9,801,627 B2 10/2017 Harris et al.
9,801,679 B2 10/2017 Trees et al.
9,802,033 B2 10/2017 Hibner et al.
9,804,618 B2 10/2017 Leimbach et al.
9,805,472 B2 10/2017 Chou et al.
9,808,244 B2 11/2017 Leimbach et al.
9,808,245 B2 11/2017 Richard et al.
9,808,246 B2 11/2017 Shelton, IV et al.
9,808,248 B2 11/2017 Hoffman
9,808,249 B2 11/2017 Shelton, IV
9,814,457 B2 11/2017 Martin et al.
9,814,460 B2 11/2017 Kimsey et al.
9,814,462 B2 11/2017 Woodard, Jr. et al.
9,814,463 B2 11/2017 Williams et al.

(56) References Cited

U.S. PATENT DOCUMENTS 9,820,699 B2 11/2017 Bingley et al.
9,820,738 B2 11/2017 Lytle, IV et al.
9,820,741 B2 11/2017 Kostrzewski
9,820,768 B2 11/2017 Gee et al.
9,826,976 B2 11/2017 Parihar et al.
9,826,977 B2 11/2017 Leimbach et al.
9,827,054 B2 11/2017 Richmond et al.
9,827,059 B2 11/2017 Robinson et al.
9,830,424 B2 11/2017 Dixon et al.
9,833,241 B2 12/2017 Huitema et al.
9,833,254 B1 12/2017 Barral et al.
9,839,419 B2 12/2017 Deck et al.
9,839,424 B2 12/2017 Zergiebel et al.
9,839,428 B2 12/2017 Baxter, III et al.
9,839,467 B2 12/2017 Harper et al.
9,839,470 B2 12/2017 Gilbert et al.
9,839,487 B2 12/2017 Dachs, II
9,844,321 B1 12/2017 Ekvall et al.
9,844,368 B2 12/2017 Boudreaux et al.
9,844,369 B2 12/2017 Huitema et al.
9,844,374 B2 12/2017 Lytle, IV et al.
9,844,375 B2 12/2017 Overmyer et al.
9,844,376 B2 12/2017 Baxter, III et al.
9,844,379 B2 12/2017 Shelton, IV et al.
9,848,058 B2 12/2017 Johnson et al.
9,848,877 B2 12/2017 Shelton, IV et al.
9,861,354 B2 1/2018 Saliman et al.
9,861,363 B2 1/2018 Chen et al.
9,861,428 B2 1/2018 Trees et al.
9,864,839 B2 1/2018 Baym et al.
9,867,612 B2 1/2018 Parihar et al.
9,867,651 B2 1/2018 Wham
9,867,670 B2 1/2018 Brannan et al.
9,867,914 B2 1/2018 Bonano et al.
9,872,609 B2 1/2018 Levy
9,872,683 B2 1/2018 Hopkins et al.
9,877,718 B2 1/2018 Weir et al.
9,877,721 B2 1/2018 Schellin et al.
9,883,860 B2 2/2018 Leimbach
9,888,864 B2 2/2018 Rondoni et al.
9,888,914 B2 2/2018 Martin et al.
9,888,919 B2 2/2018 Leimbach et al.
9,888,921 B2 2/2018 Williams et al.
9,888,975 B2 2/2018 Auld
9,895,148 B2 2/2018 Shelton, IV et al.
9,900,787 B2 2/2018 Ou
9,901,342 B2 2/2018 Shelton, IV et al.
9,901,406 B2 2/2018 State et al.
9,905,000 B2 2/2018 Chou et al.
9,907,196 B2 2/2018 Susini et al.
9,907,550 B2 3/2018 Sniffin et al.
9,913,642 B2 3/2018 Leimbach et al.
9,913,645 B2 3/2018 Zerkle et al.
9,918,326 B2 3/2018 Gilson et al.
9,918,730 B2 3/2018 Trees et al.
9,918,778 B2 3/2018 Walberg et al.
9,918,788 B2 3/2018 Paul et al.
9,922,304 B2 3/2018 DeBusk et al.
9,924,941 B2 3/2018 Burbank
9,924,944 B2 3/2018 Shelton, IV et al.
9,924,961 B2 3/2018 Shelton, IV et al.
9,931,040 B2 4/2018 Homyk et al.
9,931,118 B2 4/2018 Shelton, IV et al.
9,931,124 B2 4/2018 Gokharu
9,936,863 B2 4/2018 Tesar
9,936,942 B2 4/2018 Chin et al.
9,936,955 B2 4/2018 Miller et al.
9,936,961 B2 4/2018 Chien et al.
9,937,012 B2 4/2018 Hares et al.
9,937,014 B2 4/2018 Bowling et al.
9,937,626 B2 4/2018 Rockrohr
9,938,972 B2 4/2018 Walley
9,943,230 B2 4/2018 Kaku et al.
9,943,309 B2 4/2018 Shelton, IV et al.
9,943,312 B2 4/2018 Posada et al.
9,943,377 B2 4/2018 Yates et al.
9,943,379 B2 4/2018 Gregg, II et al.
9,943,918 B2 4/2018 Grogan et al.
9,949,785 B2 4/2018 Price et al.
9,962,157 B2 5/2018 Sapre
9,968,355 B2 5/2018 Shelton, IV et al.
9,974,595 B2 5/2018 Anderson et al.
9,980,140 B1 5/2018 Spencer et al.
9,980,769 B2 5/2018 Trees et al.
9,980,778 B2 5/2018 Ohline et al.
9,987,000 B2 6/2018 Shelton, IV et al.
9,987,068 B2 6/2018 Anderson et al.
9,987,072 B2 6/2018 McPherson
9,990,856 B2 6/2018 Kuchenbecker et al.
9,993,248 B2 6/2018 Shelton, IV et al.
9,993,258 B2 6/2018 Shelton, IV et al.
9,993,305 B2 6/2018 Andersson
10,004,491 B2 6/2018 Martin et al.
10,004,497 B2 6/2018 Overmyer et al.
10,004,500 B2 6/2018 Shelton, IV et al.
10,004,501 B2 6/2018 Shelton, IV et al.
10,004,527 B2 6/2018 Gee et al.
10,004,557 B2 6/2018 Gross
D822,206 S 7/2018 Shelton, IV et al.
10,010,322 B2 7/2018 Shelton, IV et al.
10,010,324 B2 7/2018 Huitema et al.
10,013,049 B2 7/2018 Leimbach et al.
10,016,199 B2 7/2018 Baber et al.
10,021,318 B2 7/2018 Hugosson et al.
10,022,090 B2 7/2018 Whitman
10,022,120 B2 7/2018 Martin et al.
10,022,391 B2 7/2018 Ruderman Chen et al.
10,022,568 B2 7/2018 Messerly et al.
10,028,402 B1 7/2018 Walker
10,028,744 B2 7/2018 Shelton, IV et al.
10,028,761 B2 7/2018 Leimbach et al.
10,028,788 B2 7/2018 Kang
10,034,704 B2 7/2018 Asher et al.
10,037,641 B2 7/2018 Hyde et al.
10,037,715 B2 7/2018 Toly et al.
D826,405 S 8/2018 Shelton, IV et al.
10,039,546 B2 8/2018 Williams et al.
10,039,564 B2 8/2018 Hibner et al.
10,039,565 B2 8/2018 Vezzu
10,039,589 B2 8/2018 Virshek et al.
10,041,822 B2 8/2018 Zemlok
10,044,791 B2 8/2018 Kamen et al.
10,045,704 B2 8/2018 Fagin et al.
10,045,776 B2 8/2018 Shelton, IV et al.
10,045,779 B2 8/2018 Savage et al.
10,045,781 B2 8/2018 Cropper et al.
10,045,782 B2 8/2018 Murthy Aravalli
10,045,813 B2 8/2018 Mueller
10,048,379 B2 8/2018 Markendorf et al.
10,052,044 B2 8/2018 Shelton, IV et al.
10,052,102 B2 8/2018 Baxter, III et al.
10,052,104 B2 8/2018 Shelton, IV et al.
10,054,441 B2 8/2018 Schorr et al.
10,058,393 B2 8/2018 Bonutti et al.
10,069,633 B2 9/2018 Gulati et al.
10,076,326 B2 9/2018 Yates et al.
10,080,618 B2 9/2018 Marshall et al.
10,084,833 B2 9/2018 McDonnell et al.
D831,209 S 10/2018 Huitema et al.
10,085,748 B2 10/2018 Morgan et al.
10,085,749 B2 10/2018 Cappola et al.
10,092,355 B1 10/2018 Hannaford et al.
10,095,942 B2 10/2018 Mentese et al.
10,097,578 B2 10/2018 Baldonado et al.
10,098,527 B2 10/2018 Weisenburgh, II et al.
10,098,635 B2 10/2018 Burbank
10,098,642 B2 10/2018 Baxter, III et al.
10,098,705 B2 10/2018 Brisson et al.
10,102,926 B1 10/2018 Leonardi
10,105,140 B2 10/2018 Malinouskas et al.
10,105,142 B2 10/2018 Baxter, III et al.
10,105,470 B2 10/2018 Reasoner et al.
10,111,658 B2 10/2018 Chowaniec et al.
10,111,665 B2 10/2018 Aranyi et al.

(56) References Cited

U.S. PATENT DOCUMENTS 10,111,679 B2 10/2018 Baber et al.
10,111,703 B2 10/2018 Cosman, Jr. et al.
D834,541 S 11/2018 You et al.
10,117,649 B2 11/2018 Baxter et al.
10,117,651 B2 11/2018 Whitman et al.
10,117,702 B2 11/2018 Danziger et al.
10,118,119 B2 11/2018 Sappok et al.
10,130,359 B2 11/2018 Hess et al.
10,130,360 B2 11/2018 Olson et al.
10,130,361 B2 11/2018 Yates et al.
10,130,367 B2 11/2018 Cappola et al.
10,133,248 B2 11/2018 Fitzsimmons et al.
10,135,242 B2 11/2018 Baber et al.
10,136,887 B2 11/2018 Shelton, IV et al.
10,136,891 B2 11/2018 Shelton, IV et al.
10,136,949 B2 11/2018 Felder et al.
10,136,954 B2 11/2018 Johnson et al.
10,137,245 B2 11/2018 Melker et al.
10,143,526 B2 12/2018 Walker et al.
10,143,948 B2 12/2018 Bonifas et al.
10,147,148 B2 12/2018 Wu et al.
10,149,680 B2 12/2018 Parihar et al.
10,152,789 B2 12/2018 Carnes et al.
10,154,841 B2 12/2018 Weaner et al.
10,159,044 B2 12/2018 Hrabak
10,159,481 B2 12/2018 Whitman et al.
10,159,483 B2 12/2018 Beckman et al.
10,164,466 B2 12/2018 Calderoni
10,166,025 B2 1/2019 Leimbach et al.
10,166,061 B2 1/2019 Berry et al.
10,169,862 B2 1/2019 Andre et al.
10,172,618 B2 1/2019 Shelton, IV et al.
10,172,687 B2 1/2019 Garbus et al.
10,175,096 B2 1/2019 Dickerson
10,175,127 B2 1/2019 Collins et al.
10,178,992 B2 1/2019 Wise et al.
10,179,413 B2 1/2019 Rockrohr
10,180,463 B2 1/2019 Beckman et al.
10,182,814 B2 1/2019 Okoniewski
10,182,816 B2 1/2019 Shelton, IV et al.
10,182,818 B2 1/2019 Hensel et al.
10,188,385 B2 1/2019 Kerr et al.
10,189,157 B2 1/2019 Schlegel et al.
10,190,888 B2 1/2019 Hryb et al.
10,194,891 B2 2/2019 Jeong et al.
10,194,907 B2 2/2019 Marczyk et al.
10,194,913 B2 2/2019 Nalagatla et al.
10,194,972 B2 2/2019 Yates et al.
10,197,803 B2 2/2019 Badiali et al.
10,198,965 B2 2/2019 Hart
10,201,311 B2 2/2019 Chou et al.
10,201,349 B2 2/2019 Leimbach et al.
10,201,364 B2 2/2019 Leimbach et al.
10,201,365 B2 2/2019 Boudreaux et al.
10,205,708 B1 2/2019 Fletcher et al.
10,206,605 B2 2/2019 Shelton, IV et al.
10,206,752 B2 2/2019 Hares et al.
10,213,201 B2 2/2019 Shelton, IV et al.
10,213,203 B2 2/2019 Swayze et al.
10,213,266 B2 2/2019 Zemlok et al.
10,213,268 B2 2/2019 Dachs, II
10,219,491 B2 3/2019 Stiles, Jr. et al.
10,220,522 B2 3/2019 Rockrohr
10,222,750 B2 3/2019 Bang et al.
10,226,249 B2 3/2019 Jaworek et al.
10,226,250 B2 3/2019 Beckman et al.
10,226,254 B2 3/2019 Cabrera et al.
10,226,302 B2 3/2019 Lacal et al.
10,231,634 B2 3/2019 Zand et al.
10,231,733 B2 3/2019 Ehrenfels et al.
10,231,775 B2 3/2019 Shelton, IV et al.
10,238,413 B2 3/2019 Hibner et al.
10,245,027 B2 4/2019 Shelton, IV et al.
10,245,028 B2 4/2019 Shelton, IV et al.
10,245,029 B2 4/2019 Hunter et al.
10,245,030 B2 4/2019 Hunter et al.
10,245,033 B2 4/2019 Overmyer et al.
10,245,037 B2 4/2019 Conklin et al.
10,245,038 B2 4/2019 Hopkins et al.
10,245,040 B2 4/2019 Milliman
10,251,661 B2 4/2019 Collings et al.
10,251,725 B2 4/2019 Valentine et al.
10,258,331 B2 4/2019 Shelton, IV et al.
10,258,359 B2 4/2019 Kapadia
10,258,362 B2 4/2019 Conlon
10,258,363 B2 4/2019 Worrell et al.
10,258,415 B2 4/2019 Harrah et al.
10,258,418 B2 4/2019 Shelton, IV et al.
10,258,425 B2 4/2019 Mustufa et al.
10,263,171 B2 4/2019 Wiener et al.
10,265,004 B2 4/2019 Yamaguchi et al.
10,265,035 B2 4/2019 Fehre et al.
10,265,066 B2 4/2019 Measamer et al.
10,265,068 B2 4/2019 Harris et al.
10,265,072 B2 4/2019 Shelton, IV et al.
10,265,090 B2 4/2019 Ingmanson et al.
10,265,130 B2 4/2019 Hess et al.
10,271,840 B2 4/2019 Sapre
10,271,844 B2 4/2019 Valentine et al.
10,271,850 B2 4/2019 Williams
10,271,851 B2 4/2019 Shelton, IV et al.
D847,989 S 5/2019 Shelton, IV et al.
10,278,698 B2 5/2019 Racenet
10,278,778 B2 5/2019 State et al.
10,283,220 B2 5/2019 Azizian et al.
10,285,694 B2 5/2019 Viola et al.
10,285,698 B2 5/2019 Cappola et al.
10,285,700 B2 5/2019 Scheib
10,285,705 B2 5/2019 Shelton, IV et al.
10,292,704 B2 5/2019 Harris et al.
10,292,707 B2 5/2019 Shelton, IV et al.
10,292,758 B2 5/2019 Boudreaux et al.
10,292,769 B1 5/2019 Yu
10,292,771 B2 5/2019 Wood et al.
10,293,129 B2 5/2019 Fox et al.
10,299,792 B2 5/2019 Huitema et al.
10,299,870 B2 5/2019 Connolly et al.
10,305,926 B2 5/2019 Mihan et al.
D850,617 S 6/2019 Shelton, IV et al.
10,307,159 B2 6/2019 Harris et al.
10,307,170 B2 6/2019 Parfett et al.
10,307,199 B2 6/2019 Farritor et al.
10,311,036 B1 6/2019 Hussam et al.
10,313,137 B2 6/2019 Aarnio et al.
10,314,577 B2 6/2019 Laurent et al.
10,314,582 B2 6/2019 Shelton, IV et al.
10,321,907 B2 6/2019 Shelton, IV et al.
10,321,964 B2 6/2019 Grover et al.
10,327,764 B2 6/2019 Harris et al.
10,327,779 B2 6/2019 Richard et al.
10,335,147 B2 7/2019 Rector et al.
10,335,149 B2 7/2019 Baxter, III et al.
10,335,180 B2 7/2019 Johnson et al.
10,335,227 B2 7/2019 Heard
10,339,496 B2 7/2019 Matson et al.
10,342,543 B2 7/2019 Shelton, IV et al.
10,342,602 B2 7/2019 Strobl et al.
10,342,623 B2 7/2019 Huelman et al.
10,343,102 B2 7/2019 Reasoner et al.
10,349,824 B2 7/2019 Claude et al.
10,349,939 B2 7/2019 Shelton, IV et al.
10,349,941 B2 7/2019 Marczyk et al.
10,350,016 B2 7/2019 Burbank et al.
10,357,184 B2 7/2019 Crawford et al.
10,357,246 B2 7/2019 Shelton, IV et al.
10,357,247 B2 7/2019 Shelton, IV et al.
10,362,179 B2 7/2019 Harris
10,363,032 B2 7/2019 Scheib et al.
10,363,037 B2 7/2019 Aronhalt et al.
10,368,861 B2 8/2019 Baxter, III et al.
10,368,865 B2 8/2019 Harris et al.
10,368,867 B2 8/2019 Harris et al.
10,368,876 B2 8/2019 Bhatnagar et al.
10,368,894 B2 8/2019 Madan et al.

(56) References Cited

U.S. PATENT DOCUMENTS 10,368,903 B2 8/2019 Morales et al.
10,376,263 B2 8/2019 Morgan et al.
10,376,305 B2 8/2019 Yates et al.
10,376,337 B2 8/2019 Kilroy et al.
10,376,338 B2 8/2019 Taylor et al.
10,378,893 B2 8/2019 Mankovskii
10,383,518 B2 8/2019 Abu-Tarif et al.
10,383,699 B2 8/2019 Kilroy et al.
10,384,021 B2 8/2019 Koeth et al.
10,386,990 B2 8/2019 Shikhman et al.
10,390,718 B2 8/2019 Chen et al.
10,390,794 B2 8/2019 Kuroiwa et al.
10,390,825 B2 8/2019 Shelton, IV et al.
10,390,831 B2 8/2019 Holsten et al.
10,390,895 B2 8/2019 Henderson et al.
10,398,348 B2 9/2019 Osadchy et al.
10,398,434 B2 9/2019 Shelton, IV et al.
10,398,517 B2 9/2019 Eckert et al.
10,398,521 B2 9/2019 Itkowitz et al.
10,404,521 B2 9/2019 McChord et al.
10,404,801 B2 9/2019 Martch
10,405,857 B2 9/2019 Shelton, IV et al.
10,405,863 B2 9/2019 Wise et al.
10,413,291 B2 9/2019 Worthington et al.
10,413,293 B2 9/2019 Shelton, IV et al.
10,413,297 B2 9/2019 Harris et al.
10,417,446 B2 9/2019 Takeyama
10,420,552 B2 9/2019 Shelton, IV et al.
10,420,558 B2 9/2019 Nalagatla et al.
10,420,559 B2 9/2019 Marczyk et al.
10,420,620 B2 9/2019 Rockrohr
10,420,865 B2 9/2019 Reasoner et al.
10,422,727 B2 9/2019 Pliskin
10,426,466 B2 10/2019 Contini et al.
10,426,467 B2 10/2019 Miller et al.
10,426,468 B2 10/2019 Contini et al.
10,426,471 B2 10/2019 Shelton, IV et al.
10,426,481 B2 10/2019 Aronhalt et al.
10,433,837 B2 10/2019 Worthington et al.
10,433,844 B2 10/2019 Shelton, IV et al.
10,433,849 B2 10/2019 Shelton, IV et al.
10,433,918 B2 10/2019 Shelton, IV et al.
10,441,279 B2 10/2019 Shelton, IV et al.
10,441,345 B2 10/2019 Aldridge et al.
10,448,948 B2 10/2019 Shelton, IV et al.
10,448,950 B2 10/2019 Shelton, IV et al.
10,456,137 B2 10/2019 Vendely et al.
10,456,140 B2 10/2019 Shelton, IV et al.
10,456,193 B2 10/2019 Yates et al.
10,463,365 B2 11/2019 Williams
10,463,367 B2 11/2019 Kostrzewski et al.
10,463,371 B2 11/2019 Kostrzewski
10,463,436 B2 11/2019 Jackson et al.
10,470,762 B2 11/2019 Leimbach et al.
10,470,764 B2 11/2019 Baxter, III et al.
10,470,768 B2 11/2019 Harris et al.
10,470,791 B2 11/2019 Houser
10,471,254 B2 11/2019 Sano et al.
10,478,181 B2 11/2019 Shelton, IV et al.
10,478,185 B2 11/2019 Nicholas
10,478,189 B2 11/2019 Bear et al.
10,478,190 B2 11/2019 Miller et al.
10,478,544 B2 11/2019 Friederichs et al.
10,485,450 B2 11/2019 Gupta et al.
10,485,542 B2 11/2019 Shelton, IV et al.
10,485,543 B2 11/2019 Shelton, IV et al.
10,492,783 B2 12/2019 Shelton, IV et al.
10,492,784 B2 12/2019 Beardsley et al.
10,492,785 B2 12/2019 Overmyer et al.
10,496,788 B2 12/2019 Amarasingham et al.
10,498,269 B2 12/2019 Zemlok et al.
10,499,847 B2 12/2019 Latimer et al.
10,499,891 B2 12/2019 Chaplin et al.
10,499,914 B2 12/2019 Huang et al.
10,499,915 B2 12/2019 Aranyi
10,499,994 B2 12/2019 Luks et al.
10,507,068 B2 12/2019 Kopp et al.
10,512,413 B2 12/2019 Schepis et al.
10,512,461 B2 12/2019 Gupta et al.
10,512,499 B2 12/2019 McHenry et al.
10,512,514 B2 12/2019 Nowlin et al.
10,517,588 B2 12/2019 Gupta et al.
10,517,595 B2 12/2019 Hunter et al.
10,517,596 B2 12/2019 Hunter et al.
10,517,686 B2 12/2019 Vokrot et al.
10,524,789 B2 1/2020 Swayze et al.
10,531,579 B2 1/2020 Hsiao et al.
10,531,874 B2 1/2020 Morgan et al.
10,531,929 B2 1/2020 Widenhouse et al.
10,532,330 B2 1/2020 Diallo et al.
10,536,617 B2 1/2020 Liang et al.
10,537,324 B2 1/2020 Shelton, IV et al.
10,537,325 B2 1/2020 Bakos et al.
10,537,351 B2 1/2020 Shelton, IV et al.
10,542,978 B2 1/2020 Chowaniec et al.
10,542,979 B2 1/2020 Shelton, IV et al.
10,542,982 B2 1/2020 Beckman et al.
10,542,991 B2 1/2020 Shelton, IV et al.
D876,466 S 2/2020 Kobayashi et al.
10,548,504 B2 2/2020 Shelton, IV et al.
10,548,612 B2 2/2020 Martinez et al.
10,548,673 B2 2/2020 Harris et al.
10,552,574 B2 2/2020 Sweeney
10,555,675 B2 2/2020 Satish et al.
10,555,748 B2 2/2020 Yates et al.
10,555,750 B2 2/2020 Conlon et al.
10,555,769 B2 2/2020 Worrell et al.
10,561,422 B2 2/2020 Schellin et al.
10,561,471 B2 2/2020 Nichogi
10,561,753 B2 2/2020 Thompson et al.
10,568,625 B2 2/2020 Harris et al.
10,568,626 B2 2/2020 Shelton, IV et al.
10,568,632 B2 2/2020 Miller et al.
10,568,704 B2 2/2020 Savall et al.
10,575,868 B2 3/2020 Hall et al.
10,582,928 B2 3/2020 Hunter et al.
10,582,931 B2 3/2020 Mujawar
10,582,964 B2 3/2020 Weinberg et al.
10,586,074 B2 3/2020 Rose et al.
10,588,623 B2 3/2020 Schmid et al.
10,588,625 B2 3/2020 Weaner et al.
10,588,629 B2 3/2020 Malinouskas et al.
10,588,630 B2 3/2020 Shelton, IV et al.
10,588,631 B2 3/2020 Shelton, IV et al.
10,588,632 B2 3/2020 Shelton, IV et al.
10,588,711 B2 3/2020 DiCarlo et al.
10,592,067 B2 3/2020 Merdan et al.
10,595,844 B2 3/2020 Nawana et al.
10,595,882 B2 3/2020 Parfett et al.
10,595,887 B2 3/2020 Shelton, IV et al.
10,595,930 B2 3/2020 Scheib et al.
10,595,952 B2 3/2020 Forrest et al.
10,602,007 B2 3/2020 Takano
10,602,848 B2 3/2020 Magana
10,603,036 B2 3/2020 Hunter et al.
10,603,128 B2 3/2020 Zergiebel et al.
10,610,223 B2 4/2020 Wellman et al.
10,610,224 B2 4/2020 Shelton, IV et al.
10,610,286 B2 4/2020 Wiener et al.
10,610,313 B2 4/2020 Bailey et al.
10,617,412 B2 4/2020 Shelton, IV et al.
10,617,414 B2 4/2020 Shelton, IV et al.
10,617,482 B2 4/2020 Houser et al.
10,617,484 B2 4/2020 Kilroy et al.
10,624,635 B2 4/2020 Harris et al.
10,624,667 B2 4/2020 Faller et al.
10,624,691 B2 4/2020 Wiener et al.
10,631,423 B2 4/2020 Collins et al.
10,631,858 B2 4/2020 Burbank
10,631,912 B2 4/2020 McFarlin et al.
10,631,916 B2 4/2020 Horner et al.
10,631,917 B2 4/2020 Ineson
10,631,939 B2 4/2020 Dachs, II et al.
10,639,027 B2 5/2020 Shelton, IV et al.

(56) References Cited

U.S. PATENT DOCUMENTS 10,639,034 B2 5/2020 Harris et al.
10,639,035 B2 5/2020 Shelton, IV et al.
10,639,036 B2 5/2020 Yates et al.
10,639,037 B2 5/2020 Shelton, IV et al.
10,639,039 B2 5/2020 Vendely et al.
10,639,098 B2 5/2020 Cosman et al.
10,639,111 B2 5/2020 Kopp
10,639,185 B2 5/2020 Agrawal et al.
10,653,413 B2 5/2020 Worthington et al.
10,653,476 B2 5/2020 Ross
10,653,489 B2 5/2020 Kopp
10,656,720 B1 5/2020 Holz
10,660,705 B2 5/2020 Piron et al.
10,667,809 B2 6/2020 Bakos et al.
10,667,810 B2 6/2020 Shelton, IV et al.
10,667,811 B2 6/2020 Harris et al.
10,667,877 B2 6/2020 Kapadia
10,674,897 B2 6/2020 Levy
10,675,021 B2 6/2020 Harris et al.
10,675,023 B2 6/2020 Cappola
10,675,024 B2 6/2020 Shelton, IV et al.
10,675,025 B2 6/2020 Swayze et al.
10,675,026 B2 6/2020 Harris et al.
10,675,035 B2 6/2020 Zingman
10,675,100 B2 6/2020 Frushour
10,675,104 B2 6/2020 Kapadia
10,677,764 B2 6/2020 Ross et al.
10,679,758 B2 6/2020 Fox et al.
10,682,136 B2 6/2020 Harris et al.
10,682,138 B2 6/2020 Shelton, IV et al.
10,686,805 B2 6/2020 Reybok, Jr. et al.
10,687,806 B2 6/2020 Shelton, IV et al.
10,687,809 B2 6/2020 Shelton, IV et al.
10,687,810 B2 6/2020 Shelton, IV et al.
10,687,884 B2 6/2020 Wiener et al.
10,687,905 B2 6/2020 Kostrzewski
10,695,055 B2 6/2020 Shelton, IV et al.
10,695,081 B2 6/2020 Shelton, IV et al.
10,695,134 B2 6/2020 Barral et al.
10,702,270 B2 7/2020 Shelton, IV et al.
10,702,271 B2 7/2020 Aranyi et al.
10,709,446 B2 7/2020 Harris et al.
10,716,489 B2 7/2020 Kalvoy et al.
10,716,615 B2 7/2020 Shelton, IV et al.
10,716,639 B2 7/2020 Kapadia et al.
10,717,194 B2 7/2020 Griffiths et al.
10,722,222 B2 7/2020 Aranyi
10,722,233 B2 7/2020 Wellman
10,722,292 B2 7/2020 Arya et al.
D893,717 S 8/2020 Messerly et al.
10,729,458 B2 8/2020 Stoddard et al.
10,729,509 B2 8/2020 Shelton, IV et al.
10,733,267 B2 8/2020 Pedersen
10,736,219 B2 8/2020 Seow et al.
10,736,616 B2 8/2020 Scheib et al.
10,736,628 B2 8/2020 Yates et al.
10,736,629 B2 8/2020 Shelton, IV et al.
10,736,636 B2 8/2020 Baxter, III et al.
10,736,705 B2 8/2020 Scheib et al.
10,743,872 B2 8/2020 Leimbach et al.
10,748,115 B2 8/2020 Laster et al.
10,751,052 B2 8/2020 Stokes et al.
10,751,136 B2 8/2020 Farritor et al.
10,751,768 B2 8/2020 Hersey et al.
10,755,813 B2 8/2020 Shelton, IV et al.
D896,379 S 9/2020 Shelton, IV et al.
10,758,229 B2 9/2020 Shelton, IV et al.
10,758,230 B2 9/2020 Shelton, IV et al.
10,758,294 B2 9/2020 Jones
10,758,310 B2 9/2020 Shelton, IV et al.
10,765,376 B2 9/2020 Brown, III et al.
10,765,424 B2 9/2020 Baxter, III et al.
10,765,427 B2 9/2020 Shelton, IV et al.
10,765,470 B2 9/2020 Yates et al.
10,772,630 B2 9/2020 Wixey
10,772,651 B2 9/2020 Shelton, IV et al.
10,772,673 B2 9/2020 Allen, IV et al.
10,772,688 B2 9/2020 Peine et al.
10,779,818 B2 9/2020 Zemlok et al.
10,779,821 B2 9/2020 Harris et al.
10,779,823 B2 9/2020 Shelton, IV et al.
10,779,897 B2 9/2020 Rockrohr
10,779,900 B2 9/2020 Pedros et al.
10,783,634 B2 9/2020 Nye et al.
10,786,298 B2 9/2020 Johnson
10,786,317 B2 9/2020 Zhou et al.
10,786,327 B2 9/2020 Anderson et al.
10,792,038 B2 10/2020 Becerra et al.
10,792,118 B2 10/2020 Prpa et al.
10,792,422 B2 10/2020 Douglas et al.
10,799,304 B2 10/2020 Kapadia et al.
10,803,977 B2 10/2020 Sanmugalingham
10,806,445 B2 10/2020 Penna et al.
10,806,453 B2 10/2020 Chen et al.
10,806,454 B2 10/2020 Kopp
10,806,499 B2 10/2020 Castaneda et al.
10,806,506 B2 10/2020 Gaspredes et al.
10,806,532 B2 10/2020 Grubbs et al.
10,813,638 B2 10/2020 Shelton, IV et al.
10,813,703 B2 10/2020 Swayze et al.
10,818,383 B2 10/2020 Sharifi Sedeh et al.
10,828,028 B2 11/2020 Harris et al.
10,828,030 B2 11/2020 Weir et al.
10,835,245 B2 11/2020 Swayze et al.
10,835,246 B2 11/2020 Shelton, IV et al.
10,835,247 B2 11/2020 Shelton, IV et al.
10,842,473 B2 11/2020 Scheib et al.
10,842,490 B2 11/2020 DiNardo et al.
10,842,492 B2 11/2020 Shelton, IV et al.
10,842,522 B2 11/2020 Messerly et al.
10,842,523 B2 11/2020 Shelton, IV et al.
10,842,575 B2 11/2020 Panescu et al.
10,842,897 B2 11/2020 Schwartz et al.
D904,612 S 12/2020 Wynn et al.
10,849,697 B2 12/2020 Yates et al.
10,849,700 B2 12/2020 Kopp et al.
10,856,768 B2 12/2020 Osadchy et al.
10,856,867 B2 12/2020 Shelton, IV et al.
10,856,868 B2 12/2020 Shelton, IV et al.
10,856,870 B2 12/2020 Harris et al.
10,863,984 B2 12/2020 Shelton, IV et al.
10,864,037 B2 12/2020 Mun et al.
10,864,050 B2 12/2020 Tabandeh et al.
10,872,684 B2 12/2020 McNutt et al.
10,881,399 B2 1/2021 Shelton, IV et al.
10,881,401 B2 1/2021 Baber et al.
10,881,446 B2 1/2021 Strobl
10,881,464 B2 1/2021 Odermatt et al.
10,888,321 B2 1/2021 Shelton, IV et al.
10,888,322 B2 1/2021 Morgan et al.
10,892,899 B2 1/2021 Shelton, IV et al.
10,892,995 B2 1/2021 Shelton, IV et al.
10,893,863 B2 1/2021 Shelton, IV et al.
10,893,864 B2 1/2021 Harris et al.
10,893,884 B2 1/2021 Stoddard et al.
10,898,183 B2 1/2021 Shelton, IV et al.
10,898,186 B2 1/2021 Bakos et al.
10,898,189 B2 1/2021 McDonald, II
10,898,256 B2 1/2021 Yates et al.
10,898,280 B2 1/2021 Kopp
10,898,622 B2 1/2021 Shelton, IV et al.
10,902,944 B1 1/2021 Casey et al.
10,903,685 B2 1/2021 Yates et al.
10,905,415 B2 2/2021 DiNardo et al.
10,905,418 B2 2/2021 Shelton, IV et al.
10,905,420 B2 2/2021 Jasemian et al.
10,912,559 B2 2/2021 Harris et al.
10,912,567 B2 2/2021 Shelton, IV et al.
10,912,580 B2 2/2021 Green et al.
10,912,619 B2 2/2021 Jarc et al.
10,916,415 B2 2/2021 Karancsi et al.
10,918,385 B2 2/2021 Overmyer et al.
10,930,400 B2 2/2021 Robbins et al.
D914,878 S 3/2021 Shelton, IV et al.

(56) References Cited

U.S. PATENT DOCUMENTS 10,932,705 B2 3/2021 Muhsin et al.
10,932,772 B2 3/2021 Shelton, IV et al.
10,932,784 B2 3/2021 Mozdzierz et al.
10,932,804 B2 3/2021 Scheib et al.
10,932,806 B2 3/2021 Shelton, IV et al.
10,932,872 B2 3/2021 Shelton, IV et al.
10,939,313 B2 3/2021 Eom et al.
10,943,454 B2 3/2021 Shelton, IV et al.
10,944,728 B2 3/2021 Wiener et al.
10,945,727 B2 3/2021 Shelton, IV et al.
10,950,982 B2 3/2021 Regnier et al.
10,952,708 B2 3/2021 Scheib et al.
10,954,935 B2 3/2021 O'Shea et al.
10,959,727 B2 3/2021 Hunter et al.
10,959,729 B2 3/2021 Ehrenfels et al.
10,959,744 B2 3/2021 Shelton, IV et al.
10,959,788 B2 3/2021 Grover et al.
10,960,150 B2 3/2021 Zergiebel et al.
10,966,791 B2 4/2021 Harris et al.
10,966,798 B2 4/2021 Tesar et al.
10,973,516 B2 4/2021 Shelton, IV et al.
10,973,517 B2 4/2021 Wixey
10,973,520 B2 4/2021 Shelton, IV et al.
10,973,682 B2 4/2021 Vezzu et al.
10,980,536 B2 4/2021 Weaner et al.
10,980,537 B2 4/2021 Shelton, IV et al.
10,980,560 B2 4/2021 Shelton, IV et al.
10,980,610 B2 4/2021 Rosenberg et al.
10,987,102 B2 4/2021 Gonzalez et al.
10,987,178 B2 4/2021 Shelton, IV et al.
10,992,698 B2 4/2021 Patel et al.
10,993,715 B2 5/2021 Shelton, IV et al.
10,998,098 B2 5/2021 Greene et al.
11,000,276 B2 5/2021 Shelton, IV et al.
11,000,278 B2 5/2021 Shelton, IV et al.
11,007,004 B2 5/2021 Shelton, IV et al.
11,007,022 B2 5/2021 Shelton, IV et al.
11,013,563 B2 5/2021 Shelton, IV et al.
11,026,687 B2 6/2021 Shelton, IV et al.
11,026,712 B2 6/2021 Shelton, IV et al.
11,026,713 B2 6/2021 Stokes et al.
11,026,751 B2 6/2021 Shelton, IV et al.
11,039,834 B2 6/2021 Harris et al.
11,045,191 B2 6/2021 Shelton, IV et al.
11,045,192 B2 6/2021 Harris et al.
11,045,197 B2 6/2021 Shelton, IV et al.
11,045,591 B2 6/2021 Shelton, IV et al.
11,051,817 B2 7/2021 Shelton, IV et al.
11,051,836 B2 7/2021 Shelton, IV et al.
11,051,873 B2 7/2021 Wiener et al.
11,051,876 B2 7/2021 Shelton, IV et al.
11,056,244 B2 7/2021 Shelton, IV et al.
11,058,423 B2 7/2021 Shelton, IV et al.
11,058,498 B2 7/2021 Shelton, IV et al.
11,058,501 B2 7/2021 Tokarchuk et al.
11,064,997 B2 7/2021 Shelton, IV et al.
11,069,012 B2 7/2021 Shelton, IV et al.
11,071,560 B2 7/2021 Deck et al.
11,071,595 B2 7/2021 Johnson et al.
11,076,921 B2 8/2021 Shelton, IV et al.
11,083,458 B2 8/2021 Harris et al.
11,090,047 B2 8/2021 Shelton, IV et al.
11,090,048 B2 8/2021 Fanelli et al.
11,090,075 B2 8/2021 Hunter et al.
11,096,688 B2 8/2021 Shelton, IV et al.
11,096,693 B2 8/2021 Shelton, IV et al.
11,100,631 B2 8/2021 Yates et al.
11,103,268 B2 8/2021 Shelton, IV et al.
11,109,866 B2 9/2021 Shelton, IV et al.
11,109,878 B2 9/2021 Shelton, IV et al.
11,114,195 B2 9/2021 Shelton, IV et al.
11,116,485 B2 9/2021 Scheib et al.
11,123,070 B2 9/2021 Shelton, IV et al.
11,129,611 B2 9/2021 Shelton, IV et al.
11,129,634 B2 9/2021 Scheib et al.
11,129,636 B2 9/2021 Shelton, IV et al.
11,129,669 B2 9/2021 Stulen et al.
11,129,670 B2 9/2021 Shelton, IV et al.
11,132,462 B2 9/2021 Shelton, IV et al.
11,134,942 B2 10/2021 Harris et al.
11,141,160 B2 10/2021 Shelton, IV et al.
11,141,213 B2 10/2021 Yates et al.
11,147,607 B2 10/2021 Yates et al.
11,160,551 B2 11/2021 Shelton, IV et al.
11,160,605 B2 11/2021 Shelton, IV et al.
11,166,716 B2 11/2021 Shelton, IV et al.
11,166,772 B2 11/2021 Shelton, IV et al.
11,179,150 B2 11/2021 Yates et al.
11,179,151 B2 11/2021 Shelton, IV et al.
11,179,155 B2 11/2021 Shelton, IV et al.
11,179,175 B2 11/2021 Houser et al.
11,179,204 B2 11/2021 Shelton, IV et al.
11,179,208 B2 11/2021 Yates et al.
11,185,325 B2 11/2021 Shelton, IV et al.
11,185,330 B2 11/2021 Huitema et al.
11,191,539 B2 12/2021 Overmyer et al.
11,191,540 B2 12/2021 Aronhalt et al.
11,197,668 B2 12/2021 Shelton, IV et al.
11,202,570 B2 12/2021 Shelton, IV et al.
11,207,065 B2 12/2021 Harris et al.
11,207,067 B2 12/2021 Shelton, IV et al.
11,207,090 B2 12/2021 Shelton, IV et al.
11,213,293 B2 1/2022 Worthington et al.
11,213,294 B2 1/2022 Shelton, IV et al.
11,213,359 B2 1/2022 Shelton, IV et al.
11,218,822 B2 1/2022 Morgan et al.
11,219,453 B2 1/2022 Shelton, IV et al.
11,224,426 B2 1/2022 Shelton, IV et al.
11,229,436 B2 1/2022 Shelton, IV et al.
11,229,471 B2 1/2022 Shelton, IV et al.
11,234,756 B2 2/2022 Shelton, IV et al.
11,241,230 B2 2/2022 Shelton, IV et al.
11,253,256 B2 2/2022 Harris et al.
11,253,315 B2 2/2022 Yates et al.
11,257,589 B2 2/2022 Shelton, IV et al.
11,259,806 B2 3/2022 Shelton, IV et al.
11,259,807 B2 3/2022 Shelton, IV et al.
11,259,830 B2 3/2022 Nott et al.
11,266,409 B2 3/2022 Huitema et al.
11,266,468 B2 3/2022 Shelton, IV et al.
11,272,931 B2 3/2022 Boudreaux et al.
11,273,001 B2 3/2022 Shelton, IV et al.
11,278,280 B2 3/2022 Shelton, IV et al.
11,278,281 B2 3/2022 Shelton, IV et al.
11,284,890 B2 3/2022 Nalagatla et al.
11,284,936 B2 3/2022 Shelton, IV et al.
11,291,440 B2 4/2022 Harris et al.
11,291,441 B2 4/2022 Giordano et al.
11,291,444 B2 4/2022 Boudreaux et al.
11,291,445 B2 4/2022 Shelton, IV et al.
11,291,465 B2 4/2022 Parihar et al.
11,291,495 B2 4/2022 Yates et al.
11,291,510 B2 4/2022 Shelton, IV et al.
11,298,128 B2 4/2022 Messerly et al.
11,298,129 B2 4/2022 Bakos et al.
11,298,130 B2 4/2022 Bakos et al.
11,298,148 B2 4/2022 Jayme et al.
11,304,699 B2 4/2022 Shelton, IV et al.
11,304,720 B2 4/2022 Kimball et al.
11,304,745 B2 4/2022 Shelton, IV et al.
11,304,763 B2 4/2022 Shelton, IV et al.
11,308,075 B2 4/2022 Shelton, IV et al.
11,311,306 B2 4/2022 Shelton, IV et al.
11,311,342 B2 4/2022 Parihar et al.
D950,728 S 5/2022 Bakos et al.
D952,144 S 5/2022 Boudreaux
11,317,915 B2 5/2022 Boudreaux et al.
11,317,919 B2 5/2022 Shelton, IV et al.
11,317,937 B2 5/2022 Nott et al.
11,324,557 B2 5/2022 Shelton, IV et al.
11,331,100 B2 5/2022 Boudreaux et al.
11,331,101 B2 5/2022 Harris et al.
11,337,746 B2 5/2022 Boudreaux
11,344,326 B2 5/2022 Faller et al.

(56) References Cited

U.S. PATENT DOCUMENTS 11,350,959 B2 6/2022 Messerly et al.
11,350,978 B2 6/2022 Henderson et al.
11,357,503 B2 6/2022 Bakos et al.
11,364,075 B2 6/2022 Yates et al.
11,369,377 B2 6/2022 Boudreaux et al.
11,376,002 B2 7/2022 Shelton, IV et al.
11,382,697 B2 7/2022 Shelton, IV et al.
11,389,164 B2 7/2022 Yates et al.
11,389,188 B2 7/2022 Gee et al.
11,399,858 B2 8/2022 Sawhney et al.
11,406,382 B2 8/2022 Shelton, IV et al.
11,406,390 B2 8/2022 Shelton, IV et al.
11,410,259 B2 8/2022 Harris et al.
11,762,836 B2 9/2023 Vasudevan et al.
2001/0025183 A1 9/2001 Shahidi
2001/0031950 A1 10/2001 Ryan
2001/0039419 A1 11/2001 Francischelli et al.
2001/0056237 A1 12/2001 Cane et al.
2002/0002377 A1 1/2002 Cimino
2002/0019649 A1 2/2002 Sikora et al.
2002/0022836 A1 2/2002 Goble et al.
2002/0049551 A1 4/2002 Friedman et al.
2002/0052616 A1 5/2002 Wiener et al.
2002/0052617 A1 5/2002 Anis et al.
2002/0072746 A1 6/2002 Lingenfelder et al.
2002/0077550 A1 6/2002 Rabiner et al.
2002/0138642 A1 9/2002 Miyazawa et al.
2002/0156466 A1 10/2002 Sakurai et al.
2002/0156493 A1 10/2002 Houser et al.
2002/0169584 A1 11/2002 Fu et al.
2003/0001456 A1 1/2003 Kauf et al.
2003/0009111 A1 1/2003 Cory et al.
2003/0018329 A1 1/2003 Hooven
2003/0036705 A1 2/2003 Hare et al.
2003/0046109 A1 3/2003 Uchikubo
2003/0055443 A1 3/2003 Spotnitz
2003/0069573 A1 4/2003 Kadhiresan et al.
2003/0073987 A1 4/2003 Sakurai et al.
2003/0085632 A1 5/2003 Take et al.
2003/0093503 A1 5/2003 Yamaki et al.
2003/0114851 A1 6/2003 Truckai et al.
2003/0130711 A1 7/2003 Pearson et al.
2003/0204199 A1 10/2003 Novak et al.
2003/0210812 A1 11/2003 Khamene et al.
2003/0212332 A1 11/2003 Fenton et al.
2003/0212422 A1 11/2003 Fenton et al.
2003/0223877 A1 12/2003 Anstine et al.
2003/0229344 A1 12/2003 Dycus et al.
2004/0015053 A1 1/2004 Bieger et al.
2004/0030254 A1 2/2004 Babaev
2004/0047485 A1 3/2004 Sherrit et al.
2004/0054364 A1 3/2004 Aranyi et al.
2004/0078236 A1 4/2004 Stoodley et al.
2004/0092921 A1 5/2004 Kadziauskas et al.
2004/0097919 A1 5/2004 Wellman et al.
2004/0097996 A1 5/2004 Rabiner et al.
2004/0108825 A1 6/2004 Lee et al.
2004/0176686 A1 9/2004 Hare et al.
2004/0199180 A1 10/2004 Knodel et al.
2004/0199193 A1 10/2004 Hayashi et al.
2004/0199659 A1 10/2004 Ishikawa et al.
2004/0204728 A1 10/2004 Haefner
2004/0206365 A1 10/2004 Knowlton
2004/0243147 A1 12/2004 Lipow
2004/0243148 A1 12/2004 Wasielewski
2004/0243157 A1 12/2004 Connor et al.
2004/0243435 A1 12/2004 Williams
2004/0260300 A1 12/2004 Gorensek et al.
2005/0004589 A1 1/2005 Okada et al.
2005/0020909 A1 1/2005 Moctezuma de la Barrera et al.
2005/0020918 A1 1/2005 Wilk et al.
2005/0021027 A1 1/2005 Shields et al.
2005/0021065 A1 1/2005 Yamada et al.
2005/0023324 A1 2/2005 Doll et al.
2005/0033337 A1 2/2005 Muir et al.
2005/0063575 A1 3/2005 Ma et al.
2005/0065438 A1 3/2005 Miller
2005/0070800 A1 3/2005 Takahashi
2005/0096683 A1 5/2005 Ellins et al.
2005/0100867 A1 5/2005 Hilscher et al.
2005/0131390 A1 6/2005 Heinrich et al.
2005/0139629 A1 6/2005 Schwemberger et al.
2005/0143759 A1 6/2005 Kelly
2005/0143769 A1 6/2005 White et al.
2005/0149001 A1 7/2005 Uchikubo et al.
2005/0149108 A1 7/2005 Cox
2005/0149356 A1 7/2005 Cyr et al.
2005/0165345 A1 7/2005 Laufer et al.
2005/0165390 A1 7/2005 Mauti et al.
2005/0177184 A1 8/2005 Easley
2005/0182655 A1 8/2005 Merzlak et al.
2005/0192633 A1 9/2005 Montpetit
2005/0203380 A1 9/2005 Sauer et al.
2005/0203384 A1 9/2005 Sati et al.
2005/0203504 A1 9/2005 Wham et al.
2005/0209620 A1 9/2005 Du et al.
2005/0222631 A1 10/2005 Dalal et al.
2005/0228246 A1 10/2005 Lee et al.
2005/0228425 A1 10/2005 Boukhny et al.
2005/0236474 A1 10/2005 Onuma et al.
2005/0251233 A1 11/2005 Kanzius
2005/0261581 A1 11/2005 Hughes et al.
2005/0261588 A1 11/2005 Makin et al.
2005/0273090 A1 12/2005 Nieman et al.
2005/0277913 A1 12/2005 McCary
2005/0288659 A1 12/2005 Kimura et al.
2006/0020272 A1 1/2006 Gildenberg
2006/0025816 A1 2/2006 Shelton
2006/0030797 A1 2/2006 Zhou et al.
2006/0059018 A1 3/2006 Shiobara et al.
2006/0063130 A1 3/2006 Hayman et al.
2006/0066181 A1 3/2006 Bromfield et al.
2006/0069388 A1 3/2006 Truckai et al.
2006/0079872 A1 4/2006 Eggleston
2006/0079874 A1 4/2006 Faller et al.
2006/0095046 A1 5/2006 Trieu et al.
2006/0116908 A1 6/2006 Dew et al.
2006/0136622 A1 6/2006 Rouvelin et al.
2006/0184160 A1 8/2006 Ozaki et al.
2006/0190034 A1 8/2006 Nishizawa et al.
2006/0206115 A1 9/2006 Schomer et al.
2006/0211943 A1 9/2006 Beaupre
2006/0235306 A1 10/2006 Cotter et al.
2006/0241399 A1 10/2006 Fabian
2006/0253050 A1 11/2006 Yoshimine et al.
2006/0264809 A1 11/2006 Hansmann et al.
2006/0282009 A1 12/2006 Oberg et al.
2007/0010838 A1 1/2007 Shelton et al.
2007/0016235 A1 1/2007 Tanaka et al.
2007/0016236 A1 1/2007 Beaupre
2007/0016979 A1 1/2007 Damaj et al.
2007/0027459 A1 2/2007 Horvath et al.
2007/0038080 A1 2/2007 Salisbury et al.
2007/0049947 A1 3/2007 Menn et al.
2007/0055228 A1 3/2007 Berg et al.
2007/0056596 A1 3/2007 Fanney et al.
2007/0060915 A1 3/2007 Kucklick
2007/0060935 A1 3/2007 Schwardt et al.
2007/0063618 A1 3/2007 Bromfield
2007/0066970 A1 3/2007 Ineson
2007/0078678 A1 4/2007 DiSilvestro et al.
2007/0084896 A1 4/2007 Doll et al.
2007/0106317 A1 5/2007 Shelton et al.
2007/0130771 A1 6/2007 Ehlert et al.
2007/0131034 A1 6/2007 Ehlert et al.
2007/0149881 A1 6/2007 Rabin
2007/0156019 A1 7/2007 Larkin et al.
2007/0162050 A1 7/2007 Sartor
2007/0167702 A1 7/2007 Hasser et al.
2007/0168461 A1 7/2007 Moore
2007/0173803 A1 7/2007 Wham et al.
2007/0173872 A1 7/2007 Neuenfeldt
2007/0175955 A1 8/2007 Shelton et al.
2007/0179482 A1 8/2007 Anderson

(56) References Cited

U.S. PATENT DOCUMENTS

2007/0179508 A1 8/2007 Arndt
2007/0185380 A1 8/2007 Kucklick
2007/0191713 A1 8/2007 Eichmann et al.
2007/0203744 A1 8/2007 Scholl
2007/0219481 A1 9/2007 Babaev
2007/0225556 A1 9/2007 Ortiz et al.
2007/0225690 A1 9/2007 Sekiguchi et al.
2007/0239028 A1 10/2007 Houser et al.
2007/0244478 A1 10/2007 Bahney
2007/0249941 A1 10/2007 Salehi et al.
2007/0249990 A1 10/2007 Cosmescu
2007/0260234 A1 11/2007 Mccullagh et al.
2007/0265560 A1 11/2007 Soltani et al.
2007/0270660 A1 11/2007 Caylor et al.
2007/0275348 A1 11/2007 Lemon
2007/0282195 A1 12/2007 Masini et al.
2007/0282321 A1 12/2007 Shah et al.
2007/0282333 A1 12/2007 Fortson et al.
2007/0287933 A1 12/2007 Phan et al.
2007/0293218 A1 12/2007 Meylan et al.
2008/0009848 A1 1/2008 Paraschiv et al.
2008/0013460 A1 1/2008 Allen et al.
2008/0015664 A1 1/2008 Podhajsky
2008/0015912 A1 1/2008 Rosenthal et al.
2008/0033404 A1 2/2008 Romoda et al.
2008/0040151 A1 2/2008 Moore
2008/0051812 A1 2/2008 Schmitz et al.
2008/0058585 A1 3/2008 Novak et al.
2008/0058593 A1 3/2008 Gu et al.
2008/0058775 A1 3/2008 Darian et al.
2008/0058845 A1 3/2008 Shimizu et al.
2008/0059658 A1 3/2008 Williams
2008/0077158 A1 3/2008 Haider et al.
2008/0082039 A1 4/2008 Babaev
2008/0082098 A1 4/2008 Tanaka et al.
2008/0083414 A1 4/2008 Messerges
2008/0091071 A1 4/2008 Kumar et al.
2008/0114212 A1 5/2008 Messerges
2008/0114350 A1 5/2008 Park et al.
2008/0129465 A1 6/2008 Rao
2008/0132887 A1 6/2008 Masuda et al.
2008/0140090 A1 6/2008 Aranyi et al.
2008/0167644 A1 7/2008 Shelton et al.
2008/0171938 A1 7/2008 Masuda et al.
2008/0172051 A1 7/2008 Masuda et al.
2008/0172052 A1* 7/2008 Eder .................. A61B 18/1442
606/50
2008/0177258 A1 7/2008 Govari et al.
2008/0177268 A1 7/2008 Daum et al.
2008/0177362 A1 7/2008 Phillips et al.
2008/0188878 A1 8/2008 Young
2008/0200940 A1 8/2008 Eichmann et al.
2008/0208231 A1 8/2008 Ota et al.
2008/0234708 A1 9/2008 Houser et al.
2008/0234709 A1 9/2008 Houser
2008/0234711 A1 9/2008 Houser et al.
2008/0235052 A1 9/2008 Node-Langlois et al.
2008/0243106 A1 10/2008 Coe et al.
2008/0245371 A1 10/2008 Gruber
2008/0249553 A1 10/2008 Gruber et al.
2008/0255413 A1 10/2008 Zemlok et al.
2008/0262490 A1 10/2008 Williams
2008/0262654 A1 10/2008 Omori et al.
2008/0272172 A1 11/2008 Zemlok et al.
2008/0281200 A1 11/2008 Voic et al.
2008/0281301 A1 11/2008 DeBoer et al.
2008/0281678 A1 11/2008 Keuls et al.
2008/0287948 A1 11/2008 Newton et al.
2008/0296346 A1 12/2008 Shelton, IV et al.
2008/0306759 A1 12/2008 Ilkin et al.
2008/0312953 A1 12/2008 Claus
2009/0017910 A1 1/2009 Rofougaran et al.
2009/0030311 A1 1/2009 Stulen et al.
2009/0030351 A1 1/2009 Wiener et al.
2009/0030437 A1 1/2009 Houser et al.
2009/0030438 A1 1/2009 Stulen
2009/0030439 A1 1/2009 Stulen
2009/0036750 A1 2/2009 Weinstein et al.
2009/0036794 A1 2/2009 Stubhaug et al.
2009/0036911 A1 2/2009 Stulen
2009/0036912 A1 2/2009 Wiener et al.
2009/0043253 A1 2/2009 Podaima
2009/0046146 A1 2/2009 Hoyt
2009/0048537 A1 2/2009 Lydon et al.
2009/0048589 A1 2/2009 Takashino et al.
2009/0048611 A1 2/2009 Funda et al.
2009/0054886 A1 2/2009 Yachi et al.
2009/0054894 A1 2/2009 Yachi
2009/0076409 A1 3/2009 Wu et al.
2009/0076506 A1 3/2009 Baker
2009/0082716 A1 3/2009 Akahoshi
2009/0090763 A1 4/2009 Zemlok et al.
2009/0099866 A1 4/2009 Newman
2009/0114699 A1 5/2009 Viola
2009/0118802 A1 5/2009 Mioduski et al.
2009/0128084 A1 5/2009 Johnson et al.
2009/0138006 A1 5/2009 Bales et al.
2009/0143796 A1 6/2009 Stulen et al.
2009/0143806 A1 6/2009 Witt et al.
2009/0149801 A1 6/2009 Crandall et al.
2009/0157071 A1 6/2009 Wham et al.
2009/0182577 A1 7/2009 Squilla et al.
2009/0206131 A1 8/2009 Weisenburgh, II et al.
2009/0217932 A1 9/2009 Voegele
2009/0234352 A1 9/2009 Behnke et al.
2009/0259149 A1 10/2009 Tahara et al.
2009/0259221 A1 10/2009 Tahara et al.
2009/0270853 A1 10/2009 Yachi et al.
2009/0270899 A1 10/2009 Carusillo et al.
2009/0299214 A1 12/2009 Wu et al.
2009/0306581 A1 12/2009 Claus
2009/0307681 A1 12/2009 Armado et al.
2009/0318945 A1 12/2009 Yoshimine et al.
2009/0326321 A1 12/2009 Jacobsen et al.
2009/0326336 A1 12/2009 Lemke et al.
2009/0327715 A1 12/2009 Smith et al.
2010/0016785 A1 1/2010 Takuma
2010/0030248 A1 2/2010 Palmer et al.
2010/0036370 A1 2/2010 Mirel et al.
2010/0036374 A1 2/2010 Ward
2010/0036405 A1 2/2010 Giordano et al.
2010/0038403 A1 2/2010 D'Arcangelo
2010/0057106 A1 3/2010 Sorrentino et al.
2010/0065604 A1 3/2010 Weng
2010/0069939 A1 3/2010 Konishi
2010/0069942 A1 3/2010 Shelton, IV
2010/0070417 A1 3/2010 Flynn et al.
2010/0120266 A1 5/2010 Rimborg
2010/0132334 A1 6/2010 Duclos et al.
2010/0137845 A1 6/2010 Ramstein et al.
2010/0137886 A1 6/2010 Zergiebel et al.
2010/0158307 A1 6/2010 Kubota et al.
2010/0168561 A1 7/2010 Anderson
2010/0179577 A1 7/2010 Houser
2010/0179831 A1 7/2010 Brown et al.
2010/0187283 A1 7/2010 Crainich et al.
2010/0191100 A1 7/2010 Anderson et al.
2010/0193567 A1 8/2010 Scheib et al.
2010/0198200 A1 8/2010 Horvath
2010/0198248 A1 8/2010 Vakharia
2010/0204717 A1 8/2010 Knodel
2010/0217991 A1 8/2010 Choi
2010/0234906 A1 9/2010 Koh
2010/0234996 A1 9/2010 Schreiber et al.
2010/0235689 A1 9/2010 Tian et al.
2010/0250571 A1 9/2010 Pierce et al.
2010/0258327 A1 10/2010 Esenwein et al.
2010/0268211 A1 10/2010 Mcnally et al.
2010/0280368 A1 11/2010 Can et al.
2010/0292535 A1 11/2010 Paskar
2010/0292684 A1 11/2010 Cybulski et al.
2010/0298743 A1 11/2010 Nield et al.
2010/0298851 A1 11/2010 Nield
2010/0301095 A1 12/2010 Shelton, IV et al.

(56) References Cited

U.S. PATENT DOCUMENTS

2010/0331869 A1 12/2010 Voegele et al.
2010/0331870 A1 12/2010 Wan et al.
2010/0331871 A1 12/2010 Nield et al.
2010/0331872 A1 12/2010 Houser et al.
2011/0009850 A1 1/2011 Main et al.
2011/0015631 A1* 1/2011 Wiener .................... A61N 7/00 606/42
2011/0022032 A1 1/2011 Zemlok et al.
2011/0036890 A1 2/2011 Ma
2011/0071530 A1 3/2011 Carson
2011/0077512 A1 3/2011 Boswell
2011/0087212 A1 4/2011 Aldridge et al.
2011/0087218 A1 4/2011 Boudreaux et al.
2011/0087238 A1 4/2011 Wang et al.
2011/0105895 A1 5/2011 Kornblau et al.
2011/0112569 A1 5/2011 Friedman et al.
2011/0118708 A1 5/2011 Burbank et al.
2011/0119075 A1 5/2011 Dhoble
2011/0125149 A1 5/2011 El-Galley et al.
2011/0125175 A1 5/2011 Stulen et al.
2011/0152712 A1 6/2011 Cao et al.
2011/0163147 A1 7/2011 Laurent et al.
2011/0166883 A1 7/2011 Palmer et al.
2011/0196286 A1 8/2011 Robertson et al.
2011/0196287 A1 8/2011 Robertson et al.
2011/0196398 A1 8/2011 Robertson et al.
2011/0196399 A1 8/2011 Robertson et al.
2011/0196400 A1 8/2011 Robertson et al.
2011/0196401 A1 8/2011 Robertson et al.
2011/0196403 A1 8/2011 Robertson et al.
2011/0196404 A1 8/2011 Dietz et al.
2011/0196405 A1 8/2011 Dietz
2011/0237883 A1 9/2011 Chun
2011/0251612 A1 10/2011 Faller et al.
2011/0264000 A1 10/2011 Paul et al.
2011/0264078 A1 10/2011 Lipow et al.
2011/0273465 A1 11/2011 Konishi et al.
2011/0278343 A1 11/2011 Knodel et al.
2011/0290024 A1 12/2011 Lefler
2011/0295270 A1 12/2011 Giordano et al.
2011/0306840 A1 12/2011 Allen et al.
2012/0012638 A1 1/2012 Huang et al.
2012/0021684 A1 1/2012 Schultz et al.
2012/0022519 A1 1/2012 Huang et al.
2012/0029354 A1 2/2012 Mark et al.
2012/0046662 A1 2/2012 Gilbert
2012/0059289 A1 3/2012 Nield et al.
2012/0059684 A1 3/2012 Hampapur et al.
2012/0078243 A1 3/2012 Worrell et al.
2012/0078244 A1 3/2012 Worrell et al.
2012/0078247 A1 3/2012 Worrell et al.
2012/0080336 A1 4/2012 Shelton, IV et al.
2012/0083786 A1 4/2012 Artale et al.
2012/0100517 A1 4/2012 Bowditch et al.
2012/0101488 A1 4/2012 Aldridge et al.
2012/0116265 A1 5/2012 Houser et al.
2012/0116381 A1 5/2012 Houser et al.
2012/0116394 A1 5/2012 Timm et al.
2012/0130217 A1 5/2012 Kauphusman et al.
2012/0145714 A1 6/2012 Farascioni et al.
2012/0172696 A1 7/2012 Kallback et al.
2012/0177005 A1 7/2012 Liang et al.
2012/0190981 A1 7/2012 Harris et al.
2012/0191091 A1 7/2012 Allen
2012/0191162 A1 7/2012 Villa
2012/0197619 A1 8/2012 Namer Yelin et al.
2012/0203067 A1 8/2012 Higgins et al.
2012/0203257 A1 8/2012 Stulen et al.
2012/0203785 A1 8/2012 Awada
2012/0210223 A1 8/2012 Eppolito
2012/0211542 A1 8/2012 Racenet
2012/0226150 A1 9/2012 Balicki et al.
2012/0245958 A1 9/2012 Lawrence et al.
2012/0253329 A1 10/2012 Zemlok et al.
2012/0253847 A1 10/2012 Dell'Anno et al.
2012/0265555 A1 10/2012 Cappuzzo et al.
2012/0269676 A1 10/2012 Houser et al.
2012/0289984 A1 11/2012 Houser et al.
2012/0292367 A1 11/2012 Morgan et al.
2012/0319859 A1 12/2012 Taub et al.
2012/0323265 A1 12/2012 Stulen
2013/0001121 A1 1/2013 Metzger
2013/0006241 A1 1/2013 Takashino
2013/0008677 A1 1/2013 Huifu
2013/0012970 A1 1/2013 Houser
2013/0024213 A1 1/2013 Poon
2013/0046182 A1 2/2013 Hegg et al.
2013/0046279 A1 2/2013 Niklewski et al.
2013/0046295 A1 2/2013 Kerr et al.
2013/0066647 A1 3/2013 Andrie et al.
2013/0090526 A1 4/2013 Suzuki et al.
2013/0093829 A1 4/2013 Rosenblatt et al.
2013/0096597 A1 4/2013 Anand et al.
2013/0103023 A1 4/2013 Monson et al.
2013/0103024 A1 4/2013 Monson et al.
2013/0116218 A1 5/2013 Kaplan et al.
2013/0123776 A1 5/2013 Monson et al.
2013/0123777 A1 5/2013 Monson et al.
2013/0123782 A1 5/2013 Trees et al.
2013/0144284 A1 6/2013 Behnke, II et al.
2013/0165776 A1 6/2013 Blomqvist
2013/0178853 A1 7/2013 Hyink et al.
2013/0191647 A1 7/2013 Ferrara, Jr. et al.
2013/0193188 A1 8/2013 Shelton, IV et al.
2013/0197531 A1 8/2013 Boukhny et al.
2013/0206813 A1 8/2013 Nalagatla
2013/0214025 A1 8/2013 Zemlok et al.
2013/0226207 A1 8/2013 Stulen et al.
2013/0253480 A1 9/2013 Kimball et al.
2013/0256373 A1 10/2013 Schmid et al.
2013/0267874 A1 10/2013 Marcotte et al.
2013/0268283 A1 10/2013 Vann et al.
2013/0277410 A1 10/2013 Fernandez et al.
2013/0282038 A1* 10/2013 Dannaher ...... A61B 17/320068 606/1
2013/0317837 A1 11/2013 Ballantyne et al.
2013/0321425 A1 12/2013 Greene et al.
2013/0325809 A1 12/2013 Kim et al.
2013/0331873 A1 12/2013 Ross et al.
2013/0331875 A1 12/2013 Ross et al.
2013/0338656 A1 12/2013 Irisawa et al.
2013/0345670 A1* 12/2013 Rajagopalan ........ A61B 18/042 606/1
2014/0001231 A1 1/2014 Shelton, IV et al.
2014/0001234 A1 1/2014 Shelton, IV et al.
2014/0005640 A1 1/2014 Shelton, IV et al.
2014/0005667 A1 1/2014 Stulen et al.
2014/0006132 A1 1/2014 Barker
2014/0009894 A1 1/2014 Yu
2014/0013565 A1 1/2014 MacDonald et al.
2014/0018788 A1 1/2014 Engelman et al.
2014/0029411 A1 1/2014 Nayak et al.
2014/0033926 A1 2/2014 Fassel et al.
2014/0035762 A1 2/2014 Shelton, IV et al.
2014/0066700 A1 3/2014 Wilson et al.
2014/0073893 A1 3/2014 Bencini
2014/0074076 A1 3/2014 Gertner
2014/0074091 A1 3/2014 Arya et al.
2014/0081255 A1 3/2014 Johnson et al.
2014/0081659 A1 3/2014 Nawana et al.
2014/0084949 A1 3/2014 Smith et al.
2014/0087999 A1 3/2014 Kaplan et al.
2014/0092089 A1 4/2014 Kasuya et al.
2014/0107697 A1 4/2014 Patani et al.
2014/0108035 A1 4/2014 Akbay et al.
2014/0108983 A1 4/2014 William R. et al.
2014/0117256 A1 5/2014 Mueller et al.
2014/0121669 A1 5/2014 Claus
2014/0148729 A1 5/2014 Schmitz et al.
2014/0148803 A1 5/2014 Taylor
2014/0163359 A1 6/2014 Sholev et al.
2014/0166724 A1 6/2014 Schellin et al.
2014/0171778 A1 6/2014 Tsusaka et al.
2014/0187856 A1 7/2014 Holoien et al.

(56) References Cited

U.S. PATENT DOCUMENTS

2014/0188440 A1 7/2014 Donhowe et al.
2014/0194864 A1 7/2014 Martin et al.
2014/0195052 A1 7/2014 Tsusaka et al.
2014/0204190 A1 7/2014 Rosenblatt, III et al.
2014/0226572 A1 8/2014 Thota et al.
2014/0243799 A1 8/2014 Parihar
2014/0243809 A1 8/2014 Gelfand et al.
2014/0243811 A1 8/2014 Reschke et al.
2014/0246475 A1 9/2014 Hall et al.
2014/0249557 A1 9/2014 Koch et al.
2014/0252064 A1 9/2014 Mozdzierz et al.
2014/0263541 A1 9/2014 Leimbach et al.
2014/0263552 A1 9/2014 Hall et al.
2014/0275760 A1 9/2014 Lee et al.
2014/0276749 A1 9/2014 Johnson
2014/0287393 A1 9/2014 Kumar et al.
2014/0303660 A1 10/2014 Boyden et al.
2014/0303990 A1 10/2014 Schoenefeld et al.
2014/0336943 A1 11/2014 Pellini et al.
2014/0337052 A1 11/2014 Pellini et al.
2014/0364691 A1 12/2014 Krivopisk et al.
2015/0006201 A1 1/2015 Pait et al.
2015/0025549 A1 1/2015 Kilroy et al.
2015/0032150 A1 1/2015 Ishida et al.
2015/0051452 A1 2/2015 Ciaccio
2015/0051598 A1 2/2015 Orszulak et al.
2015/0051617 A1 2/2015 Takemura et al.
2015/0053737 A1 2/2015 Leimbach et al.
2015/0053743 A1 2/2015 Yates et al.
2015/0057675 A1 2/2015 Akeel et al.
2015/0066000 A1 3/2015 An et al.
2015/0070187 A1 3/2015 Wiesner et al.
2015/0073400 A1 3/2015 Sverdlik et al.
2015/0077528 A1 3/2015 Awdeh
2015/0083774 A1 3/2015 Measamer et al.
2015/0108198 A1 4/2015 Estrella
2015/0133945 A1 5/2015 Dushyant et al.
2015/0136833 A1 5/2015 Shelton, IV et al.
2015/0140982 A1 5/2015 Postrel
2015/0141981 A1 5/2015 Price et al.
2015/0145682 A1 5/2015 Harris
2015/0148830 A1 5/2015 Stulen et al.
2015/0157354 A1 6/2015 Bales, Jr. et al.
2015/0164532 A1 6/2015 Faller et al.
2015/0173673 A1 6/2015 Toth et al.
2015/0173756 A1 6/2015 Baxter, III et al.
2015/0182220 A1 7/2015 Yates et al.
2015/0196295 A1 7/2015 Shelton, IV et al.
2015/0199109 A1 7/2015 Lee
2015/0202014 A1 7/2015 Kim et al.
2015/0208934 A1 7/2015 Sztrubel et al.
2015/0223725 A1 8/2015 Engel et al.
2015/0223868 A1 8/2015 Brandt et al.
2015/0237502 A1 8/2015 Schmidt et al.
2015/0272557 A1 10/2015 Overmyer et al.
2015/0272571 A1 10/2015 Leimbach et al.
2015/0272580 A1 10/2015 Leimbach et al.
2015/0272582 A1 10/2015 Leimbach et al.
2015/0272694 A1 10/2015 Charles
2015/0282821 A1 10/2015 Look et al.
2015/0297200 A1 10/2015 Fitzsimmons et al.
2015/0297222 A1 10/2015 Huitema et al.
2015/0297228 A1 10/2015 Huitema et al.
2015/0297311 A1 10/2015 Tesar
2015/0302157 A1 10/2015 Collar et al.
2015/0310174 A1 10/2015 Coudert et al.
2015/0313538 A1 11/2015 Bechtel et al.
2015/0317899 A1 11/2015 Dumbauld et al.
2015/0320423 A1 11/2015 Aranyi
2015/0324114 A1 11/2015 Hurley et al.
2015/0328474 A1 11/2015 Flyash et al.
2015/0332003 A1 11/2015 Stamm et al.
2015/0332196 A1 11/2015 Stiller et al.
2015/0335344 A1 11/2015 Aljuri et al.
2015/0374259 A1 12/2015 Garbey et al.
2016/0000437 A1 1/2016 Giordano et al.
2016/0001411 A1 1/2016 Alberti
2016/0015471 A1 1/2016 Piron et al.
2016/0022374 A1 1/2016 Haider et al.
2016/0034648 A1 2/2016 Mohlenbrock et al.
2016/0038224 A1 2/2016 Couture et al.
2016/0038253 A1 2/2016 Piron et al.
2016/0048780 A1 2/2016 Sethumadhavan et al.
2016/0058439 A1 3/2016 Shelton, IV et al.
2016/0066913 A1 3/2016 Swayze et al.
2016/0106516 A1 4/2016 Mesallum
2016/0106934 A1 4/2016 Hiraga et al.
2016/0121143 A1 5/2016 Mumaw et al.
2016/0157717 A1 6/2016 Gaster
2016/0158468 A1 6/2016 Tang et al.
2016/0174998 A1 6/2016 Lal et al.
2016/0175001 A1 6/2016 Hibner et al.
2016/0175025 A1 6/2016 Strobl
2016/0180045 A1 6/2016 Syed
2016/0184054 A1 6/2016 Lowe
2016/0192960 A1 7/2016 Bueno et al.
2016/0206202 A1 7/2016 Frangioni
2016/0206362 A1 7/2016 Mehta et al.
2016/0224760 A1 8/2016 Petak et al.
2016/0225551 A1 8/2016 Shedletsky
2016/0228061 A1 8/2016 Kallback et al.
2016/0228204 A1 8/2016 Quaid et al.
2016/0235303 A1 8/2016 Fleming et al.
2016/0242836 A1 8/2016 Eggers et al.
2016/0249910 A1 9/2016 Shelton, IV et al.
2016/0249920 A1 9/2016 Gupta et al.
2016/0270861 A1 9/2016 Guru et al.
2016/0278841 A1 9/2016 Panescu et al.
2016/0287312 A1 10/2016 Tegg et al.
2016/0287316 A1 10/2016 Worrell et al.
2016/0287912 A1 10/2016 Warnking
2016/0292456 A1 10/2016 Dubey et al.
2016/0296246 A1 10/2016 Schaller
2016/0302210 A1 10/2016 Thornton et al.
2016/0310055 A1 10/2016 Zand et al.
2016/0310204 A1 10/2016 Mchenry et al.
2016/0314716 A1 10/2016 Grubbs
2016/0314717 A1 10/2016 Grubbs
2016/0321400 A1 11/2016 Durrant et al.
2016/0323283 A1 11/2016 Kang et al.
2016/0331460 A1* 11/2016 Cheatham, III ..... A61B 5/0024
2016/0342753 A1 11/2016 Feazell
2016/0342916 A1 11/2016 Arceneaux et al.
2016/0345857 A1 12/2016 Jensrud et al.
2016/0350490 A1 12/2016 Martinez et al.
2016/0354162 A1 12/2016 Yen et al.
2016/0361070 A1 12/2016 Ardel et al.
2016/0367305 A1 12/2016 Hareland
2016/0367401 A1 12/2016 Claus
2016/0374723 A1 12/2016 Frankhouser et al.
2016/0374762 A1 12/2016 Case et al.
2016/0379504 A1 12/2016 Bailey et al.
2017/0000516 A1* 1/2017 Stulen ................ A61B 18/1445
2017/0027603 A1 2/2017 Pandey
2017/0042604 A1 2/2017 McFarland et al.
2017/0068792 A1 3/2017 Reiner
2017/0079530 A1 3/2017 DiMaio et al.
2017/0079730 A1 3/2017 Azizian et al.
2017/0086829 A1 3/2017 Vendely et al.
2017/0086930 A1 3/2017 Thompson et al.
2017/0105754 A1 4/2017 Boudreaux et al.
2017/0116873 A1 4/2017 Lendvay et al.
2017/0127499 A1 5/2017 Unoson et al.
2017/0132374 A1 5/2017 Lee et al.
2017/0132385 A1 5/2017 Hunter et al.
2017/0132785 A1 5/2017 Wshah et al.
2017/0143284 A1 5/2017 Sehnert et al.
2017/0164997 A1 6/2017 Johnson et al.
2017/0165008 A1 6/2017 Finley
2017/0165012 A1 6/2017 Chaplin et al.
2017/0172550 A1 6/2017 Mukherjee et al.
2017/0172565 A1 6/2017 Heneveld
2017/0172614 A1 6/2017 Scheib et al.
2017/0173262 A1 6/2017 Veltz

(56) References Cited

U.S. PATENT DOCUMENTS

2017/0177807 A1 6/2017 Fabian
2017/0189093 A1 7/2017 Houser
2017/0196583 A1 7/2017 Sugiyama
2017/0202595 A1 7/2017 Shelton, IV
2017/0202608 A1 7/2017 Shelton, IV et al.
2017/0209145 A1 7/2017 Swayze et al.
2017/0215944 A1 8/2017 Keffeler
2017/0224332 A1 8/2017 Hunter et al.
2017/0224428 A1 8/2017 Kopp
2017/0231628 A1 8/2017 Shelton, IV et al.
2017/0238991 A1 8/2017 Worrell et al.
2017/0245809 A1 8/2017 Ma et al.
2017/0245917 A1 8/2017 Sugawara
2017/0249431 A1 8/2017 Shelton, IV et al.
2017/0249432 A1 8/2017 Grantcharov
2017/0262604 A1 9/2017 Francois
2017/0265864 A1 9/2017 Hessler et al.
2017/0265943 A1 9/2017 Sela et al.
2017/0273715 A1 9/2017 Piron et al.
2017/0281186 A1 10/2017 Shelton, IV et al.
2017/0296173 A1 10/2017 Shelton, IV et al.
2017/0296185 A1 10/2017 Swensgard et al.
2017/0296213 A1 10/2017 Swensgard et al.
2017/0303984 A1 10/2017 Malackowski
2017/0303988 A1 10/2017 Hayashida et al.
2017/0304007 A1 10/2017 Piron et al.
2017/0304020 A1 10/2017 Ng et al.
2017/0311777 A1 11/2017 Hirayama et al.
2017/0312456 A1 11/2017 Phillips
2017/0325876 A1 11/2017 Nakadate et al.
2017/0325878 A1 11/2017 Messerly et al.
2017/0333111 A1 11/2017 Kabaya et al.
2017/0337043 A1 11/2017 Brincat et al.
2017/0360358 A1 12/2017 Amiot et al.
2017/0360499 A1 12/2017 Greep et al.
2017/0367583 A1 12/2017 Black et al.
2017/0367754 A1 12/2017 Narisawa
2017/0367771 A1 12/2017 Tako et al.
2017/0367772 A1 12/2017 Gunn et al.
2017/0370710 A1 12/2017 Chen et al.
2018/0008359 A1 1/2018 Randle
2018/0011983 A1 1/2018 Zuhars et al.
2018/0021058 A1 1/2018 Meglan
2018/0042659 A1 2/2018 Rupp et al.
2018/0050196 A1 2/2018 Pawsey et al.
2018/0052971 A1 2/2018 Hanina et al.
2018/0065248 A1 3/2018 Barral et al.
2018/0078170 A1 3/2018 Panescu et al.
2018/0098816 A1 4/2018 Govari et al.
2018/0108438 A1 4/2018 Ryan et al.
2018/0116662 A1 5/2018 Shelton, IV et al.
2018/0116735 A1 5/2018 Tierney et al.
2018/0122506 A1 5/2018 Grantcharov et al.
2018/0132895 A1 5/2018 Silver
2018/0144243 A1 5/2018 Hsieh et al.
2018/0153574 A1 6/2018 Faller et al.
2018/0153632 A1 6/2018 Tokarchuk et al.
2018/0154297 A1 6/2018 Maletich et al.
2018/0161062 A1 6/2018 Kaga et al.
2018/0161716 A1 6/2018 Li et al.
2018/0165780 A1 6/2018 Romeo
2018/0168575 A1 6/2018 Simms et al.
2018/0168577 A1 6/2018 Aronhalt et al.
2018/0168579 A1 6/2018 Aronhalt et al.
2018/0168592 A1 6/2018 Overmyer et al.
2018/0168598 A1 6/2018 Shelton, IV et al.
2018/0168608 A1 6/2018 Shelton, IV et al.
2018/0168609 A1 6/2018 Fanelli et al.
2018/0168610 A1 6/2018 Shelton, IV et al.
2018/0168615 A1 6/2018 Shelton, IV et al.
2018/0168618 A1 6/2018 Scott et al.
2018/0168619 A1 6/2018 Scott et al.
2018/0168623 A1 6/2018 Simms et al.
2018/0168625 A1 6/2018 Posada et al.
2018/0168633 A1 6/2018 Shelton, IV et al.
2018/0168647 A1 6/2018 Shelton, IV et al.
2018/0168648 A1 6/2018 Shelton, IV et al.
2018/0168650 A1 6/2018 Shelton, IV et al.
2018/0177383 A1 6/2018 Noonan et al.
2018/0182475 A1 6/2018 Cossler et al.
2018/0193579 A1 7/2018 Hanrahan et al.
2018/0206884 A1 7/2018 Beaupre
2018/0206905 A1 7/2018 Batchelor et al.
2018/0211726 A1 7/2018 Courtemanche et al.
2018/0214025 A1 8/2018 Homyk et al.
2018/0221005 A1 8/2018 Hamel et al.
2018/0221598 A1 8/2018 Silver
2018/0228557 A1 8/2018 Darisse et al.
2018/0233222 A1 8/2018 Daley et al.
2018/0235719 A1 8/2018 Jarc
2018/0235722 A1 8/2018 Baghdadi et al.
2018/0242967 A1 8/2018 Meade
2018/0247128 A1 8/2018 Alvi et al.
2018/0247711 A1 8/2018 Terry
2018/0250086 A1 9/2018 Grubbs
2018/0263699 A1 9/2018 Murphy et al.
2018/0263710 A1 9/2018 Sakaguchi et al.
2018/0268320 A1 9/2018 Shekhar
2018/0271520 A1 9/2018 Shelton, IV et al.
2018/0271603 A1 9/2018 Nir et al.
2018/0289427 A1 10/2018 Griffiths et al.
2018/0294060 A1 10/2018 Kassab
2018/0296286 A1 10/2018 Peine et al.
2018/0303552 A1 10/2018 Ryan et al.
2018/0304471 A1 10/2018 Tokuchi
2018/0310986 A1 11/2018 Batchelor et al.
2018/0315492 A1 11/2018 Bishop et al.
2018/0317916 A1 11/2018 Wixey
2018/0333188 A1 11/2018 Nott et al.
2018/0333207 A1 11/2018 Moctezuma De la Barrera
2018/0333209 A1 11/2018 Frushour et al.
2018/0353186 A1 12/2018 Mozdzierz et al.
2018/0357383 A1 12/2018 Allen et al.
2018/0360456 A1 12/2018 Shelton, IV et al.
2018/0366213 A1 12/2018 Fidone et al.
2018/0368930 A1 12/2018 Esterberg et al.
2019/0000569 A1 1/2019 Crawford et al.
2019/0001079 A1 1/2019 Zergiebel et al.
2019/0005641 A1 1/2019 Yamamoto
2019/0006047 A1 1/2019 Gorek et al.
2019/0025040 A1 1/2019 Andreason et al.
2019/0036688 A1 1/2019 Wasily et al.
2019/0038335 A1 2/2019 Mohr et al.
2019/0038364 A1 2/2019 Enoki
2019/0046198 A1 2/2019 Stokes et al.
2019/0053801 A1 2/2019 Wixey et al.
2019/0053866 A1 2/2019 Seow et al.
2019/0059986 A1 2/2019 Shelton, IV et al.
2019/0069949 A1 3/2019 Vrba et al.
2019/0069964 A1 3/2019 Hagn
2019/0069966 A1 3/2019 Petersen et al.
2019/0070550 A1 3/2019 Lalomia et al.
2019/0070731 A1 3/2019 Bowling et al.
2019/0083190 A1 3/2019 Graves et al.
2019/0087544 A1 3/2019 Peterson
2019/0099221 A1 4/2019 Schmidt et al.
2019/0104919 A1 4/2019 Shelton, IV et al.
2019/0110828 A1 4/2019 Despatie
2019/0110855 A1 4/2019 Barral et al.
2019/0115108 A1 4/2019 Hegedus et al.
2019/0125320 A1 5/2019 Shelton, IV et al.
2019/0125335 A1 5/2019 Shelton, IV et al.
2019/0125336 A1 5/2019 Deck et al.
2019/0125338 A1 5/2019 Shelton, IV et al.
2019/0125361 A1 5/2019 Shelton, IV et al.
2019/0125377 A1 5/2019 Shelton, IV
2019/0125378 A1 5/2019 Shelton, IV et al.
2019/0125388 A1 5/2019 Shelton, IV et al.
2019/0125430 A1 5/2019 Shelton, IV et al.
2019/0125431 A1 5/2019 Shelton, IV et al.
2019/0125432 A1 5/2019 Shelton, IV et al.
2019/0125454 A1 5/2019 Stokes et al.
2019/0125455 A1 5/2019 Shelton, IV et al.
2019/0125458 A1 5/2019 Shelton, IV et al.

(56) References Cited

U.S. PATENT DOCUMENTS

2019/0125459 A1 5/2019 Shelton, IV et al.
2019/0125476 A1 5/2019 Shelton, IV et al.
2019/0133703 A1 5/2019 Seow et al.
2019/0142535 A1 5/2019 Seow et al.
2019/0145942 A1 5/2019 Dutriez et al.
2019/0150975 A1 5/2019 Kawasaki et al.
2019/0159778 A1 5/2019 Shelton, IV et al.
2019/0163875 A1 5/2019 Allen et al.
2019/0167296 A1 6/2019 Tsubuku et al.
2019/0192157 A1 6/2019 Scott et al.
2019/0200844 A1 7/2019 Shelton, IV et al.
2019/0200905 A1 7/2019 Shelton, IV et al.
2019/0200906 A1 7/2019 Shelton, IV et al.
2019/0200977 A1 7/2019 Shelton, IV et al.
2019/0200980 A1 7/2019 Shelton, IV et al.
2019/0200981 A1 7/2019 Harris et al.
2019/0200984 A1 7/2019 Shelton, IV et al.
2019/0200985 A1 7/2019 Shelton, IV et al.
2019/0200987 A1 7/2019 Shelton, IV et al.
2019/0200988 A1 7/2019 Shelton, IV
2019/0200997 A1 7/2019 Shelton, IV et al.
2019/0201021 A1 7/2019 Shelton, IV et al.
2019/0201024 A1 7/2019 Shelton, IV et al.
2019/0201025 A1 7/2019 Shelton, IV et al.
2019/0201026 A1 7/2019 Shelton, IV et al.
2019/0201027 A1 7/2019 Shelton, IV et al.
2019/0201029 A1 7/2019 Shelton, IV et al.
2019/0201030 A1 7/2019 Shelton, IV et al.
2019/0201033 A1 7/2019 Yates et al.
2019/0201034 A1 7/2019 Shelton, IV et al.
2019/0201036 A1 7/2019 Nott et al.
2019/0201038 A1 7/2019 Yates et al.
2019/0201039 A1 7/2019 Widenhouse et al.
2019/0201040 A1 7/2019 Messerly et al.
2019/0201042 A1 7/2019 Nott et al.
2019/0201043 A1 7/2019 Shelton, IV et al.
2019/0201044 A1 7/2019 Shelton, IV et al.
2019/0201045 A1 7/2019 Yates et al.
2019/0201046 A1 7/2019 Shelton, IV et al.
2019/0201047 A1 7/2019 Yates et al.
2019/0201073 A1 7/2019 Nott et al.
2019/0201075 A1 7/2019 Shelton, IV et al.
2019/0201080 A1 7/2019 Messerly et al.
2019/0201083 A1 7/2019 Shelton, IV et al.
2019/0201085 A1 7/2019 Shelton, IV et al.
2019/0201087 A1 7/2019 Shelton, IV et al.
2019/0201090 A1 7/2019 Shelton, IV et al.
2019/0201102 A1 7/2019 Shelton, IV et al.
2019/0201104 A1 7/2019 Shelton, IV et al.
2019/0201112 A1 7/2019 Wiener et al.
2019/0201113 A1 7/2019 Shelton, IV et al.
2019/0201115 A1 7/2019 Shelton, IV et al.
2019/0201118 A1 7/2019 Shelton, IV et al.
2019/0201120 A1 7/2019 Shelton, IV et al.
2019/0201123 A1 7/2019 Shelton, IV et al.
2019/0201124 A1 7/2019 Shelton, IV et al.
2019/0201126 A1 7/2019 Shelton, IV et al.
2019/0201127 A1 7/2019 Shelton, IV et al.
2019/0201128 A1 7/2019 Yates et al.
2019/0201130 A1 7/2019 Shelton, IV et al.
2019/0201136 A1 7/2019 Shelton, IV et al.
2019/0201137 A1 7/2019 Shelton, IV et al.
2019/0201139 A1 7/2019 Shelton, IV et al.
2019/0201140 A1 7/2019 Yates et al.
2019/0201142 A1 7/2019 Shelton, IV et al.
2019/0201146 A1 7/2019 Shelton, IV et al.
2019/0201158 A1 7/2019 Shelton, IV et al.
2019/0201594 A1 7/2019 Shelton, IV et al.
2019/0204201 A1 7/2019 Shelton, IV et al.
2019/0205001 A1 7/2019 Messerly et al.
2019/0205567 A1 7/2019 Shelton, IV et al.
2019/0206551 A1 7/2019 Yates et al.
2019/0206555 A1 7/2019 Morgan et al.
2019/0206561 A1 7/2019 Shelton, IV et al.
2019/0206562 A1 7/2019 Shelton, IV et al.
2019/0206564 A1 7/2019 Shelton, IV et al.
2019/0206565 A1 7/2019 Shelton, IV
2019/0206569 A1 7/2019 Shelton, IV et al.
2019/0224434 A1 7/2019 Silver et al.
2019/0254759 A1 8/2019 Azizian
2019/0261984 A1 8/2019 Nelson et al.
2019/0269476 A1 9/2019 Bowling et al.
2019/0272917 A1 9/2019 Couture et al.
2019/0274662 A1 9/2019 Rockman et al.
2019/0274705 A1 9/2019 Sawhney et al.
2019/0274706 A1 9/2019 Nott et al.
2019/0274709 A1 9/2019 Scoggins
2019/0274710 A1 9/2019 Black
2019/0274711 A1 9/2019 Scoggins et al.
2019/0274713 A1 9/2019 Scoggins et al.
2019/0274714 A1 9/2019 Cuti et al.
2019/0274718 A1 9/2019 Denzinger et al.
2019/0274719 A1 9/2019 Stulen
2019/0274749 A1 9/2019 Brady et al.
2019/0274752 A1 9/2019 Denzinger et al.
2019/0278262 A1 9/2019 Taylor et al.
2019/0282311 A1 9/2019 Nowlin et al.
2019/0290389 A1 9/2019 Kopp
2019/0298350 A1 10/2019 Shelton, IV et al.
2019/0298352 A1 10/2019 Shelton, IV et al.
2019/0298353 A1 10/2019 Shelton, IV et al.
2019/0298464 A1 10/2019 Abbott
2019/0307520 A1 10/2019 Peine et al.
2019/0311802 A1 10/2019 Kokubo et al.
2019/0314081 A1 10/2019 Brogna
2019/0320929 A1 10/2019 Spencer et al.
2019/0321117 A1 10/2019 Itkowitz et al.
2019/0333626 A1 10/2019 Mansi et al.
2019/0343594 A1 11/2019 Garcia Kilroy et al.
2019/0374140 A1 12/2019 Tucker et al.
2019/0374292 A1 12/2019 Barral et al.
2019/0378610 A1 12/2019 Barral et al.
2020/0000470 A1 1/2020 Du et al.
2020/0000509 A1 1/2020 Hayashida et al.
2020/0038120 A1 2/2020 Ziraknejad et al.
2020/0046353 A1 2/2020 Deck et al.
2020/0054317 A1 2/2020 Pisarnwongs et al.
2020/0054321 A1 2/2020 Harris et al.
2020/0078070 A1 3/2020 Henderson et al.
2020/0078071 A1 3/2020 Asher
2020/0078076 A1 3/2020 Henderson et al.
2020/0078078 A1 3/2020 Henderson et al.
2020/0078079 A1 3/2020 Morgan et al.
2020/0078080 A1 3/2020 Henderson et al.
2020/0078081 A1 3/2020 Jayme et al.
2020/0078082 A1 3/2020 Henderson et al.
2020/0078089 A1 3/2020 Henderson et al.
2020/0078096 A1 3/2020 Barbagli et al.
2020/0078106 A1 3/2020 Henderson et al.
2020/0078110 A1 3/2020 Henderson et al.
2020/0078111 A1 3/2020 Oberkircher et al.
2020/0078112 A1 3/2020 Henderson et al.
2020/0078113 A1 3/2020 Sawhney et al.
2020/0078114 A1 3/2020 Asher et al.
2020/0078115 A1 3/2020 Asher et al.
2020/0078116 A1 3/2020 Oberkircher et al.
2020/0078117 A1 3/2020 Henderson et al.
2020/0078118 A1 3/2020 Henderson et al.
2020/0078119 A1 3/2020 Henderson et al.
2020/0078120 A1 3/2020 Aldridge et al.
2020/0081585 A1 3/2020 Petre et al.
2020/0090808 A1 3/2020 Carroll et al.
2020/0100825 A1 4/2020 Henderson et al.
2020/0100830 A1 4/2020 Henderson et al.
2020/0106220 A1 4/2020 Henderson et al.
2020/0162896 A1 5/2020 Su et al.
2020/0168323 A1 5/2020 Bullington et al.
2020/0178760 A1 6/2020 Kashima et al.
2020/0178971 A1 6/2020 Harris et al.
2020/0193600 A1 6/2020 Shameli et al.
2020/0197027 A1 6/2020 Hershberger et al.
2020/0203004 A1 6/2020 Shanbhag et al.
2020/0214699 A1 7/2020 Shelton, IV et al.
2020/0226751 A1 7/2020 Jin et al.

(56) References Cited

U.S. PATENT DOCUMENTS

| | | | |
|---|---|---|---|
| 2020/0237372 | A1 | 7/2020 | Park |
| 2020/0261078 | A1 | 8/2020 | Bakos et al. |
| 2020/0261086 | A1 | 8/2020 | Zeiner et al. |
| 2020/0261087 | A1 | 8/2020 | Timm et al. |
| 2020/0275928 | A1 | 9/2020 | Shelton, IV et al. |
| 2020/0275930 | A1 | 9/2020 | Harris et al. |
| 2020/0281665 | A1 | 9/2020 | Kopp |
| 2020/0305924 | A1 | 10/2020 | Carroll |
| 2020/0305945 | A1 | 10/2020 | Morgan et al. |
| 2020/0348662 | A1 | 11/2020 | Cella et al. |
| 2020/0405304 | A1 | 12/2020 | Mozdzierz et al. |
| 2020/0405375 | A1 | 12/2020 | Shelton, IV et al. |
| 2021/0007760 | A1 | 1/2021 | Reisin |
| 2021/0015568 | A1 | 1/2021 | Liao et al. |
| 2021/0022731 | A1 | 1/2021 | Eisinger |
| 2021/0022738 | A1 | 1/2021 | Weir et al. |
| 2021/0022809 | A1 | 1/2021 | Crawford et al. |
| 2021/0059674 | A1 | 3/2021 | Shelton, IV et al. |
| 2021/0068834 | A1 | 3/2021 | Shelton, IV et al. |
| 2021/0076966 | A1 | 3/2021 | Grantcharov et al. |
| 2021/0128149 | A1 | 5/2021 | Whitfield et al. |
| 2021/0153889 | A1 | 5/2021 | Nott et al. |
| 2021/0169516 | A1 | 6/2021 | Houser et al. |
| 2021/0176179 | A1 | 6/2021 | Shelton, IV |
| 2021/0177452 | A1 | 6/2021 | Nott et al. |
| 2021/0177489 | A1 | 6/2021 | Yates et al. |
| 2021/0186454 | A1 | 6/2021 | Behzadi et al. |
| 2021/0192914 | A1 | 6/2021 | Shelton, IV et al. |
| 2021/0201646 | A1 | 7/2021 | Shelton, IV et al. |
| 2021/0205020 | A1 | 7/2021 | Shelton, IV et al. |
| 2021/0205021 | A1 | 7/2021 | Shelton, IV et al. |
| 2021/0205028 | A1 | 7/2021 | Shelton, IV et al. |
| 2021/0205029 | A1 | 7/2021 | Wiener et al. |
| 2021/0205030 | A1 | 7/2021 | Shelton, IV et al. |
| 2021/0205031 | A1 | 7/2021 | Shelton, IV et al. |
| 2021/0212602 | A1 | 7/2021 | Shelton, IV et al. |
| 2021/0212694 | A1 | 7/2021 | Shelton, IV et al. |
| 2021/0212717 | A1 | 7/2021 | Yates et al. |
| 2021/0212719 | A1 | 7/2021 | Houser et al. |
| 2021/0212770 | A1 | 7/2021 | Messerly et al. |
| 2021/0212771 | A1 | 7/2021 | Shelton, IV et al. |
| 2021/0212774 | A1 | 7/2021 | Shelton, IV et al. |
| 2021/0212775 | A1 | 7/2021 | Shelton, IV et al. |
| 2021/0212782 | A1 | 7/2021 | Shelton, IV et al. |
| 2021/0219976 | A1 | 7/2021 | DiNardo et al. |
| 2021/0220058 | A1 | 7/2021 | Messerly et al. |
| 2021/0240852 | A1 | 8/2021 | Shelton, IV et al. |
| 2021/0241898 | A1 | 8/2021 | Shelton, IV et al. |
| 2021/0249125 | A1 | 8/2021 | Morgan et al. |
| 2021/0251487 | A1 | 8/2021 | Shelton, IV et al. |
| 2021/0259687 | A1 | 8/2021 | Gonzalez et al. |
| 2021/0259697 | A1 | 8/2021 | Shelton, IV et al. |
| 2021/0259698 | A1 | 8/2021 | Shelton, IV et al. |
| 2021/0282780 | A1 | 9/2021 | Shelton, IV et al. |
| 2021/0282781 | A1 | 9/2021 | Shelton, IV et al. |
| 2021/0306176 | A1 | 9/2021 | Park et al. |
| 2021/0315579 | A1 | 10/2021 | Shelton, IV et al. |
| 2021/0315580 | A1 | 10/2021 | Shelton, IV et al. |
| 2021/0315581 | A1 | 10/2021 | Shelton, IV et al. |
| 2021/0315582 | A1 | 10/2021 | Shelton, IV et al. |
| 2021/0322014 | A1 | 10/2021 | Shelton, IV et al. |
| 2021/0322015 | A1 | 10/2021 | Shelton, IV et al. |
| 2021/0322017 | A1 | 10/2021 | Shelton, IV et al. |
| 2021/0322018 | A1 | 10/2021 | Shelton, IV et al. |
| 2021/0322019 | A1 | 10/2021 | Shelton, IV et al. |
| 2021/0322020 | A1 | 10/2021 | Shelton, IV et al. |
| 2021/0336939 | A1 | 10/2021 | Wiener et al. |
| 2021/0353287 | A1 | 11/2021 | Shelton, IV et al. |
| 2021/0353288 | A1 | 11/2021 | Shelton, IV et al. |
| 2021/0358599 | A1 | 11/2021 | Alvi et al. |
| 2021/0361284 | A1 | 11/2021 | Shelton, IV et al. |
| 2022/0000484 | A1 | 1/2022 | Shelton, IV et al. |
| 2022/0054158 | A1 | 2/2022 | Shelton, IV et al. |
| 2022/0079591 | A1 | 3/2022 | Bakos et al. |
| 2022/0160438 | A1 | 5/2022 | Shelton, IV et al. |
| 2022/0175374 | A1 | 6/2022 | Shelton, IV et al. |

FOREIGN PATENT DOCUMENTS

| | | | |
|---|---|---|---|
| CN | 1634601 | A | 7/2005 |
| CN | 101617950 | A | 1/2010 |
| CN | 104244850 | A | 12/2014 |
| CN | 105764435 | A | 7/2016 |
| CN | 104490448 | B | 3/2017 |
| CN | 206097107 | U | 4/2017 |
| CN | 107249490 | A | 10/2017 |
| CN | 108652695 | A | 10/2018 |
| DE | 2037167 | A1 | 2/1972 |
| DE | 3016131 | A1 | 10/1981 |
| DE | 3824913 | A1 | 2/1990 |
| DE | 4002843 | C1 | 4/1991 |
| DE | 102005051367 | A1 | 4/2007 |
| DE | 102016207666 | A1 | 11/2017 |
| EP | 0000756 | B1 | 10/1981 |
| EP | 0 171 967 | A2 | 2/1986 |
| EP | 0408160 | A1 | 1/1991 |
| EP | 0 443 256 | A1 | 8/1991 |
| EP | 0 456 470 | A1 | 11/1991 |
| EP | 0473987 | A1 | 3/1992 |
| EP | 0 482 195 | B1 | 1/1996 |
| EP | 0 612 570 | B1 | 6/1997 |
| EP | 0929263 | B1 | 7/1999 |
| EP | 0 908 148 | B1 | 1/2002 |
| EP | 1214913 | A2 | 6/2002 |
| EP | 0 908 155 | B1 | 6/2003 |
| EP | 1 199 044 | B1 | 12/2005 |
| EP | 1 199 043 | B1 | 3/2006 |
| EP | 1 844 720 | A1 | 10/2007 |
| EP | 1 862 133 | A1 | 12/2007 |
| EP | 1 974 771 | A1 | 10/2008 |
| EP | 1 832 259 | B1 | 6/2009 |
| EP | 2 074 959 | A1 | 7/2009 |
| EP | 2 298 154 | A2 | 3/2011 |
| EP | 2 578 172 | A2 | 4/2013 |
| EP | 2730209 | A1 | 5/2014 |
| EP | 2732772 | A1 | 5/2014 |
| EP | 2942023 | A2 | 11/2015 |
| EP | 3047806 | A1 | 7/2016 |
| EP | 3056923 | A1 | 8/2016 |
| EP | 3095399 | A2 | 11/2016 |
| EP | 3120781 | A2 | 1/2017 |
| EP | 3135225 | A2 | 3/2017 |
| EP | 3141181 | A1 | 3/2017 |
| EP | 2 789 953 | B1 | 7/2019 |
| FR | 2838234 | A1 | 10/2003 |
| GB | 2032221 | A | 4/1980 |
| GB | 2037167 | A1 | 7/1980 |
| GB | 2379878 | B | 11/2004 |
| GB | 2509523 | A | 7/2014 |
| JP | S5373315 | A | 6/1978 |
| JP | 62292153 | A | 12/1987 |
| JP | H02-71510 | U | 5/1990 |
| JP | H04-30508 | U | 3/1992 |
| JP | H08-24266 | A | 1/1996 |
| JP | H08-275951 | A | 10/1996 |
| JP | H10-295700 | A | 11/1998 |
| JP | 2001029353 | A | 2/2001 |
| JP | 2002-263579 | A | 9/2002 |
| JP | 2003-339730 | A | 12/2003 |
| JP | 2005-027026 | A | 1/2005 |
| JP | 2005-074088 | A | 3/2005 |
| JP | 2006-217716 | A | 8/2006 |
| JP | 2007123394 | A | 5/2007 |
| JP | 2010057642 | A | 3/2010 |
| JP | 2010-194319 | A | 9/2010 |
| JP | 2012-533346 | A | 12/2012 |
| JP | 2013-078585 | A | 5/2013 |
| JP | 6095878 | B1 | 2/2017 |
| JP | 6129460 | B1 | 4/2017 |
| JP | 2017513561 | A | 6/2017 |
| JP | 6507081 | B2 | 4/2019 |
| JP | 2021-509056 | A | 3/2021 |

(56) References Cited

FOREIGN PATENT DOCUMENTS

| | | | |
|---|---|---|---|
| KR | 20140104587 | A | 8/2014 |
| KR | 101587721 | B1 | 1/2016 |
| WO | 92/22259 | A2 | 12/1992 |
| WO | 93/14708 | A1 | 8/1993 |
| WO | 94/21183 | A1 | 9/1994 |
| WO | 95/09572 | A1 | 4/1995 |
| WO | WO-9734533 | A1 | 9/1997 |
| WO | 98/26739 | A1 | 6/1998 |
| WO | 98/37815 | A1 | 9/1998 |
| WO | WO-0024322 | A1 | 5/2000 |
| WO | WO-0108578 | A1 | 2/2001 |
| WO | WO-0112089 | A1 | 2/2001 |
| WO | WO-0120892 | A2 | 3/2001 |
| WO | 01/54590 | A1 | 8/2001 |
| WO | 01/95810 | A2 | 12/2001 |
| WO | WO-03079909 | A2 | 10/2003 |
| WO | 2004/037095 | A2 | 5/2004 |
| WO | 2005/122917 | A1 | 12/2005 |
| WO | 2006/012797 | A1 | 2/2006 |
| WO | 2006/058223 | A2 | 6/2006 |
| WO | 2006/063199 | A2 | 6/2006 |
| WO | 2006/083988 | A1 | 8/2006 |
| WO | 2006/129465 | A1 | 12/2006 |
| WO | 2007/008710 | A2 | 1/2007 |
| WO | 2007/087272 | A2 | 8/2007 |
| WO | WO-2007137304 | A2 | 11/2007 |
| WO | 2007/143665 | A2 | 12/2007 |
| WO | 2008/016886 | A2 | 2/2008 |
| WO | 2008/042021 | A1 | 4/2008 |
| WO | WO-2008053485 | A1 | 5/2008 |
| WO | WO-2008056618 | A2 | 5/2008 |
| WO | WO-2008069816 | A1 | 6/2008 |
| WO | 2008/130793 | A1 | 10/2008 |
| WO | WO-2008147555 | A2 | 12/2008 |
| WO | 2009/018406 | A2 | 2/2009 |
| WO | 2009/027065 | A1 | 3/2009 |
| WO | 2011/008672 | A2 | 1/2011 |
| WO | 2011/052349 | A1 | 5/2011 |
| WO | WO-2011112931 | A1 | 9/2011 |
| WO | 2011/144911 | A1 | 11/2011 |
| WO | 2013/084420 | A1 | 6/2013 |
| WO | 2013/088891 | A1 | 6/2013 |
| WO | WO-2013143573 | A1 | 10/2013 |
| WO | WO-2014031800 | A1 | 2/2014 |
| WO | WO-2014071184 | A1 | 5/2014 |
| WO | WO-2014134196 | A1 | 9/2014 |
| WO | 2015/021333 | A1 | 2/2015 |
| WO | WO-2015129395 | A1 | 9/2015 |
| WO | WO-2016100719 | A1 | 6/2016 |
| WO | WO-2016118752 | A1 | 7/2016 |
| WO | 2016/201123 | A1 | 12/2016 |
| WO | WO-2016206015 | A1 | 12/2016 |
| WO | WO-2017011382 | A1 | 1/2017 |
| WO | WO-2017011646 | A1 | 1/2017 |
| WO | 2017/070031 | A1 | 4/2017 |
| WO | WO-2017058617 | | 4/2017 |
| WO | WO-2017058695 | A1 | 4/2017 |
| WO | WO-2017151996 | A1 | 9/2017 |
| WO | WO-2017189317 | A1 | 11/2017 |
| WO | WO-2017205308 | A1 | 11/2017 |
| WO | WO-2017210499 | A1 | 12/2017 |
| WO | WO-2017210501 | A1 | 12/2017 |
| WO | WO-2018116247 | A1 | 6/2018 |
| WO | WO-2018152141 | A1 | 8/2018 |
| WO | WO-2018176414 | A1 | 10/2018 |

OTHER PUBLICATIONS

Engel et al. "A safe robot system for craniofacial surgery", 2013 IEEE International Conference on Robotics and Automation (ICRA); May 6-10, 2013; Karlsruhe, Germany, vol. 2, Jan. 1, 2001, pp. 2020-2024.

Miller, et al., "Impact of Powered and Tissue-Specific Endoscopic Stapling Technology on Clinical and Economic Outcomes of Video-Assisted Thoracic Surgery Lobectomy Procedures: A Retrospective, Observational Study," Article, Apr. 2018, pp. 707-723, vol. 35 (Issue 5), Advances in Therapy.

Choi et al., A haptic augmented reality surgeon console for a laparoscopic surgery robot system, 2013, IEEE, p. 355-357 (Year: 2013).

"Surgical instrumentation: the true cost of instrument trays and a potential strategy for optimization"; Mhlaba et al.; Sep. 23, 2015 (Year: 2015).

Anonymous: "Titanium Key Chain Tool 1.1, Ultralight Multipurpose Key Chain Tool, Forward Cutting Can Opener—Vargo Titanium," vargooutdoors.com, Jul. 5, 2014 (Jul. 5, 2014), retrieved from the internet: https://vargooutdoors.com/titanium-key-chain-tool-1-1.html.

Shi et al., An intuitive control console for robotic syrgery system, 2014, IEEE, p. 404-407 (Year: 2014).

Slocinski et al., "Distance measure for impedance spectra for quantified evaluations," Lecture Notes on Impedance Spectroscopy, vol. 3, Taylor and Francis Group (Jul. 2012)—Book Not Attached.

Zoccali, Bruno, "A Method for Approximating Component Temperatures at Altitude Conditions Based on CFD Analysis at Sea Level Conditions," (white paper), www.tdmginc.com, Dec. 6, 2018 (9 pages).

Flores et al., "Large-scale Offloading in the Internet of Things," 2017 IEEE International Conference on Pervasive Computing and Communications Workshops (PERCOM Workshops), IEEE, pp. 479-484, Mar. 13, 2017.

Kalantarian et al., "Computation Offloading for Real-Time Health-Monitoring Devices," 2016 38th Annual International Conference of the IEEE Engineering in Medicine and Biology Society (EBMC), IEEE, pp. 4971-4974, Aug. 16, 2016.

Yuyi Mao et al., "A Survey on Mobile Edge Computing: The Communication Perspective," IEEE Communications Surveys & Tutorials, pp. 2322-2358, Jun. 13, 2017.

Khazaei et al., "Health Informatics for Neonatal Intensive Care Units: An Analytical Modeling Perspective," IEEE Journal of Translational Engineering in Health and Medicine, vol. 3, pp. 1-9, Oct. 21, 2015.

Benkmann et al., "Concept of iterative optimization of minimally invasive surgery," 2017 22nd International Conference on Methods and Models in Automation and Robotics (MMAR), IEEE pp. 443-446, Aug. 28, 2017.

Trautman, Peter, "Breaking the Human-Robot Deadlock: Surpassing Shared Control Performance Limits with Sparse Human-Robot Interaction," Robotics: Science and Systems XIIII, pp. 1-10, Jul. 12, 2017.

Miksch et al., "Utilizing temporal data abstraction for data validation and therapy planning for artificially ventilated newborn infants," Artificial Intelligence in Medicine, vol. 8, No. 6, pp. 543-576 (1996).

Horn et al., "Effective data validation of high-frequency data: Time-point-time-interval-, and trend-based methods," Computers in Biology and Medic, New York, NY, vol. 27, No. 5, pp. 389-409 (1997).

Stacey et al., "Temporal abstraction in intelligent clinical data analysis: A survey," Artificial Intelligence in Medicine, vol. 39, No. 1, pp. 1-24 (2006).

Yang et al., "A dynamic stategy for packet scheduling and bandwidth allocation based on channel quality in IEEE 802.16e OFDMA system," Journal of Network and Computer Applications, vol. 39, pp. 52-60, May 2, 2013.

Hsiao-Wei Tang, "ARCM", Video, Sep. 2012, YouTube, 5 screenshots, Retrieved from internet: <https://www.youtube.com/watch?v=UldQaxb3fRw&feature=youtu.be>.

Giannios, et al., "Visible to near-infrared refractive properties of freshly-excised human-liver tissues: marking hepatic malignancies," Article, Jun. 14, 2016, pp. 1-10, Scientific Reports 6, Article No. 27910, Nature.

Vander Heiden, et al., "Understanding the Warburg effect: the metabolic requirements of cell proliferation," Article, May 22, 2009, pp. 1-12, vol. 324, Issue 5930, Science.

Hirayama et al., "Quantitative Metabolome Profiling of Colon and Stomach Cancer Microenvironment by Capillary Electrophoresis

(56) References Cited

OTHER PUBLICATIONS

Time-of-Flight Mass Spectrometry," Article, Jun. 2009, pp. 4918-4925, vol. 69, Issue 11, Cancer Research.
Cengiz, et al., "A Tale of Two Compartments: Interstitial Versus Blood Glucose Monitoring," Article, Jun. 2009, pp. S11-S16, vol. 11, Supplement 1, Diabetes Technology & Therapeutics.
Shen, et al., "An iridium nanoparticles dispersed carbon based thick film electrochemical biosensor and its application for a single use, disposable glucose biosensor," Article, Feb. 3, 2007, pp. 106-113, vol. 125, Issue 1, Sensors and Actuators B: Chemical, Science Direct.
IEEE Std No. 177, "Standard Definitions and Methods of Measurement for Piezoelectric Vibrators," published May 1966, The Institute of Electrical and Electronics Engineers, Inc., New York, N.Y.
CRC Press, "The Measurement, Instrumentation and Sensors Handbook," 1999, Section VII, Chapter 41, Peter O'Shea, "Phase Measurement," pp. 1303-1321, ISBN 0-8493-2145-X.
"ATM-MPLS Network Interworking Version 2.0, af-aic-0178.001" ATM Standard, The ATM Forum Technical Committee, published Aug. 2003.
IEEE Std 802.3-2012 (Revision of IEEE Std 802.3-2008, published Dec. 28, 2012.
Bonaci et al., "To Make a Robot Secure: An Experimental Analysis of Cyber Security Threats Against Teleoperated Surgical Robots," May 13, 2015. Retrieved from the Internet: URL:https://arxiv.org/pdf/1504.04339v2.pdf [retrieved on Aug. 24, 2019].
Homa Alemzadeh et al., "Targeted Attacks on Teleoperated Surgical Robots: Dynamic Model-Based Detection and Mitigation," 2016 46th Annual IEEE/IFIP International Conference on Dependable Systems and Networks (DSN), IEEE, Jun. 28, 2016, pp. 395-406.
Harold I. Brandon and V. Leroy Young, Mar. 1997, Surgical Services Management vol. 3 No. 3. retrieved from the internet <https://www.surgimedics.com/Research%20Articles/Electrosurgical%20Plume/Characterization%20And%20Removal%20Of%20Electrosurgical%20Smoke.pdf> (Year: 1997).
Marshall Brain, How Microcontrollers Work, 2006, retrieved from the internet <https://web.archive.org/web/20060221235221/http://electronics.howstuffworks.com/microcontroller.htm/printable> (Year: 2006).
Sorrells, P., "Application Note AN680. Passive RFID Basics," retrieved from http://ww1.microchip.com/downloads/en/AppNotes/00680b.pdf on Feb. 26, 2020, Dec. 31, 1998, pp. 1-7.
Staub et al., "Contour-based Surgical Instrument Tracking Supported by Kinematic Prediction," Proceedings of the 2010 3rd IEEE RAS & EMBS International Conference on Biomedical Robotics and Biomechatronics, Sep. 1, 2010, pp. 746-752.
Phumzile Malindi, "5. QoS in Telemedicine," "Telemedicine," Jun. 20, 2011, IntechOpen, pp. 119-138.
Allan et al., "3-D Pose Estimation of Articulated Instruments in Robotic Minimally Invasive Surgery," IEEE Transactions on Medical Imaging, vol. 37, No. 5, May 1, 2018, pp. 1204-1213.
Kassahun et al., "Surgical Robotics Beyond Enhanced Dexterity Instrumentation: A Survey of the Machine Learning Techniques and their Role in Intelligent and Autonomous Surgical Actions." International Journal of Computer Assisted Radiology and Surgery, vol. 11, No. 4, Oct. 8, 2015, pp. 553-568.
Weede et al. "An Intelligent and Autonomous Endoscopic Guidance System for Minimally Invasive Surgery," 2013 IEEE International Conference on Robotics ad Automation (ICRA), May 6-10, 2013. Karlsruhe, Germany, May 1, 2011, pp. 5762-5768.
Altenberg et al., "Genes of Glycolysis are Ubiquitously Overexpressed in 24 Cancer Classes," Genomics, vol. 84, pp. 1014-1020 (2004).
Jiang, "'Sound of Silence' : a secure indoor wireless ultrasonic communication system," Article, 2014, pp. 46-50, Snapshots of Doctoral Research at University College Cork, School of Engineering—Electrical & Electronic Engineering, UCC, Cork, Ireland.
Li, et al., "Short-range ultrasonic communications in air using quadrature modulation," Journal, Oct. 30, 2009, pp. 2060-2072, IEEE Transactions on Ultrasonics, Ferroelectrics, and Frequency Control, vol. 56, No. 10, IEEE.
Salamon, "AI Detects Polyps Better Than Colonoscopists" Online Article, Jun. 3, 2018, Medscape Medical News, Digestive Disease Week (DDW) 2018: Presentation 133.
Misawa, et al. "Artificial Intelligence-Assisted Polyp Detection for Colonoscopy: Initial Experience," Article, Jun. 2018, pp. 2027-2029, vol. 154, Issue 8, American Gastroenterolgy Association.
Dottorato, "Analysis and Design of the Rectangular Microstrip Patch Antennas for TM0n0 operating mode,"Article, Oct. 8, 2010, pp. 1-9, Microwave Journal.
Xie et al., Development of stereo vision and master-slave controller for a compact surgical robot system, 2015, IEEE, p. 403-407 (Year: 2015).
Sun et al., Innovative effector design for simulation training in robotic surgery, 2010, IEEE, p. 1755-1759 (Year: 2010).
Nabil Simaan et al, "Intelligent Surgical Robots with Situational Awareness: From Good to Great Surgeons", DOI: 10.1115/1.2015-Sep-6 external link, Sep. 2015 (Sep. 2015), p. 3-6, Retrieved from the Internet: URL:http://memagazineselect.asmedigitalcollection.asme.org/data/journals/meena/936888/me-2015-sep6.pdf XP055530863.
Nordlinger, Christopher, "The Internet of Things and the Operating Room of the Future," May 4, 2015, https://medium.com/@chrisnordlinger/the-internet-of-things-and-the-operating-room-of-the-future-8999a143d7b1, retrieved from the internet on Apr. 27, 2021, 9 pages.
Screen captures from YouTube video clip entitled "Four ways to use the Lego Brick Separator Tool," 2 pages, uploaded on May 29, 2014 by user "Sarah Lewis". Retrieved from internet: https://www.youtube.com/watch?v=ucKiRD6U1LU (Year: 2014).
Anonymous, "Internet of Things Powers Connected Surgical Device Infrastructure Case Study", Dec. 31, 2016 (Dec. 31, 2016), Retrieved from the Internet: URL:https://www.cognizant.com/services-resources/150110_IoT_connected_surgical_devices.pdf.
Roy D Cullum, "Handbook of Engineering Design", ISBN: 9780408005586, Jan. 1, 1988 (Jan. 1, 1988), XP055578597, ISBN: 9780408005586, 10-20, Chapter 6, p. 138, right-hand column, paragraph 3.
Draijer, Matthijs et al., "Review of laser speckle contrast techniques for visualizing tissue perfusion," Lasers in Medical Science, Springer-Verlag, LO, vol. 24, No. 4, Dec. 3, 2008, pp. 639-651.
Anonymous: "Screwdriver—Wikipedia", en.wikipedia.org, Jun. 23, 2019, XP055725151, Retrieved from the Internet: URL:https://en.wikipedia.org/w/index.php?title=Screwdriver&oldid=903111203 [retrieved on Mar. 20, 2021].
Takahashi et al., "Automatic smoke evacuation in laparoscopic surgery: a simplified method for objective evaluation," Surgical Endoscopy, vol. 27, No. 8, pp. 2980-2987, Feb. 23, 2013.
Lalys, et al., "Automatic knowledge-based recognition of low-level tasks in ophthalmological procedures", Int J CARS, vol. 8, No. 1, pp. 1-49, Apr. 19, 2012.
"Principles of Video Contact Angle Analysis", Ast Products, Inc., 2006, 20 pages.
"Technology Overview", Retrieved From www.harmonicscalpel.com, Jun. 13, 2007, 3 pages.
Campbell et al., "Thermal Imaging in Surgery", Chapter 27, Medical Infrared Imaging, 2008, 3.
Duck, "Optical Properties of Tissue including Ultraviolet and Infrared Radiation", Physical Properties of Tissues, Chapter 3, 1990, pp. 43-71.
Huston et al., "Magnetic and magnetostrictive properties of cube textured nickel for magnetostrictive transducer applications", IEEE Transactions on Magnetics, vol. 9, No. 4, Dec. 1973, pp. 636-640.
Lim et al., "A review of mechanism used in laparoscopic surgical instruments", Mechanism and Machine Theory, vol. 38, No. 11, Nov. 2003, pp. 1133-1147.
Orr et al., "Overview of Bioheat Transfer", Optical-Thermal Response of Laser-Irradiated Tissue, vol. 11, 1995, pp. 367-384.
Extended European Search Report received for EP Application No. 21185280.1 mailed on Jan. 20, 2022, 10 pages.
International Preliminary Report on Patentability received for PCT Application No. PCT/US2010/041663 mailed on Jan. 17, 2012, 8 pages.

(56) References Cited

OTHER PUBLICATIONS

International Search Report and Written Opinion received for PCT Application No. PCT/US2010/041663 mailed on Feb. 17, 2011, 15 pages.
International Search Report and Written Opinion received for PCT Application No. PCT/US2018/060980 mailed on Mar. 8, 2019, 17 pages.
International Search Report and Written Opinion received for PCT Application No. PCT/US2018/060981 mailed on Feb. 20, 2019, 16 pages.
Gooch, et al., "Recommended Infection-Control Practices for Dentistry", Retrieved from the URL <http//wonder.cdc.gov/wonder/prevguid/p0000191/p0000191.asp>, May 28, 1993, 20 pages.
Incropera et al., "Fundamentals of Heat and Mass Transfer", John Wiley & Sons, 6th Edition, 2007, 1070 pages.
Sherrit et al., "Novel Horn Designs for Ultrasonic/sonic Cleaning Welding, Soldering, Cutting and Drilling", Proceedings SPIE Smart Structures Conference, vol. 4701, No. 34, Jul. 2002, pp. 353-360.

* cited by examiner 300
314
CLK
OSC/PLL
MUX
1
0
330
Serial EEPROM Interface
310
326
SIE
Hub/Device Command Decoder
312
Hub Power Logic
302
DM0
DP0
USB Transceiver
316
Suspend/Resume Logic and Frame Timer
328
SIE Interface Logic
324
Port 3 Logic
322
Port 2 Logic
304
USB Transceiver
DM1
DP1
306
USB Transceiver
DM2
DP2
Port 1 Logic
320
USB Transceiver
DM3
DP3
308
Hub Repeater
318

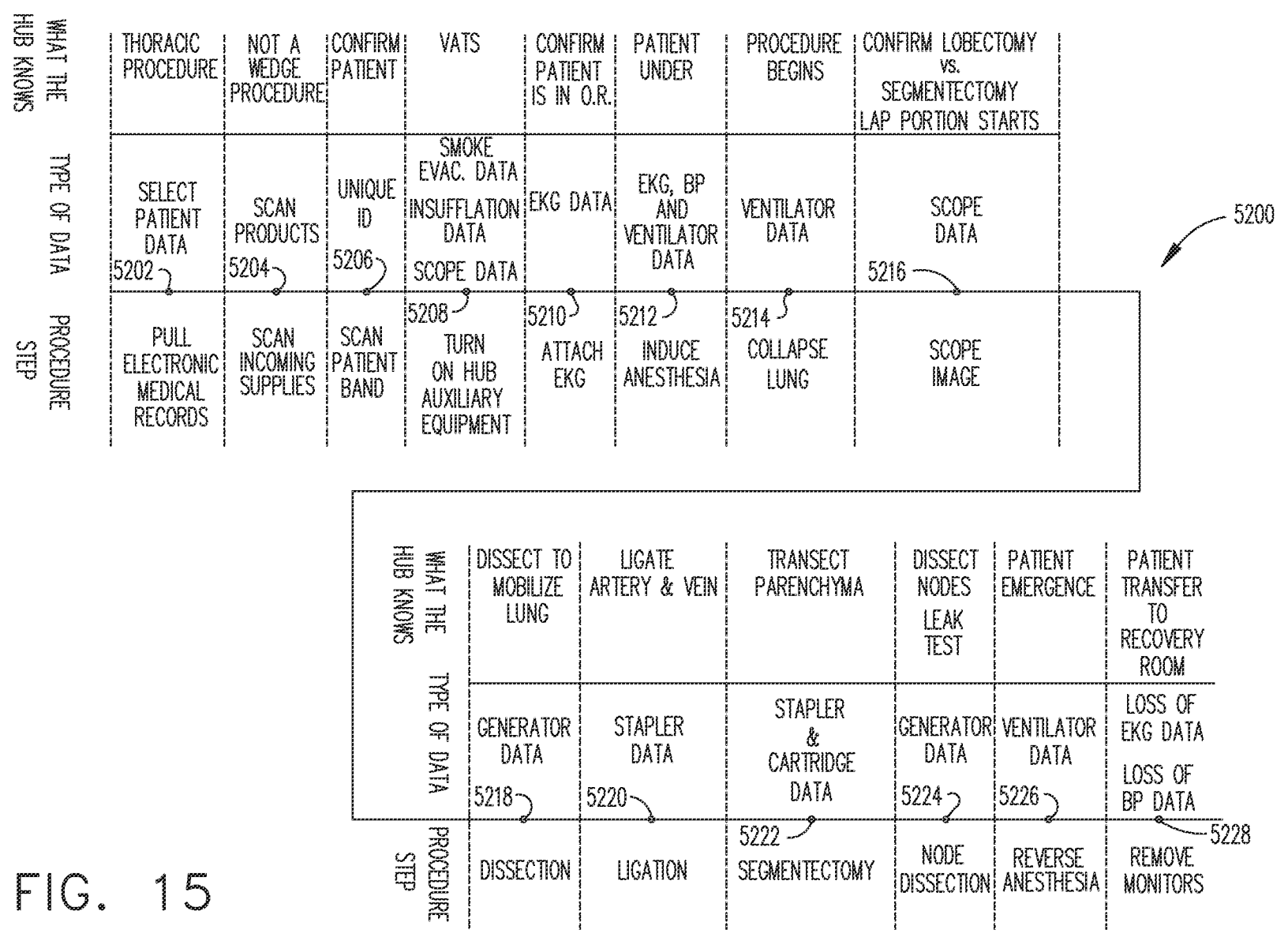

5200

| WHAT THE HUB KNOWS | THORACIC PROCEDURE | NOT A WEDGE PROCEDURE | CONFIRM PATIENT | VATS | CONFIRM PATIENT IS IN O.R. | PATIENT UNDER | PROCEDURE BEGINS | CONFIRM LOBECTOMY vs. SEGMENTECTOMY LAP PORTION STARTS |
| --- | --- | --- | --- | --- | --- | --- | --- | --- |
| TYPE OF DATA | SELECT PATIENT DATA | SCAN PRODUCTS | UNIQUE ID | SMOKE EVAC. DATA<br>INSUFFLATION DATA<br>SCOPE DATA | EKG DATA | EKG, BP AND VENTILATOR DATA | VENTILATOR DATA | SCOPE DATA |
| PROCEDURE STEP | 5202 PULL ELECTRONIC MEDICAL RECORDS | 5204 SCAN INCOMING SUPPLIES | 5206 SCAN PATIENT BAND | 5208 TURN ON HUB AUXILIARY EQUIPMENT | 5210 ATTACH EKG | 5212 INDUCE ANESTHESIA | 5214 COLLAPSE LUNG | 5216 SCOPE IMAGE |

| WHAT THE HUB KNOWS | DISSECT TO MOBILIZE LUNG | LIGATE ARTERY & VEIN | TRANSECT PARENCHYMA | DISSECT NODES<br>LEAK TEST | PATIENT EMERGENCE | PATIENT TRANSFER TO RECOVERY ROOM |
| --- | --- | --- | --- | --- | --- | --- |
| TYPE OF DATA | GENERATOR DATA | STAPLER DATA | STAPLER & CARTRIDGE DATA | GENERATOR DATA | VENTILATOR DATA | LOSS OF EKG DATA<br>LOSS OF BP DATA |
| PROCEDURE STEP | 5218 DISSECTION | 5220 LIGATION | 5222 SEGMENTECTOMY | 5224 NODE DISSECTION | 5226 REVERSE ANESTHESIA | 5228 REMOVE MONITORS |

FIG. 15

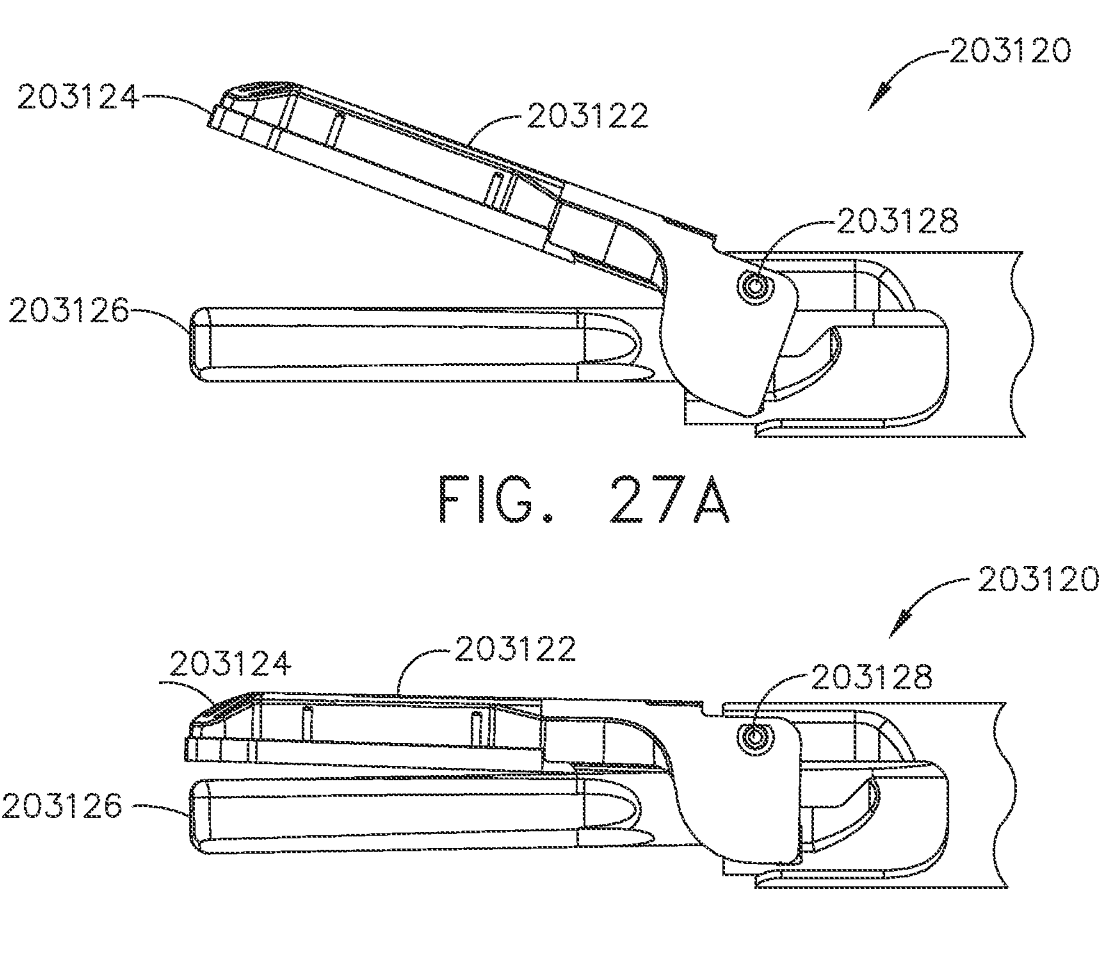
FIG. 27A
FIG. 27B
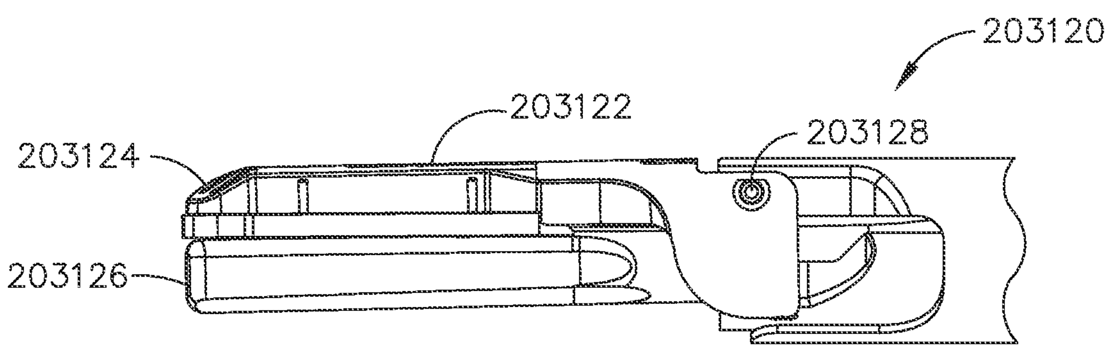
FIG. 27C 203220
203222
203224
203226
203228
203230

203300
203314
203384
203312
203302
203308
203388
203310

203352
203358
203372
203392
203412
203356
203376
230396
203416
203340
203348
203342
203344
203346
203350

ULTRASONIC ENERGY DEVICE WHICH VARIES PRESSURE APPLIED BY CLAMP ARM TO PROVIDE THRESHOLD CONTROL PRESSURE AT A CUT PROGRESSION LOCATION

CROSS-REFERENCE TO RELATED APPLICATIONS

This application is a continuation application claiming priority under 35 U.S.C. § 120 to U.S. patent application Ser. No. 16/182,238, titled ULTRASONIC ENERGY DEVICE WHICH VARIES PRESSURE APPLIED BY CLAMP ARM TO PROVIDE THRESHOLD CONTROL PRESSURE AT A CUT PROGRESSION LOCATION, filed Nov. 6, 2018, now U.S. Patent Application Publication No. 2019/0201080, which claims priority under 35 U.S.C. § 119(e) to U.S. Provisional Patent Application Ser. No. 62/729,195, titled ULTRASONIC ENERGY DEVICE WHICH VARIES PRESSURE APPLIED BY CLAMP ARM TO PROVIDE THRESHOLD CONTROL PRESSURE AT A CUT PROGRESSION LOCATION, filed on Sep. 10, 2018, the disclosure of each of which is herein incorporated by reference in its entirety.

This application is a continuation application claiming priority under 35 U.S.C. § 120 to U.S. patent application Ser. No. 16/182,238, titled ULTRASONIC ENERGY DEVICE WHICH VARIES PRESSURE APPLIED BY CLAMP ARM TO PROVIDE THRESHOLD CONTROL PRESSURE AT A CUT PROGRESSION LOCATION, filed Nov. 6, 2018, now U.S. Patent Application Publication No. 2019/0201080, which also claims priority under 35 U.S.C. § 119(e) to U.S. Provisional Patent Application Ser. No. 62/692,747, titled SMART ACTIVATION OF AN ENERGY DEVICE BY ANOTHER DEVICE, filed on Jun. 30, 2018, to U.S. Provisional Patent Application Ser. No. 62/692,748, titled SMART ENERGY ARCHITECTURE, filed on Jun. 30, 2018, and to U.S. Provisional Patent Application Ser. No. 62/692,768, titled SMART ENERGY DEVICES, filed on Jun. 30, 2018, the disclosure of each of which is herein incorporated by reference in its entirety.

This application is a continuation application claiming priority under 35 U.S.C. § 120 to U.S. patent application Ser. No. 16/182,238, titled ULTRASONIC ENERGY DEVICE WHICH VARIES PRESSURE APPLIED BY CLAMP ARM TO PROVIDE THRESHOLD CONTROL PRESSURE AT A CUT PROGRESSION LOCATION, filed Nov. 6, 2018, now U.S. Patent Application Publication No. 2019/0201080, which also claims priority under 35 U.S.C. § 119(e) to U.S. Provisional Patent Application Ser. No. 62/659,900, titled METHOD OF HUB COMMUNICATION, filed on Apr. 19, 2018, the disclosure of which is herein incorporated by reference in its entirety.

This application is a continuation application claiming priority under 35 U.S.C. § 120 to U.S. patent application Ser. No. 16/182,238, titled ULTRASONIC ENERGY DEVICE WHICH VARIES PRESSURE APPLIED BY CLAMP ARM TO PROVIDE THRESHOLD CONTROL PRESSURE AT A CUT PROGRESSION LOCATION, filed Nov. 6, 2018, now U.S. Patent Application Publication No. 2019/0201080, which also claims priority under 35 U.S.C. § 119(e) to U.S. Provisional Patent Application Ser. No. 62/650,898 filed on Mar. 30, 2018, titled CAPACITIVE COUPLED RETURN PATH PAD WITH SEPARABLE ARRAY ELEMENTS, to U.S. Provisional Patent Application Ser. No. 62/650,887, titled SURGICAL SYSTEMS WITH OPTIMIZED SENSING CAPABILITIES, filed Mar. 30, 2018, to U.S. Provisional Patent Application Ser. No. 62/650,882, titled SMOKE EVACUATION MODULE FOR INTERACTIVE SURGICAL PLATFORM, filed Mar. 30, 2018, and to U.S. Provisional Patent Application Ser. No. 62/650,877, titled SURGICAL SMOKE EVACUATION SENSING AND CONTROLS, filed Mar. 30, 2018, the disclosure of each of which is herein incorporated by reference in its entirety.

This application is a continuation application claiming priority under 35 U.S.C. § 120 to U.S. patent application Ser. No. 16/182,238, titled ULTRASONIC ENERGY DEVICE WHICH VARIES PRESSURE APPLIED BY CLAMP ARM TO PROVIDE THRESHOLD CONTROL PRESSURE AT A CUT PROGRESSION LOCATION, filed Nov. 6, 2018, now U.S. Patent Application Publication No. 2019/0201080, which also claims priority under 35 U.S.C. § 119(e) to U.S. Provisional Patent Application Ser. No. 62/640,417, titled TEMPERATURE CONTROL IN ULTRASONIC DEVICE AND CONTROL SYSTEM THEREFOR, filed Mar. 8, 2018, and to U.S. Provisional Patent Application Ser. No. 62/640,415, titled ESTIMATING STATE OF ULTRASONIC END EFFECTOR AND CONTROL SYSTEM THEREFOR, filed Mar. 8, 2018, the disclosure of each of which is herein incorporated by reference in its entirety.

This application is a continuation application claiming priority under 35 U.S.C. § 120 to U.S. patent application Ser. No. 16/182,238, titled ULTRASONIC ENERGY DEVICE WHICH VARIES PRESSURE APPLIED BY CLAMP ARM TO PROVIDE THRESHOLD CONTROL PRESSURE AT A CUT PROGRESSION LOCATION, filed Nov. 6, 2018, now U.S. Patent Application Publication No. 2019/0201080, which also claims priority under 35 U.S.C. § 119(e) to U.S. Provisional Patent Application Ser. No. 62/611,341, titled INTERACTIVE SURGICAL PLATFORM, filed Dec. 28, 2017, to U.S. Provisional Patent Application Ser. No. 62/611,340, titled CLOUD-BASED MEDICAL ANALYTICS, filed Dec. 28, 2017, and to U.S. Provisional Patent Application Ser. No. 62/611,339, titled ROBOT ASSISTED SURGICAL PLATFORM, filed Dec. 28, 2017, the disclosure of each of which is herein incorporated by reference in its entirety.

BACKGROUND

The present disclosure relates to various surgical systems. Surgical procedures are typically performed in surgical operating theaters or rooms in a healthcare facility such as, for example, a hospital. A sterile field is typically created around the patient. The sterile field may include the scrubbed team members, who are properly attired, and all furniture and fixtures in the area. Various surgical devices and systems are utilized in performance of a surgical procedure.

FIGURES

The various aspects described herein, both as to organization and methods of operation, together with further objects and advantages thereof, may best be understood by reference to the following description, taken in conjunction with the accompanying drawings as follows.

FIG. 15 is a timeline depicting situational awareness of a surgical hub, in accordance with at least one aspect of the present disclosure.

FIGS. 27A-27C are sectional views of end effector that illustrate a closure stroke of the end effector, in accordance with at least one aspect of the present disclosure.

DESCRIPTION

Figure 1:
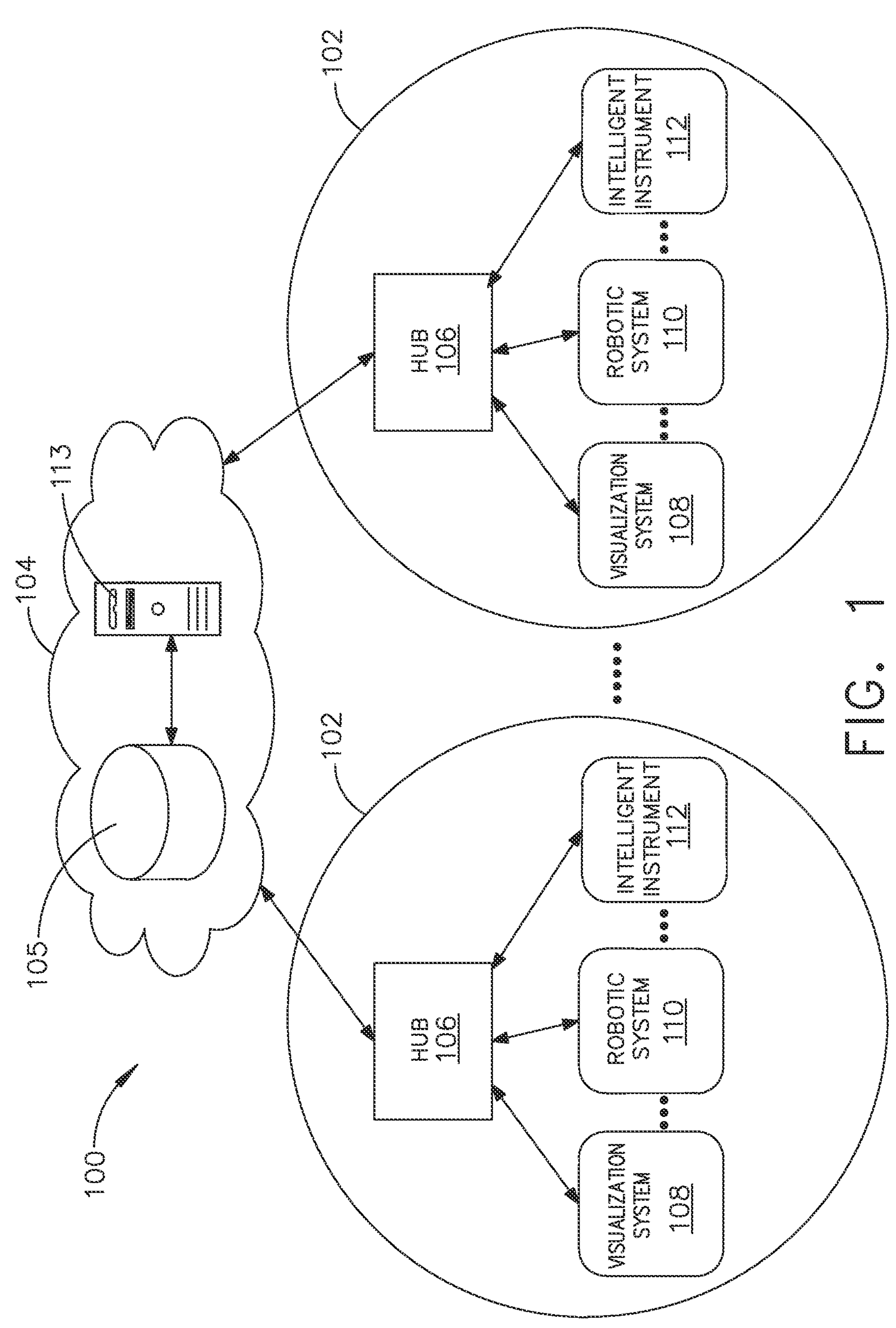
FIG. 1 is a block diagram of a computer-implemented interactive surgical system, in accordance with at least one aspect of the present disclosure.

Applicant of the present application owns the following U.S. patent applications, filed on Nov. 6, 2018, the disclosure of each of which is herein incorporated by reference in its entirety:

- U.S. patent application Ser. No. 16/182,224, titled SURGICAL NETWORK, INSTRUMENT, AND CLOUD RESPONSES BASED ON VALIDATION OF RECEIVED DATASET AND AUTHENTICATION OF ITS SOURCE AND INTEGRITY, now U.S. Pat. No. 11,308,075;
- U.S. patent application Ser. No. 16/182,230, titled SURGICAL SYSTEM FOR PRESENTING INFORMATION INTERPRETED FROM EXTERNAL DATA, now U.S. Patent Application Publication No. 2019/0200980;

U.S. patent application Ser. No. 16/182,233, titled MODIFICATION OF SURGICAL SYSTEMS CONTROL PROGRAMS BASED ON MACHINE LEARNING, now U.S. Patent Application Publication No. 2019/0201123;

U.S. patent application Ser. No. 16/182,239, titled ADJUSTMENT OF DEVICE CONTROL PROGRAMS BASED ON STRATIFIED CONTEXTUAL DATA IN ADDITION TO THE DATA, now U.S. Patent Application Publication No. 2019/0201124;

U.S. patent application Ser. No. 16/182,243, titled SURGICAL HUB AND MODULAR DEVICE RESPONSE ADJUSTMENT BASED ON SITUATIONAL AWARENESS, now U.S. Pat. No. 11,273,001;

U.S. patent application Ser. No. 16/182,248, titled DETECTION AND ESCALATION OF SECURITY RESPONSES OF SURGICAL INSTRUMENTS TO INCREASING SEVERITY THREATS, now U.S. Pat. No. 10,943,454;

U.S. patent application Ser. No. 16/182,251, titled INTERACTIVE SURGICAL SYSTEM, now U.S. Pat. No. 11,278,281;

U.S. patent application Ser. No. 16/182,260, titled AUTOMATED DATA SCALING, ALIGNMENT, AND ORGANIZING BASED ON PREDEFINED PARAMETERS WITHIN SURGICAL NETWORKS, now U.S. Pat. No. 11,056,244;

U.S. patent application Ser. No. 16/182,267, titled SENSING THE PATIENT POSITION AND CONTACT UTILIZING THE MONO-POLAR RETURN PAD ELECTRODE TO PROVIDE SITUATIONAL AWARENESS TO A SURGICAL NETWORK, now U.S. Patent Application Publication No. 2019/0201128;

U.S. patent application Ser. No. 16/182,249, titled POWERED SURGICAL TOOL WITH PREDEFINED ADJUSTABLE CONTROL ALGORITHM FOR CONTROLLING END EFFECTOR PARAMETER, now U.S. Pat. No. 11,234,756;

U.S. patent application Ser. No. 16/182,246, titled ADJUSTMENTS BASED ON AIRBORNE PARTICLE PROPERTIES, now U.S. Patent Application Publication No. 2019/0204201;

U.S. patent application Ser. No. 16/182,256, titled ADJUSTMENT OF A SURGICAL DEVICE FUNCTION BASED ON SITUATIONAL AWARENESS, now U.S. Patent Application Publication No. 2019/0201127;

U.S. patent application Ser. No. 16/182,242, titled REAL-TIME ANALYSIS OF COMPREHENSIVE COST OF ALL INSTRUMENTATION USED IN SURGERY UTILIZING DATA FLUIDITY TO TRACK INSTRUMENTS THROUGH STOCKING AND IN-HOUSE PROCESSES, now U.S. Pat. No. 11,257,589;

U.S. patent application Ser. No. 16/182,255, titled USAGE AND TECHNIQUE ANALYSIS OF SURGEON/STAFF PERFORMANCE AGAINST A BASELINE TO OPTIMIZE DEVICE UTILIZATION AND PERFORMANCE FOR BOTH CURRENT AND FUTURE PROCEDURES, now U.S. Patent Application Publication No. 2019/0201126;

U.S. patent application Ser. No. 16/182,269, titled IMAGE CAPTURING OF THE AREAS OUTSIDE THE ABDOMEN TO IMPROVE PLACEMENT AND CONTROL OF A SURGICAL DEVICE IN USE, now U.S. Pat. No. 11,304,763;

U.S. patent application Ser. No. 16/182,278, titled COMMUNICATION OF DATA WHERE A SURGICAL NETWORK IS USING CONTEXT OF THE DATA AND REQUIREMENTS OF A RECEIVING SYSTEM/USER TO INFLUENCE INCLUSION OR LINKAGE OF DATA AND METADATA TO ESTABLISH CONTINUITY, now U.S. Patent Application Publication No. 2019/0201130;

U.S. patent application Ser. No. 16/182,290, titled SURGICAL NETWORK RECOMMENDATIONS FROM REAL TIME ANALYSIS OF PROCEDURE VARIABLES AGAINST A BASELINE HIGHLIGHTING DIFFERENCES FROM THE OPTIMAL SOLUTION, now U.S. Patent Application Publication No. 2019/0201102;

U.S. patent application Ser. No. 16/182,232, titled CONTROL OF A SURGICAL SYSTEM THROUGH A SURGICAL BARRIER, now U.S. Patent Application Publication No. 2019/0201158;

U.S. patent application Ser. No. 16/182,227, titled SURGICAL NETWORK DETERMINATION OF PRIORITIZATION OF COMMUNICATION, INTERACTION, OR PROCESSING BASED ON SYSTEM OR DEVICE NEEDS, now U.S. Pat. No. 10,892,995;

U.S. patent application Ser. No. 16/182,231, titled WIRELESS PAIRING OF A SURGICAL DEVICE WITH ANOTHER DEVICE WITHIN A STERILE SURGICAL FIELD BASED ON THE USAGE AND SITUATIONAL AWARENESS OF DEVICES, now U.S. Pat. No. 10,758,310

U.S. patent application Ser. No. 16/182,229, titled ADJUSTMENT OF STAPLE HEIGHT OF AT LEAST ONE ROW OF STAPLES BASED ON THE SENSED TISSUE THICKNESS OR FORCE IN CLOSING, now U.S. Pat. No. 11,096,693;

U.S. patent application Ser. No. 16/182,234, titled STAPLING DEVICE WITH BOTH COMPULSORY AND DISCRETIONARY LOCKOUTS BASED ON SENSED PARAMETERS, now U.S. Patent Application Publication No. 2019/0200997;

U.S. patent application Ser. No. 16/182,240, titled POWERED STAPLING DEVICE CONFIGURED TO ADJUST FORCE, ADVANCEMENT SPEED, AND OVERALL STROKE OF CUTTING MEMBER BASED ON SENSED PARAMETER OF FIRING OR CLAMPING, now U.S. Patent Application Publication No. 2019/0201034; and U.S. patent application Ser. No. 16/182,235, titled VARIATION OF RADIO FREQUENCY AND ULTRASONIC POWER LEVEL IN COOPERATION WITH VARYING CLAMP ARM PRESSURE TO ACHIEVE PREDEFINED HEAT FLUX OR POWER APPLIED TO TISSUE, now U.S. Patent Application Publication No. 2019/0201044.

Applicant of the present application owns the following U.S. patent applications, filed on Sep. 10, 2018, the disclosure of each of which is herein incorporated by reference in its entirety:

U.S. Provisional Patent Application Ser. No. 62/729,183, titled A CONTROL FOR A SURGICAL NETWORK OR SURGICAL NETWORK CONNECTED DEVICE THAT ADJUSTS ITS FUNCTION BASED ON A SENSED SITUATION OR USAGE;

U.S. Provisional Patent Application Ser. No. 62/729,177, titled AUTOMATED DATA SCALING, ALIGNMENT, AND ORGANIZING BASED ON PREDEFINED PARAMETERS WITHIN A SURGICAL NETWORK BEFORE TRANSMISSION;

U.S. Provisional Patent Application Ser. No. 62/729,176, titled INDIRECT COMMAND AND CONTROL OF A FIRST OPERATING ROOM SYSTEM THROUGH THE USE OF A SECOND OPERATING ROOM SYSTEM WITHIN A STERILE FIELD WHERE THE SECOND OPERATING ROOM SYSTEM HAS PRIMARY AND SECONDARY OPERATING MODES;

U.S. Provisional Patent Application Ser. No. 62/729,185, titled POWERED STAPLING DEVICE THAT IS CAPABLE OF ADJUSTING FORCE, ADVANCEMENT SPEED, AND OVERALL STROKE OF CUTTING MEMBER OF THE DEVICE BASED ON SENSED PARAMETER OF FIRING OR CLAMPING;

U.S. Provisional Patent Application Ser. No. 62/729,184, titled POWERED SURGICAL TOOL WITH A PREDEFINED ADJUSTABLE CONTROL ALGORITHM FOR CONTROLLING AT LEAST ONE END EFFECTOR PARAMETER AND A MEANS FOR LIMITING THE ADJUSTMENT;

U.S. Provisional Patent Application Ser. No. 62/729,182, titled SENSING THE PATIENT POSITION AND CONTACT UTILIZING THE MONO POLAR RETURN PAD ELECTRODE TO PROVIDE SITUATIONAL AWARENESS TO THE HUB;

U.S. Provisional Patent Application Ser. No. 62/729,191, titled SURGICAL NETWORK RECOMMENDATIONS FROM REAL TIME ANALYSIS OF PROCEDURE VARIABLES AGAINST A BASELINE HIGHLIGHTING DIFFERENCES FROM THE OPTIMAL SOLUTION;

U.S. Provisional Patent Application Ser. No. 62/729,195, titled ULTRASONIC ENERGY DEVICE WHICH VARIES PRESSURE APPLIED BY CLAMP ARM TO PROVIDE THRESHOLD CONTROL PRESSURE AT A CUT PROGRESSION LOCATION; and U.S. Provisional Patent Application Ser. No. 62/729,186, titled WIRELESS PAIRING OF A SURGICAL DEVICE WITH ANOTHER DEVICE WITHIN A STERILE SURGICAL FIELD BASED ON THE USAGE AND SITUATIONAL AWARENESS OF DEVICES.

Applicant of the present application owns the following U.S. patent applications, filed on Aug. 28, 2018, the disclosure of each of which is herein incorporated by reference in its entirety:

U.S. patent application Ser. No. 16/115,214, titled ESTIMATING STATE OF ULTRASONIC END EFFECTOR AND CONTROL SYSTEM THEREFOR;

U.S. patent application Ser. No. 16/115,205, titled TEMPERATURE CONTROL OF ULTRASONIC END EFFECTOR AND CONTROL SYSTEM THEREFOR;

U.S. patent application Ser. No. 16/115,233, titled RADIO FREQUENCY ENERGY DEVICE FOR DELIVERING COMBINED ELECTRICAL SIGNALS;

U.S. patent application Ser. No. 16/115,208, titled CONTROLLING AN ULTRASONIC SURGICAL INSTRUMENT ACCORDING TO TISSUE LOCATION;

U.S. patent application Ser. No. 16/115,220, titled CONTROLLING ACTIVATION OF AN ULTRASONIC SURGICAL INSTRUMENT ACCORDING TO THE PRESENCE OF TISSUE;

U.S. patent application Ser. No. 16/115,232, titled DETERMINING TISSUE COMPOSITION VIA AN ULTRASONIC SYSTEM;

U.S. patent application Ser. No. 16/115,239, titled DETERMINING THE STATE OF AN ULTRASONIC ELECTROMECHANICAL SYSTEM ACCORDING TO FREQUENCY SHIFT;

U.S. patent application Ser. No. 16/115,247, titled DETERMINING THE STATE OF AN ULTRASONIC END EFFECTOR;

U.S. patent application Ser. No. 16/115,211, titled SITUATIONAL AWARENESS OF ELECTROSURGICAL SYSTEMS;

U.S. patent application Ser. No. 16/115,226, titled MECHANISMS FOR CONTROLLING DIFFERENT ELECTROMECHANICAL SYSTEMS OF AN ELECTROSURGICAL INSTRUMENT;

U.S. patent application Ser. No. 16/115,240, titled DETECTION OF END EFFECTOR IMMERSION IN LIQUID;

U.S. patent application Ser. No. 16/115,249, titled INTERRUPTION OF ENERGY DUE TO INADVERTENT CAPACITIVE COUPLING;

U.S. patent application Ser. No. 16/115,256, titled INCREASING RADIO FREQUENCY TO CREATE PAD-LESS MONOPOLAR LOOP;

U.S. patent application Ser. No. 16/115,223, titled BIPOLAR COMBINATION DEVICE THAT AUTOMATICALLY ADJUSTS PRESSURE BASED ON ENERGY MODALITY; and U.S. patent application Ser. No. 16/115,238, titled ACTIVATION OF ENERGY DEVICES.

Applicant of the present application owns the following U.S. patent applications, filed on Aug. 23, 2018, the disclosure of each of which is herein incorporated by reference in its entirety:

U.S. Provisional Patent Application Ser. No. 62/721,995, titled CONTROLLING AN ULTRASONIC SURGICAL INSTRUMENT ACCORDING TO TISSUE LOCATION; U.S. Provisional Patent Application Ser. No. 62/721,998, titled SITUATIONAL AWARENESS OF ELECTROSURGICAL SYSTEMS;

U.S. Provisional Patent Application Ser. No. 62/721,999, titled INTERRUPTION OF ENERGY DUE TO INADVERTENT CAPACITIVE COUPLING;

U.S. Provisional Patent Application Ser. No. 62/721,994, titled BIPOLAR COMBINATION DEVICE THAT AUTOMATICALLY ADJUSTS PRESSURE BASED ON ENERGY MODALITY; and U.S. Provisional Patent Application Ser. No. 62/721,996, titled RADIO FREQUENCY ENERGY DEVICE FOR DELIVERING COMBINED ELECTRICAL SIGNALS.

Applicant of the present application owns the following U.S. patent applications, filed on Jun. 30, 2018, the disclosure of each of which is herein incorporated by reference in its entirety:

U.S. Provisional Patent Application Ser. No. 62/692,747, titled SMART ACTIVATION OF AN ENERGY DEVICE BY ANOTHER DEVICE;

U.S. Provisional Patent Application Ser. No. 62/692,748, titled SMART ENERGY ARCHITECTURE; and U.S. Provisional Patent Application Ser. No. 62/692,768, titled SMART ENERGY DEVICES.

Applicant of the present application owns the following U.S. patent applications, filed on Jun. 29, 2018, the disclosure of each of which is herein incorporated by reference in its entirety:

U.S. patent application Ser. No. 16/024,090, titled CAPACITIVE COUPLED RETURN PATH PAD WITH SEPARABLE ARRAY ELEMENTS;

U.S. patent application Ser. No. 16/024,057, titled CONTROLLING A SURGICAL INSTRUMENT ACCORDING TO SENSED CLOSURE PARAMETERS;

U.S. patent application Ser. No. 16/024,067, titled SYSTEMS FOR ADJUSTING END EFFECTOR PARAMETERS BASED ON PERIOPERATIVE INFORMATION;

U.S. patent application Ser. No. 16/024,075, titled SAFETY SYSTEMS FOR SMART POWERED SURGICAL STAPLING;

U.S. patent application Ser. No. 16/024,083, titled SAFETY SYSTEMS FOR SMART POWERED SURGICAL STAPLING;

U.S. patent application Ser. No. 16/024,094, titled SURGICAL SYSTEMS FOR DETECTING END EFFECTOR TISSUE DISTRIBUTION IRREGULARITIES;

U.S. patent application Ser. No. 16/024,138, titled SYSTEMS FOR DETECTING PROXIMITY OF SURGICAL END EFFECTOR TO CANCEROUS TISSUE;

U.S. patent application Ser. No. 16/024,150, titled SURGICAL INSTRUMENT CARTRIDGE SENSOR ASSEMBLIES;

U.S. patent application Ser. No. 16/024,160, titled VARIABLE OUTPUT CARTRIDGE SENSOR ASSEMBLY;

U.S. patent application Ser. No. 16/024,124, titled SURGICAL INSTRUMENT HAVING A FLEXIBLE ELECTRODE;

U.S. patent application Ser. No. 16/024,132, titled SURGICAL INSTRUMENT HAVING A FLEXIBLE CIRCUIT;

U.S. patent application Ser. No. 16/024,141, titled SURGICAL INSTRUMENT WITH A TISSUE MARKING ASSEMBLY;

U.S. patent application Ser. No. 16/024,162, titled SURGICAL SYSTEMS WITH PRIORITIZED DATA TRANSMISSION CAPABILITIES;

U.S. patent application Ser. No. 16/024,066, titled SURGICAL EVACUATION SENSING AND MOTOR CONTROL;

U.S. patent application Ser. No. 16/024,096, titled SURGICAL EVACUATION SENSOR ARRANGEMENTS;

U.S. patent application Ser. No. 16/024,116, titled SURGICAL EVACUATION FLOW PATHS;

U.S. patent application Ser. No. 16/024,149, titled SURGICAL EVACUATION SENSING AND GENERATOR CONTROL;

U.S. patent application Ser. No. 16/024,180, titled SURGICAL EVACUATION SENSING AND DISPLAY;

U.S. patent application Ser. No. 16/024,245, titled COMMUNICATION OF SMOKE EVACUATION SYSTEM PARAMETERS TO HUB OR CLOUD IN SMOKE EVACUATION MODULE FOR INTERACTIVE SURGICAL PLATFORM;

U.S. patent application Ser. No. 16/024,258, titled SMOKE EVACUATION SYSTEM INCLUDING A SEGMENTED CONTROL CIRCUIT FOR INTERACTIVE SURGICAL PLATFORM;

U.S. patent application Ser. No. 16/024,265, titled SURGICAL EVACUATION SYSTEM WITH A COMMUNICATION CIRCUIT FOR COMMUNICATION BETWEEN A FILTER AND A SMOKE EVACUATION DEVICE; and U.S. patent application Ser. No. 16/024,273, titled DUAL IN-SERIES LARGE AND SMALL DROPLET FILTERS.

Applicant of the present application owns the following U.S. Provisional Patent Applications, filed on Jun. 28, 2018, the disclosure of each of which is herein incorporated by reference in its entirety:

U.S. Provisional Patent Application Ser. No. 62/691,228, titled A METHOD OF USING REINFORCED FLEX CIRCUITS WITH MULTIPLE SENSORS WITH ELECTROSURGICAL DEVICES;

U.S. Provisional Patent Application Ser. No. 62/691,227, titled CONTROLLING A SURGICAL INSTRUMENT ACCORDING TO SENSED CLOSURE PARAMETERS;

U.S. Provisional Patent Application Ser. No. 62/691,230, titled SURGICAL INSTRUMENT HAVING A FLEXIBLE ELECTRODE;

U.S. Provisional Patent Application Ser. No. 62/691,219, titled SURGICAL EVACUATION SENSING AND MOTOR CONTROL;

U.S. Provisional Patent Application Ser. No. 62/691,257, titled COMMUNICATION OF SMOKE EVACUATION SYSTEM PARAMETERS TO HUB OR CLOUD IN SMOKE EVACUATION MODULE FOR INTERACTIVE SURGICAL PLATFORM;

U.S. Provisional Patent Application Ser. No. 62/691,262, titled SURGICAL EVACUATION SYSTEM WITH A COMMUNICATION CIRCUIT FOR COMMUNICATION BETWEEN A FILTER AND A SMOKE EVACUATION DEVICE; and U.S. Provisional Patent Application Ser. No. 62/691,251, titled DUAL IN-SERIES LARGE AND SMALL DROPLET FILTERS.

Applicant of the present application owns the following U.S. Provisional Patent Application, filed on Apr. 19, 2018, the disclosure of which is herein incorporated by reference in its entirety:

U.S. Provisional Patent Application Ser. No. 62/659,900, titled METHOD OF HUB COMMUNICATION.

Applicant of the present application owns the following U.S. Provisional Patent Applications, filed on Mar. 30, 2018, the disclosure of each of which is herein incorporated by reference in its entirety:

U.S. Provisional Patent Application Ser. No. 62/650,898 filed on Mar. 30, 2018, titled CAPACITIVE COUPLED RETURN PATH PAD WITH SEPARABLE ARRAY ELEMENTS;

U.S. Provisional Patent Application Ser. No. 62/650,887, titled SURGICAL SYSTEMS WITH OPTIMIZED SENSING CAPABILITIES;

U.S. Provisional Patent Application Ser. No. 62/650,882, titled SMOKE EVACUATION MODULE FOR INTERACTIVE SURGICAL PLATFORM; and U.S. Provisional Patent Application Ser. No. 62/650,877, titled SURGICAL SMOKE EVACUATION SENSING AND CONTROLS.

Applicant of the present application owns the following U.S. patent applications, filed on Mar. 29, 2018, the disclosure of each of which is herein incorporated by reference in its entirety:

U.S. patent application Ser. No. 15/940,641, titled INTERACTIVE SURGICAL SYSTEMS WITH ENCRYPTED COMMUNICATION CAPABILITIES;

U.S. patent application Ser. No. 15/940,648, titled INTERACTIVE SURGICAL SYSTEMS WITH CONDITION HANDLING OF DEVICES AND DATA CAPABILITIES;

U.S. patent application Ser. No. 15/940,656, titled SURGICAL HUB COORDINATION OF CONTROL AND COMMUNICATION OF OPERATING ROOM DEVICES;

U.S. patent application Ser. No. 15/940,666, titled SPATIAL AWARENESS OF SURGICAL HUBS IN OPERATING ROOMS;

U.S. patent application Ser. No. 15/940,670, titled COOPERATIVE UTILIZATION OF DATA DERIVED FROM SECONDARY SOURCES BY INTELLIGENT SURGICAL HUBS;

U.S. patent application Ser. No. 15/940,677, titled SURGICAL HUB CONTROL ARRANGEMENTS;

U.S. patent application Ser. No. 15/940,632, titled DATA STRIPPING METHOD TO INTERROGATE PATIENT RECORDS AND CREATE ANONYMIZED RECORD;

U.S. patent application Ser. No. 15/940,640, titled COMMUNICATION HUB AND STORAGE DEVICE FOR STORING PARAMETERS AND STATUS OF A SURGICAL DEVICE TO BE SHARED WITH CLOUD BASED ANALYTICS SYSTEMS;

U.S. patent application Ser. No. 15/940,645, titled SELF DESCRIBING DATA PACKETS GENERATED AT AN ISSUING INSTRUMENT;

U.S. patent application Ser. No. 15/940,649, titled DATA PAIRING TO INTERCONNECT A DEVICE MEASURED PARAMETER WITH AN OUTCOME;

U.S. patent application Ser. No. 15/940,654, titled SURGICAL HUB SITUATIONAL AWARENESS;

U.S. patent application Ser. No. 15/940,663, titled SURGICAL SYSTEM DISTRIBUTED PROCESSING;

U.S. patent application Ser. No. 15/940,668, titled AGGREGATION AND REPORTING OF SURGICAL HUB DATA;

U.S. patent application Ser. No. 15/940,671, titled SURGICAL HUB SPATIAL AWARENESS TO DETERMINE DEVICES IN OPERATING THEATER;

U.S. patent application Ser. No. 15/940,686, titled DISPLAY OF ALIGNMENT OF STAPLE CARTRIDGE TO PRIOR LINEAR STAPLE LINE;

U.S. patent application Ser. No. 15/940,700, titled STERILE FIELD INTERACTIVE CONTROL DISPLAYS;

U.S. patent application Ser. No. 15/940,629, titled COMPUTER IMPLEMENTED INTERACTIVE SURGICAL SYSTEMS;

U.S. patent application Ser. No. 15/940,704, titled USE OF LASER LIGHT AND RED-GREEN-BLUE COLORATION TO DETERMINE PROPERTIES OF BACK SCATTERED LIGHT;

U.S. patent application Ser. No. 15/940,722, titled CHARACTERIZATION OF TISSUE IRREGULARITIES THROUGH THE USE OF MONO-CHROMATIC LIGHT REFRACTIVITY;

U.S. patent application Ser. No. 15/940,742, titled DUAL CMOS ARRAY IMAGING;

U.S. patent application Ser. No. 15/940,636, titled ADAPTIVE CONTROL PROGRAM UPDATES FOR SURGICAL DEVICES;

U.S. patent application Ser. No. 15/940,653, titled ADAPTIVE CONTROL PROGRAM UPDATES FOR SURGICAL HUBS;

U.S. patent application Ser. No. 15/940,660, titled CLOUD-BASED MEDICAL ANALYTICS FOR CUSTOMIZATION AND RECOMMENDATIONS TO A USER;

U.S. patent application Ser. No. 15/940,679, titled CLOUD-BASED MEDICAL ANALYTICS FOR LINKING OF LOCAL USAGE TRENDS WITH THE RESOURCE ACQUISITION BEHAVIORS OF LARGER DATA SET;

U.S. patent application Ser. No. 15/940,694, titled CLOUD-BASED MEDICAL ANALYTICS FOR MEDICAL FACILITY SEGMENTED INDIVIDUALIZATION OF INSTRUMENT FUNCTION;

U.S. patent application Ser. No. 15/940,634, titled CLOUD-BASED MEDICAL ANALYTICS FOR SECURITY AND AUTHENTICATION TRENDS AND REACTIVE MEASURES;

U.S. patent application Ser. No. 15/940,706, titled DATA HANDLING AND PRIORITIZATION IN A CLOUD ANALYTICS NETWORK;

U.S. patent application Ser. No. 15/940,675, titled CLOUD INTERFACE FOR COUPLED SURGICAL DEVICES;

U.S. patent application Ser. No. 15/940,627, titled DRIVE ARRANGEMENTS FOR ROBOT-ASSISTED SURGICAL PLATFORMS;

U.S. patent application Ser. No. 15/940,637, titled COMMUNICATION ARRANGEMENTS FOR ROBOT-ASSISTED SURGICAL PLATFORMS;

U.S. patent application Ser. No. 15/940,642, titled CONTROLS FOR ROBOT-ASSISTED SURGICAL PLATFORMS;

U.S. patent application Ser. No. 15/940,676, titled AUTOMATIC TOOL ADJUSTMENTS FOR ROBOT-ASSISTED SURGICAL PLATFORMS;

U.S. patent application Ser. No. 15/940,680, titled CONTROLLERS FOR ROBOT-ASSISTED SURGICAL PLATFORMS;

U.S. patent application Ser. No. 15/940,683, titled COOPERATIVE SURGICAL ACTIONS FOR ROBOT-ASSISTED SURGICAL PLATFORMS;

U.S. patent application Ser. No. 15/940,690, titled DISPLAY ARRANGEMENTS FOR ROBOT-ASSISTED SURGICAL PLATFORMS; and U.S. patent application Ser. No. 15/940,711, titled SENSING ARRANGEMENTS FOR ROBOT-ASSISTED SURGICAL PLATFORMS.

Applicant of the present application owns the following U.S. Provisional Patent Applications, filed on Mar. 28, 2018, the disclosure of each of which is herein incorporated by reference in its entirety:

U.S. Provisional Patent Application Ser. No. 62/649,302, titled INTERACTIVE SURGICAL SYSTEMS WITH ENCRYPTED COMMUNICATION CAPABILITIES;

U.S. Provisional Patent Application Ser. No. 62/649,294, titled DATA STRIPPING METHOD TO INTERROGATE PATIENT RECORDS AND CREATE ANONYMIZED RECORD;

U.S. Provisional Patent Application Ser. No. 62/649,300, titled SURGICAL HUB SITUATIONAL AWARENESS;

U.S. Provisional Patent Application Ser. No. 62/649,309, titled SURGICAL HUB SPATIAL AWARENESS TO DETERMINE DEVICES IN OPERATING THEATER;

U.S. Provisional Patent Application Ser. No. 62/649,310, titled COMPUTER IMPLEMENTED INTERACTIVE SURGICAL SYSTEMS;

U.S. Provisional Patent Application Ser. No. 62/649,291, titled USE OF LASER LIGHT AND RED-GREEN-BLUE COLORATION TO DETERMINE PROPERTIES OF BACK SCATTERED LIGHT;

U.S. Provisional Patent Application Ser. No. 62/649,296, titled ADAPTIVE CONTROL PROGRAM UPDATES FOR SURGICAL DEVICES;

U.S. Provisional Patent Application Ser. No. 62/649,333, titled CLOUD-BASED MEDICAL ANALYTICS FOR CUSTOMIZATION AND RECOMMENDATIONS TO A USER;

U.S. Provisional Patent Application Ser. No. 62/649,327, titled CLOUD-BASED MEDICAL ANALYTICS FOR SECURITY AND AUTHENTICATION TRENDS AND REACTIVE MEASURES;

U.S. Provisional Patent Application Ser. No. 62/649,315, titled DATA HANDLING AND PRIORITIZATION IN A CLOUD ANALYTICS NETWORK;

U.S. Provisional Patent Application Ser. No. 62/649,313, titled CLOUD INTERFACE FOR COUPLED SURGICAL DEVICES;

U.S. Provisional Patent Application Ser. No. 62/649,320, titled DRIVE ARRANGEMENTS FOR ROBOT-ASSISTED SURGICAL PLATFORMS;

U.S. Provisional Patent Application Ser. No. 62/649,307, titled AUTOMATIC TOOL ADJUSTMENTS FOR ROBOT-ASSISTED SURGICAL PLATFORMS; and U.S. Provisional Patent Application Ser. No. 62/649,323, titled SENSING ARRANGEMENTS FOR ROBOT-ASSISTED SURGICAL PLATFORMS.

Applicant of the present application owns the following U.S. Provisional Patent Applications, filed on Mar. 8, 2018, the disclosure of each of which is herein incorporated by reference in its entirety:

U.S. Provisional Patent Application Ser. No. 62/640,417, titled TEMPERATURE CONTROL IN ULTRASONIC DEVICE AND CONTROL SYSTEM THEREFOR; and U.S. Provisional Patent Application Ser. No. 62/640,415, titled ESTIMATING STATE OF ULTRASONIC END EFFECTOR AND CONTROL SYSTEM THEREFOR.

Applicant of the present application owns the following U.S. Provisional Patent Applications, filed on Dec. 28, 2017, the disclosure of each of which is herein incorporated by reference in its entirety:

U.S. Provisional Patent Application Serial No. U.S. Provisional Patent Application Ser. No. 62/611,341, titled INTERACTIVE SURGICAL PLATFORM;

U.S. Provisional Patent Application Ser. No. 62/611,340, titled CLOUD-BASED MEDICAL ANALYTICS; and U.S. Provisional Patent Application Ser. No. 62/611,339, titled ROBOT ASSISTED SURGICAL PLATFORM.

Before explaining various aspects of surgical devices and generators in detail, it should be noted that the illustrative examples are not limited in application or use to the details of construction and arrangement of parts illustrated in the accompanying drawings and description. The illustrative examples may be implemented or incorporated in other aspects, variations and modifications, and may be practiced or carried out in various ways. Further, unless otherwise indicated, the terms and expressions employed herein have been chosen for the purpose of describing the illustrative examples for the convenience of the reader and are not for the purpose of limitation thereof. Also, it will be appreciated that one or more of the following-described aspects, expressions of aspects, and/or examples, can be combined with any one or more of the other following-described aspects, expressions of aspects and/or examples.

Surgical Hubs

Referring to FIG. 1, a computer-implemented interactive surgical system 100 includes one or more surgical systems 102 and a cloud-based system (e.g., the cloud 104 that may include a remote server 113 coupled to a storage device 105). Each surgical system 102 includes at least one surgical hub 106 in communication with the cloud 104 that may include a remote server 113. In one example, as illustrated in FIG. 1, the surgical system 102 includes a visualization system 108, a robotic system 110, and a handheld intelligent surgical instrument 112, which are configured to communicate with one another and/or the hub 106. In some aspects, a surgical system 102 may include an M number of hubs 106, an N number of visualization systems 108, an O number of robotic systems 110, and a P number of handheld intelligent surgical instruments 112, where M, N, O, and P are integers greater than or equal to one.

In various aspects, the intelligent instruments 112 as described herein with reference to FIGS. 1-7 may be implemented as ultrasonic surgical instruments and combination energy surgical instruments 7012 as described in FIGS. 23A-23B, 24A-24B, 25-26, 27A-27C, 28A-28C, 29A-29C, 30A-30D, 31A-31D, 32A-32E. The intelligent instruments 112 (e.g., devices 1*a*-1*n*) such as ultrasonic/combination surgical instruments 7012 as described in FIGS. 23A-23B, 24A-24B, 25-26, 27A-27C, 28A-28C, 29A-29C, 30A-30D, 31A-31D, 32A-32E are configured to operate in a surgical data network 201 as described with reference to FIG. 8.

Figure 2:
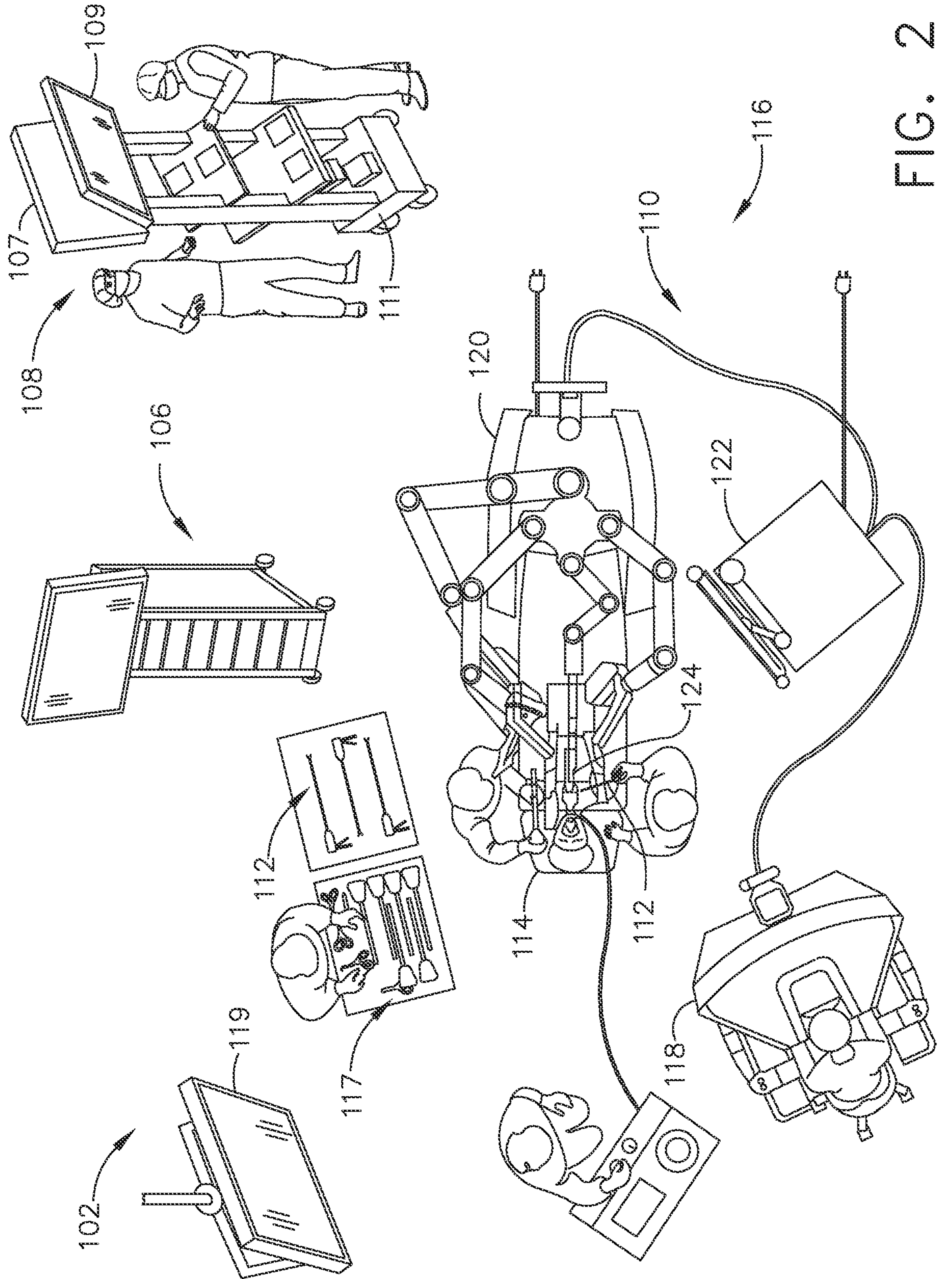
FIG. 2 is a surgical system being used to perform a surgical procedure in an operating room, in accordance with at least one aspect of the present disclosure.

FIG. 2 depicts an example of a surgical system 102 being used to perform a surgical procedure on a patient who is lying down on an operating table 114 in a surgical operating room 116. A robotic system 110 is used in the surgical procedure as a part of the surgical system 102. The robotic system 110 includes a surgeon's console 118, a patient side cart 120 (surgical robot), and a surgical robotic hub 122. The patient side cart 120 can manipulate at least one removably coupled surgical tool 117 through a minimally invasive incision in the body of the patient while the surgeon views the surgical site through the surgeon's console 118. An image of the surgical site can be obtained by a medical imaging device 124, which can be manipulated by the patient side cart 120 to orient the imaging device 124. The robotic hub 122 can be used to process the images of the surgical site for subsequent display to the surgeon through the surgeon's console 118.

Other types of robotic systems can be readily adapted for use with the surgical system 102. Various examples of robotic systems and surgical tools that are suitable for use with the present disclosure are described in U.S. Provisional Patent Application Ser. No. 62/611,339, titled ROBOT ASSISTED SURGICAL PLATFORM, filed Dec. 28, 2017, the disclosure of which is herein incorporated by reference in its entirety.

Various examples of cloud-based analytics that are performed by the cloud 104, and are suitable for use with the present disclosure, are described in U.S. Provisional Patent Application Ser. No. 62/611,340, titled CLOUD-BASED MEDICAL ANALYTICS, filed Dec. 28, 2017, the disclosure of which is herein incorporated by reference in its entirety.

In various aspects, the imaging device 124 includes at least one image sensor and one or more optical components. Suitable image sensors include, but are not limited to, Charge-Coupled Device (CCD) sensors and Complementary Metal-Oxide Semiconductor (CMOS) sensors.

The optical components of the imaging device 124 may include one or more illumination sources and/or one or more lenses. The one or more illumination sources may be directed to illuminate portions of the surgical field. The one or more image sensors may receive light reflected or refracted from the surgical field, including light reflected or refracted from tissue and/or surgical instruments.

The one or more illumination sources may be configured to radiate electromagnetic energy in the visible spectrum as well as the invisible spectrum. The visible spectrum, sometimes referred to as the optical spectrum or luminous spectrum, is that portion of the electromagnetic spectrum that is visible to (i.e., can be detected by) the human eye and may be referred to as visible light or simply light. A typical human eye will respond to wavelengths in air that are from about 380 nm to about 750 nm.

The invisible spectrum (i.e., the non-luminous spectrum) is that portion of the electromagnetic spectrum that lies below and above the visible spectrum (i.e., wavelengths below about 380 nm and above about 750 nm). The invisible spectrum is not detectable by the human eye. Wavelengths greater than about 750 nm are longer than the red visible spectrum, and they become invisible infrared (IR), microwave, and radio electromagnetic radiation. Wavelengths less than about 380 nm are shorter than the violet spectrum, and they become invisible ultraviolet, x-ray, and gamma ray electromagnetic radiation.

In various aspects, the imaging device 124 is configured for use in a minimally invasive procedure. Examples of imaging devices suitable for use with the present disclosure include, but not limited to, an arthroscope, angioscope, bronchoscope, choledochoscope, colonoscope, cytoscope, duodenoscope, enteroscope, esophagogastro-duodenoscope (gastroscope), endoscope, laryngoscope, nasopharyngo-neproscope, sigmoidoscope, thoracoscope, and uretero-scope.

In one aspect, the imaging device employs multi-spectrum monitoring to discriminate topography and underlying structures. A multi-spectral image is one that captures image data within specific wavelength ranges across the electromagnetic spectrum. The wavelengths may be separated by filters or by the use of instruments that are sensitive to particular wavelengths, including light from frequencies beyond the visible light range, e.g., IR and ultraviolet. Spectral imaging can allow extraction of additional information the human eye fails to capture with its receptors for red, green, and blue. The use of multi-spectral imaging is described in greater detail under the heading "Advanced Imaging Acquisition Module" in U.S. Provisional Patent Application Ser. No. 62/611,341, titled INTERACTIVE SURGICAL PLATFORM, filed Dec. 28, 2017, the disclosure of which is herein incorporated by reference in its entirety. Multi-spectrum monitoring can be a useful tool in relocating a surgical field after a surgical task is completed to perform one or more of the previously described tests on the treated tissue.

It is axiomatic that strict sterilization of the operating room and surgical equipment is required during any surgery. The strict hygiene and sterilization conditions required in a "surgical theater," i.e., an operating or treatment room, necessitate the highest possible sterility of all medical devices and equipment. Part of that sterilization process is the need to sterilize anything that comes in contact with the patient or penetrates the sterile field, including the imaging device 124 and its attachments and components. It will be appreciated that the sterile field may be considered a specified area, such as within a tray or on a sterile towel, that is considered free of microorganisms, or the sterile field may be considered an area, immediately around a patient, who has been prepared for a surgical procedure. The sterile field may include the scrubbed team members, who are properly attired, and all furniture and fixtures in the area.

In various aspects, the visualization system 108 includes one or more imaging sensors, one or more image-processing units, one or more storage arrays, and one or more displays that are strategically arranged with respect to the sterile field, as illustrated in FIG. 2. In one aspect, the visualization system 108 includes an interface for HL7, PACS, and EMR. Various components of the visualization system 108 are described under the heading "Advanced Imaging Acquisition Module" in U.S. Provisional Patent Application Ser. No. 62/611,341, titled INTERACTIVE SURGICAL PLATFORM, filed Dec. 28, 2017, the disclosure of which is herein incorporated by reference in its entirety.

As illustrated in FIG. 2, a primary display 119 is positioned in the sterile field to be visible to an operator at the operating table 114. In addition, a visualization tower 111 is positioned outside the sterile field. The visualization tower 111 includes a first non-sterile display 107 and a second non-sterile display 109, which face away from each other. The visualization system 108, guided by the hub 106, is configured to utilize the displays 107, 109, and 119 to coordinate information flow to operators inside and outside the sterile field. For example, the hub 106 may cause the visualization system 108 to display a snapshot of a surgical site, as recorded by an imaging device 124, on a non-sterile display 107 or 109, while maintaining a live feed of the surgical site on the primary display 119. The snapshot on the non-sterile display 107 or 109 can permit a non-sterile operator to perform a diagnostic step relevant to the surgical procedure, for example.

In one aspect, the hub 106 is also configured to route a diagnostic input or feedback entered by a non-sterile operator at the visualization tower 111 to the primary display 119 within the sterile field, where it can be viewed by a sterile operator at the operating table. In one example, the input can be in the form of a modification to the snapshot displayed on the non-sterile display 107 or 109, which can be routed to the primary display 119 by the hub 106.

Referring to FIG. 2, a surgical instrument 112 is being used in the surgical procedure as part of the surgical system 102. The hub 106 is also configured to coordinate information flow to a display of the surgical instrument 112. For example, coordinate information flow is further described in U.S. Provisional Patent Application Ser. No. 62/611,341, titled INTERACTIVE SURGICAL PLATFORM, filed Dec. 28, 2017, the disclosure of which is herein incorporated by reference in its entirety. A diagnostic input or feedback entered by a non-sterile operator at the visualization tower 111 can be routed by the hub 106 to the surgical instrument display 115 within the sterile field, where it can be viewed by the operator of the surgical instrument 112. Example surgical instruments that are suitable for use with the surgical system 102 are described under the heading "Surgical Instrument Hardware" in U.S. Provisional Patent Application Ser. No. 62/611,341, titled INTERACTIVE SURGICAL PLATFORM, filed Dec. 28, 2017, the disclosure of which is herein incorporated by reference in its entirety, for example.

Figure 3:
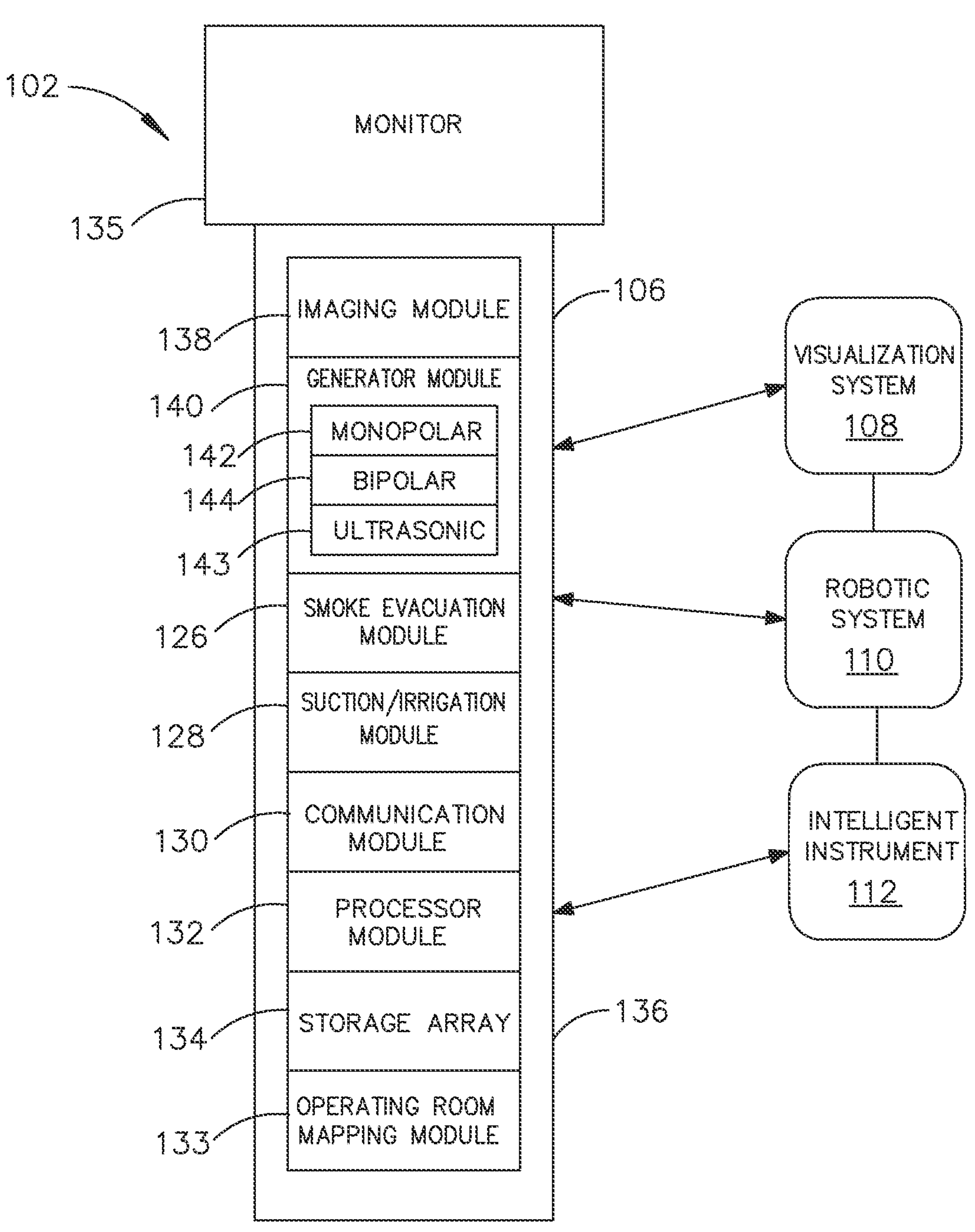
FIG. 3 is a surgical hub paired with a visualization system, a robotic system, and an intelligent instrument, in accordance with at least one aspect of the present disclosure.

Referring now to FIG. 3, a hub 106 is depicted in communication with a visualization system 108, a robotic system 110, and a handheld intelligent surgical instrument 112. The hub 106 includes a hub display 135, an imaging module 138, a generator module 140 (which can include a monopolar generator 142, a bipolar generator 144, and/or an ultrasonic generator 143), a communication module 130, a processor module 132, and a storage array 134. In certain aspects, as illustrated in FIG. 3, the hub 106 further includes a smoke evacuation module 126, a suction/irrigation module 128, and/or an OR mapping module 133.

During a surgical procedure, energy application to tissue, for sealing and/or cutting, is generally associated with smoke evacuation, suction of excess fluid, and/or irrigation of the tissue. Fluid, power, and/or data lines from different sources are often entangled during the surgical procedure. Valuable time can be lost addressing this issue during a surgical procedure. Detangling the lines may necessitate disconnecting the lines from their respective modules, which may require resetting the modules. The hub modular enclosure 136 offers a unified environment for managing the power, data, and fluid lines, which reduces the frequency of entanglement between such lines.

Aspects of the present disclosure present a surgical hub for use in a surgical procedure that involves energy application to tissue at a surgical site. The surgical hub includes a hub enclosure and a combo generator module slidably receivable in a docking station of the hub enclosure. The docking station includes data and power contacts. The combo generator module includes two or more of an ultrasonic energy generator component, a bipolar RF energy generator component, and a monopolar RF energy generator component that are housed in a single unit. In one aspect, the combo generator module also includes a smoke evacuation component, at least one energy delivery cable for connecting the combo generator module to a surgical instrument, at least one smoke evacuation component configured to evacuate smoke, fluid, and/or particulates generated by the application of therapeutic energy to the tissue, and a fluid line extending from the remote surgical site to the smoke evacuation component.

In one aspect, the fluid line is a first fluid line and a second fluid line extends from the remote surgical site to a suction and irrigation module slidably received in the hub enclosure. In one aspect, the hub enclosure comprises a fluid interface.

Certain surgical procedures may require the application of more than one energy type to the tissue. One energy type may be more beneficial for cutting the tissue, while another different energy type may be more beneficial for sealing the tissue. For example, a bipolar generator can be used to seal the tissue while an ultrasonic generator can be used to cut the sealed tissue. Aspects of the present disclosure present a solution where a hub modular enclosure 136 is configured to accommodate different generators, and facilitate an interactive communication therebetween. One of the advantages of the hub modular enclosure 136 is enabling the quick removal and/or replacement of various modules.

Aspects of the present disclosure present a modular surgical enclosure for use in a surgical procedure that involves energy application to tissue. The modular surgical enclosure includes a first energy-generator module, configured to generate a first energy for application to the tissue, and a first docking station comprising a first docking port that includes first data and power contacts, wherein the first energy-generator module is slidably movable into an electrical engagement with the power and data contacts and wherein the first energy-generator module is slidably movable out of the electrical engagement with the first power and data contacts, Further to the above, the modular surgical enclosure also includes a second energy-generator module configured to generate a second energy, different than the first energy, for application to the tissue, and a second docking station comprising a second docking port that includes second data and power contacts, wherein the second energy-generator module is slidably movable into an electrical engagement with the power and data contacts, and wherein the second energy-generator module is slidably movable out of the electrical engagement with the second power and data contacts.

In addition, the modular surgical enclosure also includes a communication bus between the first docking port and the second docking port, configured to facilitate communication between the first energy-generator module and the second energy-generator module.

Figure 5:
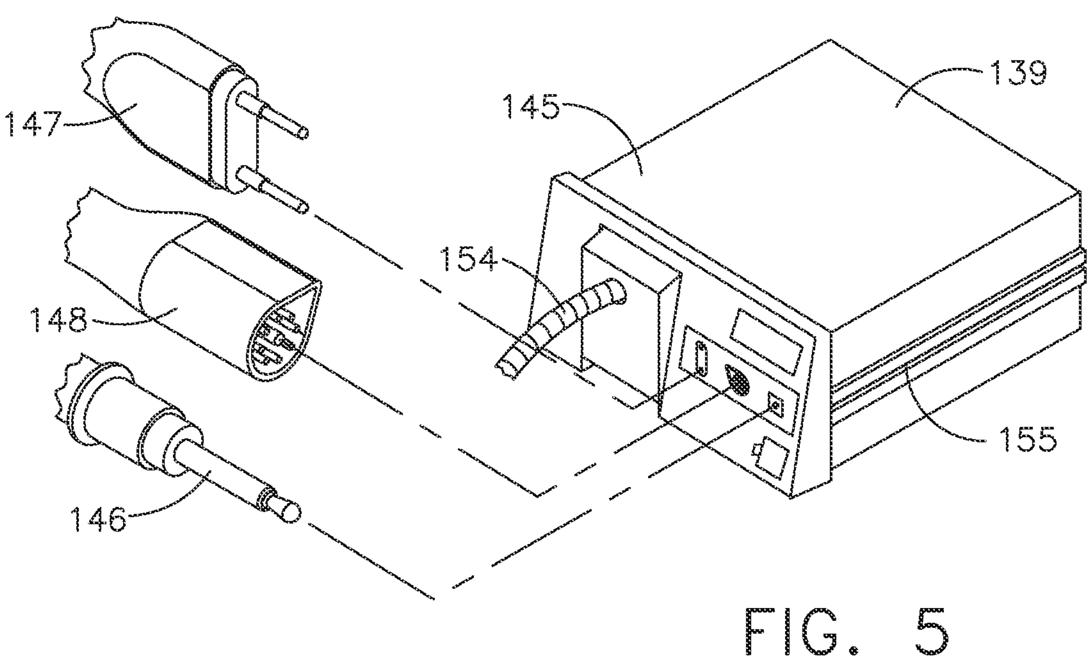
FIG. 5 is a perspective view of a combo generator module with bipolar, ultrasonic, and monopolar contacts and a smoke evacuation component, in accordance with at least one aspect of the present disclosure.

Referring to FIGS. 3-7, aspects of the present disclosure are presented for a hub modular enclosure 136 that allows the modular integration of a generator module 140, a smoke evacuation module 126, and a suction/irrigation module 128. The hub modular enclosure 136 further facilitates interactive communication between the modules 140, 126, 128. As illustrated in FIG. 5, the generator module 140 can be a generator module with integrated monopolar, bipolar, and ultrasonic components supported in a single housing unit 139 slidably insertable into the hub modular enclosure 136. As illustrated in FIG. 5, the generator module 140 can be configured to connect to a monopolar device 146, a bipolar device 147, and an ultrasonic device 148. Alternatively, the generator module 140 may comprise a series of monopolar, bipolar, and/or ultrasonic generator modules that interact through the hub modular enclosure 136. The hub modular enclosure 136 can be configured to facilitate the insertion of multiple generators and interactive communication between the generators docked into the hub modular enclosure 136 so that the generators would act as a single generator.

In one aspect, the hub modular enclosure 136 comprises a modular power and communication backplane 149 with external and wireless communication headers to enable the removable attachment of the modules 140, 126, 128 and interactive communication therebetween.

Figure 4:
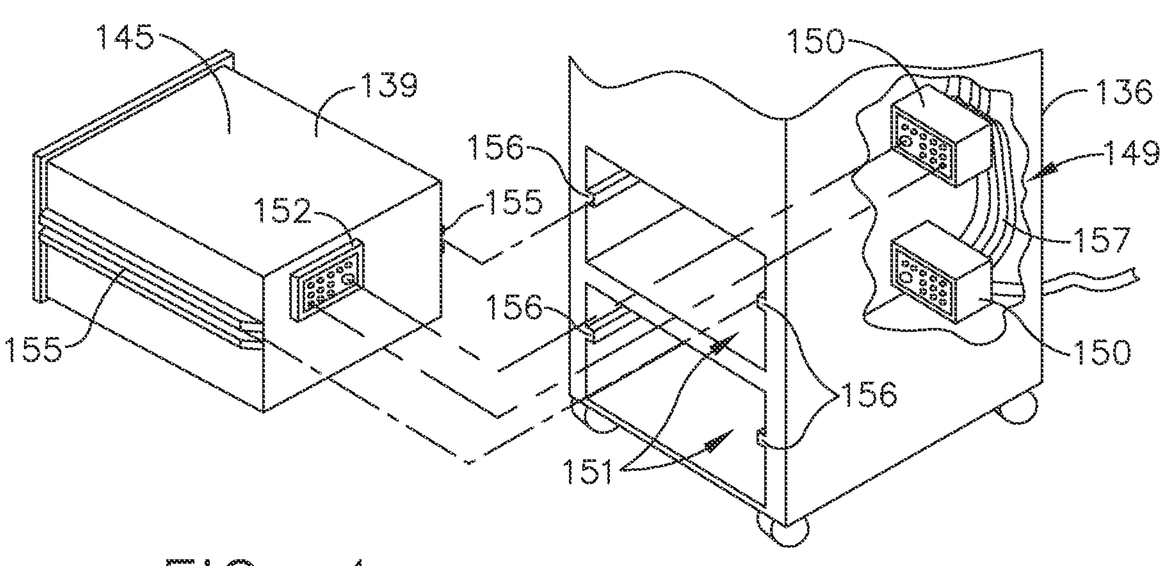
FIG. 4 is a partial perspective view of a surgical hub enclosure, and of a combo generator module slidably receivable in a drawer of the surgical hub enclosure, in accordance with at least one aspect of the present disclosure.

In one aspect, the hub modular enclosure 136 includes docking stations, or drawers, 151, herein also referred to as drawers, which are configured to slidably receive the modules 140, 126, 128. FIG. 4 illustrates a partial perspective view of a surgical hub enclosure 136, and a combo generator module 145 slidably receivable in a docking station 151 of the surgical hub enclosure 136. A docking port 152 with power and data contacts on a rear side of the combo generator module 145 is configured to engage a corresponding docking port 150 with power and data contacts of a corresponding docking station 151 of the hub modular enclosure 136 as the combo generator module 145 is slid into position within the corresponding docking station 151 of the hub module enclosure 136. In one aspect, the combo generator module 145 includes a bipolar, ultrasonic, and monopolar module and a smoke evacuation module integrated together into a single housing unit 139, as illustrated in FIG. 5.

In various aspects, the smoke evacuation module 126 includes a fluid line 154 that conveys captured/collected smoke and/or fluid away from a surgical site and to, for example, the smoke evacuation module 126. Vacuum suction originating from the smoke evacuation module 126 can draw the smoke into an opening of a utility conduit at the surgical site. The utility conduit, coupled to the fluid line, can be in the form of a flexible tube terminating at the smoke evacuation module 126. The utility conduit and the fluid line define a fluid path extending toward the smoke evacuation module 126 that is received in the hub enclosure 136.

In various aspects, the suction/irrigation module 128 is coupled to a surgical tool comprising an aspiration fluid line and a suction fluid line. In one example, the aspiration and suction fluid lines are in the form of flexible tubes extending from the surgical site toward the suction/irrigation module 128. One or more drive systems can be configured to cause irrigation and aspiration of fluids to and from the surgical site.

In one aspect, the surgical tool includes a shaft having an end effector at a distal end thereof and at least one energy treatment associated with the end effector, an aspiration tube, and an irrigation tube. The aspiration tube can have an inlet port at a distal end thereof and the aspiration tube extends through the shaft. Similarly, an irrigation tube can extend through the shaft and can have an inlet port in proximity to the energy deliver implement. The energy deliver implement is configured to deliver ultrasonic and/or RF energy to the surgical site and is coupled to the generator module 140 by a cable extending initially through the shaft.

The irrigation tube can be in fluid communication with a fluid source, and the aspiration tube can be in fluid communication with a vacuum source. The fluid source and/or the vacuum source can be housed in the suction/irrigation module 128. In one example, the fluid source and/or the vacuum source can be housed in the hub enclosure 136 separately from the suction/irrigation module 128. In such example, a fluid interface can be configured to connect the suction/irrigation module 128 to the fluid source and/or the vacuum source.

In one aspect, the modules 140, 126, 128 and/or their corresponding docking stations on the hub modular enclosure 136 may include alignment features that are configured to align the docking ports of the modules into engagement with their counterparts in the docking stations of the hub modular enclosure 136. For example, as illustrated in FIG. 4, the combo generator module 145 includes side brackets 155 that are configured to slidably engage with corresponding brackets 156 of the corresponding docking station 151 of the hub modular enclosure 136. The brackets cooperate to guide the docking port contacts of the combo generator module 145 into an electrical engagement with the docking port contacts of the hub modular enclosure 136.

In some aspects, the drawers 151 of the hub modular enclosure 136 are the same, or substantially the same size, and the modules are adjusted in size to be received in the drawers 151. For example, the side brackets 155 and/or 156 can be larger or smaller depending on the size of the module. In other aspects, the drawers 151 are different in size and are each designed to accommodate a particular module.

Furthermore, the contacts of a particular module can be keyed for engagement with the contacts of a particular drawer to avoid inserting a module into a drawer with mismatching contacts.

As illustrated in FIG. 4, the docking port 150 of one drawer 151 can be coupled to the docking port 150 of another drawer 151 through a communications link 157 to facilitate an interactive communication between the modules housed in the hub modular enclosure 136. The docking ports 150 of the hub modular enclosure 136 may alternatively, or additionally, facilitate a wireless interactive communication between the modules housed in the hub modular enclosure 136. Any suitable wireless communication can be employed, such as for example Air Titan-Bluetooth.

Figure 6:
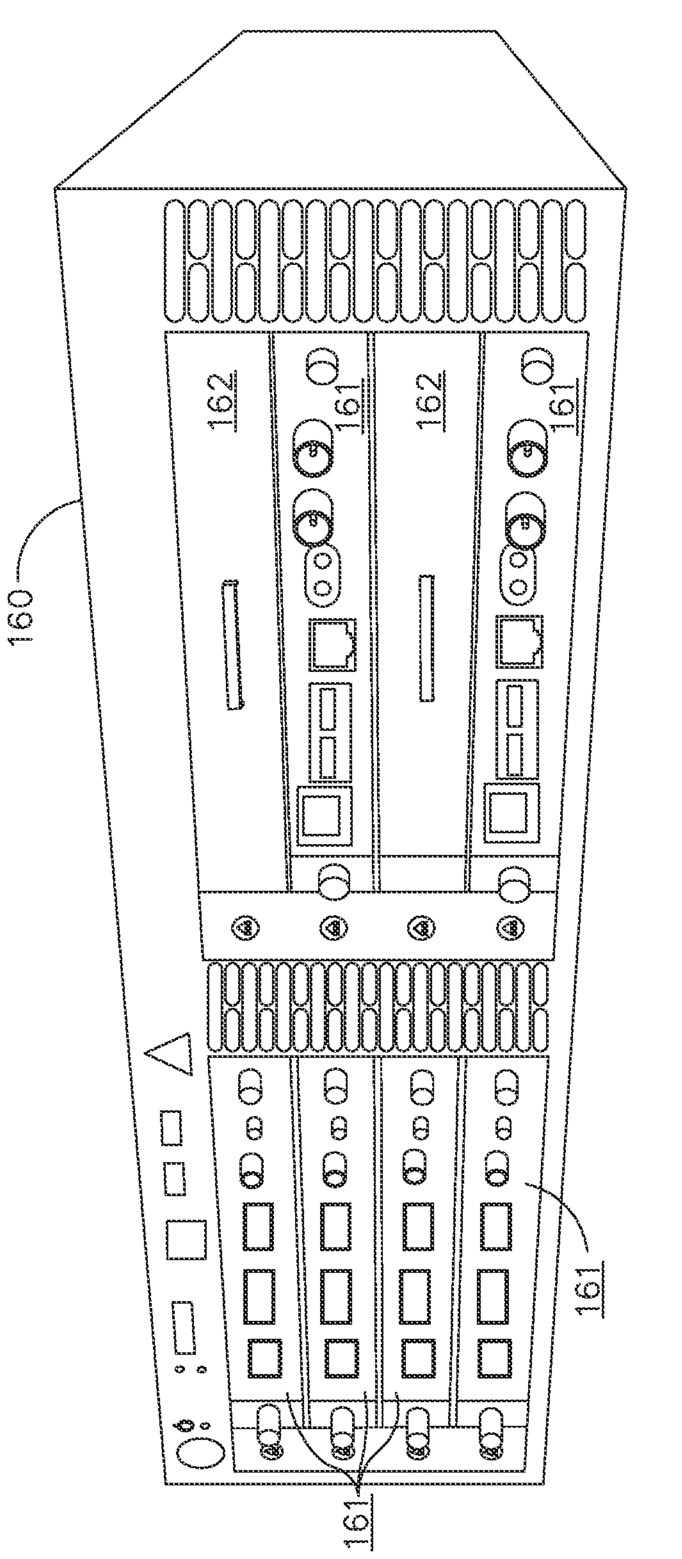
FIG. 6 illustrates individual power bus attachments for a plurality of lateral docking ports of a lateral modular housing configured to receive a plurality of modules, in accordance with at least one aspect of the present disclosure.

FIG. 6 illustrates individual power bus attachments for a plurality of lateral docking ports of a lateral modular housing 160 configured to receive a plurality of modules of a surgical hub 206. The lateral modular housing 160 is configured to laterally receive and interconnect the modules 161. The modules 161 are slidably inserted into docking stations 162 of lateral modular housing 160, which includes a backplane for interconnecting the modules 161. As illustrated in FIG. 6, the modules 161 are arranged laterally in the lateral modular housing 160. Alternatively, the modules 161 may be arranged vertically in a lateral modular housing.

Figure 7:
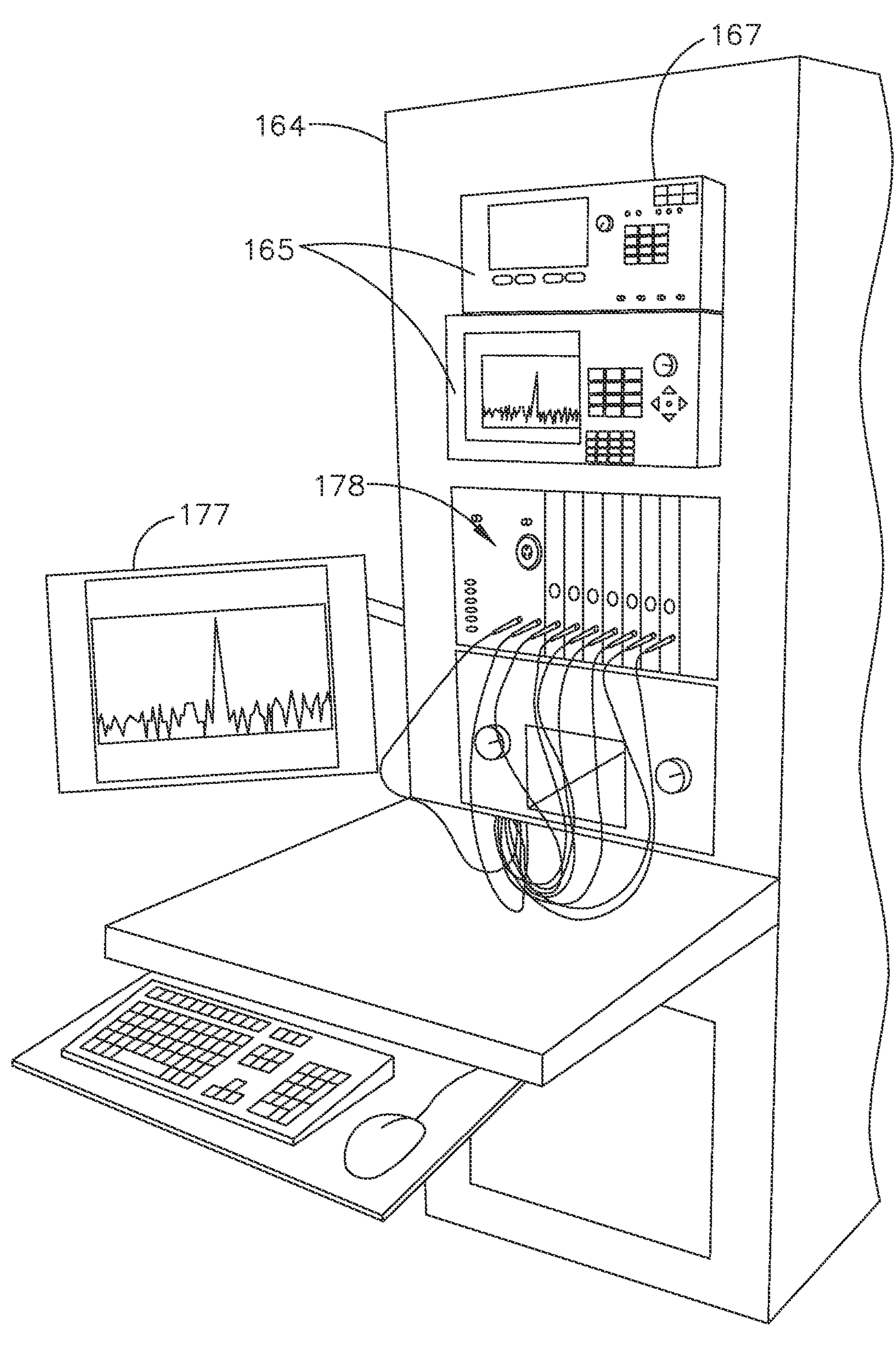
FIG. 7 illustrates a vertical modular housing configured to receive a plurality of modules, in accordance with at least one aspect of the present disclosure.

FIG. 7 illustrates a vertical modular housing 164 configured to receive a plurality of modules 165 of the surgical hub 106. The modules 165 are slidably inserted into docking stations, or drawers, 167 of vertical modular housing 164, which includes a backplane for interconnecting the modules 165. Although the drawers 167 of the vertical modular housing 164 are arranged vertically, in certain instances, a vertical modular housing 164 may include drawers that are arranged laterally. Furthermore, the modules 165 may interact with one another through the docking ports of the vertical modular housing 164. In the example of FIG. 7, a display 177 is provided for displaying data relevant to the operation of the modules 165. In addition, the vertical modular housing 164 includes a master module 178 housing a plurality of sub-modules that are slidably received in the master module 178.

In various aspects, the imaging module 138 comprises an integrated video processor and a modular light source and is adapted for use with various imaging devices. In one aspect, the imaging device is comprised of a modular housing that can be assembled with a light source module and a camera module. The housing can be a disposable housing. In at least one example, the disposable housing is removably coupled to a reusable controller, a light source module, and a camera module. The light source module and/or the camera module can be selectively chosen depending on the type of surgical procedure. In one aspect, the camera module comprises a CCD sensor. In another aspect, the camera module comprises a CMOS sensor. In another aspect, the camera module is configured for scanned beam imaging. Likewise, the light source module can be configured to deliver a white light or a different light, depending on the surgical procedure.

During a surgical procedure, removing a surgical device from the surgical field and replacing it with another surgical device that includes a different camera or a different light source can be inefficient. Temporarily losing sight of the surgical field may lead to undesirable consequences. The module imaging device of the present disclosure is configured to permit the replacement of a light source module or a camera module midstream during a surgical procedure, without having to remove the imaging device from the surgical field.

In one aspect, the imaging device comprises a tubular housing that includes a plurality of channels. A first channel is configured to slidably receive the camera module, which can be configured for a snap-fit engagement with the first channel. A second channel is configured to slidably receive the light source module, which can be configured for a snap-fit engagement with the second channel. In another example, the camera module and/or the light source module can be rotated into a final position within their respective channels. A threaded engagement can be employed in lieu of the snap-fit engagement.

In various examples, multiple imaging devices are placed at different positions in the surgical field to provide multiple views. The imaging module 138 can be configured to switch between the imaging devices to provide an optimal view. In various aspects, the imaging module 138 can be configured to integrate the images from the different imaging device.

Various image processors and imaging devices suitable for use with the present disclosure are described in U.S. Pat. No. 7,995,045, titled COMBINED SBI AND CONVENTIONAL IMAGE PROCESSOR, which issued on Aug. 9, 2011, which is herein incorporated by reference in its entirety. In addition, U.S. Pat. No. 7,982,776, titled SBI MOTION ARTIFACT REMOVAL APPARATUS AND METHOD, which issued on Jul. 19, 2011, which is herein incorporated by reference in its entirety, describes various systems for removing motion artifacts from image data. Such systems can be integrated with the imaging module 138. Furthermore, U.S. Patent Application Publication No. 2011/0306840, titled CONTROLLABLE MAGNETIC SOURCE TO FIXTURE INTRACORPOREAL APPARATUS, which published on Dec. 15, 2011, and U.S. Patent Application Publication No. 2014/0243597, titled SYSTEM FOR PERFORMING A MINIMALLY INVASIVE SURGICAL PROCEDURE, which published on Aug. 28, 2014, each of which is herein incorporated by reference in its entirety.

Figure 8:
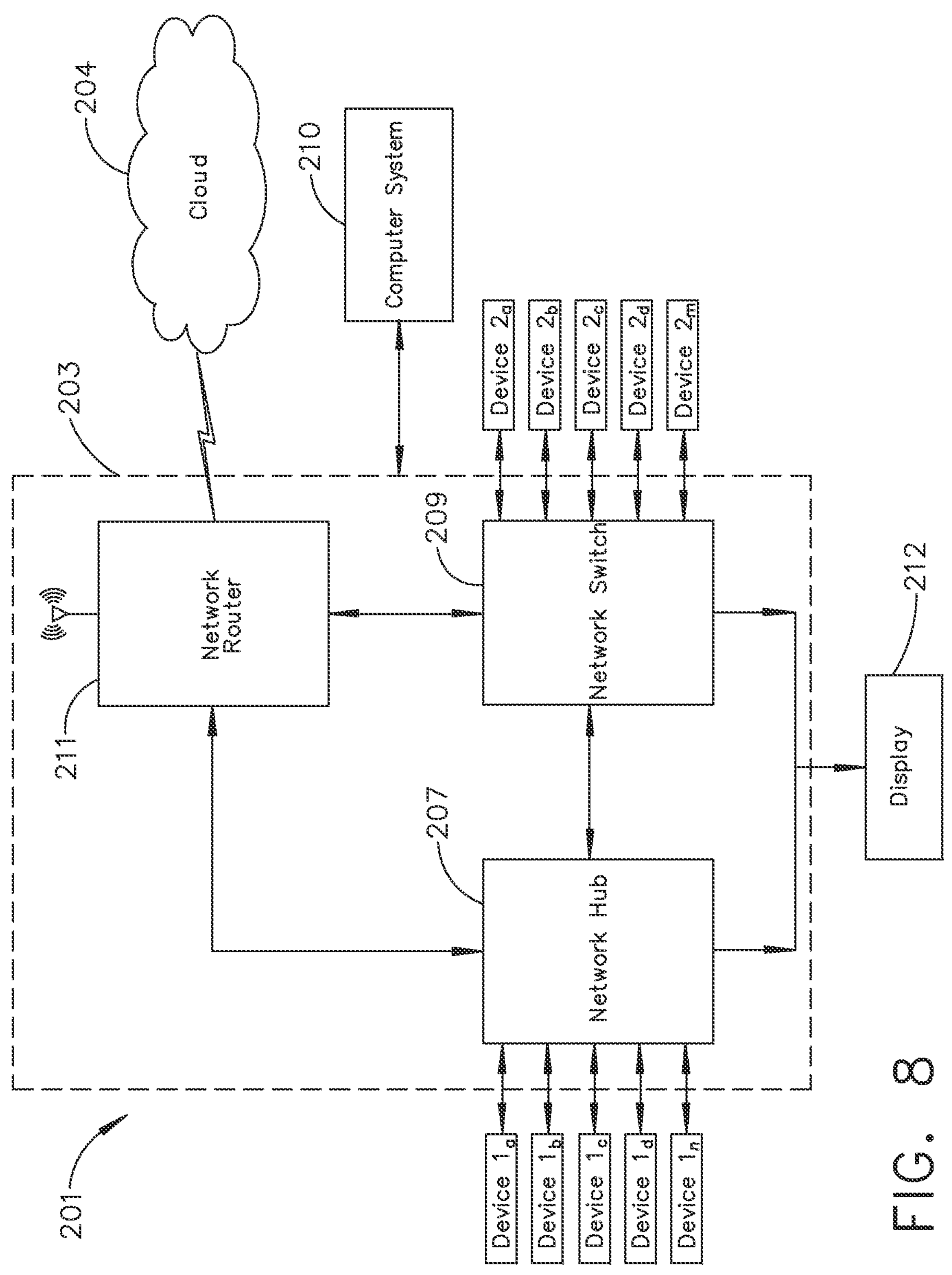
FIG. 8 illustrates a surgical data network comprising a modular communication hub configured to connect modular devices located in one or more operating theaters of a healthcare facility, or any room in a healthcare facility specially equipped for surgical operations, to the cloud, in accordance with at least one aspect of the present disclosure.

FIG. 8 illustrates a surgical data network 201 comprising a modular communication hub 203 configured to connect modular devices located in one or more operating theaters of a healthcare facility, or any room in a healthcare facility specially equipped for surgical operations, to a cloud-based system (e.g., the cloud 204 that may include a remote server 213 coupled to a storage device 205). In one aspect, the modular communication hub 203 comprises a network hub 207 and/or a network switch 209 in communication with a network router. The modular communication hub 203 also can be coupled to a local computer system 210 to provide local computer processing and data manipulation. The surgical data network 201 may be configured as passive, intelligent, or switching. A passive surgical data network serves as a conduit for the data, enabling it to go from one device (or segment) to another and to the cloud computing resources. An intelligent surgical data network includes additional features to enable the traffic passing through the surgical data network to be monitored and to configure each port in the network hub 207 or network switch 209. An intelligent surgical data network may be referred to as a manageable hub or switch. A switching hub reads the destination address of each packet and then forwards the packet to the correct port.

Modular devices 1*a*-1*n* located in the operating theater may be coupled to the modular communication hub 203. The network hub 207 and/or the network switch 209 may be coupled to a network router 211 to connect the devices 1*a*-1*n* to the cloud 204 or the local computer system 210. Data associated with the devices 1*a*-1*n* may be transferred to cloud-based computers via the router for remote data processing and manipulation. Data associated with the devices 1*a*-1*n* may also be transferred to the local computer system 210 for local data processing and manipulation. Modular devices 2*a*-2*m* located in the same operating theater also may be coupled to a network switch 209. The network switch 209 may be coupled to the network hub 207 and/or the network router 211 to connect to the devices 2*a*-2*m* to the cloud 204. Data associated with the devices 2*a*-2*n* may be transferred to the cloud 204 via the network router 211 for data processing and manipulation. Data associated with the devices 2*a*-2*m* may also be transferred to the local computer system 210 for local data processing and manipulation.

It will be appreciated that the surgical data network 201 may be expanded by interconnecting multiple network hubs 207 and/or multiple network switches 209 with multiple network routers 211. The modular communication hub 203 may be contained in a modular control tower configured to receive multiple devices 1*a*-1*n*/2*a*-2*m*. The local computer system 210 also may be contained in a modular control tower. The modular communication hub 203 is connected to a display 212 to display images obtained by some of the devices 1*a*-1*n*/2*a*-2*m*, for example during surgical procedures. In various aspects, the devices 1*a*-1*n*/2*a*-2*m* may include, for example, various modules such as an imaging module 138 coupled to an endoscope, a generator module 140 coupled to an energy-based surgical device, a smoke evacuation module 126, a suction/irrigation module 128, a communication module 130, a processor module 132, a storage array 134, a surgical device coupled to a display, and/or a non-contact sensor module, among other modular devices that may be connected to the modular communication hub 203 of the surgical data network 201.

In one aspect, the surgical data network 201 may comprise a combination of network hub(s), network switch(es), and network router(s) connecting the devices 1*a*-1*n*/2*a*-2*m* to the cloud. Any one of or all of the devices 1*a*-1*n*/2*a*-2*m* coupled to the network hub or network switch may collect data in real time and transfer the data to cloud computers for data processing and manipulation. It will be appreciated that cloud computing relies on sharing computing resources rather than having local servers or personal devices to handle software applications. The word "cloud" may be used as a metaphor for "the Internet," although the term is not limited as such. Accordingly, the term "cloud computing" may be used herein to refer to "a type of Internet-based computing," where different services—such as servers, storage, and applications—are delivered to the modular communication hub 203 and/or computer system 210 located in the surgical theater (e.g., a fixed, mobile, temporary, or field operating room or space) and to devices connected to the modular communication hub 203 and/or computer system 210 through the Internet. The cloud infrastructure may be maintained by a cloud service provider. In this context, the cloud service provider may be the entity that coordinates the usage and control of the devices 1*a*-1*n*/2*a*-2*m* located in one or more operating theaters. The cloud computing services can perform a large number of calculations based on the data gathered by smart surgical instruments, robots, and other computerized devices located in the operating theater. The hub hardware enables multiple devices or connections to be connected to a computer that communicates with the cloud computing resources and storage.

Applying cloud computer data processing techniques on the data collected by the devices 1*a*-1*n*/2*a*-2*m*, the surgical data network provides improved surgical outcomes, reduced costs, and improved patient satisfaction. At least some of the devices 1*a*-1*n*/2*a*-2*m* may be employed to view tissue states to assess leaks or perfusion of sealed tissue after a tissue sealing and cutting procedure. At least some of the devices 1*a*-1*n*/2*a*-2*m* may be employed to identify pathology, such as the effects of diseases, using the cloud-based computing to examine data including images of samples of body tissue for diagnostic purposes. This includes localization and margin confirmation of tissue and phenotypes. At least some of the devices 1*a*-1*n*/2*a*-2*m* may be employed to identify anatomical structures of the body using a variety of sensors integrated with imaging devices and techniques such as overlaying images captured by multiple imaging devices. The data gathered by the devices 1*a*-1*n*/2*a*-2*m*, including image data, may be transferred to the cloud 204 or the local computer system 210 or both for data processing and manipulation including image processing and manipulation. The data may be analyzed to improve surgical procedure outcomes by determining if further treatment, such as the application of endoscopic intervention, emerging technologies, a targeted radiation, targeted intervention, and precise robotics to tissue-specific sites and conditions, may be pursued. Such data analysis may further employ outcome analytics processing, and using standardized approaches may provide beneficial feedback to either confirm surgical treatments and the behavior of the surgeon or suggest modifications to surgical treatments and the behavior of the surgeon.

In one implementation, the operating theater devices 1*a*-1*n* may be connected to the modular communication hub 203 over a wired channel or a wireless channel depending on the configuration of the devices 1*a*-1*n* to a network hub. The network hub 207 may be implemented, in one aspect, as a local network broadcast device that works on the physical layer of the Open System Interconnection (OSI) model. The network hub provides connectivity to the devices 1*a*-1*n* located in the same operating theater network. The network hub 207 collects data in the form of packets and sends them to the router in half duplex mode. The network hub 207 does not store any media access control/Internet Protocol (MAC/IP) to transfer the device data. Only one of the devices 1*a*-1*n* can send data at a time through the network hub 207. The network hub 207 has no routing tables or intelligence regarding where to send information and broadcasts all network data across each connection and to a remote server 213 (FIG. 9) over the cloud 204. The network hub 207 can detect basic network errors such as collisions, but having all information broadcast to multiple ports can be a security risk and cause bottlenecks.

In another implementation, the operating theater devices 2*a*-2*m* may be connected to a network switch 209 over a wired channel or a wireless channel. The network switch 209 works in the data link layer of the OSI model. The network switch 209 is a multicast device for connecting the devices 2*a*-2*m* located in the same operating theater to the network. The network switch 209 sends data in the form of frames to the network router 211 and works in full duplex mode. Multiple devices 2*a*-2*m* can send data at the same time through the network switch 209. The network switch 209 stores and uses MAC addresses of the devices 2*a*-2*m* to transfer data.

The network hub 207 and/or the network switch 209 are coupled to the network router 211 for connection to the cloud 204. The network router 211 works in the network layer of the OSI model. The network router 211 creates a route for transmitting data packets received from the network hub 207 and/or network switch 211 to cloud-based computer resources for further processing and manipulation of the data collected by any one of or all the devices 1*a*-1*n*/2*a*-2*m*. The network router 211 may be employed to connect two or more different networks located in different locations, such as, for example, different operating theaters of the same healthcare facility or different networks located in different operating theaters of different healthcare facilities. The network router 211 sends data in the form of packets to the cloud 204 and works in full duplex mode. Multiple devices can send data at the same time. The network router 211 uses IP addresses to transfer data.

In one example, the network hub 207 may be implemented as a USB hub, which allows multiple USB devices to be connected to a host computer. The USB hub may expand a single USB port into several tiers so that there are more ports available to connect devices to the host system computer. The network hub 207 may include wired or wireless capabilities to receive information over a wired channel or a wireless channel. In one aspect, a wireless USB short-range, high-bandwidth wireless radio communication protocol may be employed for communication between the devices 1*a*-1*n* and devices 2*a*-2*m* located in the operating theater.

In other examples, the operating theater devices 1*a*-1*n*/2*a*-2*m* may communicate to the modular communication hub 203 via Bluetooth wireless technology standard for exchanging data over short distances (using short-wavelength UHF radio waves in the ISM band from 2.4 to 2.485 GHz) from fixed and mobile devices and building personal area networks (PANs). In other aspects, the operating theater devices 1*a*-1*n*/2*a*-2*m* may communicate to the modular communication hub 203 via a number of wireless or wired communication standards or protocols, including but not limited to Wi-Fi (IEEE 802.11 family), WiMAX (IEEE 802.16 family), IEEE 802.20, long-term evolution (LTE), and Ev-DO, HSPA+, HSDPA+, HSUPA+, EDGE, GSM, GPRS, CDMA, TDMA, DECT, and Ethernet derivatives thereof, as well as any other wireless and wired protocols that are designated as 3G, 4G, 5G, and beyond. The computing module may include a plurality of communication modules. For instance, a first communication module may be dedicated to shorter-range wireless communications such as Wi-Fi and Bluetooth, and a second communication module may be dedicated to longer-range wireless communications such as GPS, EDGE, GPRS, CDMA, WiMAX, LTE, Ev-DO, and others.

The modular communication hub 203 may serve as a central connection for one or all of the operating theater devices 1*a*-1*n*/2*a*-2*m* and handles a data type known as frames. Frames carry the data generated by the devices 1*a*-1*n*/2*a*-2*m*. When a frame is received by the modular communication hub 203, it is amplified and transmitted to the network router 211, which transfers the data to the cloud computing resources by using a number of wireless or wired communication standards or protocols, as described herein.

The modular communication hub 203 can be used as a standalone device or be connected to compatible network hubs and network switches to form a larger network. The modular communication hub 203 is generally easy to install, configure, and maintain, making it a good option for networking the operating theater devices 1*a*-1*n*/2*a*-2*m*.

Figure 9:
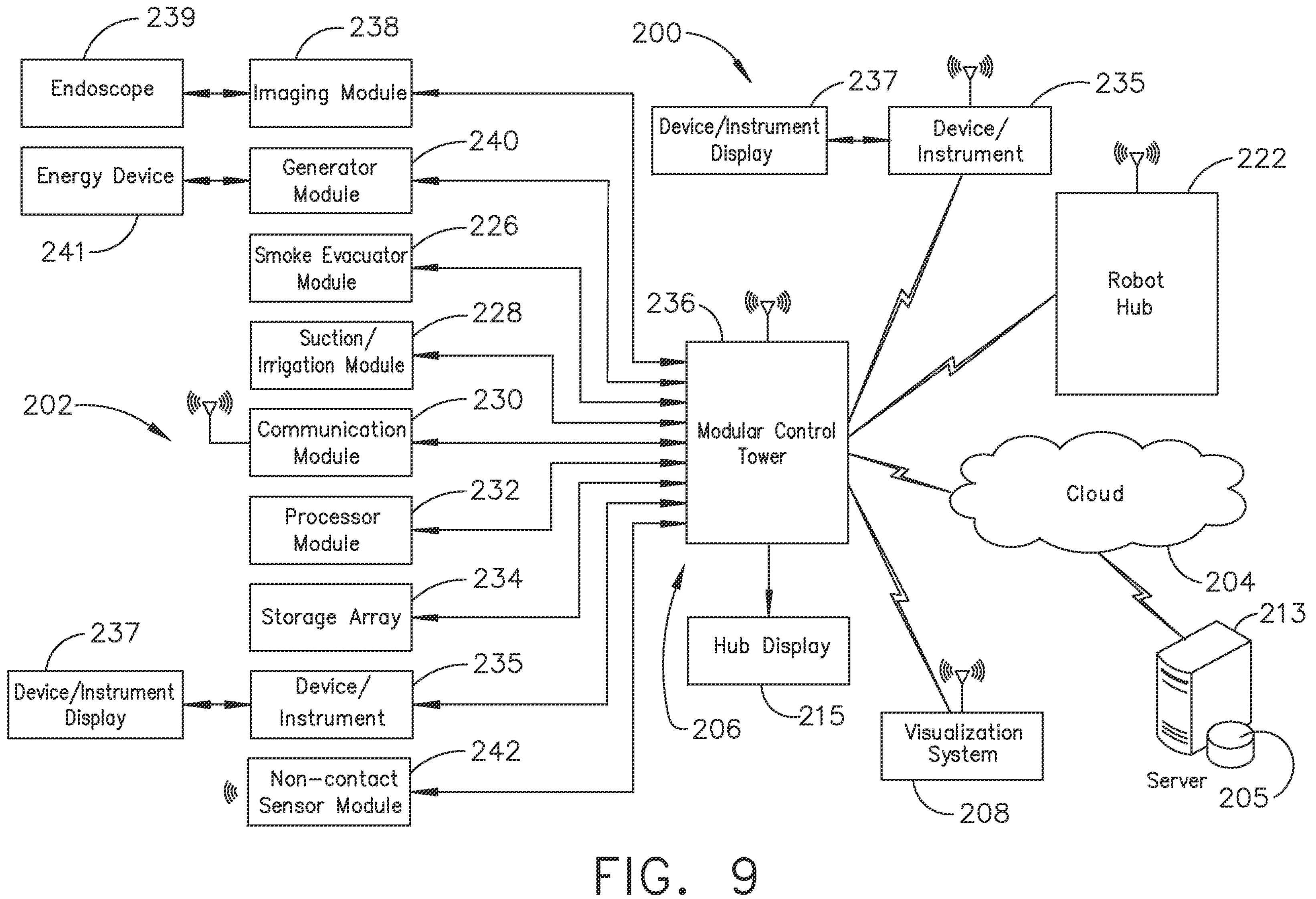
FIG. 9 illustrates a computer-implemented interactive surgical system, in accordance with at least one aspect of the present disclosure.
Figure 10:
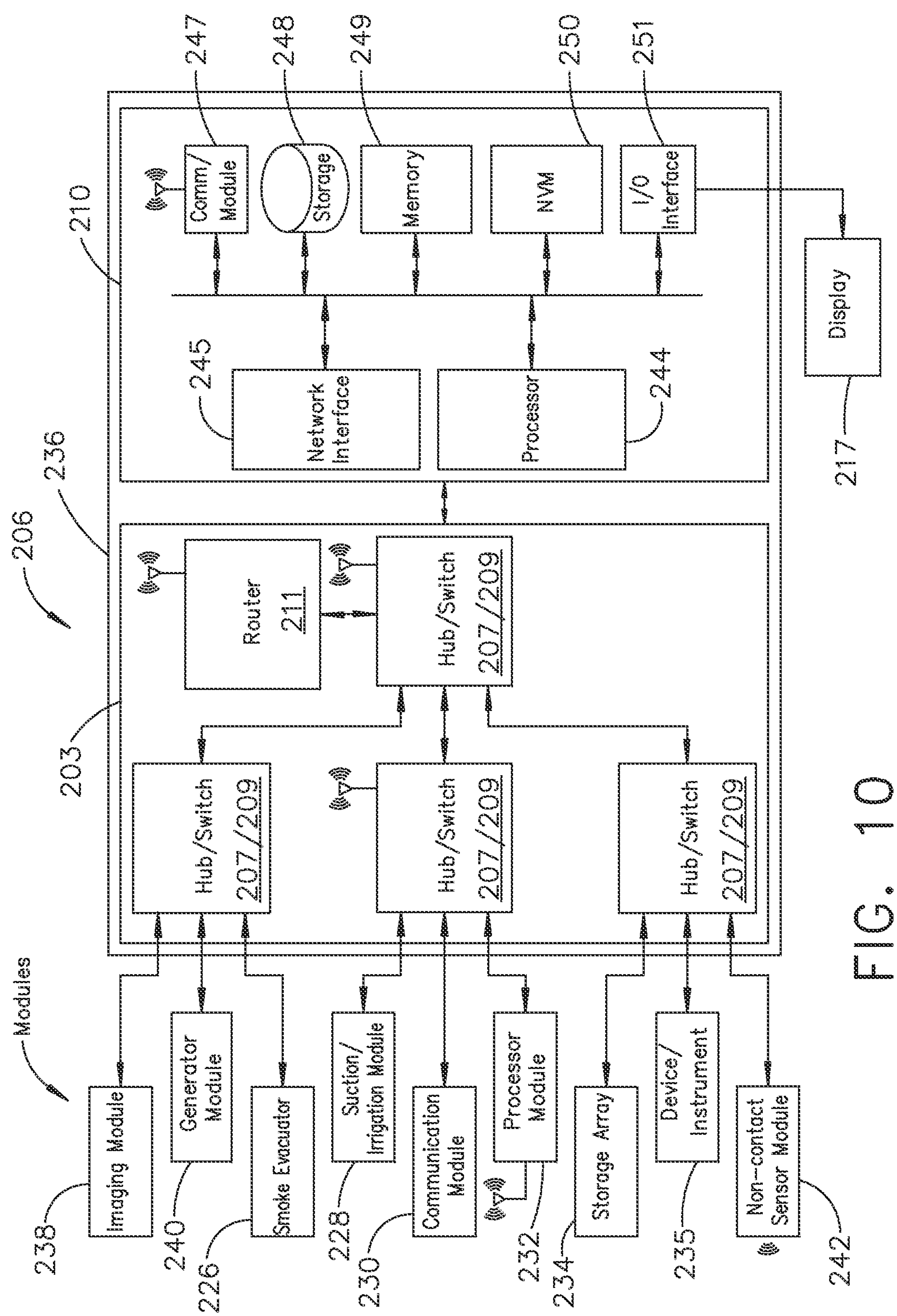
FIG. 10 illustrates a surgical hub comprising a plurality of modules coupled to the modular control tower, in accordance with at least one aspect of the present disclosure.

FIG. 9 illustrates a computer-implemented interactive surgical system 200. The computer-implemented interactive surgical system 200 is similar in many respects to the computer-implemented interactive surgical system 100. For example, the computer-implemented interactive surgical system 200 includes one or more surgical systems 202, which are similar in many respects to the surgical systems 102. Each surgical system 202 includes at least one surgical hub 206 in communication with a cloud 204 that may include a remote server 213. In one aspect, the computer-implemented interactive surgical system 200 comprises a modular control tower 236 connected to multiple operating theater devices such as, for example, intelligent surgical instruments, robots, and other computerized devices located in the operating theater. As shown in FIG. 10, the modular control tower 236 comprises a modular communication hub 203 coupled to a computer system 210. As illustrated in the example of FIG. 9, the modular control tower 236 is coupled to an imaging module 238 that is coupled to an endoscope 239, a generator module 240 that is coupled to an energy device 241, a smoke evacuator module 226, a suction/irrigation module 228, a communication module 230, a processor module 232, a storage array 234, a smart device/instrument 235 optionally coupled to a display 237, and a non-contact sensor module 242. The operating theater devices are coupled to cloud computing resources and data storage via the modular control tower 236. A robot hub 222 also may be connected to the modular control tower 236 and to the cloud computing resources. The devices/instruments 235, visualization systems 208, among others, may be coupled to the modular control tower 236 via wired or wireless communication standards or protocols, as described herein. The modular control tower 236 may be coupled to a hub display 215 (e.g., monitor, screen) to display and overlay images received from the imaging module, device/instrument display, and/or other visualization systems 208. The hub display also may display data received from devices connected to the modular control tower in conjunction with images and overlaid images.

FIG. 10 illustrates a surgical hub 206 comprising a plurality of modules coupled to the modular control tower 236. The modular control tower 236 comprises a modular communication hub 203, e.g., a network connectivity device, and a computer system 210 to provide local processing, visualization, and imaging, for example. As shown in FIG. 10, the modular communication hub 203 may be connected in a tiered configuration to expand the number of modules (e.g., devices) that may be connected to the modular communication hub 203 and transfer data associated with the modules to the computer system 210, cloud computing resources, or both. As shown in FIG. 10, each of the network hubs/switches in the modular communication hub 203 includes three downstream ports and one upstream port. The upstream network hub/switch is connected to a processor to provide a communication connection to the cloud computing resources and a local display 217. Communication to the cloud 204 may be made either through a wired or a wireless communication channel.

The surgical hub 206 employs a non-contact sensor module 242 to measure the dimensions of the operating theater and generate a map of the surgical theater using either ultrasonic or laser-type non-contact measurement devices. An ultrasound-based non-contact sensor module scans the operating theater by transmitting a burst of ultrasound and receiving the echo when it bounces off the perimeter walls of an operating theater as described under the heading "Surgical Hub Spatial Awareness Within an Operating Room" in U.S. Provisional Patent Application Ser. No. 62/611,341, titled INTERACTIVE SURGICAL PLATFORM, filed Dec. 28, 2017, which is herein incorporated by reference in its entirety, in which the sensor module is configured to determine the size of the operating theater and to adjust Bluetooth-pairing distance limits. A laser-based non-contact sensor module scans the operating theater by transmitting laser light pulses, receiving laser light pulses that bounce off the perimeter walls of the operating theater, and comparing the phase of the transmitted pulse to the received pulse to determine the size of the operating theater and to adjust Bluetooth pairing distance limits, for example.

The computer system 210 comprises a processor 244 and a network interface 245. The processor 244 is coupled to a communication module 247, storage 248, memory 249, non-volatile memory 250, and input/output interface 251 via a system bus. The system bus can be any of several types of bus structure(s) including the memory bus or memory controller, a peripheral bus or external bus, and/or a local bus using any variety of available bus architectures including, but not limited to, 9-bit bus, Industrial Standard Architecture (ISA), Micro-Charmel Architecture (MSA), Extended ISA (EISA), Intelligent Drive Electronics (IDE), VESA Local Bus (VLB), Peripheral Component Interconnect (PCI), USB, Advanced Graphics Port (AGP), Personal Computer Memory Card International Association bus (PCMCIA), Small Computer Systems Interface (SCSI), or any other proprietary bus.

The processor 244 may be any single-core or multicore processor such as those known under the trade name ARM Cortex by Texas Instruments. In one aspect, the processor may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle serial random access memory (SRAM), an internal read-only memory (ROM) loaded with StellarisWare® software, a 2 KB electrically erasable programmable read-only memory (EEPROM), and/or one or more pulse width modulation (PWM) modules, one or more quadrature encoder inputs (QEI) analogs, one or more 12-bit analog-to-digital converters (ADCs) with 12 analog input channels, details of which are available for the product datasheet.

In one aspect, the processor 244 may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The system memory includes volatile memory and non-volatile memory. The basic input/output system (BIOS), containing the basic routines to transfer information between elements within the computer system, such as during start-up, is stored in non-volatile memory. For example, the non-volatile memory can include ROM, programmable ROM (PROM), electrically programmable ROM (EPROM), EEPROM, or flash memory. Volatile memory includes random-access memory (RAM), which acts as external cache memory. Moreover, RAM is available in many forms such as SRAM, dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM).

The computer system 210 also includes removable/non-removable, volatile/non-volatile computer storage media, such as for example disk storage. The disk storage includes, but is not limited to, devices like a magnetic disk drive, floppy disk drive, tape drive, Jaz drive, Zip drive, LS-60 drive, flash memory card, or memory stick. In addition, the disk storage can include storage media separately or in combination with other storage media including, but not limited to, an optical disc drive such as a compact disc ROM device (CD-ROM), compact disc recordable drive (CD-R Drive), compact disc rewritable drive (CD-RW Drive), or a digital versatile disc ROM drive (DVD-ROM). To facilitate the connection of the disk storage devices to the system bus, a removable or non-removable interface may be employed.

It is to be appreciated that the computer system 210 includes software that acts as an intermediary between users and the basic computer resources described in a suitable operating environment. Such software includes an operating system. The operating system, which can be stored on the disk storage, acts to control and allocate resources of the computer system. System applications take advantage of the management of resources by the operating system through program modules and program data stored either in the system memory or on the disk storage. It is to be appreciated that various components described herein can be implemented with various operating systems or combinations of operating systems.

A user enters commands or information into the computer system 210 through input device(s) coupled to the I/O interface 251. The input devices include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processor through the system bus via interface port(s). The interface port(s) include, for example, a serial port, a parallel port, a game port, and a USB. The output device(s) use some of the same types of ports as input device(s). Thus, for example, a USB port may be used to provide input to the computer system and to output information from the computer system to an output device. An output adapter is provided to illustrate that there are some output devices like monitors, displays, speakers, and printers, among other output devices that require special adapters. The output adapters include, by way of illustration and not limitation, video and sound cards that provide a means of connection between the output device and the system bus. It should be noted that other devices and/or systems of devices, such as remote computer(s), provide both input and output capabilities.

The computer system 210 can operate in a networked environment using logical connections to one or more remote computers, such as cloud computer(s), or local computers. The remote cloud computer(s) can be a personal computer, server, router, network PC, workstation, microprocessor-based appliance, peer device, or other common network node, and the like, and typically includes many or all of the elements described relative to the computer system. For purposes of brevity, only a memory storage device is illustrated with the remote computer(s). The remote computer(s) is logically connected to the computer system through a network interface and then physically connected via a communication connection. The network interface encompasses communication networks such as local area networks (LANs) and wide area networks (WANs). LAN technologies include Fiber Distributed Data Interface (FDDI), Copper Distributed Data Interface (CDDI), Ethernet/IEEE 802.3, Token Ring/IEEE 802.5 and the like. WAN technologies include, but are not limited to, point-to-point links, circuit-switching networks like Integrated Services Digital Networks (ISDN) and variations thereon, packet-switching networks, and Digital Subscriber Lines (DSL).

In various aspects, the computer system 210 of FIG. 10, the imaging module 238 and/or visualization system 208, and/or the processor module 232 of FIGS. 9-10, may comprise an image processor, image-processing engine, media processor, or any specialized digital signal processor (DSP) used for the processing of digital images. The image processor may employ parallel computing with single instruction, multiple data (SIMD) or multiple instruction, multiple data (MIMD) technologies to increase speed and efficiency. The digital image-processing engine can perform a range of tasks. The image processor may be a system on a chip with multicore processor architecture.

The communication connection(s) refers to the hardware/software employed to connect the network interface to the bus. While the communication connection is shown for illustrative clarity inside the computer system, it can also be external to the computer system 210. The hardware/software necessary for connection to the network interface includes, for illustrative purposes only, internal and external technologies such as modems, including regular telephone-grade modems, cable modems, and DSL modems, ISDN adapters, and Ethernet cards.

In various aspects, the devices/instruments 235 described with reference to FIGS. 9-10, may be implemented as ultrasonic surgical instruments and combination energy surgical instruments 7012 as described in FIGS. 23A-23B, 24A-24B, 25-26, 27A-27C, 28A-28C, 29A-29C, 30A-30D, 31A-31D, 32A-32E. Accordingly, the ultrasonic/combination surgical instrument 7012 as described in FIGS. 23A-23B, 24A-24B, 25-26, 27A-27C, 28A-28C, 29A-29C, 30A-30D, 31A-31D, 32A-32E is configured to interface with the modular control tower 236 and the surgical hub 206. Once connected to the surgical hub 206, the ultrasonic/combination surgical instrument 7012 as described in FIGS. 23A-23B, 24A-24B, 25-26, 27A-27C, 28A-28C, 29A-29C, 30A-30D, 31A-31D, 32A-32E is configured to interface with the cloud 204, the server 213, other hub connected instruments, the hub display 215, or the visualization system 209, or combinations thereof. Further, once connected to hub 206, the ultrasonic/combination surgical instrument 7012 as described in FIGS. 23A-23B, 24A-24B, 25-26, 27A-27C, 28A-28C, 29A-29C, 30A-30D, 31A-31D, 32A-32E may utilize the processing circuits available in the hub local computer system 210.

Figure 11:
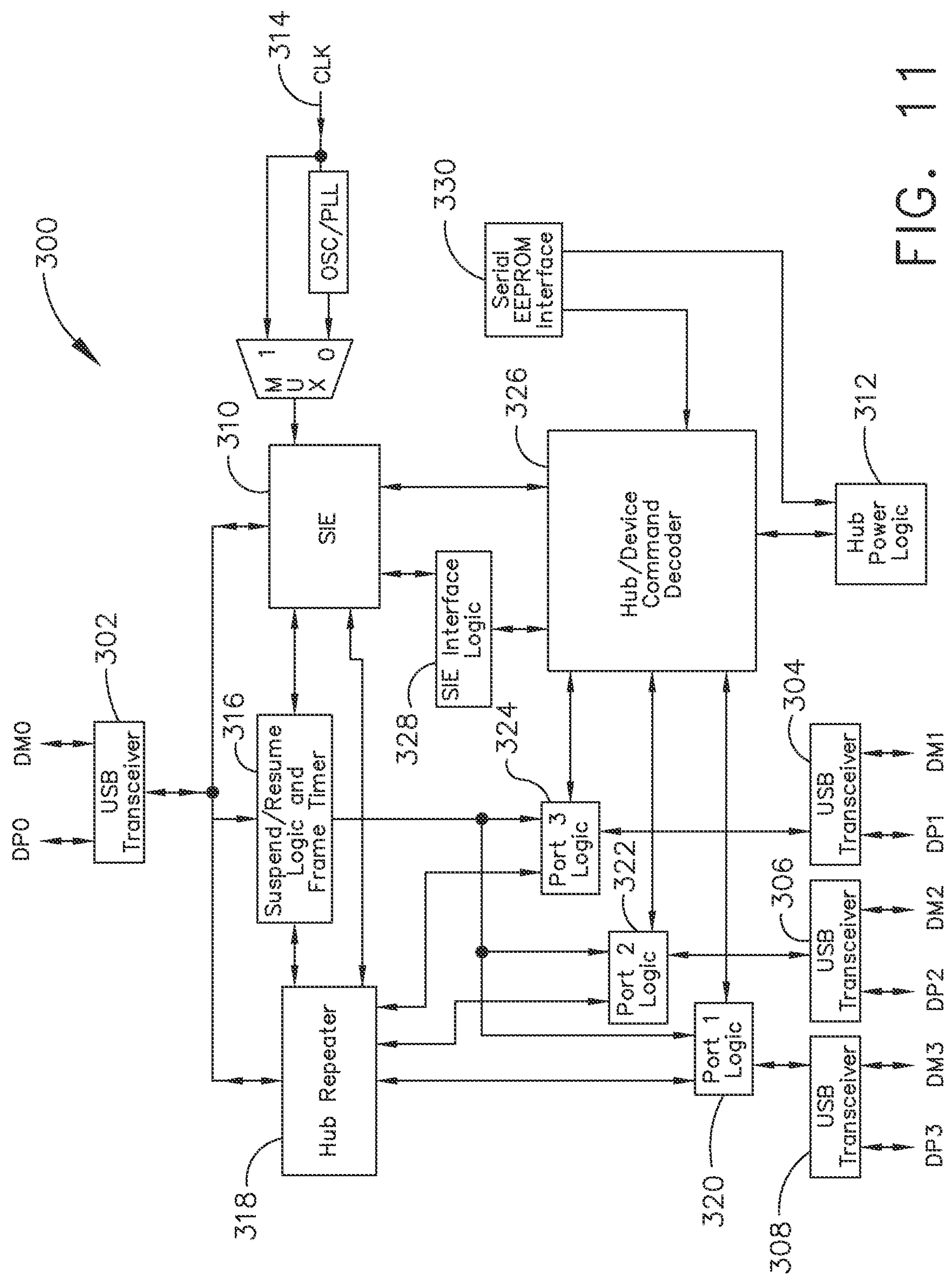
FIG. 11 illustrates one aspect of a Universal Serial Bus (USB) network hub device, in accordance with at least one aspect of the present disclosure.

FIG. 11 illustrates a functional block diagram of one aspect of a USB network hub 300 device, in accordance with at least one aspect of the present disclosure. In the illustrated aspect, the USB network hub device 300 employs a TUSB2036 integrated circuit hub by Texas Instruments. The USB network hub 300 is a CMOS device that provides an upstream USB transceiver port 302 and up to three downstream USB transceiver ports 304, 306, 308 in compliance with the USB 2.0 specification. The upstream USB transceiver port 302 is a differential root data port comprising a differential data minus (DM0) input paired with a differential data plus (DP0) input. The three downstream USB transceiver ports 304, 306, 308 are differential data ports where each port includes differential data plus (DP1-DP3) outputs paired with differential data minus (DM1-DM3) outputs.

The USB network hub 300 device is implemented with a digital state machine instead of a microcontroller, and no firmware programming is required. Fully compliant USB transceivers are integrated into the circuit for the upstream USB transceiver port 302 and all downstream USB transceiver ports 304, 306, 308. The downstream USB transceiver ports 304, 306, 308 support both full-speed and low-speed devices by automatically setting the slew rate according to the speed of the device attached to the ports. The USB network hub 300 device may be configured either in bus-powered or self-powered mode and includes a hub power logic 312 to manage power.

The USB network hub 300 device includes a serial interface engine 310 (SIE). The SIE 310 is the front end of the USB network hub 300 hardware and handles most of the protocol described in chapter 8 of the USB specification. The SIE 310 typically comprehends signaling up to the transaction level. The functions that it handles could include: packet recognition, transaction sequencing, SOP, EOP, RESET, and RESUME signal detection/generation, clock/data separation, non-return-to-zero invert (NRZI) data encoding/decoding and bit-stuffing, CRC generation and checking (token and data), packet ID (PID) generation and checking/decoding, and/or serial-parallel/parallel-serial conversion. The 310 receives a clock input 314 and is coupled to a suspend/resume logic and frame timer 316 circuit and a hub repeater circuit 318 to control communication between the upstream USB transceiver port 302 and the downstream USB transceiver ports 304, 306, 308 through port logic circuits 320, 322, 324. The SIE 310 is coupled to a command decoder 326 via interface logic 328 to control commands from a serial EEPROM via a serial EEPROM interface 330.

In various aspects, the USB network hub 300 can connect 127 functions configured in up to six logical layers (tiers) to a single computer. Further, the USB network hub 300 can connect to all peripherals using a standardized four-wire cable that provides both communication and power distribution. The power configurations are bus-powered and self-powered modes. The USB network hub 300 may be configured to support four modes of power management: a bus-powered hub, with either individual-port power management or ganged-port power management, and the self-powered hub, with either individual-port power management or ganged-port power management. In one aspect, using a USB cable, the USB network hub 300, the upstream USB transceiver port 302 is plugged into a USB host controller, and the downstream USB transceiver ports 304, 306, 308 are exposed for connecting USB compatible devices, and so forth.

Additional details regarding the structure and function of the surgical hub and/or surgical hub networks can be found in U.S. Provisional Patent Application Ser. No. 62/659,900, titled METHOD OF HUB COMMUNICATION, filed Apr. 19, 2018, which is hereby incorporated by reference herein in its entirety.

Cloud System Hardware and Functional Modules

Figure 12:
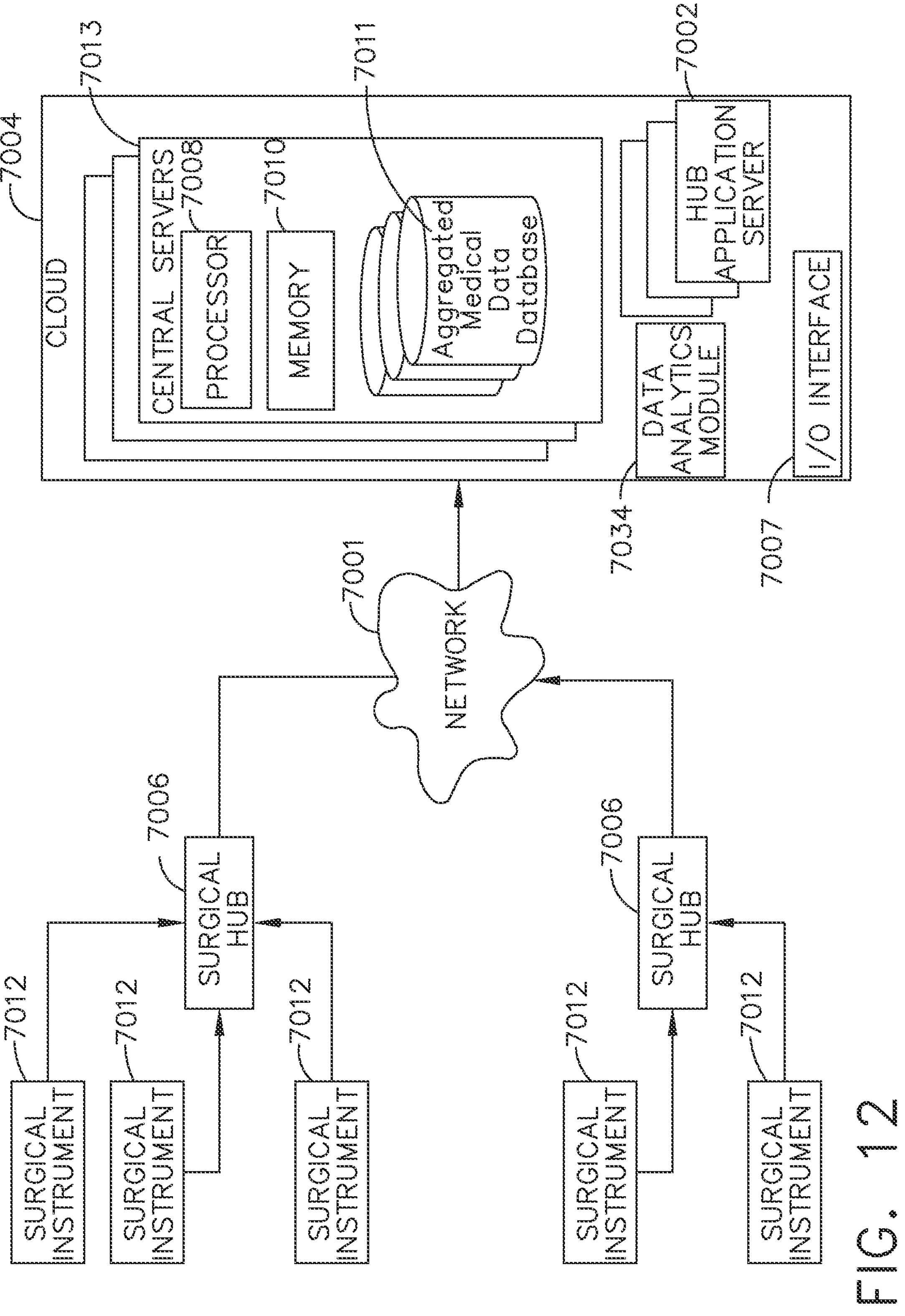
FIG. 12 is a block diagram of a cloud computing system comprising a plurality of smart surgical instruments coupled to surgical hubs that may connect to the cloud component of the cloud computing system, in accordance with at least one aspect of the present disclosure.

FIG. 12 is a block diagram of the computer-implemented interactive surgical system, in accordance with at least one aspect of the present disclosure. In one aspect, the computer-implemented interactive surgical system is configured to monitor and analyze data related to the operation of various surgical systems that include surgical hubs, surgical instruments, robotic devices and operating theaters or healthcare facilities. The computer-implemented interactive surgical system comprises a cloud-based analytics system. Although the cloud-based analytics system is described as a surgical system, it is not necessarily limited as such and could be a cloud-based medical system generally. As illustrated in FIG. 12, the cloud-based analytics system comprises a plurality of surgical instruments 7012 (may be the same or similar to instruments 112), a plurality of surgical hubs 7006 (may be the same or similar to hubs 106), and a surgical data network 7001 (may be the same or similar to network 201) to couple the surgical hubs 7006 to the cloud 7004 (may be the same or similar to cloud 204). Each of the plurality of surgical hubs 7006 is communicatively coupled to one or more surgical instruments 7012. The hubs 7006 are also communicatively coupled to the cloud 7004 of the computer-implemented interactive surgical system via the network 7001. The cloud 7004 is a remote centralized source of hardware and software for storing, manipulating, and communicating data generated based on the operation of various surgical systems. As shown in FIG. 12, access to the cloud 7004 is achieved via the network 7001, which may be the Internet or some other suitable computer network. Surgical hubs 7006 that are coupled to the cloud 7004 can be considered the client side of the cloud computing system (i.e., cloud-based analytics system). Surgical instruments 7012 are paired with the surgical hubs 7006 for control and implementation of various surgical procedures or operations as described herein.

In addition, surgical instruments 7012 may comprise transceivers for data transmission to and from their corresponding surgical hubs 7006 (which may also comprise transceivers). Combinations of surgical instruments 7012 and corresponding hubs 7006 may indicate particular locations, such as operating theaters in healthcare facilities (e.g., hospitals), for providing medical operations. For example, the memory of a surgical hub 7006 may store location data. As shown in FIG. 12, the cloud 7004 comprises central servers 7013 (which may be same or similar to remote server 113 in FIG. 1 and/or remote server 213 in FIG. 9), hub application servers 7002, data analytics modules 7034, and an input/output ("I/O") interface 7007. The central servers 7013 of the cloud 7004 collectively administer the cloud computing system, which includes monitoring requests by client surgical hubs 7006 and managing the processing capacity of the cloud 7004 for executing the requests. Each of the central servers 7013 comprises one or more processors 7008 coupled to suitable memory devices 7010 which can include volatile memory such as random-access memory (RAM) and non-volatile memory such as magnetic storage devices. The memory devices 7010 may comprise machine executable instructions that when executed cause the processors 7008 to execute the data analytics modules 7034 for the cloud-based data analysis, operations, recommendations and other operations described below. Moreover, the processors 7008 can execute the data analytics modules 7034 independently or in conjunction with hub applications independently executed by the hubs 7006. The central servers 7013 also comprise aggregated medical data databases 2212, which can reside in the memory 2210.

Based on connections to various surgical hubs 7006 via the network 7001, the cloud 7004 can aggregate data from specific data generated by various surgical instruments 7012 and their corresponding hubs 7006. Such aggregated data may be stored within the aggregated medical databases 7011 of the cloud 7004. In particular, the cloud 7004 may advantageously perform data analysis and operations on the aggregated data to yield insights and/or perform functions that individual hubs 7006 could not achieve on their own. To this end, as shown in FIG. 12, the cloud 7004 and the surgical hubs 7006 are communicatively coupled to transmit and receive information. The I/O interface 7007 is connected to the plurality of surgical hubs 7006 via the network 7001. In this way, the I/O interface 7007 can be configured to transfer information between the surgical hubs 7006 and the aggregated medical data databases 7011. Accordingly, the I/O interface 7007 may facilitate read/write operations of the cloud-based analytics system. Such read/write operations may be executed in response to requests from hubs 7006. These requests could be transmitted to the hubs 7006 through the hub applications. The I/O interface 7007 may include one or more high speed data ports, which may include universal serial bus (USB) ports, IEEE 1394 ports, as well as Wi-Fi and Bluetooth I/O interfaces for connecting the cloud 7004 to hubs 7006. The hub application servers 7002 of the cloud 7004 are configured to host and supply shared capabilities to software applications (e.g. hub applications) executed by surgical hubs 7006. For example, the hub application servers 7002 may manage requests made by the hub applications through the hubs 7006, control access to the aggregated medical data databases 7011, and perform load balancing. The data analytics modules 7034 are described in further detail with reference to FIG. 13.

The particular cloud computing system configuration described in the present disclosure is specifically designed to address various issues arising in the context of medical operations and procedures performed using medical devices, such as the surgical instruments 7012, 112. In particular, the surgical instruments 7012 may be digital surgical devices configured to interact with the cloud 7004 for implementing techniques to improve the performance of surgical operations. Various surgical instruments 7012 and/or surgical hubs 7006 may comprise touch controlled user interfaces such that clinicians may control aspects of interaction between the surgical instruments 7012 and the cloud 7004. Other suitable user interfaces for control such as auditory controlled user interfaces can also be used.

Figure 13:
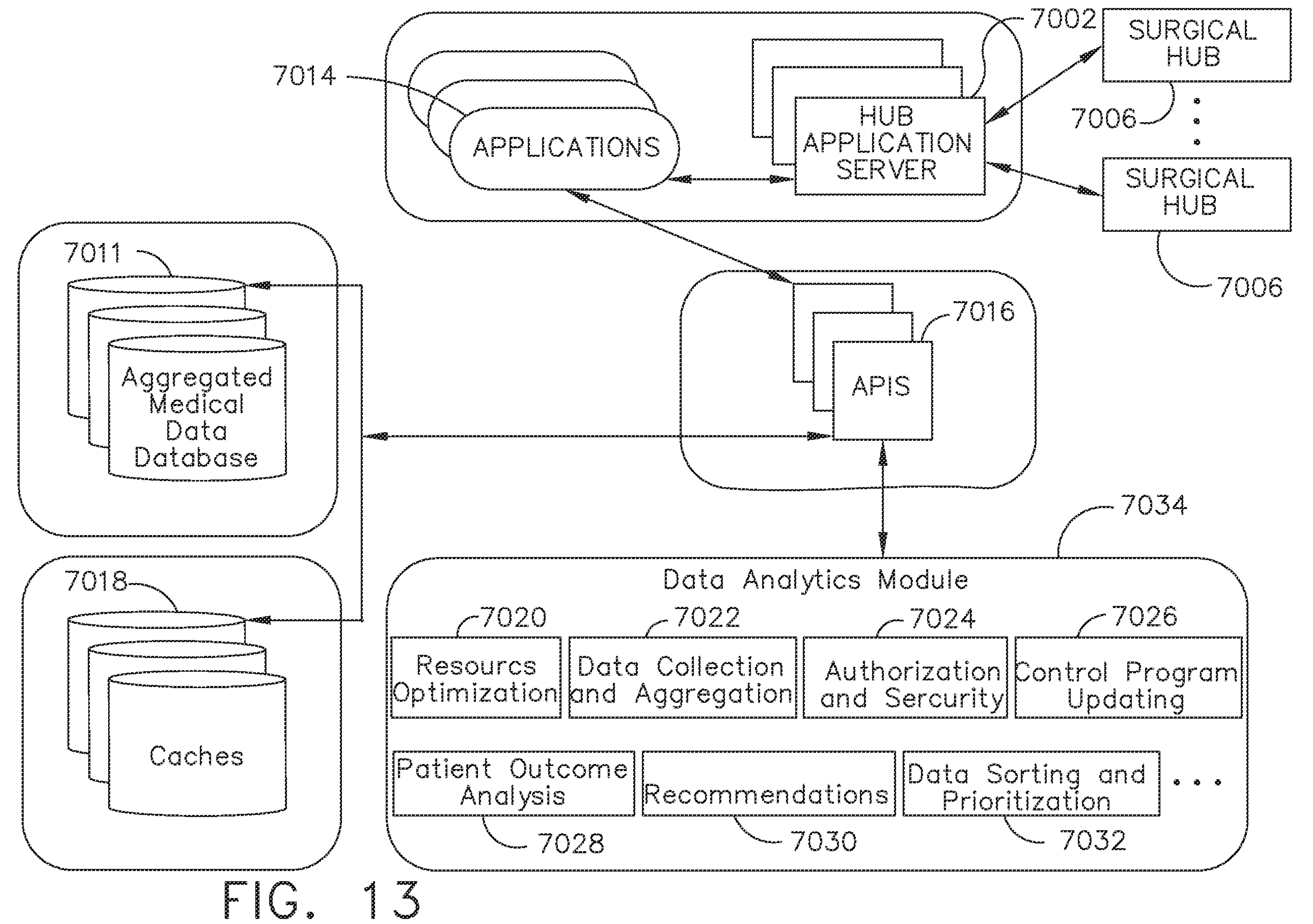
FIG. 13 is a functional module architecture of a cloud computing system, in accordance with at least one aspect of the present disclosure.

FIG. 13 is a block diagram which illustrates the functional architecture of the computer-implemented interactive surgical system, in accordance with at least one aspect of the present disclosure. The cloud-based analytics system includes a plurality of data analytics modules 7034 that may be executed by the processors 7008 of the cloud 7004 for providing data analytic solutions to problems specifically arising in the medical field. As shown in FIG. 13, the functions of the cloud-based data analytics modules 7034 may be assisted via hub applications 7014 hosted by the hub application servers 7002 that may be accessed on surgical hubs 7006. The cloud processors 7008 and hub applications 7014 may operate in conjunction to execute the data analytics modules 7034. Application program interfaces (APIs) 7016 define the set of protocols and routines corresponding to the hub applications 7014. Additionally, the APIs 7016 manage the storing and retrieval of data into and from the aggregated medical data databases 7011 for the operations of the applications 7014. The caches 7018 also store data (e.g., temporarily) and are coupled to the APIs 7016 for more efficient retrieval of data used by the applications 7014. The data analytics modules 7034 in FIG. 13 include modules for resource optimization 7020, data collection and aggregation 7022, authorization and security 7024, control program updating 7026, patient outcome analysis 7028, recommendations 7030, and data sorting and prioritization 7032. Other suitable data analytics modules could also be implemented by the cloud 7004, according to some aspects. In one aspect, the data analytics modules are used for specific recommendations based on analyzing trends, outcomes, and other data.

For example, the data collection and aggregation module 7022 could be used to generate self-describing data (e.g., metadata) including identification of notable features or configuration (e.g., trends), management of redundant data sets, and storage of the data in paired data sets which can be grouped by surgery but not necessarily keyed to actual surgical dates and surgeons. In particular, pair data sets generated from operations of surgical instruments 7012 can comprise applying a binary classification, e.g., a bleeding or a non-bleeding event. More generally, the binary classification may be characterized as either a desirable event (e.g., a successful surgical procedure) or an undesirable event (e.g., a misfired or misused surgical instrument 7012). The aggregated self-describing data may correspond to individual data received from various groups or subgroups of surgical hubs 7006. Accordingly, the data collection and aggregation module 7022 can generate aggregated metadata or other organized data based on raw data received from the surgical hubs 7006. To this end, the processors 7008 can be operationally coupled to the hub applications 7014 and aggregated medical data databases 7011 for executing the data analytics modules 7034. The data collection and aggregation module 7022 may store the aggregated organized data into the aggregated medical data databases 2212.

The resource optimization module 7020 can be configured to analyze this aggregated data to determine an optimal usage of resources for a particular or group of healthcare facilities. For example, the resource optimization module 7020 may determine an optimal order point of surgical stapling instruments 7012 for a group of healthcare facilities based on corresponding predicted demand of such instruments 7012. The resource optimization module 7020 might also assess the resource usage or other operational configurations of various healthcare facilities to determine whether resource usage could be improved. Similarly, the recommendations module 7030 can be configured to analyze aggregated organized data from the data collection and aggregation module 7022 to provide recommendations. For example, the recommendations module 7030 could recommend to healthcare facilities (e.g., medical service providers such as hospitals) that a particular surgical instrument 7012 should be upgraded to an improved version based on a higher than expected error rate, for example. Additionally, the recommendations module 7030 and/or resource optimization module 7020 could recommend better supply chain parameters such as product reorder points and provide suggestions of different surgical instrument 7012, uses thereof, or procedure steps to improve surgical outcomes. The healthcare facilities can receive such recommendations via corresponding surgical hubs 7006. More specific recommendations regarding parameters or configurations of various surgical instruments 7012 can also be provided. Hubs 7006 and/or surgical instruments 7012 each could also have display screens that display data or recommendations provided by the cloud 7004.

The patient outcome analysis module 7028 can analyze surgical outcomes associated with currently used operational parameters of surgical instruments 7012. The patient outcome analysis module 7028 may also analyze and assess other potential operational parameters. In this connection, the recommendations module 7030 could recommend using these other potential operational parameters based on yielding better surgical outcomes, such as better sealing or less bleeding. For example, the recommendations module 7030 could transmit recommendations to a surgical hub 7006 regarding when to use a particular cartridge for a corresponding stapling surgical instrument 7012. Thus, the cloud-based analytics system, while controlling for common variables, may be configured to analyze the large collection of raw data and to provide centralized recommendations over multiple healthcare facilities (advantageously determined based on aggregated data). For example, the cloud-based analytics system could analyze, evaluate, and/or aggregate data based on type of medical practice, type of patient, number of patients, geographic similarity between medical providers, which medical providers/facilities use similar types of instruments, etc., in a way that no single healthcare facility alone would be able to analyze independently.

The control program updating module 7026 could be configured to implement various surgical instrument 7012 recommendations when corresponding control programs are updated. For example, the patient outcome analysis module 7028 could identify correlations linking specific control parameters with successful (or unsuccessful) results. Such correlations may be addressed when updated control programs are transmitted to surgical instruments 7012 via the control program updating module 7026. Updates to instruments 7012 that are transmitted via a corresponding hub 7006 may incorporate aggregated performance data that was gathered and analyzed by the data collection and aggregation module 7022 of the cloud 7004. Additionally, the patient outcome analysis module 7028 and recommendations module 7030 could identify improved methods of using instruments 7012 based on aggregated performance data.

The cloud-based analytics system may include security features implemented by the cloud 7004. These security features may be managed by the authorization and security module 7024. Each surgical hub 7006 can have associated unique credentials such as username, password, and other suitable security credentials. These credentials could be stored in the memory 7010 and be associated with a permitted cloud access level. For example, based on providing accurate credentials, a surgical hub 7006 may be granted access to communicate with the cloud to a predetermined extent (e.g., may only engage in transmitting or receiving certain defined types of information). To this end, the aggregated medical data databases 7011 of the cloud 7004 may comprise a database of authorized credentials for verifying the accuracy of provided credentials. Different credentials may be associated with varying levels of permission for interaction with the cloud 7004, such as a predetermined access level for receiving the data analytics generated by the cloud 7004.

Furthermore, for security purposes, the cloud could maintain a database of hubs 7006, instruments 7012, and other devices that may comprise a "black list" of prohibited devices. In particular, a surgical hub 7006 listed on the black list may not be permitted to interact with the cloud, while surgical instruments 7012 listed on the black list may not have functional access to a corresponding hub 7006 and/or may be prevented from fully functioning when paired to its corresponding hub 7006. Additionally or alternatively, the cloud 7004 may flag instruments 7012 based on incompatibility or other specified criteria. In this manner, counterfeit medical devices and improper reuse of such devices throughout the cloud-based analytics system can be identified and addressed.

The surgical instruments 7012 may use wireless transceivers to transmit wireless signals that may represent, for example, authorization credentials for access to corresponding hubs 7006 and the cloud 7004. Wired transceivers may also be used to transmit signals. Such authorization credentials can be stored in the respective memory devices of the surgical instruments 7012. The authorization and security module 7024 can determine whether the authorization credentials are accurate or counterfeit. The authorization and security module 7024 may also dynamically generate authorization credentials for enhanced security. The credentials could also be encrypted, such as by using hash based encryption. Upon transmitting proper authorization, the surgical instruments 7012 may transmit a signal to the corresponding hubs 7006 and ultimately the cloud 7004 to indicate that the instruments 7012 are ready to obtain and transmit medical data. In response, the cloud 7004 may transition into a state enabled for receiving medical data for storage into the aggregated medical data databases 7011. This data transmission readiness could be indicated by a light indicator on the instruments 7012, for example. The cloud 7004 can also transmit signals to surgical instruments 7012 for updating their associated control programs. The cloud 7004 can transmit signals that are directed to a particular class of surgical instruments 7012 (e.g., electrosurgical instruments) so that software updates to control programs are only transmitted to the appropriate surgical instruments 7012. Moreover, the cloud 7004 could be used to implement system wide solutions to address local or global problems based on selective data transmission and authorization credentials. For example, if a group of surgical instruments 7012 are identified as having a common manufacturing defect, the cloud 7004 may change the authorization credentials corresponding to this group to implement an operational lockout of the group.

The cloud-based analytics system may allow for monitoring multiple healthcare facilities (e.g., medical facilities like hospitals) to determine improved practices and recommend changes (via the recommendations module 2030, for example) accordingly. Thus, the processors 7008 of the cloud 7004 can analyze data associated with an individual healthcare facility to identify the facility and aggregate the data with other data associated with other healthcare facilities in a group. Groups could be defined based on similar operating practices or geographical location, for example. In this way, the cloud 7004 may provide healthcare facility group wide analysis and recommendations. The cloud-based analytics system could also be used for enhanced situational awareness. For example, the processors 7008 may predictively model the effects of recommendations on the cost and effectiveness for a particular facility (relative to overall operations and/or various medical procedures). The cost and effectiveness associated with that particular facility can also be compared to a corresponding local region of other facilities or any other comparable facilities.

The data sorting and prioritization module 7032 may prioritize and sort data based on criticality (e.g., the severity of a medical event associated with the data, unexpectedness, suspiciousness). This sorting and prioritization may be used in conjunction with the functions of the other data analytics modules 7034 described above to improve the cloud-based analytics and operations described herein. For example, the data sorting and prioritization module 7032 can assign a priority to the data analysis performed by the data collection and aggregation module 7022 and patient outcome analysis modules 7028. Different prioritization levels can result in particular responses from the cloud 7004 (corresponding to a level of urgency) such as escalation for an expedited response, special processing, exclusion from the aggregated medical data databases 7011, or other suitable responses. Moreover, if necessary, the cloud 7004 can transmit a request (e.g. a push message) through the hub application servers for additional data from corresponding surgical instruments 7012. The push message can result in a notification displayed on the corresponding hubs 7006 for requesting supporting or additional data. This push message may be required in situations in which the cloud detects a significant irregularity or outlier and the cloud cannot determine the cause of the irregularity. The central servers 7013 may be programmed to trigger this push message in certain significant circumstances, such as when data is determined to be different from an expected value beyond a predetermined threshold or when it appears security has been comprised, for example.

In various aspects, the surgical instrument(s) 7012 described above with reference to FIGS. 12 and 13, may be implemented as ultrasonic surgical instruments and combination energy surgical instruments 7012 as described in FIGS. 23A-23B, 24A-24B, 25-26, 27A-27C, 28A-28C, 29A-29C, 30A-30D, 31A-31D, 32A-32E. Accordingly, the as ultrasonic surgical instrument and combination energy surgical instrument 7012 as described in FIGS. 23A-23B, 24A-24B, 25-26, 27A-27C, 28A-28C, 29A-29C, 30A-30D, 31A-31D, 32A-32E is configured to interface with the surgical hub 7006 and the network 2001, which is configured to interface with cloud 7004. Accordingly, the processing power provided by the central servers 7013 and the data analytics module 7034 are configured to process information (e.g., data and control) from the as ultrasonic surgical instrument and combination energy surgical instrument 7012 as described in FIGS. 23A-23B, 24A-24B, 25-26, 27A-27C, 28A-28C, 29A-29C, 30A-30D, 31A-31D, 32A-32E.

Additional details regarding the cloud analysis system can be found in U.S. Provisional Patent Application Ser. No. 62/659,900, titled METHOD OF HUB COMMUNICATION, filed Apr. 19, 2018, which is hereby incorporated by reference herein in its entirety.

Situational Awareness

Although an "intelligent" device including control algorithms that respond to sensed data can be an improvement over a "dumb" device that operates without accounting for sensed data, some sensed data can be incomplete or inconclusive when considered in isolation, i.e., without the context of the type of surgical procedure being performed or the type of tissue that is being operated on. Without knowing the procedural context (e.g., knowing the type of tissue being operated on or the type of procedure being performed), the control algorithm may control the modular device incorrectly or suboptimally given the particular context-free sensed data. For example, the optimal manner for a control algorithm to control a surgical instrument in response to a particular sensed parameter can vary according to the particular tissue type being operated on. This is due to the fact that different tissue types have different properties (e.g., resistance to tearing) and thus respond differently to actions taken by surgical instruments. Therefore, it may be desirable for a surgical instrument to take different actions even when the same measurement for a particular parameter is sensed. As one specific example, the optimal manner in which to control a surgical stapling and cutting instrument in response to the instrument sensing an unexpectedly high force to close its end effector will vary depending upon whether the tissue type is susceptible or resistant to tearing. For tissues that are susceptible to tearing, such as lung tissue, the instrument's control algorithm would optimally ramp down the motor in response to an unexpectedly high force to close to avoid tearing the tissue. For tissues that are resistant to tearing, such as stomach tissue, the instrument's control algorithm would optimally ramp up the motor in response to an unexpectedly high force to close to ensure that the end effector is clamped properly on the tissue. Without knowing whether lung or stomach tissue has been clamped, the control algorithm may make a suboptimal decision.

Figure 14:
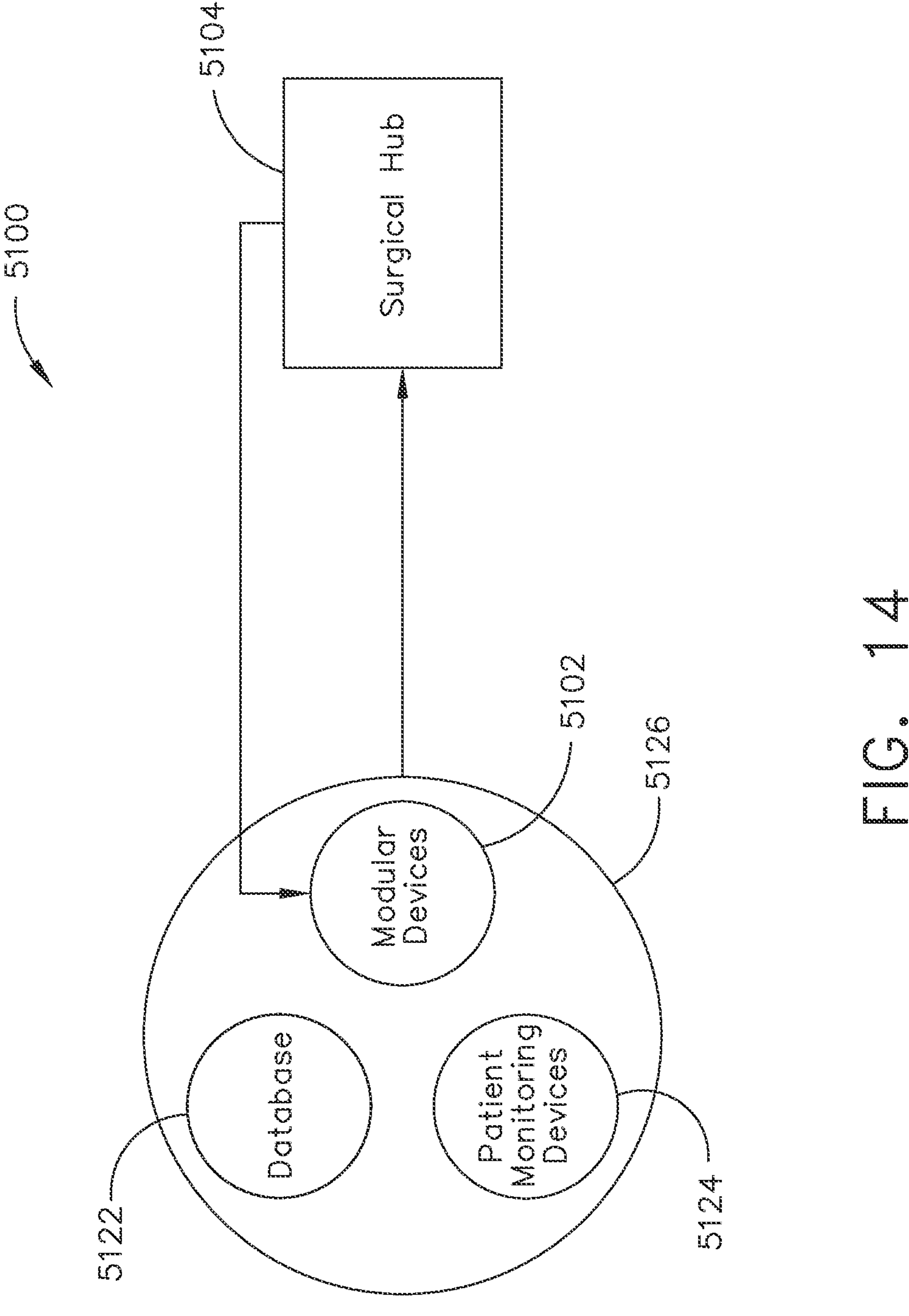
FIG. 14 illustrates a diagram of a situationally aware surgical system, in accordance with at least one aspect of the present disclosure.

One solution utilizes a surgical hub including a system that is configured to derive information about the surgical procedure being performed based on data received from various data sources and then control the paired modular devices accordingly. In other words, the surgical hub is configured to infer information about the surgical procedure from received data and then control the modular devices paired to the surgical hub based upon the inferred context of the surgical procedure. FIG. 14 illustrates a diagram of a situationally aware surgical system 5100, in accordance with at least one aspect of the present disclosure. In some exemplifications, the data sources 5126 include, for example, the modular devices 5102 (which can include sensors configured to detect parameters associated with the patient and/or the modular device itself), databases 5122 (e.g., an EMR database containing patient records), and patient monitoring devices 5124 (e.g., a blood pressure (BP) monitor and an electrocardiography (EKG) monitor).

A surgical hub 5104, which may be similar to the hub 106 in many respects, can be configured to derive the contextual information pertaining to the surgical procedure from the data based upon, for example, the particular combination(s) of received data or the particular order in which the data is received from the data sources 5126. The contextual information inferred from the received data can include, for example, the type of surgical procedure being performed, the particular step of the surgical procedure that the surgeon is performing, the type of tissue being operated on, or the body cavity that is the subject of the procedure. This ability by some aspects of the surgical hub 5104 to derive or infer information related to the surgical procedure from received data can be referred to as "situational awareness." In one exemplification, the surgical hub 5104 can incorporate a situational awareness system, which is the hardware and/or programming associated with the surgical hub 5104 that derives contextual information pertaining to the surgical procedure from the received data.

The situational awareness system of the surgical hub 5104 can be configured to derive the contextual information from the data received from the data sources 5126 in a variety of different ways. In one exemplification, the situational awareness system includes a pattern recognition system, or machine learning system (e.g., an artificial neural network), that has been trained on training data to correlate various inputs (e.g., data from databases 5122, patient monitoring devices 5124, and/or modular devices 5102) to corresponding contextual information regarding a surgical procedure. In other words, a machine learning system can be trained to accurately derive contextual information regarding a surgical procedure from the provided inputs. In another exemplification, the situational awareness system can include a lookup table storing pre-characterized contextual information regarding a surgical procedure in association with one or more inputs (or ranges of inputs) corresponding to the contextual information. In response to a query with one or more inputs, the lookup table can return the corresponding contextual information for the situational awareness system for controlling the modular devices 5102. In one exemplification, the contextual information received by the situational awareness system of the surgical hub 5104 is associated with a particular control adjustment or set of control adjustments for one or more modular devices 5102. In another exemplification, the situational awareness system includes a further machine learning system, lookup table, or other such system, which generates or retrieves one or more control adjustments for one or more modular devices 5102 when provided the contextual information as input.

A surgical hub 5104 incorporating a situational awareness system provides a number of benefits for the surgical system 5100. One benefit includes improving the interpretation of sensed and collected data, which would in turn improve the processing accuracy and/or the usage of the data during the course of a surgical procedure. To return to a previous example, a situationally aware surgical hub 5104 could determine what type of tissue was being operated on; therefore, when an unexpectedly high force to close the surgical instrument's end effector is detected, the situationally aware surgical hub 5104 could correctly ramp up or ramp down the motor of the surgical instrument for the type of tissue.

As another example, the type of tissue being operated can affect the adjustments that are made to the compression rate and load thresholds of a surgical stapling and cutting instrument for a particular tissue gap measurement. A situationally aware surgical hub 5104 could infer whether a surgical procedure being performed is a thoracic or an abdominal procedure, allowing the surgical hub 5104 to determine whether the tissue clamped by an end effector of the surgical stapling and cutting instrument is lung (for a thoracic procedure) or stomach (for an abdominal procedure) tissue. The surgical hub 5104 could then adjust the compression rate and load thresholds of the surgical stapling and cutting instrument appropriately for the type of tissue.

As yet another example, the type of body cavity being operated in during an insufflation procedure can affect the function of a smoke evacuator. A situationally aware surgical hub 5104 could determine whether the surgical site is under pressure (by determining that the surgical procedure is utilizing insufflation) and determine the procedure type. As a procedure type is generally performed in a specific body cavity, the surgical hub 5104 could then control the motor rate of the smoke evacuator appropriately for the body cavity being operated in. Thus, a situationally aware surgical hub 5104 could provide a consistent amount of smoke evacuation for both thoracic and abdominal procedures.

As yet another example, the type of procedure being performed can affect the optimal energy level for an ultrasonic surgical instrument or radio frequency (RF) electrosurgical instrument to operate at. Arthroscopic procedures, for example, require higher energy levels because the end effector of the ultrasonic surgical instrument or RF electrosurgical instrument is immersed in fluid. A situationally aware surgical hub 5104 could determine whether the surgical procedure is an arthroscopic procedure. The surgical hub 5104 could then adjust the RF power level or the ultrasonic amplitude of the generator (i.e., "energy level") to compensate for the fluid filled environment. Relatedly, the type of tissue being operated on can affect the optimal energy level for an ultrasonic surgical instrument or RF electrosurgical instrument to operate at. A situationally aware surgical hub 5104 could determine what type of surgical procedure is being performed and then customize the energy level for the ultrasonic surgical instrument or RF electrosurgical instrument, respectively, according to the expected tissue profile for the surgical procedure. Furthermore, a situationally aware surgical hub 5104 can be configured to adjust the energy level for the ultrasonic surgical instrument or RF electrosurgical instrument throughout the course of a surgical procedure, rather than just on a procedure-by-procedure basis. A situationally aware surgical hub 5104 could determine what step of the surgical procedure is being performed or will subsequently be performed and then update the control algorithms for the generator and/or ultrasonic surgical instrument or RF electrosurgical instrument to set the energy level at a value appropriate for the expected tissue type according to the surgical procedure step.

As yet another example, data can be drawn from additional data sources 5126 to improve the conclusions that the surgical hub 5104 draws from one data source 5126. A situationally aware surgical hub 5104 could augment data that it receives from the modular devices 5102 with contextual information that it has built up regarding the surgical procedure from other data sources 5126. For example, a situationally aware surgical hub 5104 can be configured to determine whether hemostasis has occurred (i.e., whether bleeding at a surgical site has stopped) according to video or image data received from a medical imaging device. However, in some cases the video or image data can be inconclusive. Therefore, in one exemplification, the surgical hub 5104 can be further configured to compare a physiologic measurement (e.g., blood pressure sensed by a BP monitor communicably connected to the surgical hub 5104) with the visual or image data of hemostasis (e.g., from a medical imaging device 124 (FIG. 2) communicably coupled to the surgical hub 5104) to make a determination on the integrity of the staple line or tissue weld. In other words, the situational awareness system of the surgical hub 5104 can consider the physiological measurement data to provide additional context in analyzing the visualization data. The additional context can be useful when the visualization data may be inconclusive or incomplete on its own.

Another benefit includes proactively and automatically controlling the paired modular devices 5102 according to the particular step of the surgical procedure that is being performed to reduce the number of times that medical personnel are required to interact with or control the surgical system 5100 during the course of a surgical procedure. For example, a situationally aware surgical hub 5104 could proactively activate the generator to which an RF electrosurgical instrument is connected if it determines that a subsequent step of the procedure requires the use of the instrument. Proactively activating the energy source allows the instrument to be ready for use a soon as the preceding step of the procedure is completed.

As another example, a situationally aware surgical hub 5104 could determine whether the current or subsequent step of the surgical procedure requires a different view or degree of magnification on the display according to the feature(s) at the surgical site that the surgeon is expected to need to view. The surgical hub 5104 could then proactively change the displayed view (supplied by, e.g., a medical imaging device for the visualization system 108) accordingly so that the display automatically adjusts throughout the surgical procedure.

As yet another example, a situationally aware surgical hub 5104 could determine which step of the surgical procedure is being performed or will subsequently be performed and whether particular data or comparisons between data will be required for that step of the surgical procedure. The surgical hub 5104 can be configured to automatically call up data screens based upon the step of the surgical procedure being performed, without waiting for the surgeon to ask for the particular information.

Another benefit includes checking for errors during the setup of the surgical procedure or during the course of the surgical procedure. For example, a situationally aware surgical hub 5104 could determine whether the operating theater is setup properly or optimally for the surgical procedure to be performed. The surgical hub 5104 can be configured to determine the type of surgical procedure being performed, retrieve the corresponding checklists, product location, or setup needs (e.g., from a memory), and then compare the current operating theater layout to the standard layout for the type of surgical procedure that the surgical hub 5104 determines is being performed. In one exemplification, the surgical hub 5104 can be configured to compare the list of items for the procedure scanned by a suitable scanner, for example, and/or a list of devices paired with the surgical hub 5104 to a recommended or anticipated manifest of items and/or devices for the given surgical procedure. If there are any discontinuities between the lists, the surgical hub 5104 can be configured to provide an alert indicating that a particular modular device 5102, patient monitoring device 5124, and/or other surgical item is missing. In one exemplification, the surgical hub 5104 can be configured to determine the relative distance or position of the modular devices 5102 and patient monitoring devices 5124 via proximity sensors, for example. The surgical hub 5104 can compare the relative positions of the devices to a recommended or anticipated layout for the particular surgical procedure. If there are any discontinuities between the layouts, the surgical hub 5104 can be configured to provide an alert indicating that the current layout for the surgical procedure deviates from the recommended layout.

As another example, a situationally aware surgical hub 5104 could determine whether the surgeon (or other medical personnel) was making an error or otherwise deviating from the expected course of action during the course of a surgical procedure. For example, the surgical hub 5104 can be configured to determine the type of surgical procedure being performed, retrieve the corresponding list of steps or order of equipment usage (e.g., from a memory), and then compare the steps being performed or the equipment being used during the course of the surgical procedure to the expected steps or equipment for the type of surgical procedure that the surgical hub 5104 determined is being performed. In one exemplification, the surgical hub 5104 can be configured to provide an alert indicating that an unexpected action is being performed or an unexpected device is being utilized at the particular step in the surgical procedure.

Overall, the situational awareness system for the surgical hub 5104 improves surgical procedure outcomes by adjusting the surgical instruments (and other modular devices 5102) for the particular context of each surgical procedure (such as adjusting to different tissue types) and validating actions during a surgical procedure. The situational awareness system also improves surgeons' efficiency in performing surgical procedures by automatically suggesting next steps, providing data, and adjusting displays and other modular devices 5102 in the surgical theater according to the specific context of the procedure.

Referring now to FIG. 15, a timeline 5200 depicting situational awareness of a hub, such as the surgical hub 106 or 206 (FIGS. 1-11), for example, is depicted. The timeline 5200 is an illustrative surgical procedure and the contextual information that the surgical hub 106, 206 can derive from the data received from the data sources at each step in the surgical procedure. The timeline 5200 depicts the typical steps that would be taken by the nurses, surgeons, and other medical personnel during the course of a lung segmentectomy procedure, beginning with setting up the operating theater and ending with transferring the patient to a post-operative recovery room.

The situationally aware surgical hub 106, 206 receives data from the data sources throughout the course of the surgical procedure, including data generated each time medical personnel utilize a modular device that is paired with the surgical hub 106, 206. The surgical hub 106, 206 can receive this data from the paired modular devices and other data sources and continually derive inferences (i.e., contextual information) about the ongoing procedure as new data is received, such as which step of the procedure is being performed at any given time. The situational awareness system of the surgical hub 106, 206 is able to, for example, record data pertaining to the procedure for generating reports, verify the steps being taken by the medical personnel, provide data or prompts (e.g., via a display screen) that may be pertinent for the particular procedural step, adjust modular devices based on the context (e.g., activate monitors, adjust the field of view (FOV) of the medical imaging device, or change the energy level of an ultrasonic surgical instrument or RF electrosurgical instrument), and take any other such action described above.

As the first step 5202 in this illustrative procedure, the hospital staff members retrieve the patient's EMR from the hospital's EMR database. Based on select patient data in the EMR, the surgical hub 106, 206 determines that the procedure to be performed is a thoracic procedure.

Second step 5204, the staff members scan the incoming medical supplies for the procedure. The surgical hub 106, 206 cross-references the scanned supplies with a list of supplies that are utilized in various types of procedures and confirms that the mix of supplies corresponds to a thoracic procedure. Further, the surgical hub 106, 206 is also able to determine that the procedure is not a wedge procedure (because the incoming supplies either lack certain supplies that are necessary for a thoracic wedge procedure or do not otherwise correspond to a thoracic wedge procedure).

Third step 5206, the medical personnel scan the patient band via a scanner that is communicably connected to the surgical hub 106, 206. The surgical hub 106, 206 can then confirm the patient's identity based on the scanned data.

Fourth step 5208, the medical staff turns on the auxiliary equipment. The auxiliary equipment being utilized can vary according to the type of surgical procedure and the techniques to be used by the surgeon, but in this illustrative case they include a smoke evacuator, insufflator, and medical imaging device. When activated, the auxiliary equipment that are modular devices can automatically pair with the surgical hub 106, 206 that is located within a particular vicinity of the modular devices as part of their initialization process. The surgical hub 106, 206 can then derive contextual information about the surgical procedure by detecting the types of modular devices that pair with it during this pre-operative or initialization phase. In this particular example, the surgical hub 106, 206 determines that the surgical procedure is a VATS procedure based on this particular combination of paired modular devices. Based on the combination of the data from the patient's EMR, the list of medical supplies to be used in the procedure, and the type of modular devices that connect to the hub, the surgical hub 106, 206 can generally infer the specific procedure that the surgical team will be performing. Once the surgical hub 106, 206 knows what specific procedure is being performed, the surgical hub 106, 206 can then retrieve the steps of that procedure from a memory or from the cloud and then cross-reference the data it subsequently receives from the connected data sources (e.g., modular devices and patient monitoring devices) to infer what step of the surgical procedure the surgical team is performing.

Fifth step 5210, the staff members attach the EKG electrodes and other patient monitoring devices to the patient. The EKG electrodes and other patient monitoring devices are able to pair with the surgical hub 106, 206. As the surgical hub 106, 206 begins receiving data from the patient monitoring devices, the surgical hub 106, 206 thus confirms that the patient is in the operating theater.

Sixth step 5212, the medical personnel induce anesthesia in the patient. The surgical hub 106, 206 can infer that the patient is under anesthesia based on data from the modular devices and/or patient monitoring devices, including EKG data, blood pressure data, ventilator data, or combinations thereof, for example. Upon completion of the sixth step S212, the pre-operative portion of the lung segmentectomy procedure is completed and the operative portion begins.

Seventh step 5214, the patient's lung that is being operated on is collapsed (while ventilation is switched to the contralateral lung). The surgical hub 106, 206 can infer from the ventilator data that the patient's lung has been collapsed, for example. The surgical hub 106, 206 can infer that the operative portion of the procedure has commenced as it can compare the detection of the patient's lung collapsing to the expected steps of the procedure (which can be accessed or retrieved previously) and thereby determine that collapsing the lung is the first operative step in this particular procedure.

Eighth step 5216, the medical imaging device (e.g., a scope) is inserted and video from the medical imaging device is initiated. The surgical hub 106, 206 receives the medical imaging device data (i.e., video or image data) through its connection to the medical imaging device. Upon receipt of the medical imaging device data, the surgical hub 106, 206 can determine that the laparoscopic portion of the surgical procedure has commenced. Further, the surgical hub 106, 206 can determine that the particular procedure being performed is a segmentectomy, as opposed to a lobectomy (note that a wedge procedure has already been discounted by the surgical hub 106, 206 based on data received at the second step 5204 of the procedure). The data from the medical imaging device 124 (FIG. 2) can be utilized to determine contextual information regarding the type of procedure being performed in a number of different ways, including by determining the angle at which the medical imaging device is oriented with respect to the visualization of the patient's anatomy, monitoring the number or medical imaging devices being utilized (i.e., that are activated and paired with the surgical hub 106, 206), and monitoring the types of visualization devices utilized. For example, one technique for performing a VATS lobectomy places the camera in the lower anterior corner of the patient's chest cavity above the diaphragm, whereas one technique for performing a VATS segmentectomy places the camera in an anterior intercostal position relative to the segmental fissure. Using pattern recognition or machine learning techniques, for example, the situational awareness system can be trained to recognize the positioning of the medical imaging device according to the visualization of the patient's anatomy. As another example, one technique for performing a VATS lobectomy utilizes a single medical imaging device, whereas another technique for performing a VATS segmentectomy utilizes multiple cameras. As yet another example, one technique for performing a VATS segmentectomy utilizes an infrared light source (which can be communicably coupled to the surgical hub as part of the visualization system) to visualize the segmental fissure, which is not utilized in a VATS lobectomy. By tracking any or all of this data from the medical imaging device, the surgical hub 106, 206 can thereby determine the specific type of surgical procedure being performed and/or the technique being used for a particular type of surgical procedure.

Ninth step 5218, the surgical team begins the dissection step of the procedure. The surgical hub 106, 206 can infer that the surgeon is in the process of dissecting to mobilize the patient's lung because it receives data from the RF or ultrasonic generator indicating that an energy instrument is being fired. The surgical hub 106, 206 can cross-reference the received data with the retrieved steps of the surgical procedure to determine that an energy instrument being fired at this point in the process (i.e., after the completion of the previously discussed steps of the procedure) corresponds to the dissection step. In certain instances, the energy instrument can be an energy tool mounted to a robotic arm of a robotic surgical system.

Tenth step 5220, the surgical team proceeds to the ligation step of the procedure. The surgical hub 106, 206 can infer that the surgeon is ligating arteries and veins because it receives data from the surgical stapling and cutting instrument indicating that the instrument is being fired. Similarly to the prior step, the surgical hub 106, 206 can derive this inference by cross-referencing the receipt of data from the surgical stapling and cutting instrument with the retrieved steps in the process. In certain instances, the surgical instrument can be a surgical tool mounted to a robotic arm of a robotic surgical system.

Eleventh step 5222, the segmentectomy portion of the procedure is performed. The surgical hub 106, 206 can infer that the surgeon is transecting the parenchyma based on data from the surgical stapling and cutting instrument, including data from its cartridge. The cartridge data can correspond to the size or type of staple being fired by the instrument, for example. As different types of staples are utilized for different types of tissues, the cartridge data can thus indicate the type of tissue being stapled and/or transected. In this case, the type of staple being fired is utilized for parenchyma (or other similar tissue types), which allows the surgical hub 106, 206 to infer that the segmentectomy portion of the procedure is being performed.

Twelfth step 5224, the node dissection step is then performed. The surgical hub 106, 206 can infer that the surgical team is dissecting the node and performing a leak test based on data received from the generator indicating that an RF or ultrasonic instrument is being fired. For this particular procedure, an RF or ultrasonic instrument being utilized after parenchyma was transected corresponds to the node dissection step, which allows the surgical hub 106, 206 to make this inference. It should be noted that surgeons regularly switch back and forth between surgical stapling/cutting instruments and surgical energy (i.e., RF or ultrasonic) instruments depending upon the particular step in the procedure because different instruments are better adapted for particular tasks. Therefore, the particular sequence in which the stapling/cutting instruments and surgical energy instruments are used can indicate what step of the procedure the surgeon is performing. Moreover, in certain instances, robotic tools can be utilized for one or more steps in a surgical procedure and/or handheld surgical instruments can be utilized for one or more steps in the surgical procedure. The surgeon(s) can alternate between robotic tools and handheld surgical instruments and/or can use the devices concurrently, for example. Upon completion of the twelfth step 5224, the incisions are closed up and the post-operative portion of the procedure begins.

Thirteenth step 5226, the patient's anesthesia is reversed. The surgical hub 106, 206 can infer that the patient is emerging from the anesthesia based on the ventilator data (i.e., the patient's breathing rate begins increasing), for example.

Lastly, the fourteenth step 5228 is that the medical personnel remove the various patient monitoring devices from the patient. The surgical hub 106, 206 can thus infer that the patient is being transferred to a recovery room when the hub loses EKG, BP, and other data from the patient monitoring devices. As can be seen from the description of this illustrative procedure, the surgical hub 106, 206 can determine or infer when each step of a given surgical procedure is taking place according to data received from the various data sources that are communicably coupled to the surgical hub 106, 206.

Situational awareness is further described in U.S. Provisional Patent Application Ser. No. 62/659,900, titled METHOD OF HUB COMMUNICATION, filed Apr. 19, 2018, which is herein incorporated by reference in its entirety. In certain instances, operation of a robotic surgical system, including the various robotic surgical systems disclosed herein, for example, can be controlled by the hub 106,

206 based on its situational awareness and/or feedback from the components thereof and/or based on information from the cloud 104.

In one aspect, as described hereinbelow with reference to FIGS. 24-40, the modular device 5102 is implemented as ultrasonic surgical instruments and combination energy surgical instruments 7012 as described in FIGS. 23A-23B, 24A-24B, 25-26, 27A-27C, 28A-28C, 29A-29C, 30A-30D, 31A-31D, 32A-32E. Accordingly, the modular device 5102 implemented as an ultrasonic surgical instrument and combination energy surgical instrument 7012 as described in FIGS. 23A-23B, 24A-24B,25-26, 27A-27C, 28A-28C, 29A-29C, 30A-30D, 31A-31D, 32A-32E is configured to operate as a data source 5126 and to interact with the database 5122 and patient monitoring devices 5124. The modular device 5102 implemented as a ultrasonic surgical instrument and combination energy surgical instrument 7012 as described in FIGS. 23A-23B, 24A-24B, 25-26, 27A-27C, 28A-28C, 29A-29C, 30A-30D, 31A-31D, 32A-32E is further configured to interact with the surgical hub 5104 to provide information (e.g., data and control) to the surgical hub 5104 and receive information (e.g., data and control) from the surgical hub 5104.

In one aspect, as described hereinbelow with reference to FIGS. 24-40, the modular device 5102 is implemented as ultrasonic surgical instruments and combination energy surgical instruments 7012 as described in FIGS. 23A-23B, 24A-24B, 25-26, 27A-27C, 28A-29C, 30A-30D, 31A-31D, 32A-32E. Accordingly, the modular device 5102 implemented as a ultrasonic surgical instrument and combination energy surgical instrument 7012 as described in FIGS. 23A-23B, 24A-24B, 25-26, 27A-27C, 28A-28C, 29A-29C, 30A-30D, 31A-31D, 32A-32E is configured to operate as a data source 5126 and to interact with the database 5122 and patient monitoring devices 5124. The modular device 5102 implemented as a ultrasonic surgical instrument and combination energy surgical instrument 7012 as described in FIGS. 23A-23B, 24A-24B, 25-26, 27A-27C, 28A-28C, 29A-29C, 30A-30D, 31A-31D, 32A-32E is further configured to interact with the surgical hub 5104 to provide information (e.g., data and control) to the surgical hub 5104 and receive information (e.g., data and control) from the surgical hub 5104.

Generator Hardware

Figure 16:
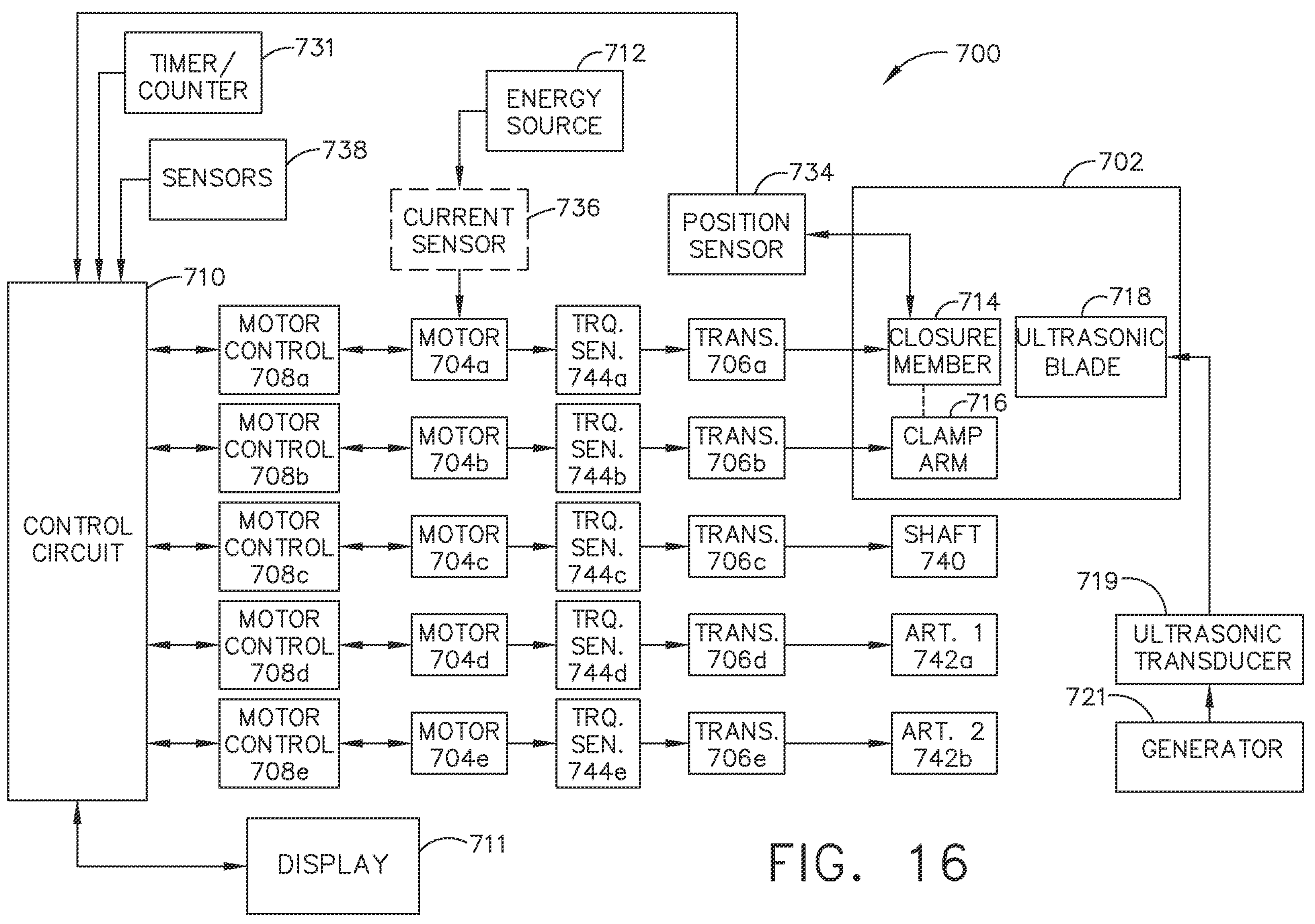
FIG. 16 is a schematic diagram of a robotic surgical instrument configured to operate a surgical tool described herein, in accordance with at least one aspect of the present disclosure.

FIG. 16 is a schematic diagram of a robotic surgical instrument 700 configured to operate a surgical tool described herein according to one aspect of this disclosure. The robotic surgical instrument 700 may be programmed or configured to control distal/proximal translation of a displacement member, distal/proximal displacement of a closure tube, shaft rotation, and articulation, either with single or multiple articulation drive links. In one aspect, the surgical instrument 700 may be programmed or configured to individually control a firing member, a closure member, a shaft member, or one or more articulation members, or combinations thereof. The surgical instrument 700 comprises a control circuit 710 configured to control motor-driven firing members, closure members, shaft members, or one or more articulation members, or combinations thereof.

In one aspect, the robotic surgical instrument 700 comprises a control circuit 710 configured to control a clamp arm 716 and a closure member 714 portion of an end effector 702, an ultrasonic blade 718 coupled to an ultrasonic transducer 719 excited by an ultrasonic generator 721, a shaft 740, and one or more articulation members 742*a*, 742*b* via a plurality of motors 704*a*-704*e*. A position sensor 734 may be configured to provide position feedback of the closure member 714 to the control circuit 710. Other sensors 738 may be configured to provide feedback to the control circuit 710. A timer/counter 731 provides timing and counting information to the control circuit 710. An energy source 712 may be provided to operate the motors 704*a*-704*e*, and a current sensor 736 provides motor current feedback to the control circuit 710. The motors 704*a*-704*e* can be operated individually by the control circuit 710 in an open-loop or closed-loop feedback control.

In one aspect, the control circuit 710 may comprise one or more microcontrollers, microprocessors, or other suitable processors for executing instructions that cause the processor or processors to perform one or more tasks. In one aspect, a timer/counter 731 provides an output signal, such as the elapsed time or a digital count, to the control circuit 710 to correlate the position of the closure member 714 as determined by the position sensor 734 with the output of the timer/counter 731 such that the control circuit 710 can determine the position of the closure member 714 at a specific time (t) relative to a starting position or the time (t) when the closure member 714 is at a specific position relative to a starting position. The timer/counter 731 may be configured to measure elapsed time, count external events, or time external events.

In one aspect, the control circuit 710 may be programmed to control functions of the end effector 702 based on one or more tissue conditions. The control circuit 710 may be programmed to sense tissue conditions, such as thickness, either directly or indirectly, as described herein. The control circuit 710 may be programmed to select a firing control program or closure control program based on tissue conditions. A firing control program may describe the distal motion of the displacement member. Different firing control programs may be selected to better treat different tissue conditions. For example, when thicker tissue is present, the control circuit 710 may be programmed to translate the displacement member at a lower velocity and/or with lower power. When thinner tissue is present, the control circuit 710 may be programmed to translate the displacement member at a higher velocity and/or with higher power. A closure control program may control the closure force applied to the tissue by the clamp arm 716. Other control programs control the rotation of the shaft 740 and the articulation members 742*a*, 742*b*.

In one aspect, the control circuit 710 may generate motor set point signals. The motor set point signals may be provided to various motor controllers 708*a*-708*e*. The motor controllers 708*a*-708*e* may comprise one or more circuits configured to provide motor drive signals to the motors 704*a*-704*e* to drive the motors 704*a*-704*e* as described herein. In some examples, the motors 704*a*-704*e* may be brushed DC electric motors. For example, the velocity of the motors 704*a*-704*e* may be proportional to the respective motor drive signals. In some examples, the motors 704*a*-704*e* may be brushless DC electric motors, and the respective motor drive signals may comprise a PWM signal provided to one or more stator windings of the motors 704*a*-704*e*. Also, in some examples, the motor controllers 708*a*-708*e* may be omitted and the control circuit 710 may generate the motor drive signals directly.

In one aspect, the control circuit 710 may initially operate each of the motors 704*a*-704*e* in an open-loop configuration for a first open-loop portion of a stroke of the displacement member. Based on the response of the robotic surgical instrument 700 during the open-loop portion of the stroke, the control circuit 710 may select a firing control program in a closed-loop configuration. The response of the instrument may include a translation distance of the displacement member during the open-loop portion, a time elapsed during the open-loop portion, the energy provided to one of the motors 704*a*-704*e* during the open-loop portion, a sum of pulse widths of a motor drive signal, etc. After the open-loop portion, the control circuit 710 may implement the selected firing control program for a second portion of the displacement member stroke. For example, during a closed-loop portion of the stroke, the control circuit 710 may modulate one of the motors 704*a*-704*e* based on translation data describing a position of the displacement member in a closed-loop manner to translate the displacement member at a constant velocity.

In one aspect, the motors 704*a*-704*e* may receive power from an energy source 712. The energy source 712 may be a DC power supply driven by a main alternating current power source, a battery, a super capacitor, or any other suitable energy source. The motors 704*a*-704*e* may be mechanically coupled to individual movable mechanical elements such as the closure member 714, clamp arm 716, shaft 740, articulation 742*a*, and articulation 742*b* via respective transmissions 706*a*-706*e*. The transmissions 706*a*-706*e* may include one or more gears or other linkage components to couple the motors 704*a*-704*e* to movable mechanical elements. A position sensor 734 may sense a position of the closure member 714. The position sensor 734 may be or include any type of sensor that is capable of generating position data that indicate a position of the closure member 714. In some examples, the position sensor 734 may include an encoder configured to provide a series of pulses to the control circuit 710 as the closure member 714 translates distally and proximally. The control circuit 710 may track the pulses to determine the position of the closure member 714. Other suitable position sensors may be used, including, for example, a proximity sensor. Other types of position sensors may provide other signals indicating motion of the closure member 714. Also, in some examples, the position sensor 734 may be omitted. Where any of the motors 704*a*-704*e* is a stepper motor, the control circuit 710 may track the position of the closure member 714 by aggregating the number and direction of steps that the motor 704 has been instructed to execute. The position sensor 734 may be located in the end effector 702 or at any other portion of the instrument. The outputs of each of the motors 704*a*-704*e* include a torque sensor 744*a*-744*e* to sense force and have an encoder to sense rotation of the drive shaft.

In one aspect, the control circuit 710 is configured to drive a firing member such as the closure member 714 portion of the end effector 702. The control circuit 710 provides a motor set point to a motor control 708*a*, which provides a drive signal to the motor 704*a*. The output shaft of the motor 704*a* is coupled to a torque sensor 744*a*. The torque sensor 744*a* is coupled to a transmission 706*a* which is coupled to the closure member 714. The transmission 706*a* comprises movable mechanical elements such as rotating elements and a firing member to control the movement of the closure member 714 distally and proximally along a longitudinal axis of the end effector 702. In one aspect, the motor 704*a* may be coupled to the knife gear assembly, which includes a knife gear reduction set that includes a first knife drive gear and a second knife drive gear. A torque sensor 744*a* provides a firing force feedback signal to the control circuit 710. The firing force signal represents the force required to fire or displace the closure member 714. A position sensor 734 may be configured to provide the position of the closure member 714 along the firing stroke or the position of the firing member as a feedback signal to the control circuit 710. The end effector 702 may include additional sensors 738 configured to provide feedback signals to the control circuit 710. When ready to use, the control circuit 710 may provide a firing signal to the motor control 708*a*. In response to the firing signal, the motor 704*a* may drive the firing member distally along the longitudinal axis of the end effector 702 from a proximal stroke start position to a stroke end position distal to the stroke start position. As the closure member 714 translates distally, the clamp arm 716 closes towards the ultrasonic blade 718.

In one aspect, the control circuit 710 is configured to drive a closure member such as the clamp arm 716 portion of the end effector 702. The control circuit 710 provides a motor set point to a motor control 708*b*, which provides a drive signal to the motor 704*b*. The output shaft of the motor 704*b* is coupled to a torque sensor 744*b*. The torque sensor 744*b* is coupled to a transmission 706*b* which is coupled to the clamp arm 716. The transmission 706*b* comprises movable mechanical elements such as rotating elements and a closure member to control the movement of the clamp arm 716 from the open and closed positions. In one aspect, the motor 704*b* is coupled to a closure gear assembly, which includes a closure reduction gear set that is supported in meshing engagement with the closure spur gear. The torque sensor 744*b* provides a closure force feedback signal to the control circuit 710. The closure force feedback signal represents the closure force applied to the clamp arm 716. The position sensor 734 may be configured to provide the position of the closure member as a feedback signal to the control circuit 710. Additional sensors 738 in the end effector 702 may provide the closure force feedback signal to the control circuit 710. The pivotable clamp arm 716 is positioned opposite the ultrasonic blade 718. When ready to use, the control circuit 710 may provide a closure signal to the motor control 708*b*. In response to the closure signal, the motor 704*b* advances a closure member to grasp tissue between the clamp arm 716 and the ultrasonic blade 718.

In one aspect, the control circuit 710 is configured to rotate a shaft member such as the shaft 740 to rotate the end effector 702. The control circuit 710 provides a motor set point to a motor control 708*c*, which provides a drive signal to the motor 704*c*. The output shaft of the motor 704*c* is coupled to a torque sensor 744*c*. The torque sensor 744*c* is coupled to a transmission 706*c* which is coupled to the shaft 740. The transmission 706*c* comprises movable mechanical elements such as rotating elements to control the rotation of the shaft 740 clockwise or counterclockwise up to and over 360°. In one aspect, the motor 704*c* is coupled to the rotational transmission assembly, which includes a tube gear segment that is formed on (or attached to) the proximal end of the proximal closure tube for operable engagement by a rotational gear assembly that is operably supported on the tool mounting plate. The torque sensor 744*c* provides a rotation force feedback signal to the control circuit 710. The rotation force feedback signal represents the rotation force applied to the shaft 740. The position sensor 734 may be configured to provide the position of the closure member as a feedback signal to the control circuit 710. Additional sensors 738 such as a shaft encoder may provide the rotational position of the shaft 740 to the control circuit 710.

In one aspect, the control circuit 710 is configured to articulate the end effector 702. The control circuit 710 provides a motor set point to a motor control 708*d*, which provides a drive signal to the motor 704*d*. The output shaft of the motor 704*d* is coupled to a torque sensor 744*d*. The torque sensor 744*d* is coupled to a transmission 706*d* which is coupled to an articulation member 742*a*. The transmission 706*d* comprises movable mechanical elements such as articulation elements to control the articulation of the end effector 702 ±65°. In one aspect, the motor 704*d* is coupled to an articulation nut, which is rotatably journaled on the proximal end portion of the distal spine portion and is rotatably driven thereon by an articulation gear assembly. The torque sensor 744*d* provides an articulation force feedback signal to the control circuit 710. The articulation force feedback signal represents the articulation force applied to the end effector 702. Sensors 738, such as an articulation encoder, may provide the articulation position of the end effector 702 to the control circuit 710.

In another aspect, the articulation function of the robotic surgical system 700 may comprise two articulation members, or links, 742*a*, 742*b*. These articulation members 742*a*, 742*b* are driven by separate disks on the robot interface (the rack) which are driven by the two motors 708*d*, 708*e*. When the separate firing motor 704*a* is provided, each of articulation links 742*a*, 742*b* can be antagonistically driven with respect to the other link in order to provide a resistive holding motion and a load to the head when it is not moving and to provide an articulation motion as the head is articulated. The articulation members 742*a*, 742*b* attach to the head at a fixed radius as the head is rotated. Accordingly, the mechanical advantage of the push-and-pull link changes as the head is rotated. This change in the mechanical advantage may be more pronounced with other articulation link drive systems.

In one aspect, the one or more motors 704*a*-704*e* may comprise a brushed DC motor with a gearbox and mechanical links to a firing member, closure member, or articulation member. Another example includes electric motors 704*a*-704*e* that operate the movable mechanical elements such as the displacement member, articulation links, closure tube, and shaft. An outside influence is an unmeasured, unpredictable influence of things like tissue, surrounding bodies, and friction on the physical system. Such outside influence can be referred to as drag, which acts in opposition to one of electric motors 704*a*-704*e*. The outside influence, such as drag, may cause the operation of the physical system to deviate from a desired operation of the physical system.

In one aspect, the position sensor 734 may be implemented as an absolute positioning system. In one aspect, the position sensor 734 may comprise a magnetic rotary absolute positioning system implemented as an AS5055EQFT single-chip magnetic rotary position sensor available from Austria Microsystems, AG. The position sensor 734 may interface with the control circuit 710 to provide an absolute positioning system. The position may include multiple Hall-effect elements located above a magnet and coupled to a CORDIC processor, also known as the digit-by-digit method and Volder's algorithm, that is provided to implement a simple and efficient algorithm to calculate hyperbolic and trigonometric functions that require only addition, subtraction, bitshift, and table lookup operations.

In one aspect, the control circuit 710 may be in communication with one or more sensors 738. The sensors 738 may be positioned on the end effector 702 and adapted to operate with the robotic surgical instrument 700 to measure the various derived parameters such as the gap distance versus time, tissue compression versus time, and anvil strain versus time. The sensors 738 may comprise a magnetic sensor, a magnetic field sensor, a strain gauge, a load cell, a pressure sensor, a force sensor, a torque sensor, an inductive sensor such as an eddy current sensor, a resistive sensor, a capacitive sensor, an optical sensor, and/or any other suitable sensor for measuring one or more parameters of the end effector 702. The sensors 738 may include one or more sensors. The sensors 738 may be located on the clamp arm 716 to determine tissue location using segmented electrodes. The torque sensors 744*a*-744*e* may be configured to sense force such as firing force, closure force, and/or articulation force, among others. Accordingly, the control circuit 710 can sense (1) the closure load experienced by the distal closure tube and its position, (2) the firing member at the rack and its position, (3) what portion of the ultrasonic blade 718 has tissue on it, and (4) the load and position on both articulation rods.

In one aspect, the one or more sensors 738 may comprise a strain gauge, such as a micro-strain gauge, configured to measure the magnitude of the strain in the clamp arm 716 during a clamped condition. The strain gauge provides an electrical signal whose amplitude varies with the magnitude of the strain. The sensors 738 may comprise a pressure sensor configured to detect a pressure generated by the presence of compressed tissue between the clamp arm 716 and the ultrasonic blade 718. The sensors 738 may be configured to detect impedance of a tissue section located between the clamp arm 716 and the ultrasonic blade 718 that is indicative of the thickness and/or fullness of tissue located therebetween.

In one aspect, the sensors 738 may be implemented as one or more limit switches, electromechanical devices, solid-state switches, Hall-effect devices, magneto-resistive (MR) devices, giant magneto-resistive (GMR) devices, magnetometers, among others. In other implementations, the sensors 738 may be implemented as solid-state switches that operate under the influence of light, such as optical sensors, IR sensors, ultraviolet sensors, among others. Still, the switches may be solid-state devices such as transistors (e.g., FET, junction FET, MOSFET, bipolar, and the like). In other implementations, the sensors 738 may include electrical conductorless switches, ultrasonic switches, accelerometers, and inertial sensors, among others.

In one aspect, the sensors 738 may be configured to measure forces exerted on the clamp arm 716 by the closure drive system. For example, one or more sensors 738 can be at an interaction point between the closure tube and the clamp arm 716 to detect the closure forces applied by the closure tube to the clamp arm 716. The forces exerted on the clamp arm 716 can be representative of the tissue compression experienced by the tissue section captured between the clamp arm 716 and the ultrasonic blade 718. The one or more sensors 738 can be positioned at various interaction points along the closure drive system to detect the closure forces applied to the clamp arm 716 by the closure drive system. The one or more sensors 738 may be sampled in real time during a clamping operation by the processor of the control circuit 710. The control circuit 710 receives real-time sample measurements to provide and analyze time-based information and assess, in real time, closure forces applied to the clamp arm 716.

In one aspect, a current sensor 736 can be employed to measure the current drawn by each of the motors 704*a*-704*e*. The force required to advance any of the movable mechanical elements such as the closure member 714 corresponds to the current drawn by one of the motors 704*a*-704*e*. The force is converted to a digital signal and provided to the control circuit 710. The control circuit 710 can be configured to simulate the response of the actual system of the instrument in the software of the controller. A displacement member can be actuated to move the closure member 714 in the end effector 702 at or near a target velocity. The robotic surgical instrument 700 can include a feedback controller, which can be one of any feedback controllers, including, but not limited to a PID, a state feedback, a linear-quadratic (LQR), and/or an adaptive controller, for example. The robotic surgical instrument 700 can include a power source to convert the signal from the feedback controller into a physical input such as case voltage, PWM voltage, frequency modulated voltage, current, torque, and/or force, for example. Additional details are disclosed in U.S. patent application Ser. No. 15/636,829, titled CLOSED LOOP VELOCITY CONTROL TECHNIQUES FOR ROBOTIC SURGICAL INSTRUMENT, filed Jun. 29, 2017, which is herein incorporated by reference in its entirety.

Figure 17:
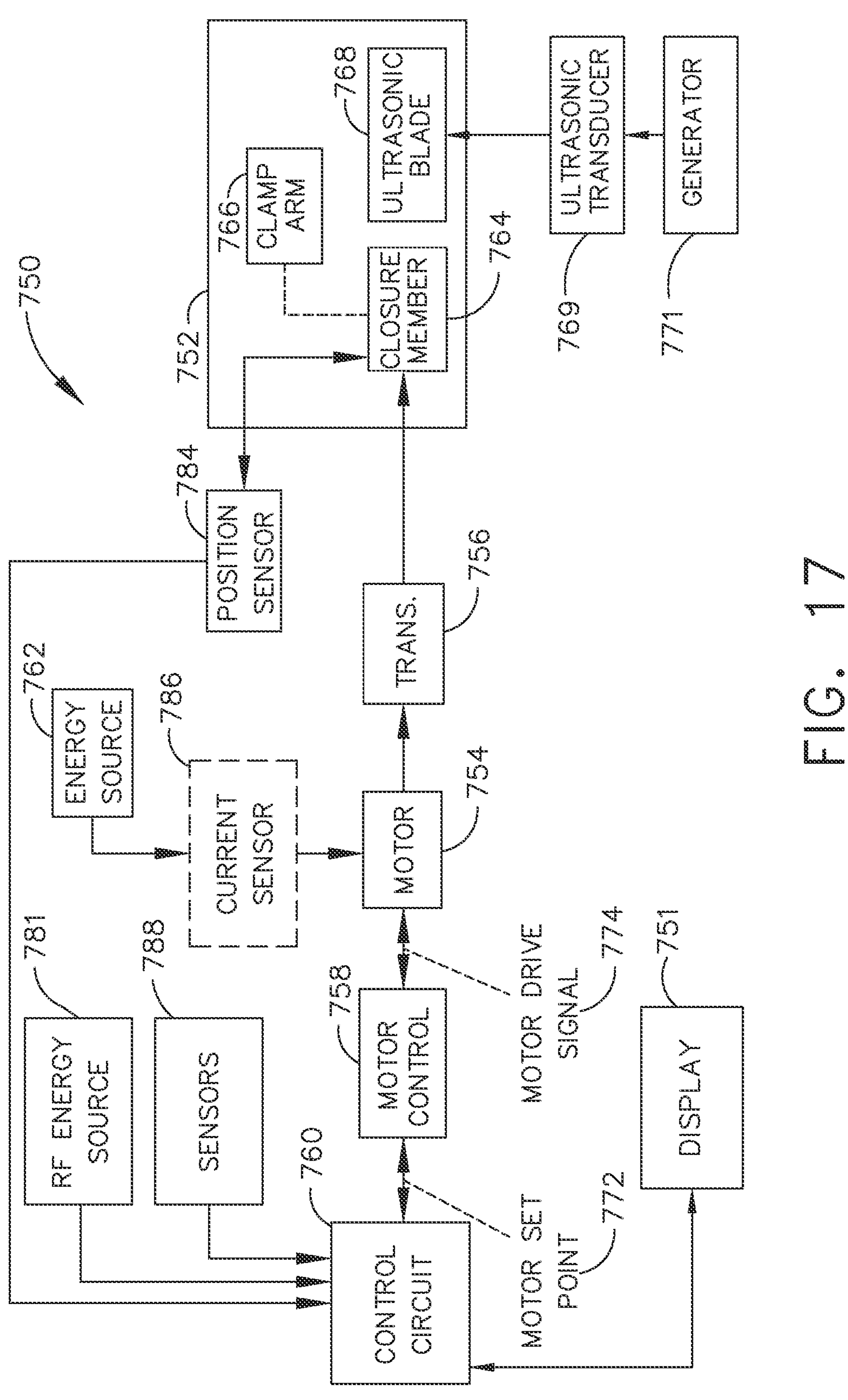
FIG. 17 illustrates a block diagram of a surgical instrument programmed to control the distal translation of a displacement member, in accordance with at least one aspect of the present disclosure.

FIG. 17 illustrates a schematic diagram of a surgical instrument 750 configured to control the distal translation of a displacement member according to one aspect of this disclosure. In one aspect, the surgical instrument 750 is programmed to control the distal translation of a displacement member such as the closure member 764. The surgical instrument 750 comprises an end effector 752 that may comprise a clamp arm 766, a closure member 764, and an ultrasonic blade 768 coupled to an ultrasonic transducer 769 driven by an ultrasonic generator 771.

The position, movement, displacement, and/or translation of a linear displacement member, such as the closure member 764, can be measured by an absolute positioning system, sensor arrangement, and position sensor 784. Because the closure member 764 is coupled to a longitudinally movable drive member, the position of the closure member 764 can be determined by measuring the position of the longitudinally movable drive member employing the position sensor 784. Accordingly, in the following description, the position, displacement, and/or translation of the closure member 764 can be achieved by the position sensor 784 as described herein. A control circuit 760 may be programmed to control the translation of the displacement member, such as the closure member 764. The control circuit 760, in some examples, may comprise one or more microcontrollers, microprocessors, or other suitable processors for executing instructions that cause the processor or processors to control the displacement member, e.g., the closure member 764, in the manner described. In one aspect, a timer/counter 781 provides an output signal, such as the elapsed time or a digital count, to the control circuit 760 to correlate the position of the closure member 764 as determined by the position sensor 784 with the output of the timer/counter 781 such that the control circuit 760 can determine the position of the closure member 764 at a specific time (t) relative to a starting position. The timer/counter 781 may be configured to measure elapsed time, count external events, or time external events.

The control circuit 760 may generate a motor set point signal 772. The motor set point signal 772 may be provided to a motor controller 758. The motor controller 758 may comprise one or more circuits configured to provide a motor drive signal 774 to the motor 754 to drive the motor 754 as described herein. In some examples, the motor 754 may be a brushed DC electric motor. For example, the velocity of the motor 754 may be proportional to the motor drive signal 774. In some examples, the motor 754 may be a brushless DC electric motor and the motor drive signal 774 may comprise a PWM signal provided to one or more stator windings of the motor 754. Also, in some examples, the motor controller 758 may be omitted, and the control circuit 760 may generate the motor drive signal 774 directly.

The motor 754 may receive power from an energy source 762. The energy source 762 may be or include a battery, a super capacitor, or any other suitable energy source. The motor 754 may be mechanically coupled to the closure member 764 via a transmission 756. The transmission 756 may include one or more gears or other linkage components to couple the motor 754 to the closure member 764. A position sensor 784 may sense a position of the closure member 764. The position sensor 784 may be or include any type of sensor that is capable of generating position data that indicate a position of the closure member 764. In some examples, the position sensor 784 may include an encoder configured to provide a series of pulses to the control circuit 760 as the closure member 764 translates distally and proximally. The control circuit 760 may track the pulses to determine the position of the closure member 764. Other suitable position sensors may be used, including, for example, a proximity sensor. Other types of position sensors may provide other signals indicating motion of the closure member 764. Also, in some examples, the position sensor 784 may be omitted. Where the motor 754 is a stepper motor, the control circuit 760 may track the position of the closure member 764 by aggregating the number and direction of steps that the motor 754 has been instructed to execute. The position sensor 784 may be located in the end effector 752 or at any other portion of the instrument.

The control circuit 760 may be in communication with one or more sensors 788. The sensors 788 may be positioned on the end effector 752 and adapted to operate with the surgical instrument 750 to measure the various derived parameters such as gap distance versus time, tissue compression versus time, and anvil strain versus time. The sensors 788 may comprise a magnetic sensor, a magnetic field sensor, a strain gauge, a pressure sensor, a force sensor, an inductive sensor such as an eddy current sensor, a resistive sensor, a capacitive sensor, an optical sensor, and/or any other suitable sensor for measuring one or more parameters of the end effector 752. The sensors 788 may include one or more sensors.

The one or more sensors 788 may comprise a strain gauge, such as a micro-strain gauge, configured to measure the magnitude of the strain in the clamp arm 766 during a clamped condition. The strain gauge provides an electrical signal whose amplitude varies with the magnitude of the strain. The sensors 788 may comprise a pressure sensor configured to detect a pressure generated by the presence of compressed tissue between the clamp arm 766 and the ultrasonic blade 768. The sensors 788 may be configured to detect impedance of a tissue section located between the clamp arm 766 and the ultrasonic blade 768 that is indicative of the thickness and/or fullness of tissue located therebetween.

The sensors 788 may be is configured to measure forces exerted on the clamp arm 766 by a closure drive system. For example, one or more sensors 788 can be at an interaction point between a closure tube and the clamp arm 766 to detect the closure forces applied by a closure tube to the clamp arm 766. The forces exerted on the clamp arm 766 can be representative of the tissue compression experienced by the tissue section captured between the clamp arm 766 and the ultrasonic blade 768. The one or more sensors 788 can be positioned at various interaction points along the closure drive system to detect the closure forces applied to the clamp arm 766 by the closure drive system. The one or more sensors 788 may be sampled in real time during a clamping operation by a processor of the control circuit 760. The control circuit 760 receives real-time sample measurements to provide and analyze time-based information and assess, in real time, closure forces applied to the clamp arm 766.

A current sensor 786 can be employed to measure the current drawn by the motor 754. The force required to advance the closure member 764 corresponds to the current drawn by the motor 754. The force is converted to a digital signal and provided to the control circuit 760.

The control circuit 760 can be configured to simulate the response of the actual system of the instrument in the software of the controller. A displacement member can be actuated to move a closure member 764 in the end effector 752 at or near a target velocity. The surgical instrument 750 can include a feedback controller, which can be one of any feedback controllers, including, but not limited to a PID, a state feedback, LQR, and/or an adaptive controller, for example. The surgical instrument 750 can include a power source to convert the signal from the feedback controller into a physical input such as case voltage, PWM voltage, frequency modulated voltage, current, torque, and/or force, for example.

The actual drive system of the surgical instrument 750 is configured to drive the displacement member, cutting member, or closure member 764, by a brushed DC motor with gearbox and mechanical links to an articulation and/or knife system. Another example is the electric motor 754 that operates the displacement member and the articulation driver, for example, of an interchangeable shaft assembly. An outside influence is an unmeasured, unpredictable influence of things like tissue, surrounding bodies and friction on the physical system. Such outside influence can be referred to as drag which acts in opposition to the electric motor 754. The outside influence, such as drag, may cause the operation of the physical system to deviate from a desired operation of the physical system.

Various example aspects are directed to a surgical instrument 750 comprising an end effector 752 with motor-driven surgical sealing and cutting implements. For example, a motor 754 may drive a displacement member distally and proximally along a longitudinal axis of the end effector 752. The end effector 752 may comprise a pivotable clamp arm 766 and, when configured for use, an ultrasonic blade 768 positioned opposite the clamp arm 766. A clinician may grasp tissue between the clamp arm 766 and the ultrasonic blade 768, as described herein. When ready to use the instrument 750, the clinician may provide a firing signal, for example by depressing a trigger of the instrument 750. In response to the firing signal, the motor 754 may drive the displacement member distally along the longitudinal axis of the end effector 752 from a proximal stroke begin position to a stroke end position distal of the stroke begin position. As the displacement member translates distally, the closure member 764 with a cutting element positioned at a distal end, may cut the tissue between the ultrasonic blade 768 and the clamp arm 766.

In various examples, the surgical instrument 750 may comprise a control circuit 760 programmed to control the distal translation of the displacement member, such as the closure member 764, for example, based on one or more tissue conditions. The control circuit 760 may be programmed to sense tissue conditions, such as thickness, either directly or indirectly, as described herein. The control circuit 760 may be programmed to select a control program based on tissue conditions. A control program may describe the distal motion of the displacement member. Different control programs may be selected to better treat different tissue conditions. For example, when thicker tissue is present, the control circuit 760 may be programmed to translate the displacement member at a lower velocity and/or with lower power. When thinner tissue is present, the control circuit 760 may be programmed to translate the displacement member at a higher velocity and/or with higher power.

In some examples, the control circuit 760 may initially operate the motor 754 in an open loop configuration for a first open loop portion of a stroke of the displacement member. Based on a response of the instrument 750 during the open loop portion of the stroke, the control circuit 760 may select a firing control program. The response of the instrument may include, a translation distance of the displacement member during the open loop portion, a time elapsed during the open loop portion, energy provided to the motor 754 during the open loop portion, a sum of pulse widths of a motor drive signal, etc. After the open loop portion, the control circuit 760 may implement the selected firing control program for a second portion of the displacement member stroke. For example, during the closed loop portion of the stroke, the control circuit 760 may modulate the motor 754 based on translation data describing a position of the displacement member in a closed loop manner to translate the displacement member at a constant velocity. Additional details are disclosed in U.S. patent application Ser. No. 15/720,852, titled SYSTEM AND METHODS FOR CONTROLLING A DISPLAY OF A SURGICAL INSTRUMENT, filed Sep. 29, 2017, which is herein incorporated by reference in its entirety.

Figure 18:
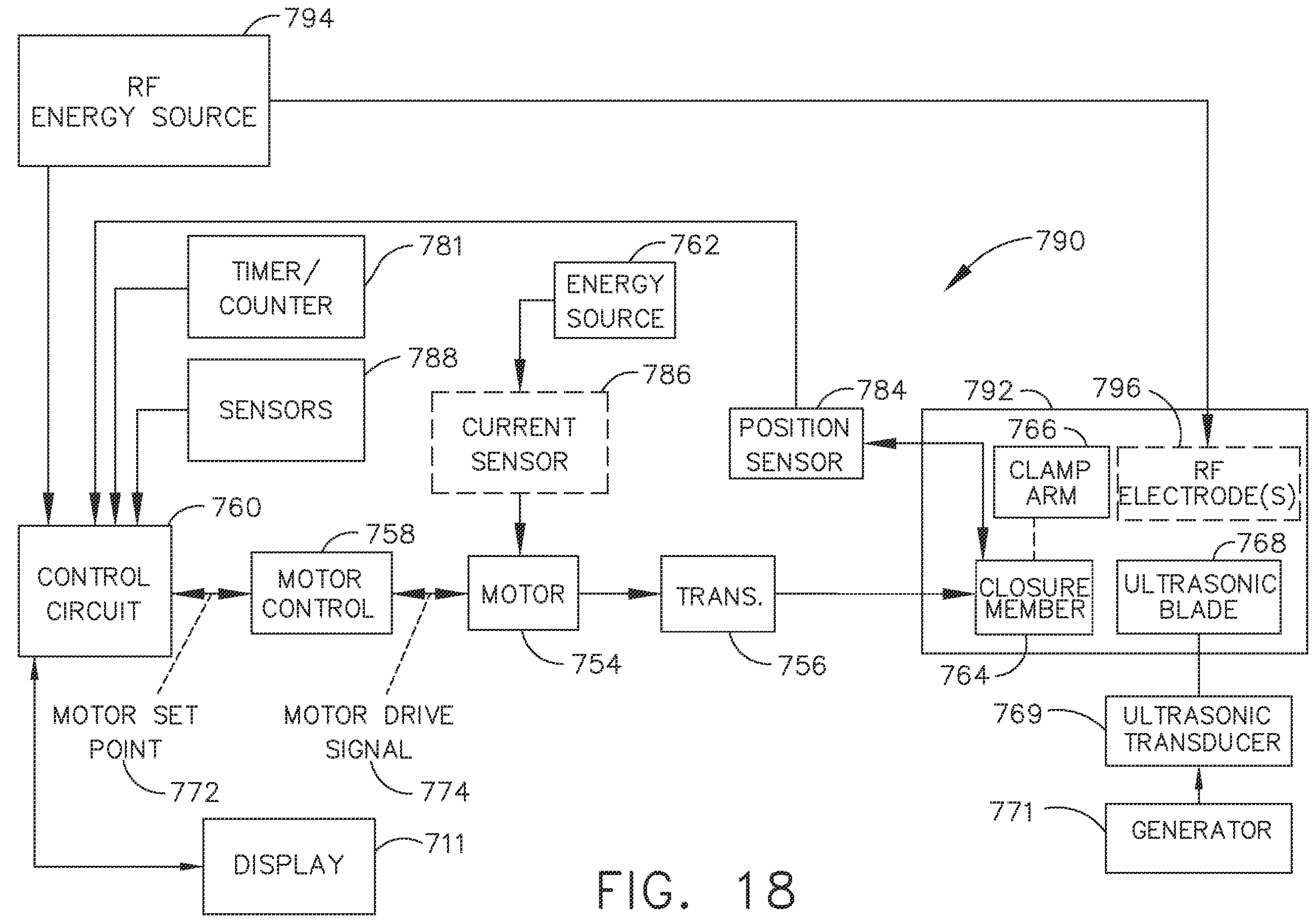
FIG. 18 is a schematic diagram of a surgical instrument configured to control various functions, in accordance with at least one aspect of the present disclosure.

FIG. 18 illustrates a schematic diagram of a surgical instrument 750 configured to control the distal translation of a displacement member according to one aspect of this disclosure. In one aspect, the surgical instrument 750 is programmed to control the distal translation of a displacement member such as the closure member 764. The surgical instrument 750 comprises an end effector 752 that may comprise a clamp arm 766, a closure member 764, and an ultrasonic blade 768 coupled to an ultrasonic transducer 769 driven by an ultrasonic generator 771.

The position, movement, displacement, and/or translation of a linear displacement member, such as the closure member 764, can be measured by an absolute positioning system, sensor arrangement, and position sensor 784. Because the closure member 764 is coupled to a longitudinally movable drive member, the position of the closure member 764 can be determined by measuring the position of the longitudinally movable drive member employing the position sensor 784. Accordingly, in the following description, the position, displacement, and/or translation of the closure member 764 can be achieved by the position sensor 784 as described herein. A control circuit 760 may be programmed to control the translation of the displacement member, such as the closure member 764. The control circuit 760, in some examples, may comprise one or more microcontrollers, microprocessors, or other suitable processors for executing instructions that cause the processor or processors to control the displacement member, e.g., the closure member 764, in the manner described. In one aspect, a timer/counter 781 provides an output signal, such as the elapsed time or a digital count, to the control circuit 760 to correlate the position of the closure member 764 as determined by the position sensor 784 with the output of the timer/counter 781 such that the control circuit 760 can determine the position of the closure member 764 at a specific time (t) relative to a starting position. The timer/counter 781 may be configured to measure elapsed time, count external events, or time external events.

The control circuit 760 may generate a motor set point signal 772. The motor set point signal 772 may be provided to a motor controller 758. The motor controller 758 may comprise one or more circuits configured to provide a motor drive signal 774 to the motor 754 to drive the motor 754 as described herein. In some examples, the motor 754 may be a brushed DC electric motor. For example, the velocity of the motor 754 may be proportional to the motor drive signal 774. In some examples, the motor 754 may be a brushless DC electric motor and the motor drive signal 774 may comprise a PWM signal provided to one or more stator windings of the motor 754. Also, in some examples, the motor controller 758 may be omitted, and the control circuit 760 may generate the motor drive signal 774 directly.

The motor 754 may receive power from an energy source 762. The energy source 762 may be or include a battery, a super capacitor, or any other suitable energy source. The motor 754 may be mechanically coupled to the closure member 764 via a transmission 756. The transmission 756 may include one or more gears or other linkage components to couple the motor 754 to the closure member 764. A position sensor 784 may sense a position of the closure member 764. The position sensor 784 may be or include any type of sensor that is capable of generating position data that indicate a position of the closure member 764. In some examples, the position sensor 784 may include an encoder configured to provide a series of pulses to the control circuit 760 as the closure member 764 translates distally and proximally. The control circuit 760 may track the pulses to determine the position of the closure member 764. Other suitable position sensors may be used, including, for example, a proximity sensor. Other types of position sensors may provide other signals indicating motion of the closure member 764. Also, in some examples, the position sensor 784 may be omitted. Where the motor 754 is a stepper motor, the control circuit 760 may track the position of the closure member 764 by aggregating the number and direction of steps that the motor 754 has been instructed to execute. The position sensor 784 may be located in the end effector 752 or at any other portion of the instrument.

The control circuit 760 may be in communication with one or more sensors 788. The sensors 788 may be positioned on the end effector 752 and adapted to operate with the surgical instrument 750 to measure the various derived parameters such as gap distance versus time, tissue compression versus time, and anvil strain versus time. The sensors 788 may comprise a magnetic sensor, a magnetic field sensor, a strain gauge, a pressure sensor, a force sensor, an inductive sensor such as an eddy current sensor, a resistive sensor, a capacitive sensor, an optical sensor, and/or any other suitable sensor for measuring one or more parameters of the end effector 752. The sensors 788 may include one or more sensors.

The one or more sensors 788 may comprise a strain gauge, such as a micro-strain gauge, configured to measure the magnitude of the strain in the clamp arm 766 during a clamped condition. The strain gauge provides an electrical signal whose amplitude varies with the magnitude of the strain. The sensors 788 may comprise a pressure sensor configured to detect a pressure generated by the presence of compressed tissue between the clamp arm 766 and the ultrasonic blade 768. The sensors 788 may be configured to detect impedance of a tissue section located between the clamp arm 766 and the ultrasonic blade 768 that is indicative of the thickness and/or fullness of tissue located therebetween.

The sensors 788 may be is configured to measure forces exerted on the clamp arm 766 by a closure drive system. For example, one or more sensors 788 can be at an interaction point between a closure tube and the clamp arm 766 to detect the closure forces applied by a closure tube to the clamp arm 766. The forces exerted on the clamp arm 766 can be representative of the tissue compression experienced by the tissue section captured between the clamp arm 766 and the ultrasonic blade 768. The one or more sensors 788 can be positioned at various interaction points along the closure drive system to detect the closure forces applied to the clamp arm 766 by the closure drive system. The one or more sensors 788 may be sampled in real time during a clamping operation by a processor of the control circuit 760. The control circuit 760 receives real-time sample measurements to provide and analyze time-based information and assess, in real time, closure forces applied to the clamp arm 766.

A current sensor 786 can be employed to measure the current drawn by the motor 754. The force required to advance the closure member 764 corresponds to the current drawn by the motor 754. The force is converted to a digital signal and provided to the control circuit 760.

The control circuit 760 can be configured to simulate the response of the actual system of the instrument in the software of the controller. A displacement member can be actuated to move a closure member 764 in the end effector 752 at or near a target velocity. The surgical instrument 750 can include a feedback controller, which can be one of any feedback controllers, including, but not limited to a PID, a state feedback, LQR, and/or an adaptive controller, for example. The surgical instrument 750 can include a power source to convert the signal from the feedback controller into a physical input such as case voltage, PWM voltage, frequency modulated voltage, current, torque, and/or force, for example.

The actual drive system of the surgical instrument 750 is configured to drive the displacement member, cutting member, or closure member 764, by a brushed DC motor with gearbox and mechanical links to an articulation and/or knife system. Another example is the electric motor 754 that operates the displacement member and the articulation driver, for example, of an interchangeable shaft assembly. An outside influence is an unmeasured, unpredictable influence of things like tissue, surrounding bodies and friction on the physical system. Such outside influence can be referred to as drag which acts in opposition to the electric motor 754. The outside influence, such as drag, may cause the operation of the physical system to deviate from a desired operation of the physical system.

Various example aspects are directed to a surgical instrument 750 comprising an end effector 752 with motor-driven surgical sealing and cutting implements. For example, a motor 754 may drive a displacement member distally and proximally along a longitudinal axis of the end effector 752. The end effector 752 may comprise a pivotable clamp arm 766 and, when configured for use, an ultrasonic blade 768 positioned opposite the clamp arm 766. A clinician may grasp tissue between the clamp arm 766 and the ultrasonic blade 768, as described herein. When ready to use the instrument 750, the clinician may provide a firing signal, for example by depressing a trigger of the instrument 750. In response to the firing signal, the motor 754 may drive the displacement member distally along the longitudinal axis of the end effector 752 from a proximal stroke begin position to a stroke end position distal of the stroke begin position. As the displacement member translates distally, the closure member 764 with a cutting element positioned at a distal end, may cut the tissue between the ultrasonic blade 768 and the clamp arm 766.

In various examples, the surgical instrument 750 may comprise a control circuit 760 programmed to control the distal translation of the displacement member, such as the closure member 764, for example, based on one or more tissue conditions. The control circuit 760 may be programmed to sense tissue conditions, such as thickness, either directly or indirectly, as described herein. The control circuit 760 may be programmed to select a control program based on tissue conditions. A control program may describe the distal motion of the displacement member. Different control programs may be selected to better treat different tissue conditions. For example, when thicker tissue is present, the control circuit 760 may be programmed to translate the displacement member at a lower velocity and/or with lower power. When thinner tissue is present, the control circuit 760 may be programmed to translate the displacement member at a higher velocity and/or with higher power.

In some examples, the control circuit 760 may initially operate the motor 754 in an open loop configuration for a first open loop portion of a stroke of the displacement member. Based on a response of the instrument 750 during the open loop portion of the stroke, the control circuit 760 may select a firing control program. The response of the instrument may include, a translation distance of the displacement member during the open loop portion, a time elapsed during the open loop portion, energy provided to the motor 754 during the open loop portion, a sum of pulse widths of a motor drive signal, etc. After the open loop portion, the control circuit 760 may implement the selected firing control program for a second portion of the displacement member stroke. For example, during the closed loop portion of the stroke, the control circuit 760 may modulate the motor 754 based on translation data describing a position of the displacement member in a closed loop manner to translate the displacement member at a constant velocity. Additional details are disclosed in U.S. patent application Ser. No. 15/720,852, titled SYSTEM AND METHODS FOR CONTROLLING A DISPLAY OF A SURGICAL INSTRUMENT, filed Sep. 29, 2017, which is herein incorporated by reference in its entirety.

FIG. 18 is a schematic diagram of a surgical instrument 790 configured to control various functions according to one aspect of this disclosure. In one aspect, the surgical instrument 790 is programmed to control distal translation of a displacement member such as the closure member 764. The surgical instrument 790 comprises an end effector 792 that may comprise a clamp arm 766, a closure member 764, and an ultrasonic blade 768 which may be interchanged with or work in conjunction with one or more RF electrodes 796 (shown in dashed line). The ultrasonic blade 768 is coupled to an ultrasonic transducer 769 driven by an ultrasonic generator 771.

In one aspect, sensors 788 may be implemented as a limit switch, electromechanical device, solid-state switches, Hall-effect devices, MR devices, GMR devices, magnetometers, among others. In other implementations, the sensors 638 may be solid-state switches that operate under the influence of light, such as optical sensors, IR sensors, ultraviolet sensors, among others. Still, the switches may be solid-state devices such as transistors (e.g., FET, junction FET, MOSFET, bipolar, and the like). In other implementations, the sensors 788 may include electrical conductorless switches, ultrasonic switches, accelerometers, and inertial sensors, among others.

In one aspect, the position sensor 784 may be implemented as an absolute positioning system comprising a magnetic rotary absolute positioning system implemented as an AS5055EQFT single-chip magnetic rotary position sensor available from Austria Microsystems, AG. The position sensor 784 may interface with the control circuit 760 to provide an absolute positioning system. The position may include multiple Hall-effect elements located above a magnet and coupled to a CORDIC processor, also known as the digit-by-digit method and Volder's algorithm, that is provided to implement a simple and efficient algorithm to calculate hyperbolic and trigonometric functions that require only addition, subtraction, bitshift, and table lookup operations.

In some examples, the position sensor 784 may be omitted. Where the motor 754 is a stepper motor, the control circuit 760 may track the position of the closure member 764 by aggregating the number and direction of steps that the motor has been instructed to execute. The position sensor 784 may be located in the end effector 792 or at any other portion of the instrument.

The control circuit 760 may be in communication with one or more sensors 788. The sensors 788 may be positioned on the end effector 792 and adapted to operate with the surgical instrument 790 to measure the various derived parameters such as gap distance versus time, tissue compression versus time, and anvil strain versus time. The sensors 788 may comprise a magnetic sensor, a magnetic field sensor, a strain gauge, a pressure sensor, a force sensor, an inductive sensor such as an eddy current sensor, a resistive sensor, a capacitive sensor, an optical sensor, and/or any other suitable sensor for measuring one or more parameters of the end effector 792. The sensors 788 may include one or more sensors.

An RF energy source 794 is coupled to the end effector 792 and is applied to the RF electrode 796 when the RF electrode 796 is provided in the end effector 792 in place of the ultrasonic blade 768 or to work in conjunction with the ultrasonic blade 768. For example, the ultrasonic blade is made of electrically conductive metal and may be employed as the return path for electrosurgical RF current. The control circuit 760 controls the delivery of the RF energy to the RF electrode 796.

Additional details are disclosed in U.S. patent application Ser. No. 15/636,096, titled SURGICAL SYSTEM COUPLABLE WITH STAPLE CARTRIDGE AND RADIO FREQUENCY CARTRIDGE, AND METHOD OF USING SAME, filed Jun. 28, 2017, which is herein incorporated by reference in its entirety.

Figure 19:
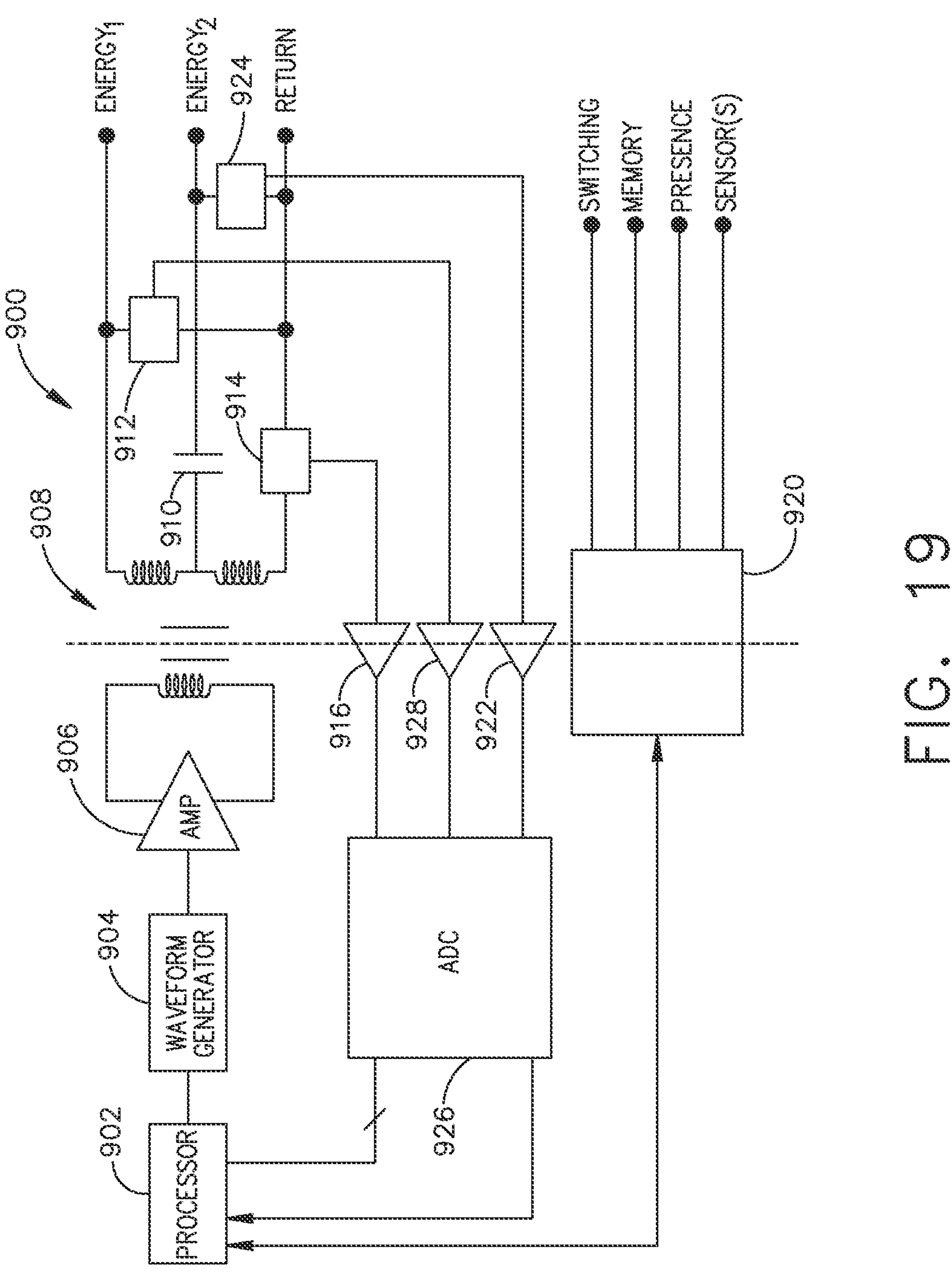
FIG. 19 illustrates an example of a generator, in accordance with at least one aspect of the present disclosure.

FIG. 19 illustrates an example of a generator 900, which is one form of a generator configured to couple to an ultrasonic instrument and further configured to execute adaptive ultrasonic blade control algorithms in a surgical data network comprising a modular communication hub. The generator 900 is configured to deliver multiple energy modalities to a surgical instrument. The generator 900 provides RF and ultrasonic signals for delivering energy to a surgical instrument either independently or simultaneously. The RF and ultrasonic signals may be provided alone or in combination and may be provided simultaneously. As noted above, at least one generator output can deliver multiple energy modalities (e.g., ultrasonic, bipolar or monopolar RF, irreversible and/or reversible electroporation, and/or microwave energy, among others) through a single port, and these signals can be delivered separately or simultaneously to the end effector to treat tissue. The generator 900 comprises a processor 902 coupled to a waveform generator 904. The processor 902 and waveform generator 904 are configured to generate a variety of signal waveforms based on information stored in a memory coupled to the processor 902, not shown for clarity of disclosure. The digital information associated with a waveform is provided to the waveform generator 904 which includes one or more DAC circuits to convert the digital input into an analog output. The analog output is fed to an amplifier 1106 for signal conditioning and amplification. The conditioned and amplified output of the amplifier 906 is coupled to a power transformer 908. The signals are coupled across the power transformer 908 to the secondary side, which is in the patient isolation side. A first signal of a first energy modality is provided to the surgical instrument between the terminals labeled $ENERGY_1$ and RETURN. A second signal of a second energy modality is coupled across a capacitor 910 and is provided to the surgical instrument between the terminals labeled $ENERGY_2$ and RETURN. It will be appreciated that more than two energy modalities may be output and thus the subscript "n" may be used to designate that up to n $ENERGY_n$ terminals may be provided, where n is a positive integer greater than 1. It also will be appreciated that up to "n" return paths $RETURN_n$ may be provided without departing from the scope of the present disclosure.

A first voltage sensing circuit 912 is coupled across the terminals labeled $ENERGY_1$ and the RETURN path to measure the output voltage therebetween. A second voltage sensing circuit 924 is coupled across the terminals labeled $ENERGY_2$ and the RETURN path to measure the output voltage therebetween. A current sensing circuit 914 is disposed in series with the RETURN leg of the secondary side of the power transformer 908 as shown to measure the output current for either energy modality. If different return paths are provided for each energy modality, then a separate current sensing circuit should be provided in each return leg. The outputs of the first and second voltage sensing circuits 912, 924 are provided to respective isolation transformers 916, 922 and the output of the current sensing circuit 914 is provided to another isolation transformer 918. The outputs of the isolation transformers 916, 928, 922 in the on the primary side of the power transformer 908 (non-patient isolated side) are provided to a one or more ADC circuit 926. The digitized output of the ADC circuit 926 is provided to the processor 902 for further processing and computation. The output voltages and output current feedback information can be employed to adjust the output voltage and current provided to the surgical instrument and to compute output impedance, among other parameters. Input/output communications between the processor 902 and patient isolated circuits is provided through an interface circuit 920. Sensors also may be in electrical communication with the processor 902 by way of the interface circuit 920.

In one aspect, the impedance may be determined by the processor 902 by dividing the output of either the first voltage sensing circuit 912 coupled across the terminals labeled $ENERGY_1$/RETURN or the second voltage sensing circuit 924 coupled across the terminals labeled $ENERGY_2$/RETURN by the output of the current sensing circuit 914 disposed in series with the RETURN leg of the secondary side of the power transformer 908. The outputs of the first and second voltage sensing circuits 912, 924 are provided to separate isolations transformers 916, 922 and the output of the current sensing circuit 914 is provided to another isolation transformer 916. The digitized voltage and current sensing measurements from the ADC circuit 926 are provided the processor 902 for computing impedance. As an example, the first energy modality $ENERGY_1$ may be ultrasonic energy and the second energy modality $ENERGY_2$ may be RF energy. Nevertheless, in addition to ultrasonic and bipolar or monopolar RF energy modalities, other energy modalities include irreversible and/or reversible electroporation and/or microwave energy, among others. Also, although the example illustrated in FIG. 19 shows a single return path RETURN may be provided for two or more energy modalities, in other aspects, multiple return paths $RETURN_n$ may be provided for each energy modality $ENERGY_n$. Thus, as described herein, the ultrasonic transducer impedance may be measured by dividing the output of the first voltage sensing circuit 912 by the current sensing circuit 914 and the tissue impedance may be measured by dividing the output of the second voltage sensing circuit 924 by the current sensing circuit 914.

As shown in FIG. 19, the generator 900 comprising at least one output port can include a power transformer 908 with a single output and with multiple taps to provide power in the form of one or more energy modalities, such as ultrasonic, bipolar or monopolar RF, irreversible and/or reversible electroporation, and/or microwave energy, among others, for example, to the end effector depending on the type of treatment of tissue being performed. For example, the generator 900 can deliver energy with higher voltage and lower current to drive an ultrasonic transducer, with lower voltage and higher current to drive RF electrodes for sealing tissue, or with a coagulation waveform for spot coagulation using either monopolar or bipolar RF electrosurgical electrodes. The output waveform from the generator 900 can be steered, switched, or filtered to provide the frequency to the end effector of the surgical instrument. The connection of an ultrasonic transducer to the generator 900 output would be preferably located between the output labeled $ENERGY_1$ and RETURN as shown in FIG. 18. In one example, a connection of RF bipolar electrodes to the generator 900 output would be preferably located between the output labeled $ENERGY_2$ and RETURN. In the case of monopolar output, the preferred connections would be active electrode (e.g., pencil or other probe) to the $ENERGY_2$ output and a suitable return pad connected to the RETURN output.

Additional details are disclosed in U.S. Patent Application Publication No. 2017/0086914, titled TECHNIQUES FOR OPERATING GENERATOR FOR DIGITALLY GENERATING ELECTRICAL SIGNAL WAVEFORMS AND SURGICAL INSTRUMENTS, which published on Mar. 30, 2017, which is herein incorporated by reference in its entirety.

As used throughout this description, the term "wireless" and its derivatives may be used to describe circuits, devices, systems, methods, techniques, communications channels, etc., that may communicate data through the use of modulated electromagnetic radiation through a non-solid medium. The term does not imply that the associated devices do not contain any wires, although in some aspects they might not. The communication module may implement any of a number of wireless or wired communication standards or protocols, including but not limited to Wi-Fi (IEEE 802.11 family), WiMAX (IEEE 802.16 family), IEEE 802.20, long term evolution (LTE), Ev-DO, HSPA+, HSDPA+, HSUPA+, EDGE, GSM, GPRS, CDMA, TDMA, DECT, Bluetooth, Ethernet derivatives thereof, as well as any other wireless and wired protocols that are designated as 3G, 4G, 5G, and beyond. The computing module may include a plurality of communication modules. For instance, a first communication module may be dedicated to shorter range wireless communications such as Wi-Fi and Bluetooth and a second communication module may be dedicated to longer range wireless communications such as GPS, EDGE, GPRS, CDMA, WiMAX, LTE, Ev-DO, and others.

As used herein a processor or processing unit is an electronic circuit which performs operations on some external data source, usually memory or some other data stream. The term is used herein to refer to the central processor (central processing unit) in a system or computer systems (especially systems on a chip (SoCs)) that combine a number of specialized "processors."

As used herein, a system on a chip or system on chip (SoC or SOC) is an integrated circuit (also known as an "IC" or "chip") that integrates all components of a computer or other electronic systems. It may contain digital, analog, mixed-signal, and often radio-frequency functions—all on a single substrate. A SoC integrates a microcontroller (or microprocessor) with advanced peripherals like graphics processing unit (GPU), Wi-Fi module, or coprocessor. A SoC may or may not contain built-in memory.

As used herein, a microcontroller or controller is a system that integrates a microprocessor with peripheral circuits and memory. A microcontroller (or MCU for microcontroller unit) may be implemented as a small computer on a single integrated circuit. It may be similar to a SoC; an SoC may include a microcontroller as one of its components. A microcontroller may contain one or more core processing units (CPUs) along with memory and programmable input/output peripherals. Program memory in the form of Ferroelectric RAM, NOR flash or OTP ROM is also often included on chip, as well as a small amount of RAM. Microcontrollers may be employed for embedded applications, in contrast to the microprocessors used in personal computers or other general purpose applications consisting of various discrete chips.

As used herein, the term controller or microcontroller may be a stand-alone IC or chip device that interfaces with a peripheral device. This may be a link between two parts of a computer or a controller on an external device that manages the operation of (and connection with) that device.

Any of the processors or microcontrollers described herein, may be implemented by any single core or multicore processor such as those known under the trade name ARM Cortex by Texas Instruments. In one aspect, the processor may be an LM4F230H5QR ARM Cortex-M4F Processor Core, available from Texas Instruments, for example, comprising on-chip memory of 256 KB single-cycle flash memory, or other non-volatile memory, up to 40 MHz, a prefetch buffer to improve performance above 40 MHz, a 32 KB single-cycle serial random access memory (SRAM), internal read-only memory (ROM) loaded with StellarisWare® software, 2 KB electrically erasable programmable read-only memory (EEPROM), one or more pulse width modulation (PWM) modules, one or more quadrature encoder inputs (QEI) analog, one or more 12-bit Analog-to-Digital Converters (ADC) with 12 analog input channels, details of which are available for the product datasheet.

In one aspect, the processor may comprise a safety controller comprising two controller-based families such as TMS570 and RM4x known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

Modular devices include the modules (as described in connection with FIGS. 3 and 9, for example) that are receivable within a surgical hub and the surgical devices or instruments that can be connected to the various modules in order to connect or pair with the corresponding surgical hub. The modular devices include, for example, intelligent surgical instruments, medical imaging devices, suction/irrigation devices, smoke evacuators, energy generators, ventilators, insufflators, and displays. The modular devices described herein can be controlled by control algorithms. The control algorithms can be executed on the modular device itself, on the surgical hub to which the particular modular device is paired, or on both the modular device and the surgical hub (e.g., via a distributed computing architecture). In some exemplifications, the modular devices' control algorithms control the devices based on data sensed by the modular device itself (i.e., by sensors in, on, or connected to the modular device). This data can be related to the patient being operated on (e.g., tissue properties or insufflation pressure) or the modular device itself (e.g., the rate at which a knife is being advanced, motor current, or energy levels). For example, a control algorithm for a surgical stapling and cutting instrument can control the rate at which the instrument's motor drives its knife through tissue according to resistance encountered by the knife as it advances.

Figure 20:
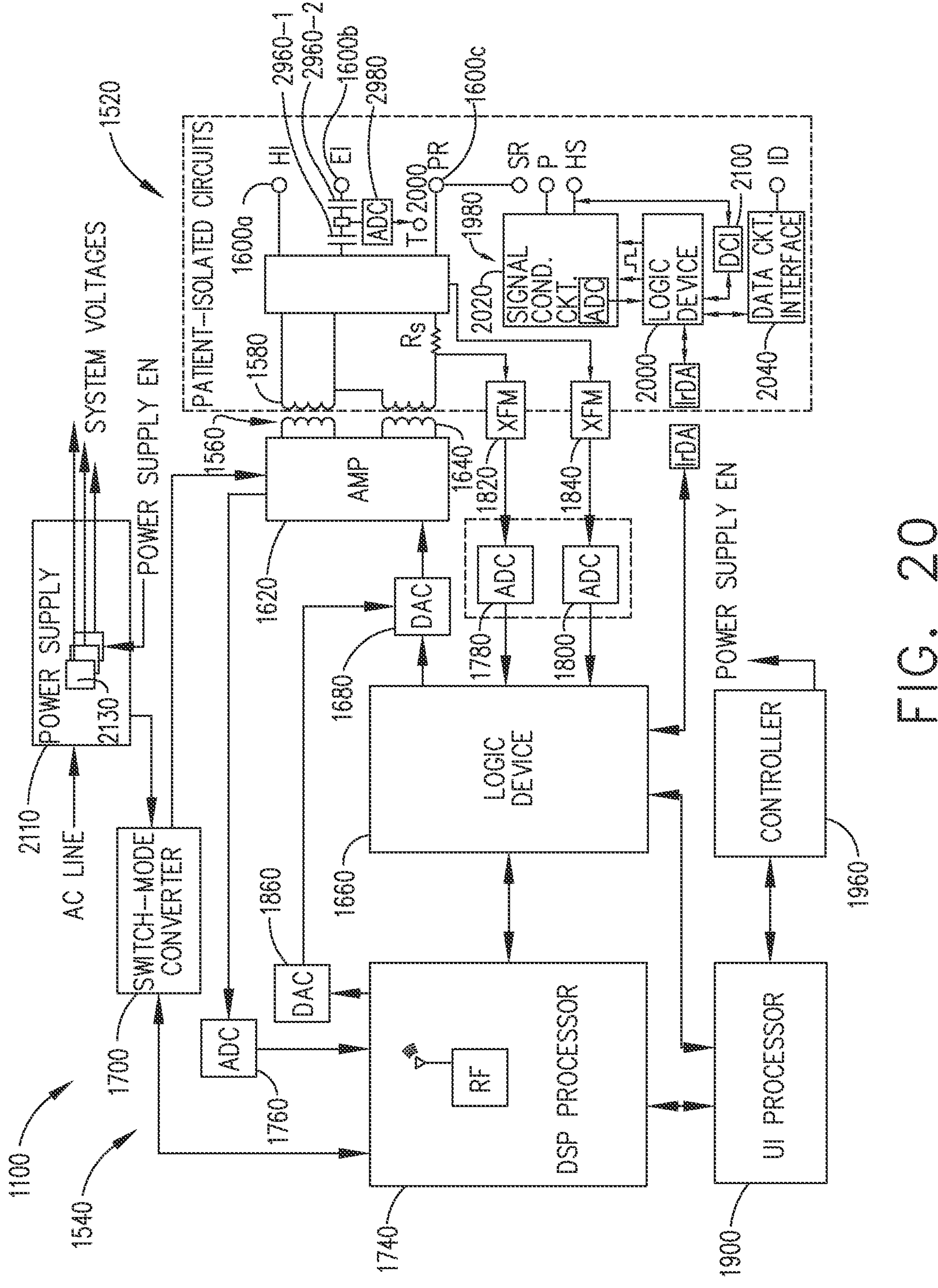
FIG. 20 is a structural view of a generator architecture, in accordance with at least one aspect of the present disclosure.

FIG. 20 is a simplified block diagram of one aspect of the generator 1100 for providing inductorless tuning as described above, among other benefits. With reference to FIG. 20, the generator 1100 may comprise a patient isolated stage 1520 in communication with a non-isolated stage 1540 via a power transformer 1560. A secondary winding 1580 of the power transformer 1560 is contained in the isolated stage 1520 and may comprise a tapped configuration (e.g., a center-tapped or non-center tapped configuration) to define drive signal outputs 1600*a*, 1600*b*, 1600*c* for outputting drive signals to different surgical devices, such as, for example, an ultrasonic surgical device 1104 and an electrosurgical device 1106. In particular, drive signal outputs 1600*a*, 1600*b*, 1600*c* may output a drive signal (e.g., a 420V RMS drive signal) to an ultrasonic surgical device 1104, and drive signal outputs 1600*a*, 1600*b*, 1600*c* may output a drive signal (e.g., a 100V RMS drive signal) to an electrosurgical device 1106, with output 1600*b* corresponding to the center tap of the power transformer 1560. The non-isolated stage 1540 may comprise a power amplifier 1620 having an output connected to a primary winding 1640 of the power transformer 1560. In certain aspects the power amplifier 1620 may comprise a push-pull amplifier, for example. The non-isolated stage 1540 may further comprise a programmable logic device 1660 for supplying a digital output to a digital-to-analog converter (DAC) 1680, which in turn supplies a corresponding analog signal to an input of the power amplifier 1620. In certain aspects the programmable logic device 1660 may comprise a field-programmable gate array (FPGA), for example. The programmable logic device 1660, by virtue of controlling the power amplifier's 1620 input via the DAC 1680, may therefore control any of a number of parameters (e.g., frequency, waveform shape, waveform amplitude) of drive signals appearing at the drive signal outputs 1600*a*, 1600*b*, 1600*c*. In certain aspects and as discussed below, the programmable logic device 1660, in conjunction with a processor (e.g., processor 1740 discussed below), may implement a number of digital signal processing (DSP)-based and/or other control algorithms to control parameters of the drive signals output by the generator 1100.

Power may be supplied to a power rail of the power amplifier 1620 by a switch-mode regulator 1700. In certain aspects the switch-mode regulator 1700 may comprise an adjustable buck regulator, for example. As discussed above, the non-isolated stage 1540 may further comprise a processor 1740, which in one aspect may comprise a DSP processor such as an ADSP-21469 SHARC DSP, available from Analog Devices, Norwood, Mass., for example. In certain aspects the processor 1740 may control operation of the switch-mode power converter 1700 responsive to voltage feedback data received from the power amplifier 1620 by the processor 1740 via an analog-to-digital converter (ADC) 1760. In one aspect, for example, the processor 1740 may receive as input, via the ADC 1760, the waveform envelope of a signal (e.g., an RF signal) being amplified by the power amplifier 1620. The processor 1740 may then control the switch-mode regulator 1700 (e.g., via a pulse-width modulated (PWM) output) such that the rail voltage supplied to the power amplifier 1620 tracks the waveform envelope of the amplified signal. By dynamically modulating the rail voltage of the power amplifier 1620 based on the waveform envelope, the efficiency of the power amplifier 1620 may be significantly improved relative to a fixed rail voltage amplifier scheme. The processor 1740 may be configured for wired or wireless communication.

In certain aspects, the programmable logic device 1660, in conjunction with the processor 1740, may implement a direct digital synthesizer (DDS) control scheme to control the waveform shape, frequency and/or amplitude of drive signals output by the generator 1100. In one aspect, for example, the programmable logic device 1660 may implement a DDS control algorithm by recalling waveform samples stored in a dynamically-updated look-up table (LUT), such as a RAM LUT which may be embedded in an FPGA. This control algorithm is particularly useful for ultrasonic applications in which an ultrasonic transducer, such as the ultrasonic transducer 1120, may be driven by a clean sinusoidal current at its resonant frequency. Because other frequencies may excite parasitic resonances, minimizing or reducing the total distortion of the motional branch current may correspondingly minimize or reduce undesirable resonance effects. Because the waveform shape of a drive signal output by the generator 1100 is impacted by various sources of distortion present in the output drive circuit (e.g., the power transformer 1560, the power amplifier 1620), voltage and current feedback data based on the drive signal may be input into an algorithm, such as an error control algorithm implemented by the processor 1740, which compensates for distortion by suitably pre-distorting or modifying the waveform samples stored in the LUT on a dynamic, ongoing basis (e.g., in real-time). In one aspect, the amount or degree of pre-distortion applied to the LUT samples may be based on the error between a computed motional branch current and a desired current waveform shape, with the error being determined on a sample-by sample basis. In this way, the pre-distorted LUT samples, when processed through the drive circuit, may result in a motional branch drive signal having the desired waveform shape (e.g., sinusoidal) for optimally driving the ultrasonic transducer. In such aspects, the LUT waveform samples will therefore not represent the desired waveform shape of the drive signal, but rather the waveform shape that is required to ultimately produce the desired waveform shape of the motional branch drive signal when distortion effects are taken into account.

The non-isolated stage 1540 may further comprise an ADC 1780 and an ADC 1800 coupled to the output of the power transformer 1560 via respective isolation transformers 1820, 1840 for respectively sampling the voltage and current of drive signals output by the generator 1100. In certain aspects, the ADCs 1780, 1800 may be configured to sample at high speeds (e.g., 80 Msps) to enable oversampling of the drive signals. In one aspect, for example, the sampling speed of the ADCs 1780, 1800 may enable approximately 200× (depending on drive frequency) oversampling of the drive signals. In certain aspects, the sampling operations of the ADCs 1780, 1800 may be performed by a single ADC receiving input voltage and current signals via a two-way multiplexer. The use of high-speed sampling in aspects of the generator 1100 may enable, among other things, calculation of the complex current flowing through the motional branch (which may be used in certain aspects to implement DDS-based waveform shape control described above), accurate digital filtering of the sampled signals, and calculation of real power consumption with a high degree of precision. Voltage and current feedback data output by the ADCs 1780, 1800 may be received and processed (e.g., FIFO buffering, multiplexing) by the programmable logic device 1660 and stored in data memory for subsequent retrieval by, for example, the processor 1740. As noted above, voltage and current feedback data may be used as input to an algorithm for pre-distorting or modifying LUT waveform samples on a dynamic and ongoing basis. In certain aspects, this may require each stored voltage and current feedback data pair to be indexed based on, or otherwise associated with, a corresponding LUT sample that was output by the programmable logic device 1660 when the voltage and current feedback data pair was acquired. Synchronization of the LUT samples and the voltage and current feedback data in this manner contributes to the correct timing and stability of the pre-distortion algorithm.

In certain aspects, the voltage and current feedback data may be used to control the frequency and/or amplitude (e.g., current amplitude) of the drive signals. In one aspect, for example, voltage and current feedback data may be used to determine impedance phase, e.g., the phase difference between the voltage and current drive signals. The frequency of the drive signal may then be controlled to minimize or reduce the difference between the determined impedance phase and an impedance phase setpoint (e.g., 0°), thereby minimizing or reducing the effects of harmonic distortion and correspondingly enhancing impedance phase measurement accuracy. The determination of phase impedance and a frequency control signal may be implemented in the processor 1740, for example, with the frequency control signal being supplied as input to a DDS control algorithm implemented by the programmable logic device 1660.

The impedance phase may be determined through Fourier analysis. In one aspect, the phase difference between the generator voltage $V_g(t)$ and generator current $I_g(t)$ driving signals may be determined using the Fast Fourier Transform (FFT) or the Discrete Fourier Transform (DFT) as follows:

$$V_g(t) = A_1\cos(2\pi f_0 t + \varphi_1)$$

$$I_g(t) = A_2\cos(2\pi f_0 t + \varphi_2)$$

$$V_g(f) = \frac{A_1}{2}(\delta(f - f_0) + \delta(f + f_0))\exp\left(j2\pi f\frac{\varphi_1}{2\pi f_0}\right)$$

$$I_g(f) = \frac{A_2}{2}(\delta(f - f_0) + \delta(f + f_0))\exp\left(j2\pi f\frac{\varphi_2}{2\pi f_0}\right)$$

Evaluating the Fourier Transform at the frequency of the sinusoid yields:

$$V_g(f_0) = \frac{A_1}{2}\delta(0)\exp(j\varphi_1) \quad \arg V(f_0) = \varphi_1$$

$$I_g(f_0) = \frac{A_2}{2}\delta(0)\exp(j\varphi_2) \quad \arg I(f_0) = \varphi_2$$

Other approaches include weighted least-squares estimation, Kalman filtering, and space-vector-based techniques.

Virtually all of the processing in an FFT or DFT technique may be performed in the digital domain with the aid of the 2-channel high speed ADC 1780, 1800, for example. In one technique, the digital signal samples of the voltage and current signals are Fourier transformed with an FFT or a DFT. The phase angle φ at any point in time can be calculated by:

$$\varphi=2\pi ft+\varphi_0$$

Where φ is the phase angle, f is the frequency, t is time, and $\varphi_0$ is the phase at t=0.

Another technique for determining the phase difference between the voltage $V_g(t)$ and current $I_g(t)$ signals is the zero-crossing method and produces highly accurate results. For voltage $V_g(t)$ and current $I_g(t)$ signals having the same frequency, each negative to positive zero-crossing of voltage signal $V_g(t)$ triggers the start of a pulse, while each negative to positive zero-crossing of current signal $I_g(t)$ triggers the end of the pulse. The result is a pulse train with a pulse width proportional to the phase angle between the voltage signal and the current signal. In one aspect, the pulse train may be passed through an averaging filter to yield a measure of the phase difference. Furthermore, if the positive to negative zero crossings also are used in a similar manner, and the results averaged, any effects of DC and harmonic components can be reduced. In one implementation, the analog voltage $V_g(t)$ and current $I_g(t)$ signals are converted to digital signals that are high if the analog signal is positive and low if the analog signal is negative. High accuracy phase estimates require sharp transitions between high and low. In one aspect, a Schmitt trigger along with an RC stabilization network may be employed to convert the analog signals into digital signals. In other aspects, an edge triggered RS flip-flop and ancillary circuitry may be employed. In yet another aspect, the zero-crossing technique may employ an eXclusive OR (XOR) gate.

Other techniques for determining the phase difference between the voltage and current signals include Lissajous figures and monitoring the image; methods such as the three-voltmeter method, the crossed-coil method, vector voltmeter and vector impedance methods; and using phase standard instruments, phase-locked loops, and other techniques as described in Phase Measurement, Peter O'Shea, 2000 CRC Press LLC, <http://www.engnetbase.com>, which is incorporated herein by reference.

In another aspect, for example, the current feedback data may be monitored in order to maintain the current amplitude of the drive signal at a current amplitude setpoint. The current amplitude setpoint may be specified directly or determined indirectly based on specified voltage amplitude and power setpoints. In certain aspects, control of the current amplitude may be implemented by control algorithm, such as, for example, a proportional-integral-derivative (PID) control algorithm, in the processor 1740. Variables controlled by the control algorithm to suitably control the current amplitude of the drive signal may include, for example, the scaling of the LUT waveform samples stored in the programmable logic device 1660 and/or the full-scale output voltage of the DAC 1680 (which supplies the input to the power amplifier 1620) via a DAC 1860.

The non-isolated stage 1540 may further comprise a processor 1900 for providing, among other things, user interface (UI) functionality. In one aspect, the processor 1900 may comprise an Atmel AT91 SAM9263 processor having an ARM 926EJ-S core, available from Atmel Corporation, San Jose, Calif., for example. Examples of UI functionality supported by the processor 1900 may include audible and visual user feedback, communication with peripheral devices (e.g., via a Universal Serial Bus (USB) interface), communication with a foot switch 1430, communication with an input device 2150 (e.g., a touch screen display) and communication with an output device 2140 (e.g., a speaker). The processor 1900 may communicate with the processor 1740 and the programmable logic device (e.g., via a serial peripheral interface (SPI) bus). Although the processor 1900 may primarily support UI functionality, it may also coordinate with the processor 1740 to implement hazard mitigation in certain aspects. For example, the processor 1900 may be programmed to monitor various aspects of user input and/or other inputs (e.g., touch screen inputs 2150, foot switch 1430 inputs, temperature sensor inputs 2160) and may disable the drive output of the generator 1100 when an erroneous condition is detected.

Figure 21:
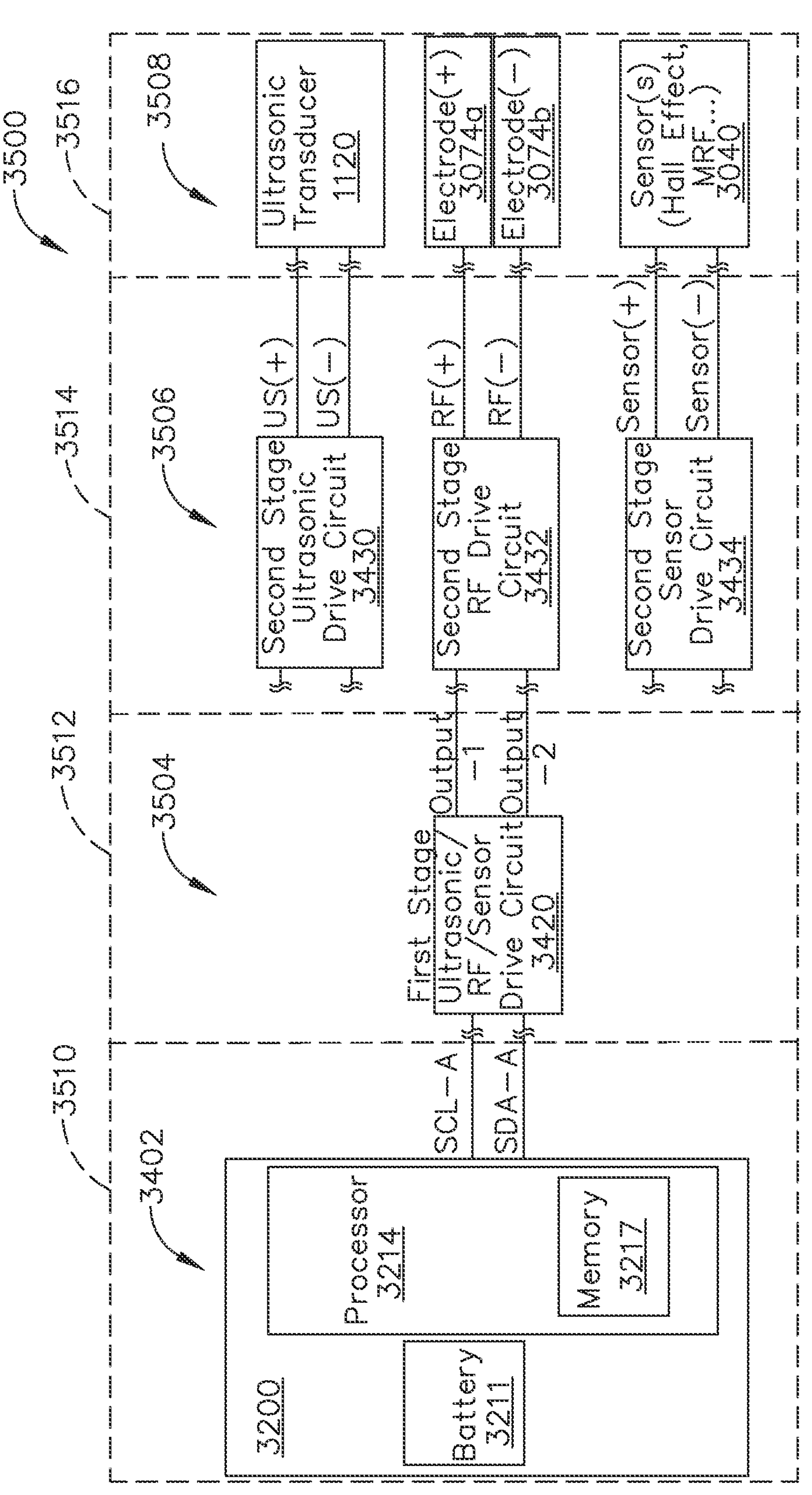
FIG. 21 illustrates a generator circuit partitioned into multiple stages where a first stage circuit is common to the second stage circuit, in accordance with at least one aspect of the present disclosure.

FIG. 21 illustrates a generator circuit 3500 partitioned into multiple stages where a first stage circuit 3504 is common to the second stage circuit 3506, in accordance with at least one aspect of the present disclosure. In one aspect, the surgical instruments of surgical system 1000 described herein may comprise generator circuit 3500 partitioned into multiple stages. For example, the surgical instruments of surgical system 1000 may comprise the generator circuit 3500 partitioned into at least two circuits: the first stage circuit 3504 and the second stage circuit 3506 of amplification enabling operation of high-frequency (RF) energy only, ultrasonic energy only, and/or a combination of RF energy and ultrasonic energy. A combination modular shaft assembly 3514 may be powered by a common first stage circuit 3504 located within the handle assembly 3512 and a modular second stage circuit 3506 integral to the modular shaft assembly 3514. As previously discussed throughout this description in connection with the surgical instruments of surgical system 1000, a battery assembly 3510 and the shaft assembly 3514 are configured to mechanically and electrically connect to the handle assembly 3512. The end effector assembly is configured to mechanically and electrically connect the shaft assembly 3514.

As shown in the example of FIG. 21, the battery assembly 3510 portion of the surgical instrument comprises a first control circuit 3502, which includes the control circuit 3200 previously described. The handle assembly 3512, which connects to the battery assembly 3510, comprises a common first stage drive circuit 3420. As previously discussed, the first stage drive circuit 3420 is configured to drive ultrasonic, high-frequency (RF) current, and sensor loads. The output of the common first stage drive circuit 3420 can drive any one of the second stage circuits 3506 such as the second stage ultrasonic drive circuit 3430, the second stage high-frequency (RF) current drive circuit 3432, and/or the second stage sensor drive circuit 3434. The common first stage drive circuit 3420 detects which second stage circuit 3506 is located in the shaft assembly 3514 when the shaft assembly 3514 is connected to the handle assembly 3512. Upon the shaft assembly 3514 being connected to the handle assembly 3512, the common first stage drive circuit 3420 determines which one of the second stage circuits 3506 (e.g., the second stage ultrasonic drive circuit 3430, the second stage RF drive circuit 3432, and/or the second stage sensor drive circuit 3434) is located in the shaft assembly 3514. The information is provided to the control circuit 3200 located in the handle assembly 3512 in order to supply a suitable digital waveform to the second stage circuit 3506 to drive the appropriate load, e.g., ultrasonic, RF, or sensor. It will be appreciated that identification circuits may be included in various assemblies 3516 in third stage circuit 3508 such as the ultrasonic transducer 1120, the electrodes 3074*a*, 3074*b*, or the sensors 3440. Thus, when a third stage circuit 3508 is connected to a second stage circuit 3506, the second stage circuit 3506 knows the type of load that is required based on the identification information.

Figure 22:
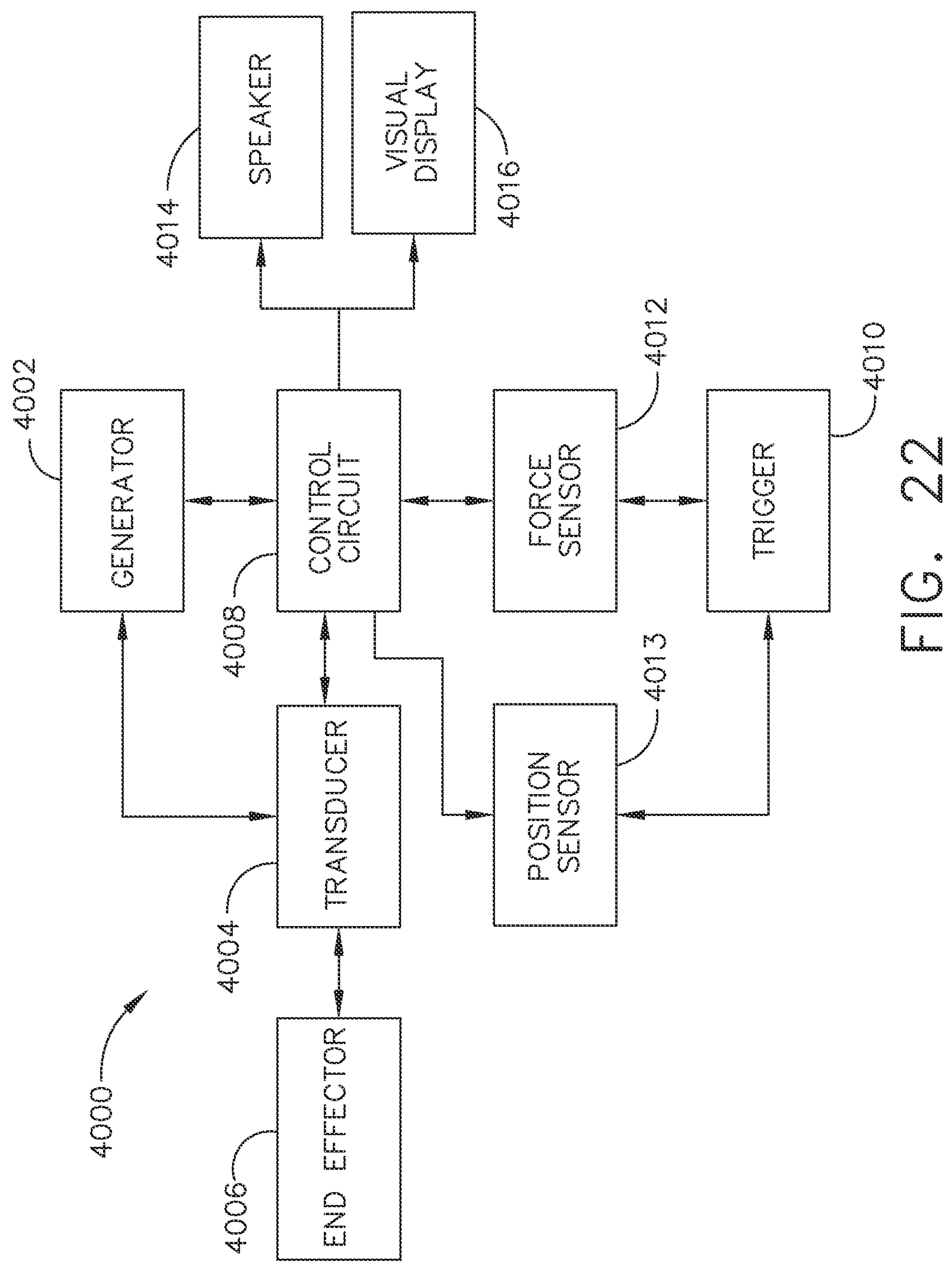
FIG. 22 illustrates a diagram of one aspect of a surgical instrument comprising a feedback system for use with a surgical instrument, according to one aspect of the present disclosure.

FIG. 22 illustrates a diagram of a surgical system 4000, which represents one aspect of the surgical system 1000, comprising a feedback system for use with any one of the surgical instruments of surgical system 1000, which may include or implement many of the features described herein. The surgical system 4000 may include a generator 4002 coupled to a surgical instrument that includes an end effector 4006, which may be activated when a clinician operates a trigger 4010. In various aspects, the end effector 4006 may include an ultrasonic blade to deliver ultrasonic vibration to carry out surgical coagulation/cutting treatments on living tissue. In other aspects the end effector 4006 may include electrically conductive elements coupled to an electrosurgical high-frequency current energy source to carry out surgical coagulation or cauterization treatments on living tissue and either a mechanical knife with a sharp edge or an ultrasonic blade to carry out cutting treatments on living tissue. When the trigger 4010 is actuated, a force sensor 4012 may generate a signal indicating the amount of force being applied to the trigger 4010. In addition to, or instead of a force sensor 4012, the surgical instrument may include a position sensor 4013, which may generate a signal indicating the position of the trigger 4010 (e.g., how far the trigger has been depressed or otherwise actuated). In one aspect, the position sensor 4013 may be a sensor positioned with an outer tubular sheath or reciprocating tubular actuating member located within the outer tubular sheath of the surgical instrument. In one aspect, the sensor may be a Hall-effect sensor or any suitable transducer that varies its output voltage in response to a magnetic field. The Hall-effect sensor may be used for proximity switching, positioning, speed detection, and current sensing applications. In one aspect, the Hall-effect sensor operates as an analog transducer, directly returning a voltage. With a known magnetic field, its distance from the Hall plate can be determined.

A control circuit 4008 may receive the signals from the sensors 4012 and/or 4013. The control circuit 4008 may include any suitable analog or digital circuit components. The control circuit 4008 also may communicate with the generator 4002 and/or a transducer 4004 to modulate the power delivered to the end effector 4006 and/or the generator level or ultrasonic blade amplitude of the end effector 4006 based on the force applied to the trigger 4010 and/or the position of the trigger 4010 and/or the position of the outer tubular sheath described above relative to a reciprocating tubular actuating member located within an outer tubular sheath (e.g., as measured by a Hall-effect sensor and magnet combination). For example, as more force is applied to the trigger 4010, more power and/or higher ultrasonic blade amplitude may be delivered to the end effector 4006. According to various aspects, the force sensor 4012 may be replaced by a multi-position switch.

According to various aspects, the end effector 4006 may include a clamp or clamping mechanism. When the trigger 4010 is initially actuated, the clamping mechanism may close, clamping tissue between a clamp arm and the end effector 4006. As the force applied to the trigger increases (e.g., as sensed by force sensor 4012) the control circuit 4008 may increase the power delivered to the end effector 4006 by the transducer 4004 and/or the generator level or ultrasonic blade amplitude brought about in the end effector 4006. In one aspect, trigger position, as sensed by position sensor 4013 or clamp or clamp arm position, as sensed by position sensor 4013 (e.g., with a Hall-effect sensor), may be used by the control circuit 4008 to set the power and/or amplitude of the end effector 4006. For example, as the trigger is moved further towards a fully actuated position, or the clamp or clamp arm moves further towards the ultrasonic blade (or end effector 4006), the power and/or amplitude of the end effector 4006 may be increased.

According to various aspects, the surgical instrument of the surgical system 4000 also may include one or more feedback devices for indicating the amount of power delivered to the end effector 4006. For example, a speaker 4014 may emit a signal indicative of the end effector power. According to various aspects, the speaker 4014 may emit a series of pulse sounds, where the frequency of the sounds indicates power. In addition to, or instead of the speaker 4014, the surgical instrument may include a visual display 4016. The visual display 4016 may indicate end effector power according to any suitable method. For example, the visual display 4016 may include a series of LEDs, where end effector power is indicated by the number of illuminated LEDs. The speaker 4014 and/or visual display 4016 may be driven by the control circuit 4008. According to various aspects, the surgical instrument may include a ratcheting device connected to the trigger 4010. The ratcheting device may generate an audible sound as more force is applied to the trigger 4010, providing an indirect indication of end effector power. The surgical instrument may include other features that may enhance safety. For example, the control circuit 4008 may be configured to prevent power from being delivered to the end effector 4006 in excess of a predetermined threshold. Also, the control circuit 4008 may implement a delay between the time when a change in end effector power is indicated (e.g., by speaker 4014 or visual display 4016), and the time when the change in end effector power is delivered. In this way, a clinician may have ample warning that the level of ultrasonic power that is to be delivered to the end effector 4006 is about to change.

In one aspect, the ultrasonic or high-frequency current generators of the surgical system 1000 may be configured to generate the electrical signal waveform digitally such that the desired using a predetermined number of phase points stored in a lookup table to digitize the wave shape. The phase points may be stored in a table defined in a memory, a field programmable gate array (FPGA), or any suitable non-volatile memory.

Advanced Energy Device Control Algorithms

Various control algorithms for ultrasonic surgical instruments and combination energy surgical instruments (e.g., ultrasonic/monopolar surgical instruments, monopolar/bipolar surgical instruments, ultrasonic/bipolar surgical instruments, and other such combination energy devices) are described herein. For the sake of clarity, surgical instruments will be referenced as surgical instrument 7012 in this section of the present disclosure, although the disclosure of this section could also apply to other surgical instruments referenced above such as surgical instrument 112, 700.

In various aspects, a control algorithm for an ultrasonic surgical instrument 7012 can be configured to apply a variable clamp arm pressure over the cycle time or the tissue coagulation/cut process of a surgical operation to create a constant proximal-to-distal pressure profile. The constant pressure profile means that each portion of tissue held within the end effector of surgical instrument 7012 along the proximal to distal end of the end effector experiences the same or substantially same pressure resulting from the force applied by the end effector clamp arm. This may advantageously result in better coagulation of surgically cut tissue. The control algorithm can be applied by a control circuit and/or a surgical hub. The constant proximal-to-distal pressure profile may involve applying the control algorithm to vary the pressure applied by the clamp arm to provide a threshold control pressure at the cut progression location. The cut progression location can be represented by the progression of a corresponding weld/coagulation focal point determined by the control circuit and/or surgical hub. Thus, the pressure may be varied based on the focal point. The threshold control pressure may be a constant pressure applied to the tissue regardless of the amount of the end effector that is active. That is, the applied pressure does not change (or at least does not significantly change) despite any changes in the extent of tissue loading of the end effector.

A tissue bite or portion of tissue may be loaded into the end effector for surgical treatment, such as by loading the distal end of the end effector with tissue first. In this way, contact may initially be made at a distal point of the end effector. A distal portion of one or more of the ultrasonic blade and clamp arm could grasp the tissue at this distal point. The initial pressure applied by the clamp arm may be determined or adjusted (e.g., from a default pressure level) by a control circuit and/or surgical hub based on the size of the tissue bite initially being grasped, which corresponds to an amount of the blade being utilized at the start (an initial tissue loading of the end effector). After surgical cutting of tissue, surgical coagulation/sealing may be performed by the surgical instrument 7012, such as by ultrasonic vibration of the ultrasonic blade and/or delivery of an RF electrical signal waveform output from the generator to RF electrodes. In the coagulation process, the progression of the weld may be used to adjust the applied clamp pressure. Specifically, the pressure of the clamp arm can adjust over the progression of the weld as the cut/weld focal point shifts along the blade.

In order to better grasp the tissue at the distal point, one or more of the blade and clamp arm could be biased or offset to create a preferential initial contact point at the distal end. Subsequently, the remaining portion of the clamp arm may then be broadly loaded in a distal to proximal manner. Stated differently, in this distal start closure stroke configuration, the offset ultrasonic blade may deflect so as to fully close against the tissue and clamp arm fully at the end effector distal end followed by deflecting further in the proximal direction. The deflections of the blade and clamp arm may be approximately equal or balanced relative to each other. The distal start closure stroke configuration is described in more detail below. The clamp arm pressure can also be varied from the initial pressure by the control circuit and/or surgical hub based on the degree that the end effector is loaded with the tissue and the progression through the weld. Also, the clamp arm pressure can be varied based on the measured tissue impedance (e.g., via a pressure, resistive, or other suitable sensor 788 in the end effector). Moreover, depending on which energy modality or modalities of the surgical instrument 7012 are selected, the power level of one or more of RF and ultrasonic energy delivered to the end effector can also be varied based on the measured tissue impedance. Other types of electrosurgical energy besides RF and ultrasonic energy could also be used.

As discussed above, the tissue loading might commence at the tip or distal end of the end effector such that the first contact between the ultrasonic blade and the clamp arm is at the tip. The surgical hub and/or control circuit can be configured to vary pressure applied by the clamp arm based on the extent of blade utilization, which could be determined via position sensor 784 (referred to in this portion of the present disclosure as position sensor 784, although position sensor 784 may also refer to position sensor 734, 4013 or others as described above). In particular, the application of clamp pressure can be controlled so that the clamp arm and ultrasonic blade do not apply pressure at portions of the end effector that do not contain tissue. In other words, the application of clamp pressure is tailored to those portions of the end effector in which tissue is located between the ultrasonic blade and clamp arm. This may advantageously reduce temperatures and heat residing in the ultrasonic blade after activation of the generator of the surgical instrument 7012. To elaborate further, when the generator delivers energy to the end effector, the portions of the end effector in which tissue is not located receive a relatively lower force so energy delivered to these portions is reduced. Consequently, after activating the generator, the peak temperatures and heat of the ultrasonic blade are reduced.

This targeted application of force by the clamp arm can be achieved based on motorized or manual closure control, tip first closure of the end effector, and feedback provided to the control circuit and/or surgical hub. The feedback could include thermally induced changes in the resonant frequency and electrical continuity (or discontinuity). The feedback could be received by the control circuit via circuitry that comprises the ultrasonic blade and a clamp arm/ultrasonic blade interface (e.g., clamp tissue pad). The changes or shift in the resonant frequency of the transducer may be used as feedback to determine the extent of the tissue loading. In this way, the feedback may be used to adjust applied clamp pressure. Furthermore, the control circuit may control the motor of the surgical instrument to implement the closure stroke so that the end effector closes at a point which is distal to the proximal-most point of the grasped tissue. In this way, a gap may be maintained between the clamp arm and ultrasonic blade at a point which is proximal to the proximal-most point of the grasped tissue.

Sensors 788 (referenced as sensors 788 in this portion of the present disclosure, although they could also refer to sensors 738 or other sensors described above) of the surgical instrument 7012 may provide end effector closure signals as input to the control circuit. Using this input, the control circuit can determine the current closure position of the end effector. When the control circuit determines that the end effector is merely closed at the tip portions (e.g., distal tip or proximal tip) or at some other sub-portion of the end effector length (e.g., the distal half of the end effector), the control circuit may reduce displacement of the ultrasonic blade. To this end, power provided to the ultrasonic transducer may be reduced. This reduction in displacement might beneficially prevent or reduce excessive wear of the clamp arm tissue pad at the distal tip. This excessive wear generally is caused by high distal forces or pressure at the distal tip (corresponding to the distal start closure stroke configuration) and inherent high distal displacement corresponding to displacement profiles associated with ultrasonic blades.

In general, when the tissue does not fully occupy the space between the jaws of the end effector, reducing the surface area of the clamp arm being compressed against the blade reduces the wasteful transmission of electrosurgical energy (e.g., including ultrasonic and RF energy) to the clamp arm and/or tissue pad. In other words, the adjustment in clamp arm pressure enables relatively more electrosurgical energy to be directed towards the tissue rather than undesirably being transmitted to other parts of the end effector. Because the pressure applied by the clamp arm is controlled based on the extent of tissue loading, a constant pressure may be applied to the tissue regardless of how much of the end effector is in an active state. The pressure may further be adjusted based on progression of the surgical coagulation/cutting treatment by the surgical instrument 7012.

Furthermore, the feedback circuitry comprising the ultrasonic blade and clamp pad can also comprise sensor 788 for sensing impedance of the tissue located between the clamp arm and the ultrasonic blade. In this case, the ultrasonic blade and associated waveguide that terminates at the blade could serve as part of the return path for the feedback circuitry. The sensed impedance can indicate a status of the coagulation/cut cycle. That is, for example, comparing the tissue impedance to a threshold may be indicative of a weld progression of the tissue, such as a progression of the weld/coagulation focal point. The focal point may be indicative of how well formed a fibrin clot is for coagulation, for example. In this way, the detected tissue impedance can enable the control circuit and/or surgical hub to adjust power provided to the ultrasonic transducer and the force applied by the clamp arm.

Although at least some portion of the control algorithm(s) disclosed herein can be performed by surgical hubs (alone or in conjunction with associated control circuits of surgical instruments), the functions of the control algorithm(s) are described as performed by control circuits for the sake of clarity. Also for clarity, the control circuit of surgical instrument 7012 in this portion of the present disclosure is labeled control circuit 710, although control circuit 710 can be the same or similar to control circuits 760, 3200, 3502, 4008. Control circuit 710 may be a part of the generator 4002 itself (referred to as generator 4002 for clarity although generator 4002 can be the same or similar to generator 140, 145, 240, 721, 771, 900, 1100) or another part of the surgical instrument 7012 that is remote from the generator 4002. In various aspects, the surgical instrument 7012 (e.g, ultrasonic surgical instrument) as described in FIGS. 23A-23B, 24A-24B, 25-26, 27A-27C, 28A-28C, 29A-29C, 30A-30D, 31A-31D, 32A-32E, is configured to operate with situational awareness in a hub environment, such as the surgical hub 106 or 206 (FIGS. 1-11), for example, as depicted by the timeline 5200.

Figure 23A:
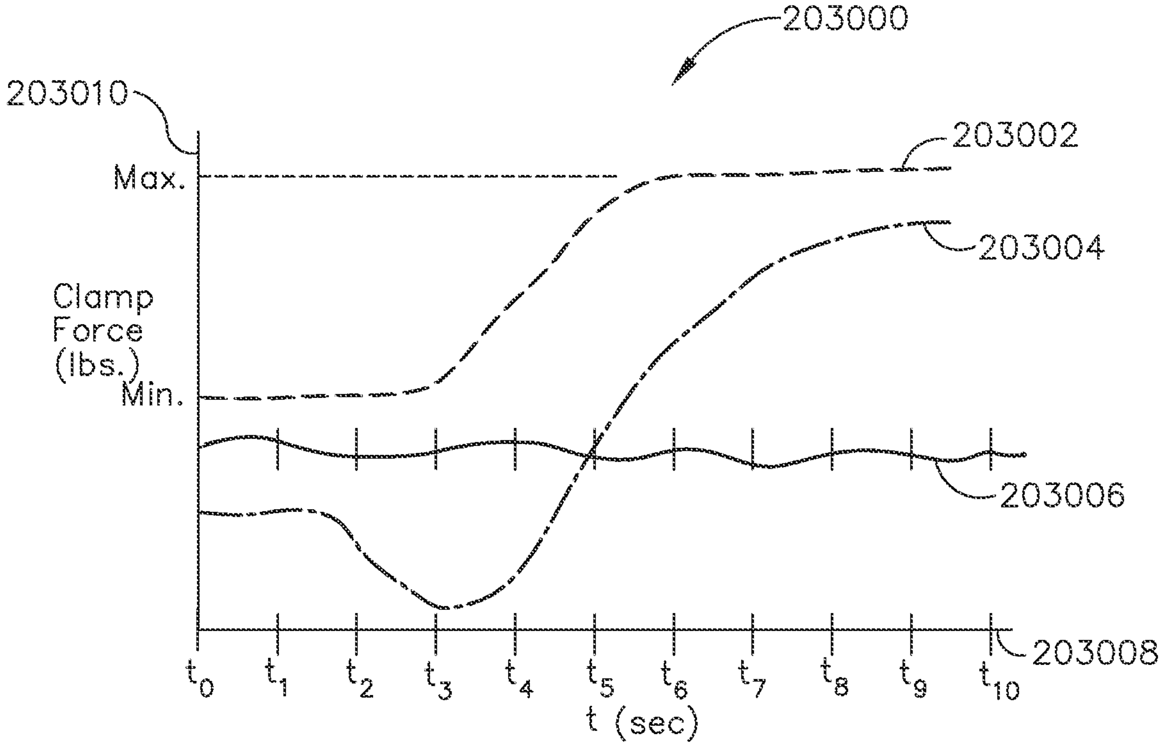
FIG. 23A-23B are graphs including a graph of clamp force as a function of time and an associated graph of a coagulation/cut focal point, in accordance with at least one aspect of the present disclosure.
Figure 23B:
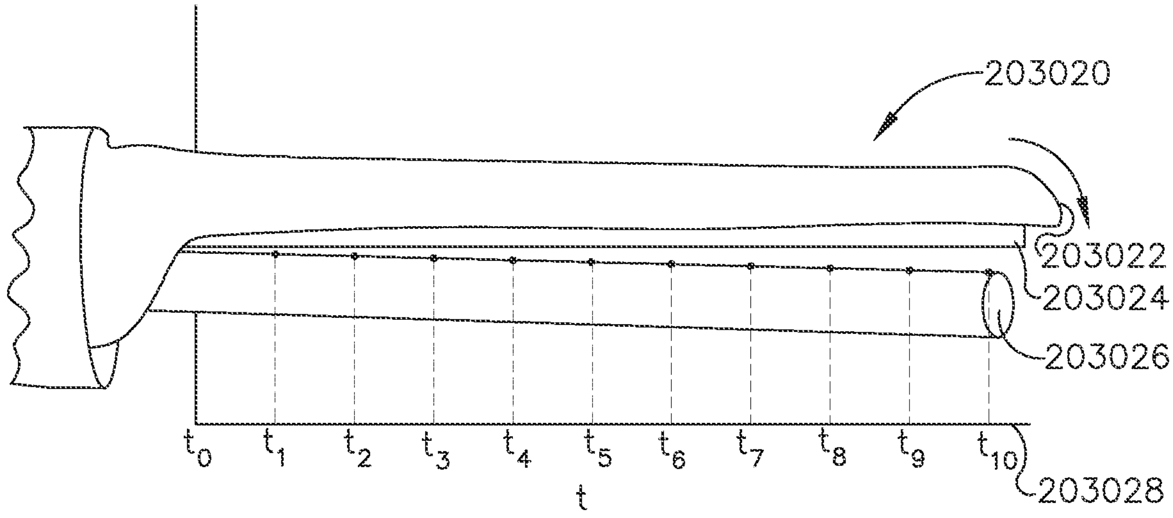

FIG. 23A-23B are graphs 203000, 203020 including a graph of clamp force as a function of time and an associated graph of a coagulation/cut focal point, in accordance with at least one aspect of the present disclosure. In FIG. 23A, the y-axis 203010 denotes force while the x-axis 203008 denotes time. The dashed line 203002 represents the force applied by the clamp arm over time and tracks the application of force by the clamp arm from the minimum force at time $t_0$ to maximum force at time $t_{10}$. Clamp force may be measured in suitable units, such as pounds (lbs). The time spanning initial time $t_0$ to time $t_{10}$ can define a surgical cycle of the surgical instrument 7012. The dash-and-dot line 203004 represents the measured tissue impedance over the surgical cycle. As can be seen on graph 203000, the measured tissue impedance decreases from its initial level at time $t_0$ to the low point at time $t_3$, demonstrating the drop in impedance resulting from the commencement of surgical treatment (the so-called "bathtub" portion of the impedance curve). After time $t_3$, the tissue impedance line 203004 rises as the tissue being treated begins to dry out. This desiccation results in an increase in tissue impedance. FIG. 23A shows how this increase in tissue impedance line 203004 corresponds to an increase in the applied force line 203002. The increase in applied force may assist in cutting the tissue and welding the denatured tissue as the surgical cycle is completed.

In particular, the control circuit 710 may execute the control algorithm to provide a constant proximal-to-distal pressure profile. By providing such a threshold control pressure, the tissue seal formed during the coagulation stage advantageously may be more uniform and secure. Accordingly, the solid line 203006, which indicates a measured pressure applied to the tissue in the end effector, stays the same or roughly constant throughout the surgical cycle. The tissue pressure line 203006 may correspond to the pressure applied at the leading edge of the end effector, where surgical coagulation and cutting occur. Clamp force can be a function of the progress of the tissue coagulation process. This relationship may be used to provide the constant tissue pressure. Thus, while tissue may be coagulated and cut at the proximal sections of the end effector, increasing clamp force at the distal section results in better coupling of the tissue to the distal sections of the ultrasonic blade. In this way, each section of tissue (which spans the proximal to distal sections of the end effector) could experience the same or approximately similar pressure. As the tissue weld progresses, the control circuit may control the clamp arm to progressive closure, which is demonstrated by graph 203000. Also, the clamp arm may be cambered to the ultrasonic wave guide that terminates into the ultrasonic blade.

FIG. 23B shows that the focal point of the surgical coagulation and cutting operation on the tissue shifts along the length of ultrasonic blade 203026 (similar to or the same as ultrasonic blade 718, 768 or other ultrasonic blades described above) over the course of the surgical cycle. As shown in FIG. 23B, the focal point shifts in a proximal to distal direction over time, but the focal point could also shift in a distal to proximal direction. The former possibility corresponds to a proximal start closure stroke configuration while the latter corresponds to a distal start closure stroke configuration. As discussed above, the control circuit 710 may be configured to determine the cut/weld focal point based on one or more of the resonant frequency and electrical continuity feedback measures. Graph 203020 also portrays clamp arm 203022 (similar to the same as clamp arm 716, 766 or other clamp arms described above). Clamp arm 203022 can comprise clamp tissue pad 203024, which may be formed from TEFLON® or some other suitable low-friction material. The pad 203024 may be mounted for cooperation with the blade 203026, with pivotal movement of the clamp arm 203022 positioning the clamp pad 203024 in substantially parallel relationship to, and in contact with, the ultrasonic blade 203026. By this construction, a tissue bite to be clamped may be grasped between the tissue pad 203024 and the ultrasonic blade 203026. The tissue pad 203024 may be provided with a sawtooth-like configuration including a plurality of axially spaced, proximally extending gripping teeth to enhance the gripping of tissue in cooperation with the ultrasonic blade 203026. The control circuit 710 may control the clamp arm 203022 to transition from between an open position and a closed position, including various intermediate positions in between. The control circuit 710 may vary the pressure applied by the clamp arm 203022 based on a shift in the weld focal point along the ultrasonic blade 203026 or an extent of tissue loading in the end effector. The x-axis 203028 of graph 203020 represents the surgical cycle in the same manner that x-axis 203008 does.

Figures 24A, 24B:
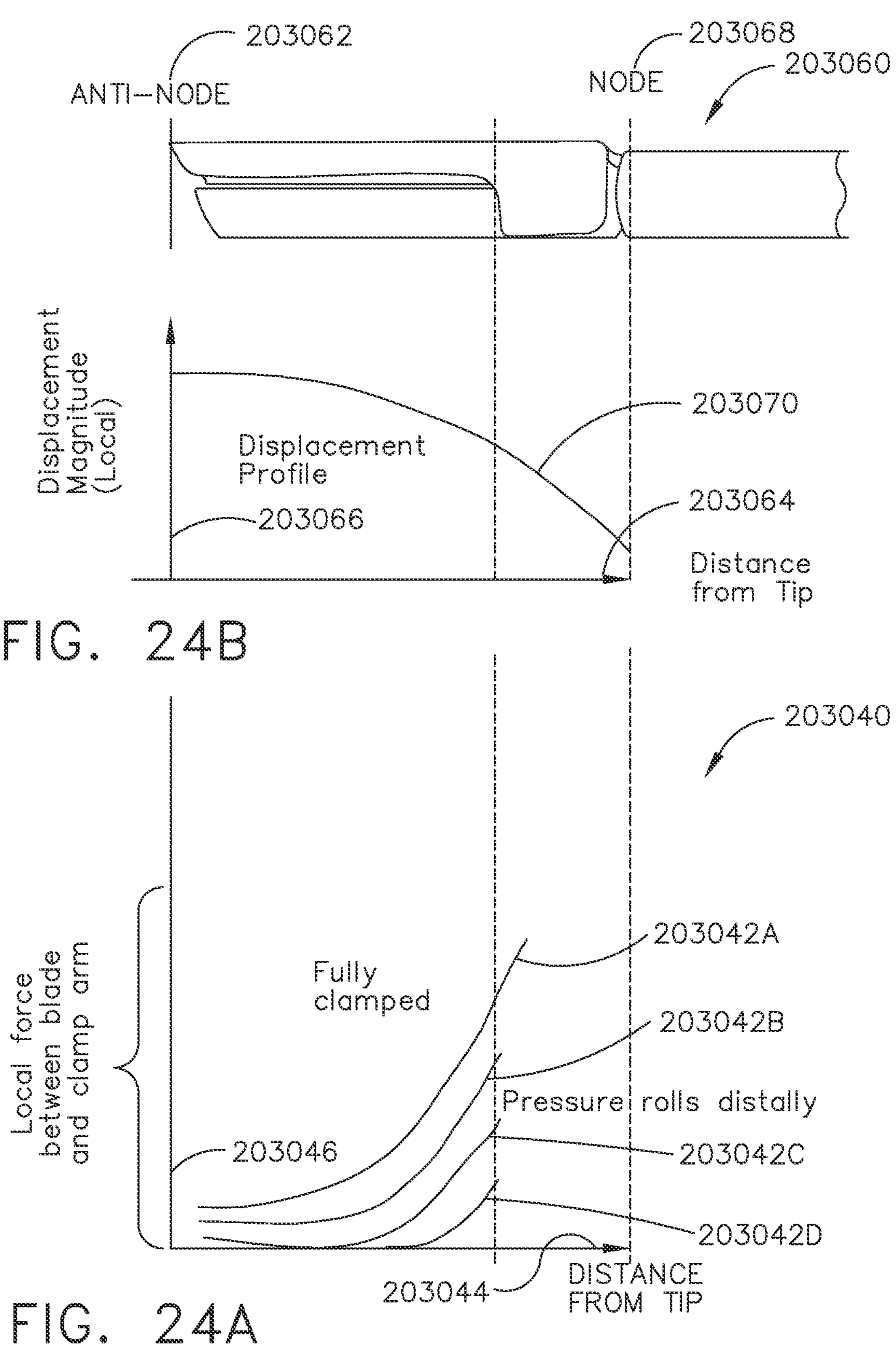
FIGS. 24A-24B are graphs including a graph of clamp force as a function of distance from the distal tip of the end effector and a graph of blade displacement as a function of distance from the distal tip, in accordance with at least one aspect of the present disclosure.

FIGS. 24A-24B are graphs 203040, 203060 including a graph 203040 of clamp force as a function of distance from the distal tip of the end effector and a graph 203060 of blade displacement as a function of distance from the distal tip, in accordance with at least one aspect of the present disclosure. FIG. 24A illustrates how the clamp pressure between the ultrasonic blade 203026 and clamp arm 203022 varies as a function of the distance from the distal tip relative to the tissue. Specifically, the graph 203040 includes a plurality of clamp pressure curves 203042A-203042D showing how the control circuit 710 can adjust the applied clamp pressure depending on the position of the tissue. To this end, the control circuit 710 may determine the closure position of one or more of the ultrasonic blade 203026 and clamp arm 203022. The x-axis 203044, 203064 denotes distance from the distal tip of the end effector while the y-axis 203046, 203066 denotes applied clamp force. In the proximal start closure stroke configuration of FIG. 24A, the applied clamp pressure rolls in a distal direction during the closure motion so that the closure stroke is at the fully clamped state at the distal tip. Put differently, the clamp pressure may be maximal when the distance from the distal tip is minimal. High amplitude of clamp pressure may be necessarily to surgically manipulate the tissue such as manipulating the structure of a blood vessel as desired.

FIG. 24B illustrates the corresponding displacement profile of the ultrasonic blade 203026 as a function of distance from the tip of the end effector. In the graph 203060, the x-axis 203064 again denotes distance from the distal tip while the y-axis 203066 denotes the magnitude of displacement of the ultrasonic blade 203026. Relatedly, the zero point of the x-axis corresponds an anti-node 203062 while the maximal point corresponds to a node 203068 of the ultrasonic blade 203026. The anti-node 203062 can be defined as a local absolute maximum in which the displacement or vibration of the ultrasonic blade 203026 is maximal. The node 203068 can be defined as a local absolute minimum in which the displacement or vibration of the ultrasonic blade 203026 is minimal. In general, the distance between the adjacent node and anti-nodes can be one-quarter wavelength of the drive or resonant frequency of the ultrasonic blade 203026. As illustrated by the graph 203060, at the anti-node 203062, the occurrence of the positive maximum extent of ultrasonic vibration of the ultrasonic blade 203026 overlaps with the maximal distance away from the distal tip. This would also occur at the next anti-node corresponding to the negative maximum extent of ultrasonic vibration, although this is not shown in FIG. 24B. At the point (node 203068) of minimum distance away from the distal tip, the ultrasonic vibration is minimal so as to fully clamp or grasp tissue between the ultrasonic blade 203026 and clamp arm 203022. This change in ultrasonic displacement as a function of distance of tip is represented by displacement line 203070.

In contrast to the proximal start closure stroke configuration, the present disclosure may contemplate a distal start closure stroke configuration in which first closing the distal tip of the end effector ultimately assists in advantageously attaining heat mitigation. Heat mitigation can occur by configuring the control circuit 710 to control clamp pressure according to the extent of tissue loading in the end effector. Specifically, pressure may be provided only at points of intersection where ultrasonic blade 203026 and clamp arm 203022 grasp tissue therebetween. By preventing or reducing pressure at portions of the end effector where no tissue resides, peak temperatures and residual heat after energy delivery from the generator 4002 are reduced. In this way, relatively more energy is transmitted to the tissue instead of the electrically conductive clamp arm tissue pad 203024. The clamp pad 203024 may be formed of a molded, carbon filled polytetraflouroethylene or some other suitable material and additionally may be secured to the underside of clamp arm 203022, as described in U.S. Patent Application Publication No. 2017/0164997, titled METHOD OF TREATING TISSUE USING END EFFECTOR WITH ULTRASONIC AND ELECTROSURGICAL FEATURES, published on Jun. 15, 2017, which is herein incorporated by reference in its entirety.

Also, the clamp tissue pad 203024 may be electrically conducive based on the use of conductive fillers (e.g. carbon, carbon nanotubes, metallic particles, etc.). Electrical current could flow through the surgical instrument 7012 from the ultrasonic blade 203026 to the tissue pad 203024 via isolated electrical circuitry, which enables the application of therapeutic or sub-therapeutic RF energy to the tissue by the end effector (e.g., via RF electrode 796). When the surgical instrument 7012 includes RF electrode 796, the control circuit 710 can be configured to adjust one or more of a power level of the RF energy and a power level of the electrosurgical energy based on determined tissue impedance. More details regarding conductive pads may be found in U.S. Pat. No. 9,764,164, titled ULTRASONIC SURGICAL INSTRUMENTS, issued on Sep. 19, 2017, which is herein incorporated by reference in its entirety. Other aspects of combination bipolar RF and ultrasonic architectures of surgical instrument 7012 are described in U.S. Pat. No. 9,017,326, titled IMPEDANCE MONITORING APPARATUS, SYSTEM, AND METHOD FOR ULTRASONIC SURGICAL INSTRUMENTS, issued on Apr. 28, 2015; U.S. Pat. No. 10,022,568, titled DEVICES AND TECHNIQUES FOR CUTTING AND COAGULATING TISSUE, issued on Jul. 17, 2018; and U.S. Patent Application Publication No. 2017/0164997, titled METHOD OF TREATING TISSUE USING END EFFECTOR WITH ULTRASONIC AND ELECTROSURGICAL FEATURES, published on Jun. 15, 2017, all of which are herein incorporated by reference in their entirety.

The control circuit 710 may control the motor of the surgical instrument 7012 to adjust the closure of the clamp arm 203022 and/or the movement of the ultrasonic blade 203026 for heat mitigation and energy efficiency. To this end, only a part of the full length of the end effector could be used to grasp and treat tissue. For example, only the distal end of the end effector could initially close on a tissue bite followed by progressively more tissue loading in the proximal direction. In this distal start closure stroke configuration, the applied force by the clamp arm is increased until reaching the full closure stroke threshold while the clamp arm 203022 and/or ultrasonic blade 203026 gradually deform to fully compress against tissue while maintaining a slight gap therebetween in portions of the end effector that do not contain tissue. When the full closure stroke of the end effector is attained, the clamp tissue pad 203024 may contact the entire length of the tissue treating portion of the ultrasonic blade 203026. In this way, the control circuit can be configured to close the end effector at a distal end of the end effector prior to closing non-distal end portions of the end effector. The pressure profile of the tissue treating or end effecting portion of the ultrasonic blade 203026 is described in more detail below.

An offset, sloping, or otherwise curved ultrasonic blade 203026 can assist in facilitating distal tip first closure of the clamp arm 203022. More detail regarding closing the distal tip of the end effector first (distal start closure stroke configuration) and the offset ultrasonic blade 203026 may be found in U.S. Pat. No. 8,444,663, titled ULTRASONIC SURGICAL SHEARS AND TISSUE PAD FOR THE SAME, issued on May 21, 2013; U.S. Pat. No. 10,004,527, titled ULTRASONIC SURGICAL INSTRUMENT WITH STAGED CLAMPING, issued on Jun. 26, 2018; U.S. Patent Application Publication No. 2018/0153574, titled HEADPIECE AND BLADE CONFIGURATIONS FOR ULTRASONIC SURGICAL INSTRUMENT, published on Jun. 7, 2018; U.S. Patent Application Publication No. 2018/0153574, titled HEADPIECE AND BLADE CONFIGURATIONS FOR ULTRASONIC SURGICAL INSTRUMENT, issued on Jun. 7, 2018; and U.S. Patent Application Publication No. 2018/0014848, titled ULTRASONIC SURGICAL INSTRUMENTS HAVING OFFSET BLADES, published on Jan. 18, 2018, all of which are herein incorporated by reference in their entirety. As discussed above, the ultrasonic blade 203026 and/or clamp arm 203022 may be compliant so that the control circuit 710 causes the ultrasonic blade 203026 and/or clamp arm 203022 to deform as the applied clamp force increases. FIGS. 32A-32E illustrate how this deformation may occur as tissue treatment proceeds. In general, the end effector should be in a full closure state prior to application of electrosurgical energy. Also, a first deflection of the offset ultrasonic blade can correspond to a second deflection of the offset clamp arm. The first and second deflection could be shaped according to a closure pressure profile implemented by the control circuit 710 to provide relatively greater pressure in the proximal portion of the end effector.

The control circuit 710 may use feedback to control the end effector for heat mitigation as described above. For example, the control circuit 710 could monitor the resonant frequency of the ultrasonic blade 203026. In particular, the generator 4002 may include a tuning inductor for tuning out the static capacitance at a resonant frequency so that substantially all of generator's current output flows into the motional branch. The motional branch current, along with the drive voltage, define the impedance and phase magnitude. Accordingly, the current output of the generator 4002 represents the motional branch current, thus enabling the generator 4002 to maintain its drive output at the ultrasonic transducer's resonant frequency. The control circuit 710 can monitor drive signals of the generator 4002 that correlate to the resonant frequency. The generator 4002 may deliver electrosurgical energy to the end effector to weld tissue based on generating the drive signal. As a surgical treatment cycle proceeds, the resonant frequency changes due to changes in the material stiffness of the tissue. In turn, the change in material stiffness occurs because of the rapid accumulation of thermal energy in the ultrasonic blade 203026, as electrosurgical energy is being delivered. The control circuit 710 is configured to evaluate this dynamic thermal response via frequency changes or frequency slope (e.g., first derivative of frequency or frequency change with respect to time), such as based on comparison to a frequency threshold parameter value. Additionally or alternatively, the control circuit 710 can compare the change in resonant frequency relative to an initial frequency value determined at the start of electrosurgical energy activation, which can be recorded to the memory of the surgical instrument 7012. Based on electrical signals generated by the generator 4002, the control circuit 710 may determine and compare frequency slope or frequency changes against corresponding thresholds. Specifically, the control circuit 710 may determine: (i) when the frequency slope is above the associated threshold parameter value and (ii) when the frequency change is above a frequency floor. Above a frequency floor means, for example, that the drop in frequency does not exceed a predetermined threshold drop relative to the determined initial frequency value. Based on one or more of these determinations, the control circuit 710 (e.g., via the motor) can control the ultrasonic blade 203026 and/or clamp arm 203022 to reduce closure force/stroke when the frequency monitoring conditions (i), (ii) are met. As such, the control circuit 710 may determine a resonant frequency measure indicative of a thermally induced change in resonant frequency to calculate a tissue weld/seal focal point.

In this way, the control circuit 710 causes the applied clamp force or pressure to "back off", to beneficially minimize the delivery of thermal energy to the clamp pad 203024 at locations that are proximal to the proximal extent of the grasped tissue. More details regarding resonant frequency monitoring can be found in U.S. Pat. No. 8,512,365, titled SURGICAL INSTRUMENTS, issued Aug. 20, 2013; and U.S. Pat. No. 9,788,851, titled SURGICAL INSTRUMENT WITH TISSUE DENSITY SENSING, issued on Oct. 17, 2017; both of which are herein incorporated by reference in their entirety. Furthermore, the control circuit 710 can be programed to follow a set limit defining the permissible extent to which the control circuit 710 backs off on closure force or stroke. The set limit could be determined in order to prevent tissue from slipping out or otherwise escaping from the grasp of the end effector. In addition, the surgical instrument 7012 could be designed to provide user feedback such as visual, audible, tactile, haptic, vibratory, or some other feedback to the user that is indicative of the current closure state. For example, the user feedback (e.g., light emitting diode, graphical user interface, buzzer, computer generated sound, handle vibration etc.) might indicate when the end effector closes at a point proximal the proximal extent of the grasped tissue. In situations where the user selects an override setting for overriding the automatic closure control feature of the surgical instrument 7012, this user feedback can be particularly helpful to inform the user of closure status.

As another example of feedback, the control circuit 710 could monitor the electrical impedance of the surgical instrument 7012. In various aspects, the surgical instrument 7012 may conduct electrical current between the ultrasonic blade 203026 and the clamp arm tissue pad 203024 for delivery of electrosurgical energy. By monitoring this electrical current (or lack thereof), tissue impedance, or transducer impedance based on an end effector sensor 788 and/or drive signal of generator 4002, the control circuit 710 may determine the amount of tissue loading in the end effector. In particular, the control circuit 710 may be programmed to detect and maintain an impedance of the circuit comprising the blade 203026 and the clamp arm tissue pad 203024 above a predetermined threshold. This maintained impedance can correspond or approximately correspond to an electrical short. As such, the electrical short means electrical discontinuity exists between the ultrasonic blade 203026 and the clamp arm tissue pad 203024. Therefore, minimal thermal energy is delivered to the portion of the clamp arm tissue pad 203024 located proximally to the proximal extent of the grasped tissue. To arrive at this desired lack of electrical continuity, the control circuit 710 could perform the reduction or backing off of the closure force or stroke as described above. As such, the control circuit 710 may determine an electrical continuity measure to calculate a tissue weld/seal focal point.

On the other hand, when the end effector is not fully closed, the feedback received by the control circuit 710 may be used to reduce the output of the generator 4002. The output of the generator 4002 might be ultrasonic and/or bipolar RF electrosurgical energy, depending on the energy modality configuration of the surgical instrument 7012. By reducing the ultrasonic displacement of ultrasonic blade 203026 and/or RF power conducted via RF electrode 796, the control circuit 710 may prevent or lower instances of relatively high power densities at the distal tip of the end effector. This is especially true given that the ultrasonic vibration of ultrasonic blade 203026 is generally relatively high at the distal tip. In any case, avoiding these high power densities may advantageously stop or reduce excessive wearing or deterioration of the clamp arm tissue pad 203024. The acoustic drive impedance of the ultrasonic blade 203026 could also be used to assess jaw closure state. Additionally or alternatively, a closure switch of the surgical instrument 7012 such as a handle closure switch could indicate when the clamp arm 203022 and/or ultrasonic blade 203026 is closed, as described for example in U.S. Pat. No. 9,724,118, titled TECHNIQUES FOR CUTTING AND COAGULATING TISSUE FOR ULTRASONIC SURGICAL INSTRUMENTS, issued on Aug. 8, 2017, which is herein incorporated by reference in its entirety. Position sensor 734 or motor current also could be used to determine jaw closure state.

Figure 25:
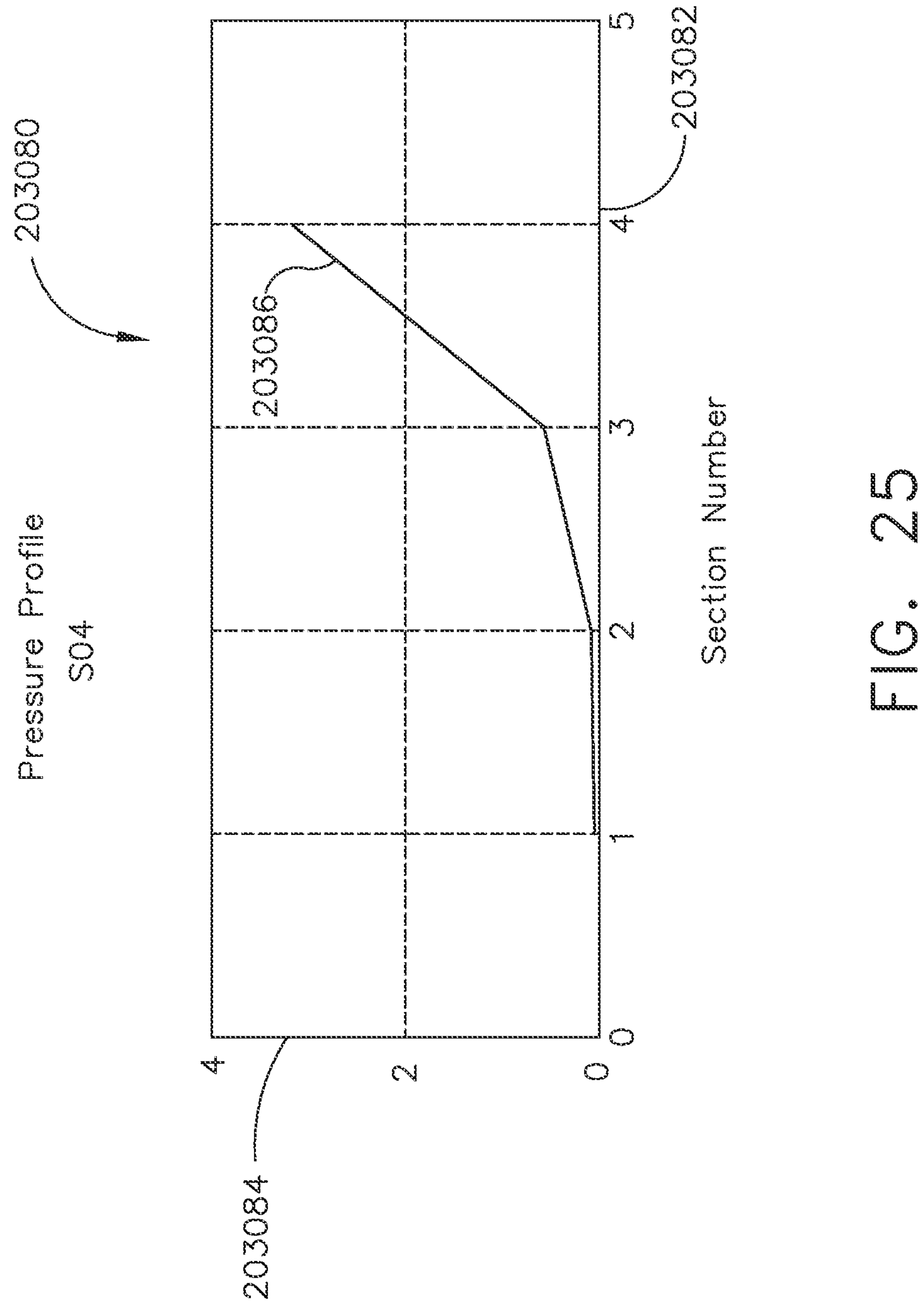
FIG. 25 is a graph of a clamp force distribution as a function of various sections along the length of the end effector, in accordance with at least one aspect of the present disclosure.

FIG. 25 is a graph 203080 of a clamp force distribution as a function of various sections along the length of the end effector, in accordance with at least one aspect of the present disclosure. The x-axis 203082 denotes a section along the length of the end effector, including section numbers 1 through 5. The y-axis 203084 denotes gradients of pressure measured in suitable units ranging from 1 through 4. The units could be pounds (lbs), for example. Section 1 represents the distal-most portion while section 4 represents the proximal-most portion of the end effector. The measured force can be determined by the control circuit 710 based on the sensor 788, such as a pressure sensor. The pressure output signal of pressure sensor 788 used to generate graph 203080 has been averaged or summed to smooth the clamp pressure line 203086. In other words, peaks and valleys in the pressure line 203086 that might result from irregularities in the pad 203024 (e.g., teeth in the clamp pad 203024) or sensor 788 are softened or smoothed out in graph 203080. As illustrated by graph 203080, the force distribution in the proximal half of the end effector is relatively higher than the force distribution in the distal half of the end effector. In other words, the pressure profile ratio of the end effector is below the value 1.

The pressure profile ratio can be defined as the sum of pressure applied in the distal portion divided by the sum of pressure applied in the proximal portion of the end effector. Therefore, pressure profile ratios >1 indicate that the end effector is distal tip loaded while pressure profile ratios <1 indicate proximal loaded status. A distal tip loaded end effector may have more cumulative pressure on the distal half while a proximal loaded end effector has more cumulative pressure on the proximal half. As demonstrated by graph 203080, the end effector measured by pressure sensor 788 is proximally loaded. The proximally loaded status may be assessed from a position in which no tissue is contained within the end effector. One such example can be seen in FIG. 32A. The relatively higher force applied in the proximal portion of the end effector may result from the greater degree of curvature or offset between the ultrasonic blade 203026 and clamp arm 203022 in the distal portion relative to the proximal portion. Proximally loading the end effector may be desirable because the ultrasonic blade 203026 generally may ultrasonically vibrate to a greater extent towards to the distal portions. That is, the displacement of the ultrasonic blade 203026 might be greater at the distal portion than the proximal portion of the end effector. The relatively high clamp pressure applied at the proximal portion can advantageously ensure a more uniform application of electrosurgical energy to the tissue, thereby attaining a more secure cutting/coagulation surgical treatment.

Figure 26:
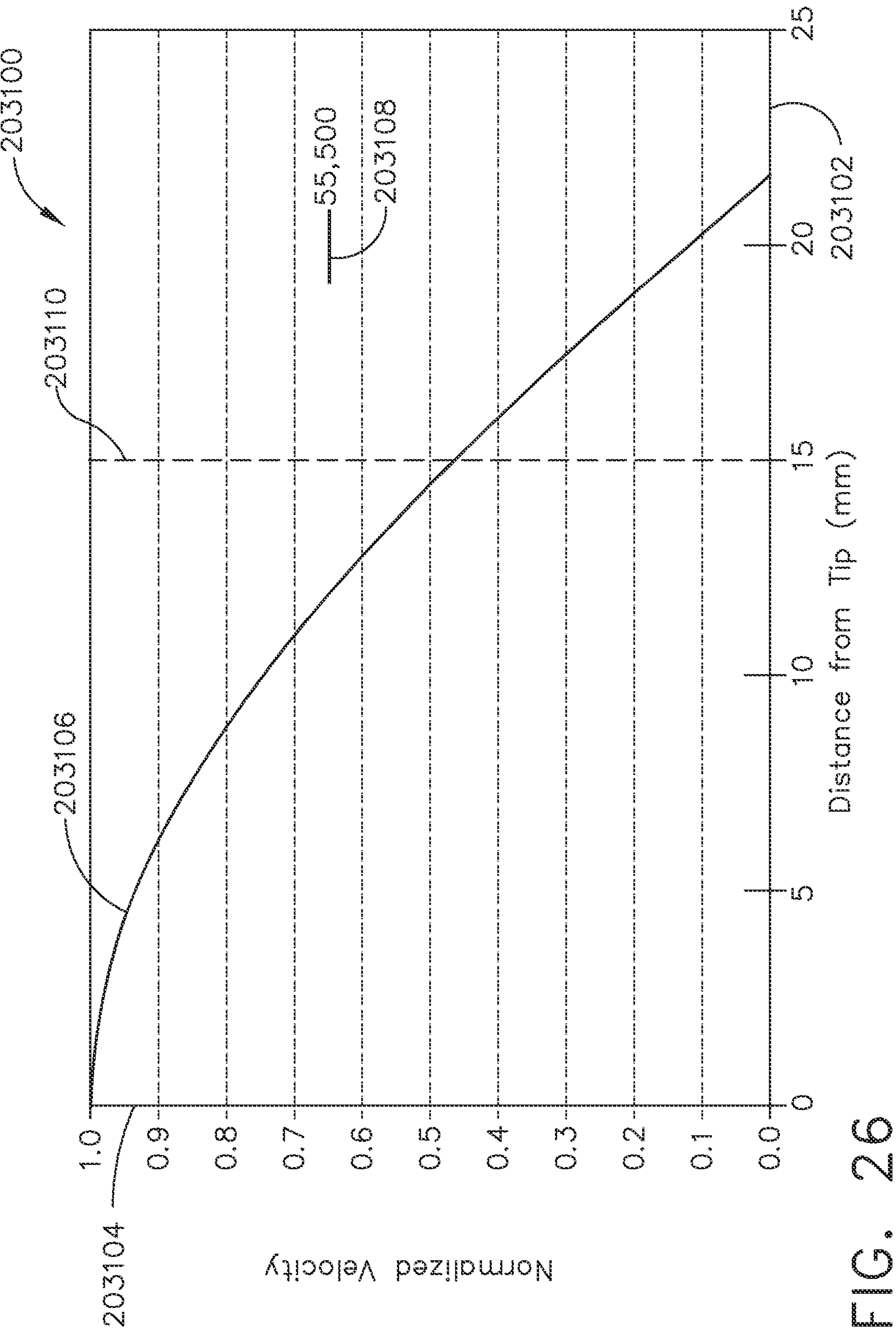
FIG. 26 is a graph of blade displacement profile as a function of distance from the distal tip of the end effector, in accordance with at least one aspect of the present disclosure.

FIG. 26 is a graph 203100 of blade displacement profile as a function of distance from the distal tip of the end effector, in accordance with at least one aspect of the present disclosure. The x-axis 203102 denotes distance from the distal tip of the end effector, which is shown in units of millimeters (mm) on graph 203100. The y-axis 203104 denotes the normalized velocity (on a scale ranging from 0 to 1) of the ultrasonic blade 203026. When normalized, the velocity profile as shown in 203100 is coterminous or overlaps with the displacement profile of the ultrasonic blade 203026. In addition, the driven resonant frequency 203108 of the ultrasonic blade 203026 defines the effective wavelength of the displacement or velocity profile. As shown in FIG. 26, the driven resonant frequency 203108 is 55.5 kilohertz (kHz), although other suitable resonant frequency values are possible as well. The driven resonant frequency 203108 is a factor of the material, geometry, and thermal condition of the surgical instrument 7012. Also shown in FIG. 26 is the tissue treatment border 203110 of the end effector. The tissue treatment border 203110 indicates the length of the tissue treating (e.g., cutting and coagulation) portion of the end effector and is approximately 15 mm from the distal tip in graph 203100. The velocity-distance line 203106 represents the change in normalized velocity as a function of distance from the distal tip.

Stated another way, the tissue treating portion spans 15 mm from the distal tip of the end effector, as measured in the proximal direction. The velocity and/or displacement profile as portrayed in graph 203100 demonstrates that the velocity and/or displacement of the ultrasonic blade 203026 is maximal at the distal tip and decreases to the minimal value as the distance from the distal tip increases to the maximum. Accordingly, providing a preferential distribution of clamp force towards the proximal portion of the end effector as shown in FIG. 25, can allow for a more uniform power deposition along the length of the end effector. Power deposition is a function of the coefficient of friction, the velocity, and the applied force or pressure. Thus, as discussed above, matching the relatively high distal velocity to a relatively low distal pressure and matching the relatively low proximal velocity to a relatively high proximal pressure can result in more uniform cutting of tissue, as determined with respect to time. When the end effector is fully closed such that it has reached the full closure stroke, the resulting pressure or force profile is higher in the proximal half or quarter of the end effector, so graph 203080 shows how the pressure or force profile ratio is <1. Also, the deflections of the ultrasonic blade 203026 and clamp arm 203022 can be equivalent or match over the course of the closure stroke of the end effector.

FIGS. 27A-27C are sectional views of end effector 203120 that illustrate a closure stroke of the end effector, in accordance with at least one aspect of the present disclosure. The progression of the closure stroke as portrayed in FIGS. 27A-27C demonstrates a proximal start configuration closure stroke. In FIG. 27A, the end effector 203120 (which may be the same or similar to end effectors described above, including end effector 702, 752, 792, 4006) is at a more open position than in FIGS. 27B-27C. Clamp arm 203122 includes clamp arm tissue pad 203124, which may be the same or similar as pad 203024. In FIG. 27A, the clamp arm 203122 is spaced away from the ultrasonic blade 203126 so that clamp arm tissue pad 203124 initially begins to contact or touch the blade at the most proximal portion of the clamp arm tissue pad 203124. The clamp arm 203122 is sloped or angled upwards relative to a horizontal axis defined by the end effector 203120. Accordingly, the opening between the clamp arm 203122 and ultrasonic blade 203126 increases in the distal direction away from pivot point 203128. The clamp arm 203122 and ultrasonic blade 203126 may pivot about pivot point 203128.

Although FIG. 27A does not depict tissue grasped by the end effector 203120, in operation, tissue may be located in end effector 203120 such that the end effector 203120 compresses against tissue at the proximal-most extent of pad 203124 to being tissue treatment in FIG. 27A. In FIG. 27B, the clamp arm 203122 is further along in the closure stroke of the end effector 203120. As such, most or all of the proximal portion of the end effector is in the closed position. Accordingly, FIG. 27B shows that the proximal-most extent of the pad 203124 contacts the ultrasonic blade 203126, while the portions of the pad 203124 immediately distal to the proximal-most extent are also almost closed or contacting the ultrasonic blade 203126. Again, the gap between the clamp arm 203122 and the ultrasonic blade 203126 increases in the distal direction away from pivot point 203128. FIG. 27C illustrates the full closure position of the end effector 203120. In FIG. 27C, the full extent of the clamp arm 203122 and pad 203124 contacts the ultrasonic blade 203126 to obtain the full closure stroke. Thus, clamp pressure is applied to all portions of the end effector 203120, as reflected in FIG. 28C. The closure progression of the proximal start configuration as depicted in FIGS. 27A-27C demonstrates how clamp pressure or force rolls in the distal direction.

Figures 28A, 28B, 28C:
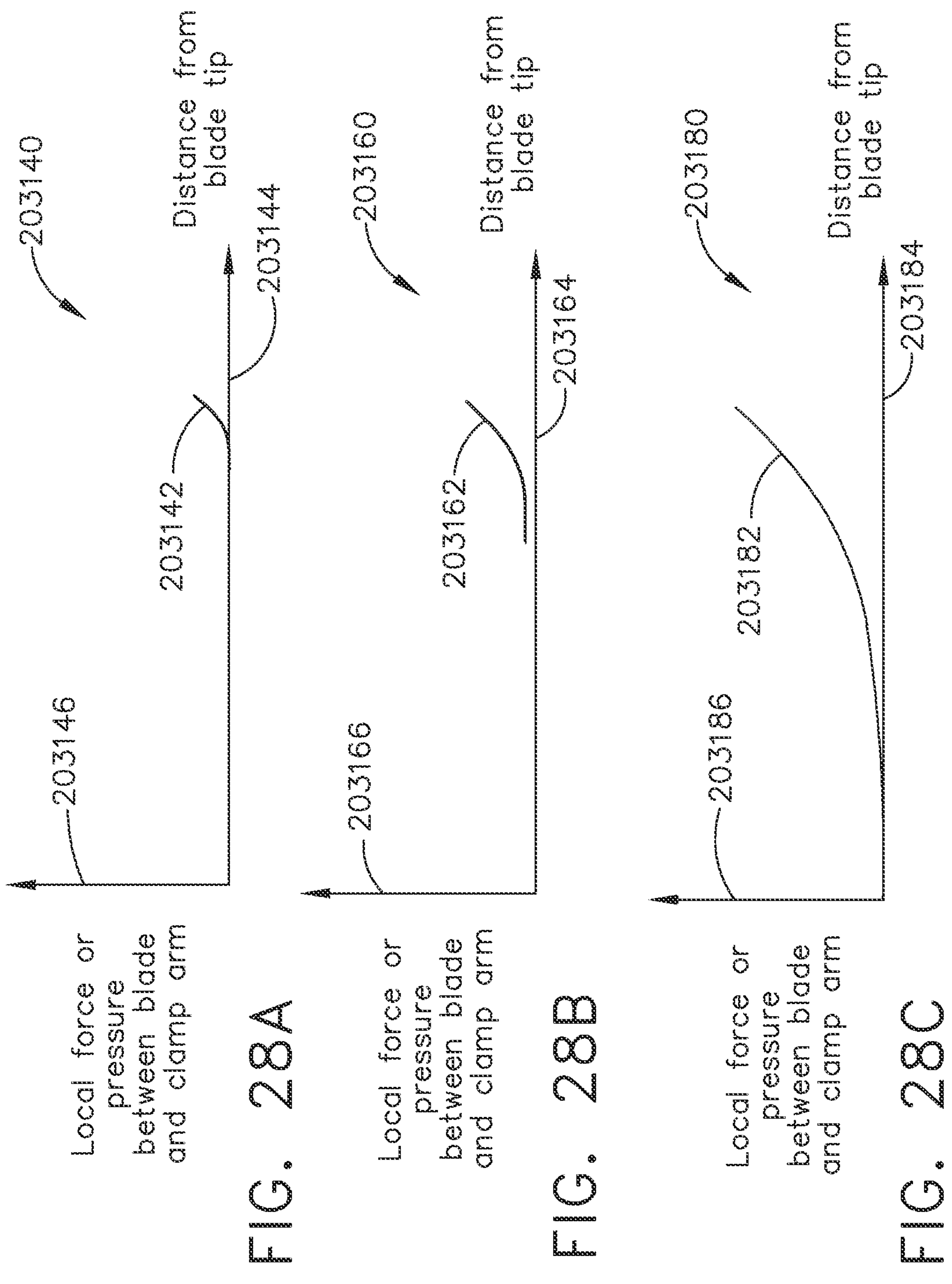
FIGS. 28A-28C are graphs of clamp force applied between the blade and clamp arm as a function of distance from the distal tip of the end effector corresponding to the sectional views of FIGS. 27A-27C, in accordance with at least one aspect of the present disclosure.

FIGS. 28A-28C are graphs 203140, 203160, 203180 of clamp force applied between the blade and clamp arm as a function of distance from the distal tip of the end effector 203120 corresponding to the sectional views of FIGS. 27A-27C, in accordance with at least one aspect of the present disclosure. The applied clamp pressure or force plotted in graphs 203140, 203160, 203180 can be measured by pressure sensor 788. In the graphs 203140, 203160, 203180, the x-axis 203144, 203164, 203184 denotes the distance from the distal tip of end effector 203120. The y-axis 203146, 203166, 203186 denotes the clamp arm pressure or force applied between the clamp arm 203122 and the ultrasonic blade 203126. The applied clamp force line 203142, 203162, 203184 illustrates the clamp pressure as a function of distance from the distal tip of end effector 203120. As described above, the applied clamp pressure first begins at the proximal-most extent of clamp arm tissue pad 203124, adjacent to pivot point 203128. This is demonstrated by FIG. 28A. In FIG. 28B, the clamp pressure has begun to spread distally. Accordingly, the applied clamp force line 203162 starts at a more leftward point than that of applied clamp force line 203142. Moreover, the clamp pressure at the proximal-most extent of clamp arm tissue pad 20312 is greater in FIG. 28B than in FIG. 28A. That is, the amplitude at the rightmost portion of the applied clamp force line 203162 is greater than the corresponding amplitude of applied clamp force line 203142.

In FIG. 28C, the applied clamp force line 203182 starts at an even more leftward point than that of applied clamp force line 203162. In fact, clamp pressure is applied at all points spanning the x-axis 203184. The clamp pressure at the proximal-most extent of clamp arm tissue pad 20312 is greater in FIG. 28C than either of FIG. 28B and FIG. 28A.

The graph 203180 of FIG. 28C illustrates the applied pressure in a full closure stroke or position of the end effector 203120. In the full closure state of the end effector 203120, it may be desirable for the control circuit 710 to implement computer executable logic or rules that ensure the end effector 203120 reaches the full closure stroke prior to application of energy by the generator 4002. As discussed above, the full closure stroke is achieved when the end effector 203120 closes along its entire available length. By delivering electrosurgical energy to the tissue only after attaining the full closure position, better tissue sealing may be performed. In particular, homeostasis can be maximized or improved based on the full closure stroke laterally displacing the inner layers and approximating the outer layers of the tissue so that these layers may be joined during delivery of electrosurgical energy. That is, optimum vessel sealing may occur when the inner muscle layer of a vessel is separated and moved away from the adventitia layer prior to the application of electrosurgical energy. The outer tissue layers could form more reliable tissue welds or seals (e.g., tunica adventitia, serosal covering, etc.).

One example of such rules executed by the control circuit 710 includes a rule in which if the user activates the large vessel or advanced hemostasis mode of the surgical instrument 7012, the control circuit 710 verifies that the end effector 203120 has reaches the full closure stroke. This verification could occur via a handle closure or full closure switch of the surgical instrument 7012, for example. When the closure switch is not in the closed position, this indicates the end effector 203120 is not fully closed. Consequently, the surgical instrument 7012 may generate an alert such as an audible beeping sound or visual, audible, tactile, haptic, vibratory alert, or some other suitable alert. In some aspects, the surgical instrument 7012 may have mechanical components to control application of relatively high clamp force for displacing vessel structure (e.g., approximating adventitia) and of relatively low clamp force for energy delivery. More details regarding such rules and vessel structure manipulation for cutting and sealing tissue may be found in U.S. Pat. No. 8,779,648, titled ULTRASONIC DEVICE FOR CUTTING AND COAGULATING WITH STEPPED OUTPUT, issued on Jul. 15, 2014; U.S. Pat. No. 9,241,728, titled SURGICAL INSTRUMENT WITH MULTIPLE CLAMPING MECHANISMS, issued on Jan. 26, 2016; U.S. Pat. No. 9,743,947, titled END EFFECTOR WITH A CLAMP ARM ASSEMBLY AND BLADE, issued on Aug. 29, 2017; all of which are herein incorporated by reference in their entirety.

Figure 29A:
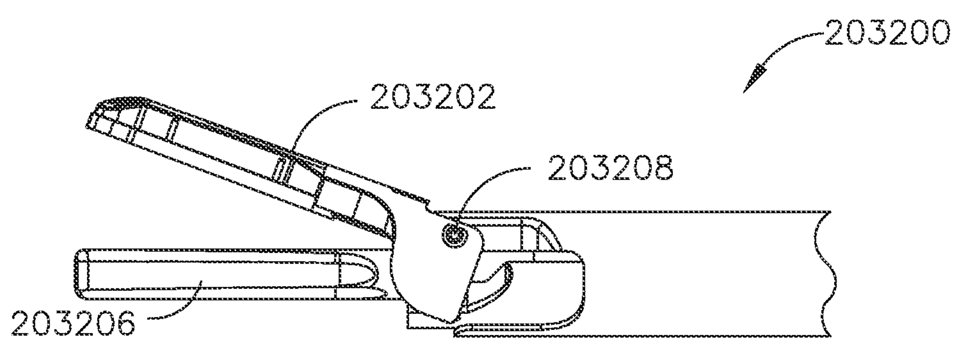
FIGS. 29A-29C are sectional views of the end effector that illustrate a proximal start closure stroke configuration, in accordance with at least one aspect of the present disclosure.
Figure 29B:
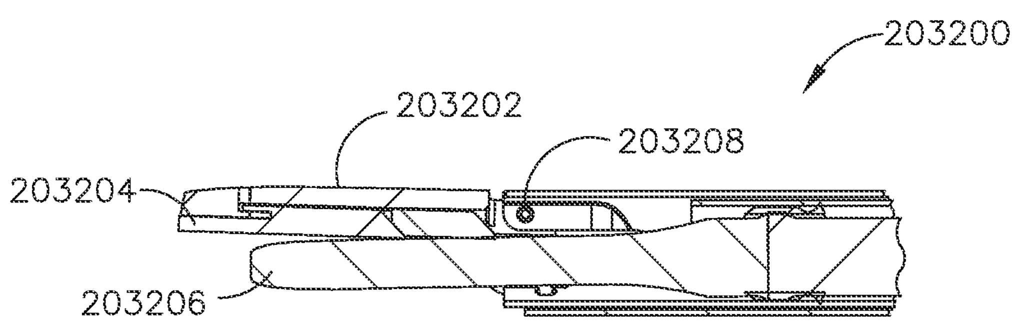
Figure 29C:
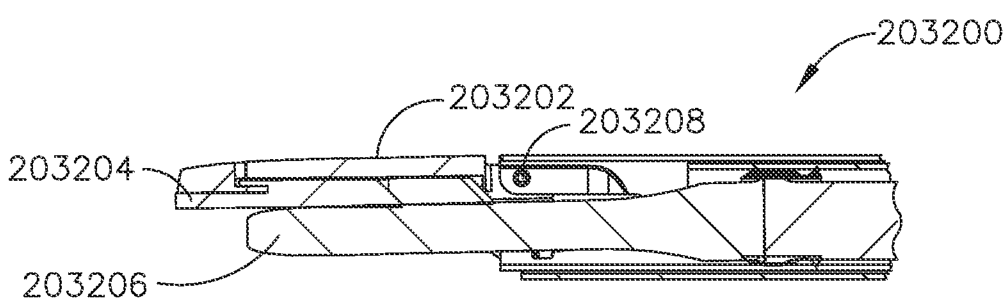

FIGS. 29A-29C are sectional views of the end effector 203200 that illustrate a proximal start closure stroke configuration, in accordance with at least one aspect of the present disclosure. As shown in FIG. 29A, the end effector 203200 starts in an open position in which clamp arm 203202 and ultrasonic blade 203206 define a relatively large gap in between each other. Clamp arm 203202 includes clamp arm tissue pad 203204, which may the same or similar as pad 203024, 203124. In FIG. 29B, the clamp arm 203202 has pivoted inwards with respect to pivot point 203208 so that the proximal portion of clamp arm tissue pad 203204 contacts tissue (not shown) located on the pad 203204. In other words, the end effector 203200 closes proximally first so as to apply full clamp pressure to only the proximal portion of the grasped tissue while clamp force progressively rolls or expands in the distal direction. As the end effector 203000 reaches the full closure stroke depicted in FIG. 29C, more clamp pressure is gradually distally. In FIG. 29C, the full closure pressure profile or force distribution is achieved in the full closure position of end effector 203000. As discussed above, relatively more clamp pressure can be applied in the proximal portion of the end effecting portion of the ultrasonic blade 203026 to account for the relatively low proximal velocity of the ultrasonic blade 203026, for example.

Figures 30A, 31A:
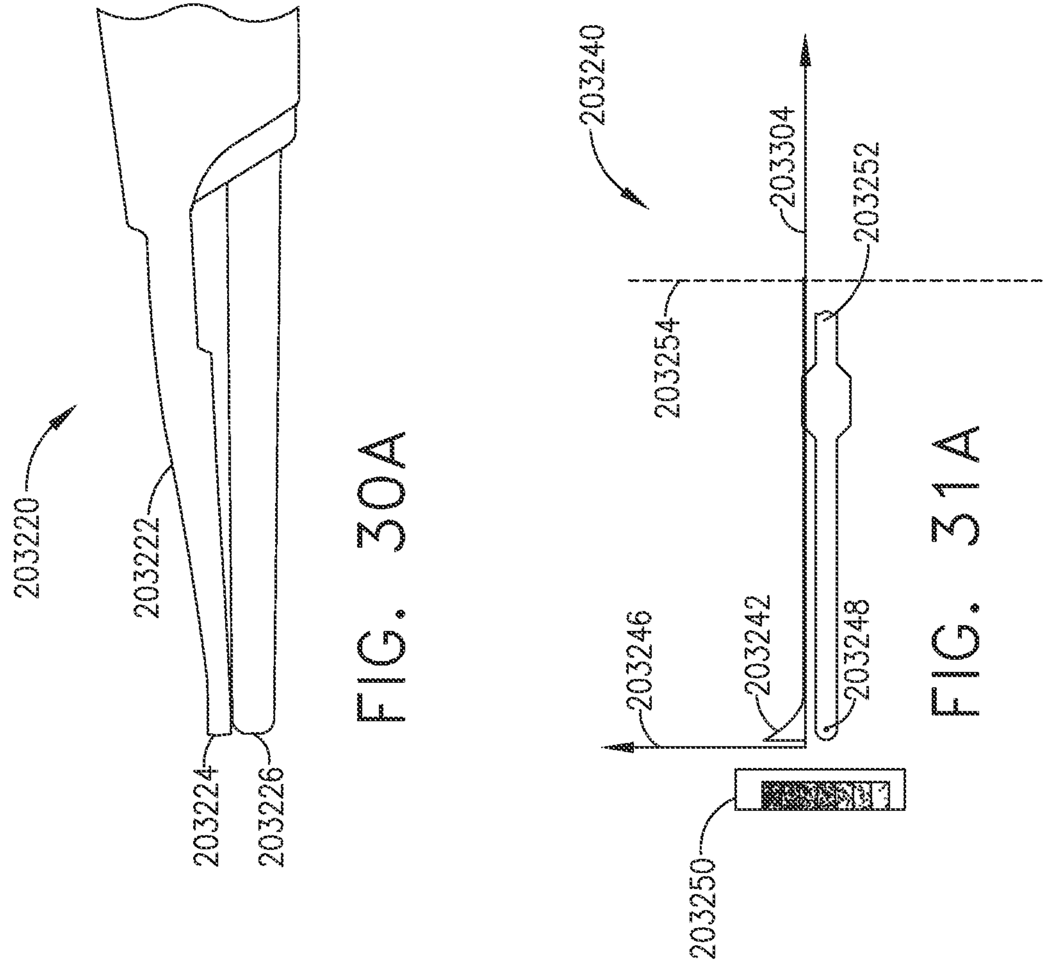
FIGS. 30A-30D are sectional views of the end effector that illustrate a distal start closure stroke configuration and indicate associated part stresses, in accordance with at least one aspect of the present disclosure.
FIGS. 31A-31D are graphs of clamp force applied between the ultrasonic blade and clamp arm as a function of distance from the distal tip of the end effector corresponding to the sectional views of FIGS. 30A-30D, in accordance with at least one aspect of the present disclosure.
Figures 30B, 31B:
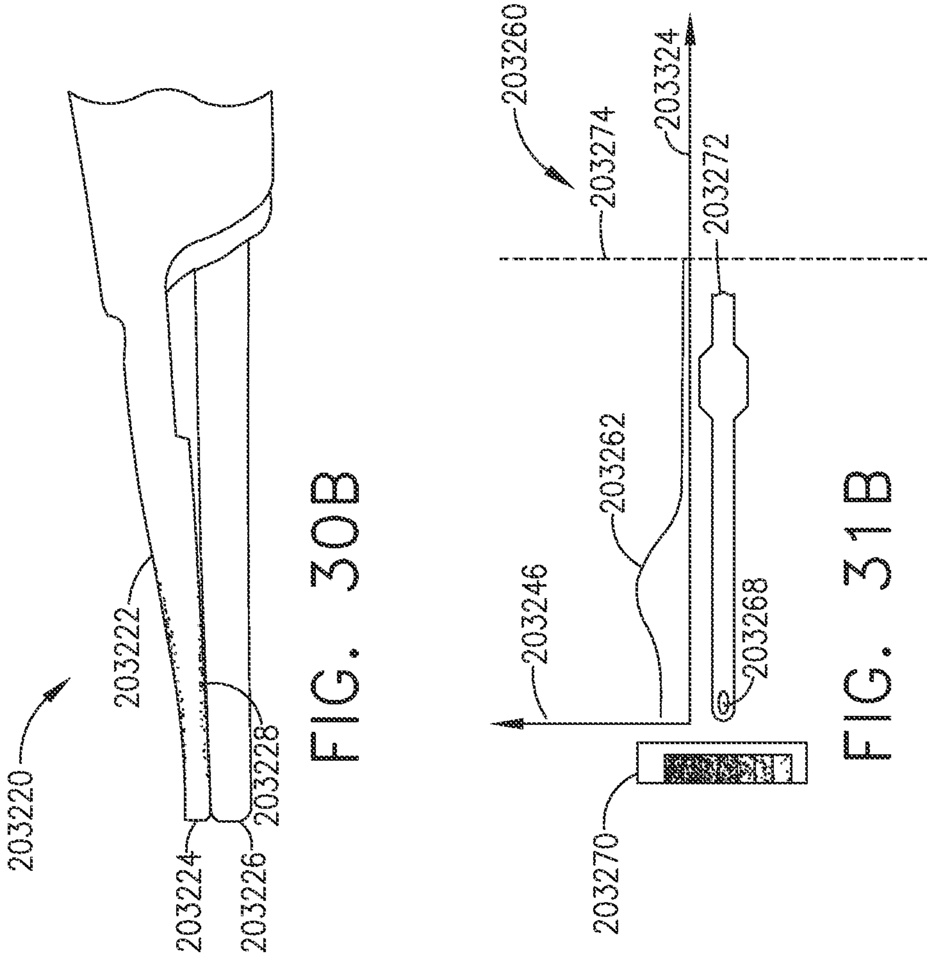
Figures 30C, 31C:
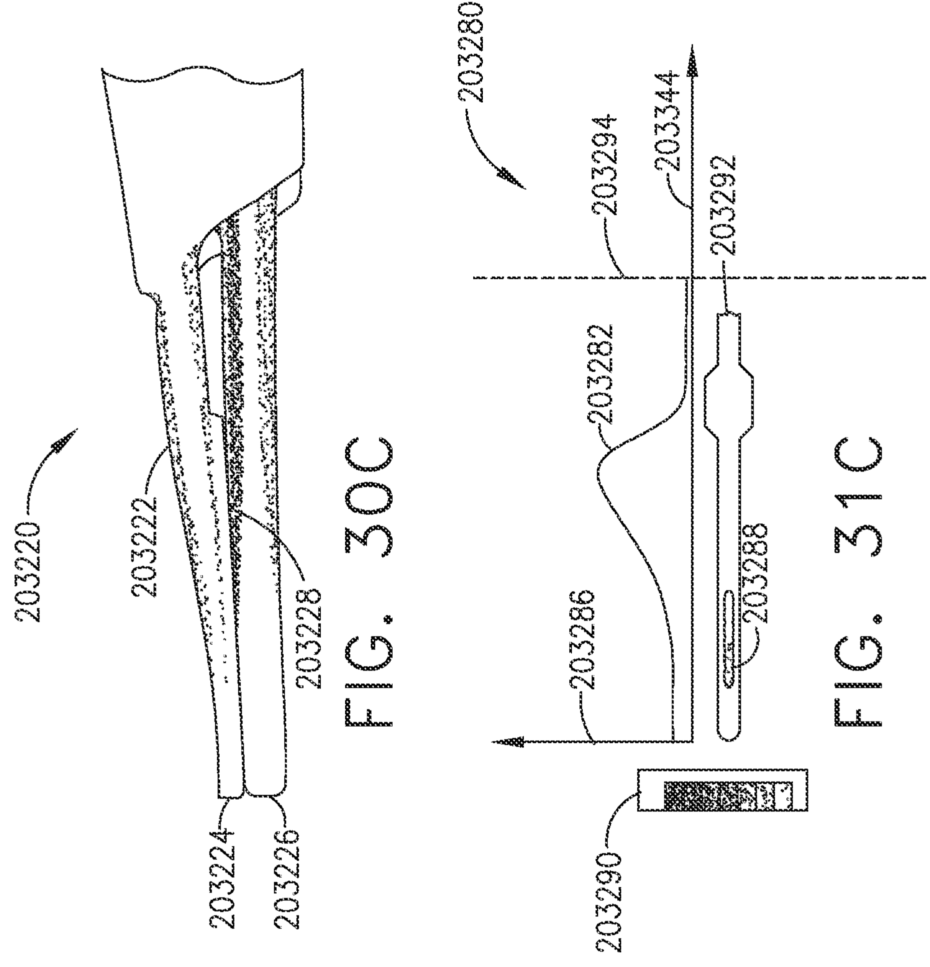

FIGS. 30A-30D are sectional views of the end effector 203220 that illustrate a distal start closure stroke configuration and indicate associated part stresses, in accordance with at least one aspect of the present disclosure. In the distal start closure stroke configuration, the end effector 203220 first closes at the distal tip, as illustrated in FIG. 30A and as described above. Thus, the control circuit is configured to control closure of the clamp arm 203224 by pivoting the clamp arm 203224 to create an initial contact point of the ultrasonic blade 203226 and clamp arm 203224 at a distal end of the end effector 203220. In FIG. 30A, the distal tip of clamp arm 203224 contacts ultrasonic blade 203226. In this way, the clamp arm tissue pad 203224 of clamp arm 203224 compresses against the grasped tissue at the distal portion first. Unlike in FIGS. 29A-29C, the applied clamp pressure in FIGS. 30A-30D rolls in the proximal direction. Also, the ultrasonic blade 203226 may be curved, sloped, or otherwise offset to allow for closing at the distal tip first. FIG. 30B depicts the end effector 203220 starting to apply more clamp pressure at the clamp arm tissue pad 203224, moving in the proximal direction. As such, the contours 203228 illustrate the associated part stresses in response to this increased bending of the clamp arm 203224. FIG. 30C shows the continued progression of the applied clamp pressure, in which a majority of the tissue treating portion of the end effector 203220 is in the fully compression position. The tissue treating portion may refer to the portion of the end effector that includes the clamp arm tissue pad 203224. As can be seen in FIGS. 30A-30D, the pad 203224 does not extend to the intersection between the clamp arm 203224 and ultrasonic blade 203226 at the proximal portion of end effector 203220. Based on this configuration, the end effector has a slight proximal gap 203230, which can be beneficial for heat mitigation as described above.

Figures 30D, 31D:
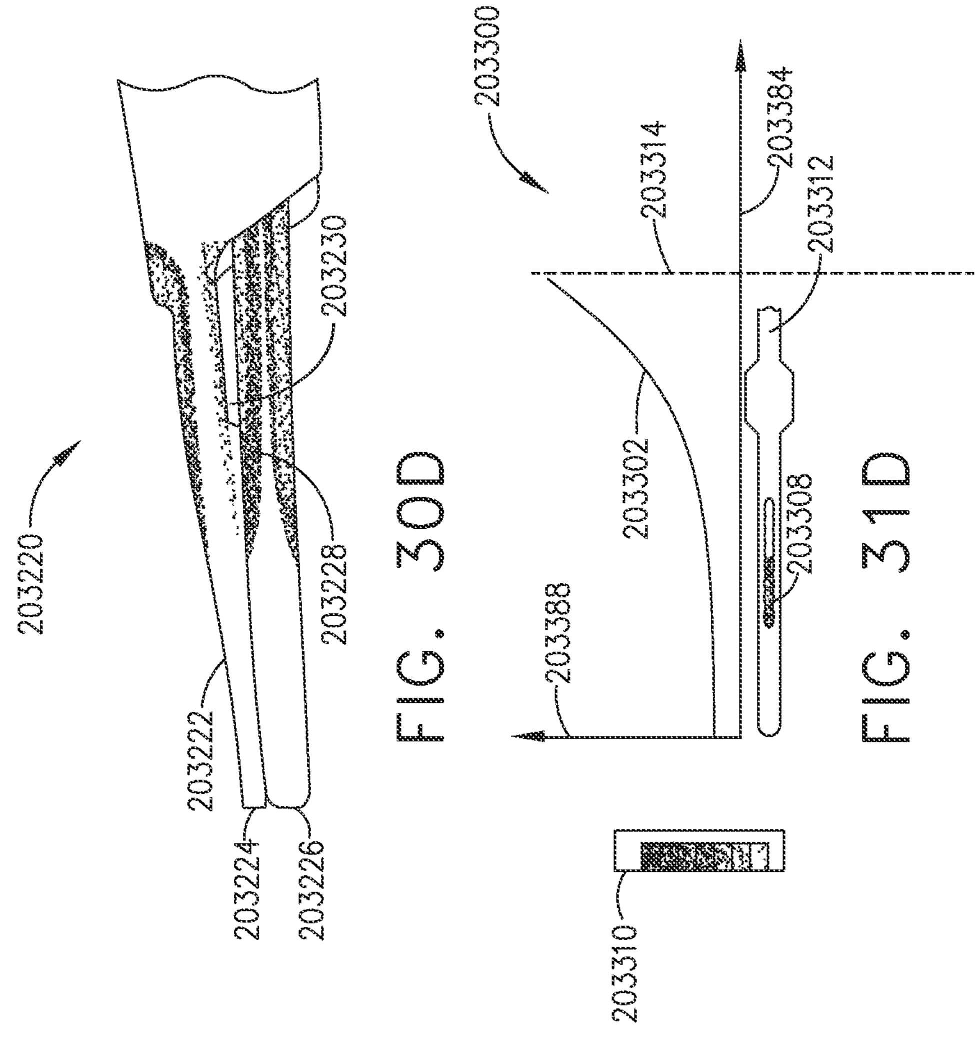

In FIG. 30D, the end effector 203220 has achieved the full closure stroke, while advantageously maintaining the proximal gap 203230. As the end effector 203220 progressively approaches a full closure position, one or more of the clamp arm 203224 and ultrasonic blade 203226 progressively realizes greater part stresses arising from the increased bending force that is exerted. In accordance, the part stresses gradually increase in correspondence with the transition from FIGS. 30A, 30C, 30C to 30D. Consequently, the greatest occurrence of contours 203228 occurs in FIG. 30D. As illustrated in FIGS. 30A-30D and moving in a proximal direction, incrementally more of the clamp arm tissue pad 203224 becomes active as more of the end effector 203220 closes. The depicted closure sequence culminates in FIG. 30D in which the entire available surface area of pad 203224 is used to compress against grasped tissue and ultrasonic blade 203226 while the portion of the end effector 203220 that is proximal to the proximal extent of the pad 203224 and grasped tissue defines the proximal gap 203230. Although the pad 203224 may terminate at the distal-most extent of the proximal gap 203230, the pad 203224 could also extend into the proximal gap 203230. Even where the pad 203224 extends in this way, the clamp arm 203222 is recessed to assist in defining the proximal gap 203230. In the proximal gap 203230, less electrosurgical energy is delivered, which may advantageously reduce the temperatures and heat residing in the ultrasonic blade 203226 after activating energy delivery by the generator 4002. The control circuit 710 may be configured to execute matching or corresponding deflections of the clamp arm 203224 and ultrasonic blade 203226 such that each of the clamp arm 203224 and ultrasonic blade 203226 deform, deflect, or bend to the same extent in transitioning from the configuration of FIG. 30A to FIG. 30D.

Moreover, the applied clamp pressure as well as displacement and velocity of ultrasonic blade 203226 can be controlled depending on the progression of the closure stroke. For example, when the end effector 203220 is only closed at the distal tip or approximately only the distal portion (e.g., in FIGS. 30A-30B), the displacement and/or velocity of the ultrasonic blade 203226 can be reduced in order to prevent excessive wear or deterioration of the pad 203224. Thus, ultrasonic oscillation can be reduced when the end effector 203220 is not fully closed. As described above, displacement may be relatively high at the distal tip portion, so reduction in blade displacement may be desirable for the distal start closure configuration of the end effector 203220. Additionally, the control circuit 710 may be configured to control closure of one or more of the clamp arm 203222 and ultrasonic blade 203226 to vary the pressure applied to provide a threshold control pressure based on the cut progression location (e.g., corresponding weld focal point). For example, as the end effector 203220 advances from FIGS. 30A to 30D, a surgical cut or coagulation focal point may shift along the length of the ultrasonic blade 203226, which can be used to adjust applied clamp pressure. The shift may be proximal or distal, depending on the selected closure stroke configuration, for example. When the focal point is at the center portion of the distal half of the end effector 203220, for example, relatively more pressure may be applied at that center portion while relative less pressure might be applied at locations distal to the center portion.

Additionally or alternatively to adjustments to clamp arm forces based on cut/coagulation focal point, the control circuit 710 may generally apply a relatively lower distal pressure and higher proximal force to address the displacement or velocity profile of the ultrasonic blade 203226. As discussed above, the displacement or velocity of the ultrasonic blade 203226 is relatively higher at distal portions, so applied forces may be lower at those portions compared to proximal portions. The ultrasonic blade 203226 may be made of a suitable material, such as titanium metal or alloy. More specifically, the titanium alloy could be a grade 5 alpha/beta titanium alloy such as Ti-6Al-4V or it could be some other suitable metal. The clamp arm 203224 could also be made of a suitable material such as stainless steel and more particularly, a precipitation-hardened 17-4 stainless steel. Also, the clamp arm tissue pad 203224 may be electrically conductive based on conductive fillers (e.g., carbon, carbon nanotubes, metallic particles) so that the surgical instrument 7012 can conduct electrical current from the ultrasonic blade 203226 to the pad 203224 via isolated electrical conduits after the end effector 203220 is fully closed. This way, electrosurgical energy such as therapeutic or sub-therapeutic RF can be delivered to the grasped tissue.

FIGS. 31A-31D are graphs 203240, 203260, 203280, 203300 of clamp force applied between the ultrasonic blade 203226 and clamp arm 203224 as a function of distance from the distal tip of the end effector 203220 corresponding to the sectional views of FIGS. 30A-30D, in accordance with at least one aspect of the present disclosure. The graphs 203240, 203260, 203280, 203300 contain legends 203250, 203270, 203290, 203310, respectively, which has different dot patterns denoting the associated degree of force due to compression between the ultrasonic blade 203226 and clamp arm 203224, for example. Pressure contours 203308 are plotted along the corresponding blade models 203252, 203272, 203292, 203312, which are a generic depiction of the length of ultrasonic blade 203226. The pressure contours 203308 may be indicative of the amount and location of component stresses applied relative to the distance away from the distal tip of the end effector 203220. The dotted line 203254, 203274, 203294, 203314 denotes the proximal end of the tissue effecting portion (e.g., the proximal end of the pad 203224) of the end effector 203220. As can be seen in FIGS. 31A-31D, the pressure contours 203308 start at the distal tip of the end effector 203220 and transition proximally towards the dotted line 203254, 203274, 203294, 203314. In the graphs 203240, 203260, 203280, 203300, the x-axis 203244, 203264, 203284, 203304 denotes the distance from the distal tip of the end effector 203220.

The y-axis 203246, 203266, 203286, 203306 denotes the applied clamp force resulting from contact between the ultrasonic blade 203226 and clamp arm 203224. The applied force is represented by the applied force line 203242, 203262, 203282, 203302. In FIG. 14A, the applied clamp force only occurs at the distal tip, which corresponds to the distal tip first closure of the distal start closure stroke configuration. The application of the clamp force gradually shifts proximally, as illustrated by the change in applied force line 203242, 203262, 203282, 203302 from FIGS. 31A to 31D. Furthermore, the amplitude of the applied clamp force also gradually increases from FIGS. 31A to 31D. The graphs 203240, 203260, 203280, 203300 may display a similar progression in clamp force as that depicted in FIGS. 28A-28C, except that the two series of graphs progress in opposite directions. Nonetheless, the distributed force or pressure profile depicted in graph 203300 may mirror that of graph 203180. That is, although FIGS. 31A to 31D depict applied pressure transitioning proximally while FIGS. 28A-28C depict pressure transitioning distally, the force profile when the full closure stroke is achieved is the same or similar regardless of the selected closure stroke configuration. The component stresses of the closure stroke according to FIGS. 31A-31D are represented by indicators 203248, 203268, 203288, 203308. Additionally, the position sensor 784 or other sensor 788 could be used to detect the vessel location along the length of the ultrasonic blade 203226 for grasped tissue. This detection might be used to adjust the closure stroke in real-time so as to target the blood vessel for application of maximum force on top of the vessel. This detection could also be used to refrain from applying power into portions of the end effector 203220 that do not contact tissue. This could be useful for heat mitigation.

Figures 32A, 32B, 32C, 32D, 32E:
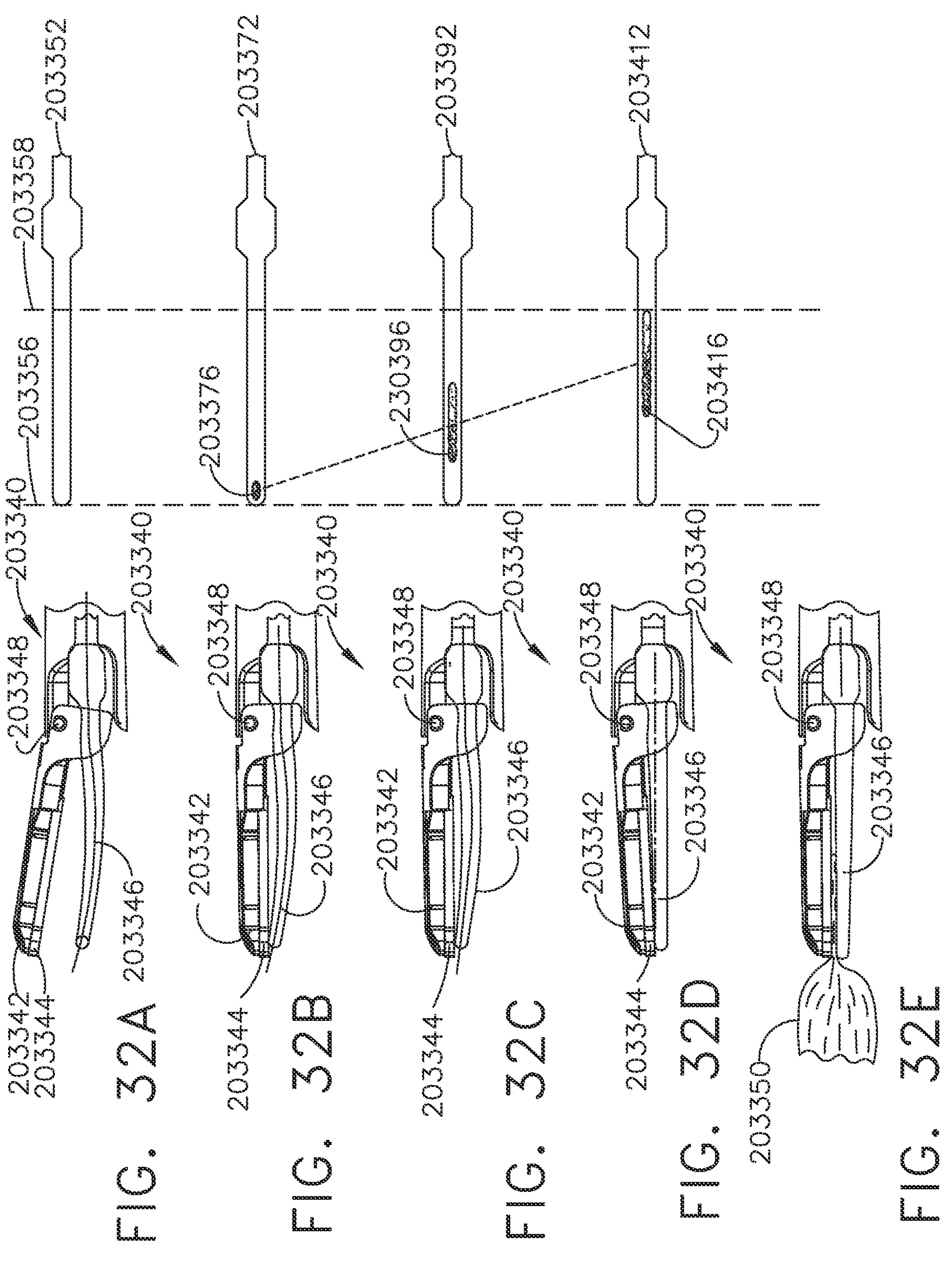
FIG. 32A-32E are sectional views of the end effector that illustrate a distal start closure stroke configuration and indicate associated part stresses, in accordance with at least one aspect of the present disclosure.

FIGS. 32A-32E are sectional views of the end effector 203340 that illustrate a distal start closure stroke configuration and indicate associated part stresses, in accordance with at least one aspect of the present disclosure. As can be seen in FIG. 32A-32E, the ultrasonic blade 203346 is curved and is deformable so that the curvature of ultrasonic blade 203346 flattens or bottoms out in the full closure stroke, as depicted in FIGS. 32D-32E. Accordingly, the axis of ultrasonic blade 203346 is offset. The ultrasonic blade 203346 and clamp arm 203342 pivot about pivot point 203348. The clamp arm 203342 includes clamp arm tissue pad 203344. FIGS. 32A-32E illustrate the progression of distal tip first closure on tissue 203350 for application of electrosurgical energy through pad 203344. In FIG. 32B, the distal tip of curved ultrasonic blade 203346 contacts the distal tip of clamp arm 203342 based on pivoting one or more of ultrasonic blade 203346 and clamp arm 203342 toward each other. The ultrasonic blade 203346 and clamp arm 203342 may move approximately an equal distance towards each other during the duration of the closure stroke. The end effector 203340 may compress against the proximal-most extent of the tissue 203350 at this point. The control circuit 710 may be configured to determine an initial clamp pressure to be applied based on the size of the tissue 203350 initially loaded into end effector 203340.

As can be seen in FIGS. 32B-32C, the deflection of curved ultrasonic blade 203346 continues and rolls proximally. Simultaneously, more of the tissue 203350 is grasped. The deflection may comprise bottoming out the curved ultrasonic blade 203346 by incrementally reducing the instantaneous curvature of the curved ultrasonic blade 203346. At FIG. 32D, the curved ultrasonic blade 203346 is fully bottomed out such that the end effector 203340 is fully closed (i.e, reached the full closure stroke). A portion of the grasped tissue 203350 is fully compressed against the ultrasonic blade 203346 and clamp arm 203342 in the full closure position so that electrosurgical energy can be delivered through the pad 203344 for cutting and coagulation. The distal to proximal span of the grasped tissue within the end effector 203340 defines the tissue contact area. This tissue contact area may generate a significant amount of heat. For thermal mitigation or reduction, instead of fully bottoming out, the end effector 203340 maintains a deflection of the ultrasonic blade 203346 that is proximal to the proximal most portion of the tissue contact area. This is shown in FIGS. 32A-32E. Thus, the control circuit 7012 may maintain a gap between the ultrasonic blade 203346 and clamp arm 203342 at a point proximal to a proximal end of the tissue. As compared to the fully closed position depicted in FIG. 32D, the portions of the pad 203344 that are not treating tissue (the portions of pad 203344 proximal to the proximal-most extent of tissue contact area) do not receive as much thermal energy. Consequently, peak temperatures and heat residing in the ultrasonic blade 203346 after application of electrosurgical energy is reduced.

Also shown in ultrasonic blade 203346 are blade models 203352, 203372, 203392, 203412, which illustrate the progression of clamp force along the length of the end effector 203340. First dotted line 203356 represents the distal tip while second dotted line 203358 represents the proximal end of the end effector 203340. The second dotted line 203358 also may represent the proximal-most extent of the tissue 203350 or where the tissue 203350 stops. In the blade model 203352, no force is applied to the ultrasonic blade 203346. In the blade model 203372, the distal tip of the ultrasonic blade 203346 contacts the corresponding portion of clamp arm 203342, so some force is applied to the distal portion of the ultrasonic blade 203346. Areas of greater applied force may be denoted by darker shading of the pressure contours 203376, 203396, 203416. Accordingly, relatively high force represented by pressure contour 203376 is applied to the distal tip in blade model 203372. In the blade model 203392, the end effector 203340 is more partially closed in the proximal direction, so the pressure contour 203396 spans a greater length of the end effector 203340. The pressure contour 203396 may vary depending on the location of the cut/weld focal point so as to provide a constant threshold pressure on the tissue 203350. In the blade model 203392, the end effector 203340 is fully closed and applied clamp force has completed moving proximally during the closure motion. Consequently, the pressure contour 203396 spans an even greater length and terminates at the second dotted line 203358.

EXAMPLES

Various aspects of the subject matter described herein are set out in the following numbered examples:

Example 1—A surgical instrument comprises an end effector, an ultrasonic transducer, a control circuit, and the control circuit coupled to the end effector. The end effector comprises: an ultrasonic blade configured to ultrasonically oscillate against tissue; and a clamp arm configured to pivot relative to the ultrasonic blade. The ultrasonic transducer is acoustically coupled to the ultrasonic blade. The ultrasonic transducer is configured to ultrasonically oscillate the ultrasonic blade in response to a drive signal from a generator. The end effector is configured to receive electrosurgical energy from the generator to treat tissue based on the drive signal. The control circuit is configured to: determine one or more of a resonant frequency measure indicative of a thermally induced change in resonant frequency and an electrical continuity measure; calculate a weld focal point based on one or more of the resonant frequency measure and electrical continuity measure; control closure of the clamp arm to vary a pressure applied by the clamp arm to provide a threshold control pressure to the tissue loaded into the end effector, wherein the pressure is varied based on a corresponding weld focal point; and maintain a gap between the ultrasonic blade and clamp arm at a point proximal to a proximal end of the tissue.

Example 2—The surgical instrument of Example 1, wherein the control circuit is further configured to determine an initial pressure applied by the clamp arm based on a size of the tissue initially loaded into the end effector.

Example 3—The surgical instrument of Examples 1 or 2, wherein the control circuit is further configured to vary the pressure applied by the clamp arm based on a shift in the weld focal point along the ultrasonic blade.

Example 4—The surgical instrument of Example 3, wherein the control circuit is further configured to vary the pressure applied by the clamp arm based on an extent of the tissue loaded into the end effector.

Example 5—The surgical instrument of Examples 1, 2, 3, or 4, wherein the control circuit is further configured to control closure of the clamp arm by pivoting the clamp arm to create an initial contact point of the ultrasonic blade and clamp arm at a distal end of the end effector.

Example 6—The surgical instrument of Examples 1, 2, 3, 4, or 5, further comprising the generator configured to deliver electrosurgical energy to the end effector to treat tissue based on generating the drive signal.

Example 7—The surgical instrument of Examples 1, 2, 3, 4, 5, or 6, further comprising a radio frequency (RF) electrode configured to deliver RF energy to the tissue, wherein the control circuit is further configured to adjust one or more of a power level of the RF energy and a power level of the electrosurgical energy based on tissue impedance.

Example 8—A method of using a surgical instrument to provide a threshold control pressure, wherein the surgical instrument comprises: an end effector comprising: a ultrasonic blade configured to ultrasonically oscillate against tissue; and a clamp arm configured to pivot relative to the ultrasonic blade; an ultrasonic transducer acoustically coupled to the ultrasonic blade, the ultrasonic transducer configured to ultrasonically oscillate the ultrasonic blade in response to the drive signal; and a control circuit coupled to the end effector, wherein the end effector is configured to receive electrosurgical energy from a generator to weld tissue based on a generated drive signal and wherein the method comprises: determining, by the control circuit, one or more of a resonant frequency measure indicative of a thermally induced change in resonant frequency and a electrical continuity measure; calculating, by the control circuit, a weld focal point based on one or more of the resonant frequency measure and electrical continuity measure; controlling, by the control circuit, closure of the clamp arm to vary a pressure applied by the clamp arm to provide the threshold control pressure to the tissue loaded into the end effector, wherein the pressure is varied based on a corresponding weld focal point; and maintaining, by the control circuit, a gap between the ultrasonic blade and clamp arm at a point proximal to a proximal end of the tissue.

Example 9—The method of Example 8, further comprising determining, by the control circuit, an initial pressure applied by the clamp arm based on a size of the tissue initially loaded into the end effector.

Example 10—The method of Examples 8 or 9, further comprising varying, by the control circuit, the pressure applied by the clamp arm based on a shift in the weld focal point along the ultrasonic blade.

Example 11—The method of Example 10, further comprising varying, by the control circuit, the pressure applied by the clamp arm based on an extent of the tissue loaded into the end effector.

Example 12—The method of Examples 8, 9, 10, or 11 further comprising controlling, by the control circuit, closure of the clamp arm by pivoting the clamp arm to create an initial contact point of the ultrasonic blade and clamp arm at a distal end of the end effector.

Example 13—The method of Examples 8, 9, 10, 11, or 12, further comprising loading the tissue into the end effector from the distal end to a proximal end of the end effector.

Example 14—The method of Examples 8, 9, 10, 11, 12, or 13, further comprising adjusting, by the control circuit, one or more of a power level of RF energy and a power level of the electrosurgical energy based on tissue impedance, wherein the surgical instrument further comprises a radio frequency (RF) electrode configured to deliver RF energy to the tissue.

Example 15—A surgical system comprising: a surgical hub configured to receive a clamp pressure algorithm transmitted from a cloud computing system, wherein the surgical hub is communicatively coupled to the cloud computing system; and a surgical instrument communicatively coupled to the surgical hub, wherein the surgical instrument comprises: an end effector comprising: an offset ultrasonic blade configured to ultrasonically oscillate against tissue; and an offset clamp arm configured to pivot relative to the ultrasonic blade; and an ultrasonic transducer acoustically coupled to the ultrasonic blade, the ultrasonic transducer configured to ultrasonically oscillate the ultrasonic blade in response to a drive signal from a generator, wherein the end effector is configured to receive electrosurgical energy from the generator to weld tissue based on the drive signal; and a control circuit configured to perform the clamp pressure algorithm to: determine one or more of a resonant frequency measure indicative of a thermally induced change in resonant frequency and a electrical continuity measure; calculate an extent of tissue loaded into the end effector based on one or more of the resonant frequency measure and electrical continuity measure; and vary pressure applied by the clamp arm according to a closure pressure profile comprising a first pressure in a proximal half of the end effector that is greater than a second pressure in a distal half of the end effector and to maintain a gap between the ultrasonic blade and clamp arm at a point proximal to a proximal end of the tissue loaded into the end effector when the end effector is fully closed.

Example 16—The surgical system of Example 15, wherein the control circuit is further configured to close the end effector at a distal end of the end effector prior to closing non-distal end portions of the end effector.

Example 17—The surgical system of Examples 15 or 16, further comprising: terminating, by the generator, application of the third power level for a third dwell time; determining, by the control circuit, a fourth tissue impedance point; and applying, by the generator, a fourth power level to reach the fourth tissue impedance point.

Example 18—The surgical system of Example 17, wherein the first and second deflection are shaped according to the closure pressure profile to provide the first pressure.

Example 19—The surgical system of Examples 15, 16, 17, or 18, wherein the control circuit is further configured to determine a closure position of the clamp arm.

Example 20—The method of Example 19, wherein the control circuit is further configured to reduce the ultrasonic oscillation of the ultrasonic blade when the end effector is not in fully closed.

While several forms have been illustrated and described, it is not the intention of Applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. Those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution.

Instructions used to program logic to perform various disclosed aspects can be stored within a memory in the system, such as dynamic random access memory (DRAM), cache, flash memory, or other storage. Furthermore, the instructions can be distributed via a network or by way of other computer readable media. Thus a machine-readable medium may include any mechanism for storing or transmitting information in a form readable by a machine (e.g., a computer), but is not limited to, floppy diskettes, optical disks, compact disc, read-only memory (CD-ROMs), and magneto-optical disks, read-only memory (ROMs), random access memory (RAM), erasable programmable read-only memory (EPROM), electrically erasable programmable read-only memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, etc.). Accordingly, the non-transitory computer-readable medium includes any type of tangible machine-readable medium suitable for storing or transmitting electronic instructions or information in a form readable by a machine (e.g., a computer).

As used in any aspect herein, the term "control circuit" may refer to, for example, hardwired circuitry, programmable circuitry (e.g., a computer processor including one or more individual instruction processing cores, processing unit, processor, microcontroller, microcontroller unit, controller, digital signal processor (DSP), programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein "control circuit" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

As used in any aspect herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

As used in any aspect herein, the terms "component," "system," "module" and the like can refer to a computer-related entity, either hardware, a combination of hardware and software, software, or software in execution.

As used in any aspect herein, an "algorithm" refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

A network may include a packet switched network. The communication devices may be capable of communicating with each other using a selected packet switched network communications protocol. One example communications protocol may include an Ethernet communications protocol which may be capable permitting communication using a Transmission Control Protocol/Internet Protocol (TCP/IP). The Ethernet protocol may comply or be compatible with the Ethernet standard published by the Institute of Electrical and Electronics Engineers (IEEE) titled "IEEE 802.3 Standard", published in December, 2008 and/or later versions of this standard. Alternatively or additionally, the communication devices may be capable of communicating with each other using an X.25 communications protocol. The X.25 communications protocol may comply or be compatible with a standard promulgated by the International Telecommunication Union-Telecommunication Standardization Sector (ITU-T). Alternatively or additionally, the communication devices may be capable of communicating with each other using a frame relay communications protocol. The frame relay communications protocol may comply or be compatible with a standard promulgated by Consultative Committee for International Telegraph and Telephone (CCITT) and/or the American National Standards Institute (ANSI). Alternatively or additionally, the transceivers may be capable of communicating with each other using an Asynchronous Transfer Mode (ATM) communications protocol. The ATM communications protocol may comply or be compatible with an ATM standard published by the ATM Forum titled "ATM-MPLS Network Interworking 2.0" published August 2001, and/or later versions of this standard. Of course, different and/or after-developed connection-oriented network communication protocols are equally contemplated herein.

Unless specifically stated otherwise as apparent from the foregoing disclosure, it is appreciated that, throughout the foregoing disclosure, discussions using terms such as "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures or characteristics may be combined in any suitable manner in one or more aspects.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

The invention claimed is:

1. A surgical hub, comprising:

a control circuit, configured to:

transmit a first control signal to a surgical instrument to cause a force to be applied to a tissue by a clamp arm of the surgical instrument;

determine a focal point between the clamp arm and the tissue based on an electrical continuity feedback measurement obtained from the surgical instrument, wherein the focal point is defined as a point of contact between the clamp arm and the tissue;

detect a shift in the focal point; and transmit a second control signal to the surgical instrument to vary the force applied by the clamp arm according to the detected shift in the focal point.

2. The surgical hub of claim 1, wherein the control circuit is configured to determine the focal point based on a resonant frequency of an ultrasonic blade of the surgical instrument.

3. The surgical hub of claim 1, wherein the control circuit is further configured to detect a proximal to distal shift in the focal point relative to the clamp arm.

4. The surgical hub of claim 1, wherein the control circuit is further configured to detect a distal to proximal shift in the focal point relative to the clamp arm.

5. A surgical system, comprising:

a surgical instrument comprising a clamp arm and an electrode, the electrode configured to apply energy to a tissue; and a control circuit, configured to:

transmit a first control signal to the surgical instrument to cause the clamp arm to apply a force to the tissue;

determine a focal point between the clamp arm and the tissue based on an electrical continuity feedback measurement obtained from the electrode, wherein the focal point is defined as a point of contact between the clamp arm and the tissue;

monitor movement of the focal point; and transmit a second control signal to the surgical instrument to vary the force applied by the clamp arm according to the monitored movement of the focal point.

6. The surgical system of claim 5, wherein the clamp arm comprises a tissue pad, and wherein the focal point is defined as a point of contact between the tissue pad and the tissue.

7. The surgical system of claim 6, wherein the tissue pad comprises axially spaced, proximally extending gripping teeth.

8. The surgical system of claim 5, wherein the surgical instrument comprises an ultrasonic blade, and wherein the focal point is determined based on a resonant frequency of the ultrasonic blade.

9. The surgical system of claim 5, wherein the control circuit is further configured to detect a proximal to distal shift in the focal point relative to the clamp arm.

10. The surgical system of claim 5, wherein the control circuit is further configured to detect a distal to proximal shift in the focal point relative to the clamp arm.

* * * * *